US012746288B2

(12) United States Patent
Liu et al.

(10) Patent No.: US 12,746,288 B2
(45) Date of Patent: Sep. 29, 2026

(54) IONIZABLE CATIONIC LIPID ANALOG MATERIAL AND USE THEREOF AS DRUG DELIVERY CARRIER

(71) Applicant: GUANGZHOU LIDE BIOMEDICINE TECHNOLOGY CO., LTD., Guangzhou (CN)

(72) Inventors: Zhijia Liu, Guangzhou (CN); Zhicheng Le, Guangzhou (CN); Zepeng He, Guangzhou (CN); Yongming Chen, Guangzhou (CN)

(73) Assignee: GUANGZHOU LIDE BIOMEDICINE TECHNOLOGY CO., LTD., Guangzhou (CN)

( * ) Notice: Subject to any disclaimer, the term of this patent is extended or adjusted under 35 U.S.C. 154(b) by 457 days.

(21) Appl. No.: 18/231,831

(22) Filed: Aug. 9, 2023

(65) Prior Publication Data

US 2023/0390402 A1 Dec. 7, 2023

Related U.S. Application Data

(63) Continuation of application No. PCT/CN2021/136176, filed on Dec. 7, 2021.

(30) Foreign Application Priority Data

Feb. 9, 2021 (CN) ......................... 202110183414.2

(51) Int. Cl.

| | |
|---|---|
| ***A61K 47/54*** | (2017.01) |
| ***A61K 9/51*** | (2006.01) |
| ***C07C 237/22*** | (2006.01) |
| ***C07D 207/09*** | (2006.01) |
| ***C07D 295/13*** | (2006.01) |
| ***C12N 15/88*** | (2006.01) |

(52) U.S. Cl.

CPC .......... *A61K 47/543* (2017.08); *A61K 9/5123* (2013.01); *A61K 47/545* (2017.08); *C07C 237/22* (2013.01); *C07D 207/09* (2013.01); *C07D 295/13* (2013.01); *C12N 15/88* (2013.01)

(58) Field of Classification Search

None

See application file for complete search history.

(56) References Cited

U.S. PATENT DOCUMENTS

2006/0148734 A1 7/2006 Camilleri et al.

FOREIGN PATENT DOCUMENTS

| | | | |
|---|---|---|---|
| CN | 111087332 | A | 5/2020 |
| CN | 111892707 | A | 11/2020 |
| JP | 2015501309 | A | 1/2015 |

OTHER PUBLICATIONS

International Search Report of PCT Patent Application No. PCT/CN2021/136176 issued on Feb. 15, 2022.

Le Z. C. et al., Combinatorial Synthesis of Redox-Responsive Cationic Polypeptoids for Intracellular Protein Delivery Application, Science China Chemistry, Aug. 13, 2020.

Extended European Search Report of counterpart European Patent Application No. 21925480.2 issued on Nov. 4, 2024.

Mark Damen et al., Structure-delivery relationships of lysine-based gemini surfactants and their lipoplexes, Soft Matter, Jan. 1, 2014, pp. 5702-5714, vol. 10, No. 31.

Xu Ping et al., Parallel Synthesis of α-Acylamino Amide Library by Ugi four-component Condensation Reaction, Journal of Chinese Pharmaceutical Sciences, 2001, pp. 9-13, vol. 10, No. 1.

*Primary Examiner* — Samantha L Shterengarts

(57) ABSTRACT

The present disclosure discloses an ionizable cationic lipid analog material and use thereof as a drug delivery carrier. In the present disclosure, a series of cationic lipid analog materials are reasonably designed, and a preparation method of the cationic lipid analog materials involves mild reaction conditions, a simple process, and excellent stability. The cationic lipid analog materials have excellent biocompatibility, and can allow an efficient and safe intracellular delivery of a biomacromolecular drug. The cationic lipid analog materials can also be used as delivery carriers for other types of drugs.

20 Claims, 14 Drawing Sheets

IONIZABLE CATIONIC LIPID ANALOG MATERIAL AND USE THEREOF AS DRUG DELIVERY CARRIER

CROSS-REFERENCE TO RELATED APPLICATIONS

The present application is a continuation application of PCT application No. PCT/CN2021/136176 filed on Dec. 7, 2021, which claims the benefit of Chinese Patent Application No. 202110183414.2 filed on Feb. 9, 2021. The contents of all of the aforementioned applications are incorporated by reference herein in their entirety.

TECHNICAL FIELD

The present disclosure relates to the technical field of biomedicine, and in particular to an ionizable cationic lipid analog material and use thereof as a drug delivery carrier.

BACKGROUND

Biomacromolecular drugs refer to biomacromolecules derived in vivo or synthesized ex vivo using modern biotechnological methods, which are used for the diagnosis, prevention, or treatment of diseases. Biomacromolecules mainly include proteins, polypeptides, antibodies, and nucleic acids, and play important roles in biological activities. Biomacromolecular drugs have excellent target selectivity and high efficacy, and exhibit advantages such as definite efficacy and minimal side effects in clinical treatment, making them an important research direction in drug development. However, compared with small-molecule drugs, biomacromolecular drugs face challenges related to their large sizes and molecular weights, negatively or positively charged surfaces, and difficulties in crossing cell membranes of target cells to enter the target cells. A lot of efforts have been conducted by researchers to allow the efficient delivery of biomacromolecular drugs, and many biomacromolecular drug delivery carriers have been developed, including liposomes, cationic polymers, nanoparticles, and the like. However, these carriers still have problems such as low delivery efficiency. Improving the delivery effectiveness of biomacromolecular drugs, maintaining their activity and stability during delivery, overcoming various biological barriers in the body, and achieving precise intracellular delivery are still major difficulties and development directions in the research of drug delivery systems for biomacromolecular drugs.

SUMMARY

An objective of the present disclosure is to overcome the shortcomings of the prior art and provide an ionizable cationic lipid analog material, and the cationic lipid analog material can efficiently allow an intracellular delivery of a biomacromolecular drug.

To achieve the above objective, the present disclosure adopts the following technical solutions:

The present disclosure provides an ionizable cationic lipid analog material with a structure shown in formula (I):

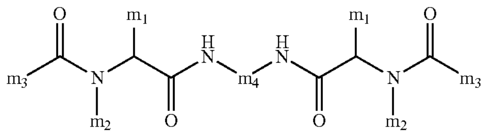

I where $m_1$ is independently selected from the group consisting of a branched alkyl, phenyl, and a heteroatom-containing aryl;

$m_2$ is

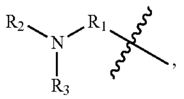

$R_1$ is an alkyl, $R_2$ is an alkyl, $R_3$ is an alkyl or phenyl, or $R_2$ and $R_3$ are connected as a cyclic group or a heterocyclic group;

$m_3$ is independently selected from the group consisting of a linear alkyl, a linear alkenyl, and

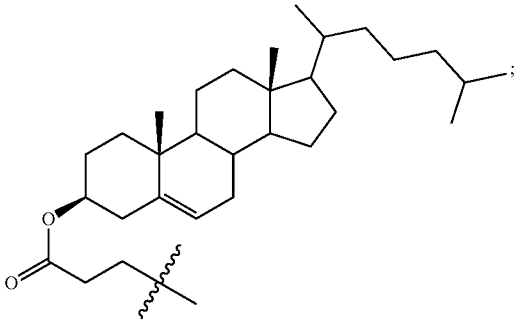 [SMILES: *CCC(=O)O[C@H]1CC[C@@]2(C)C(=CCC3C4CCC(C(C)CCCC(C)C)[C@@]4(C)CCC32)C1]

and $m_4$ is independently selected from the group consisting of a linear alkyl, an ether bond-containing linear alkyl, and a N-heterocycle-containing alkyl.

In the cationic lipid analog material of the present disclosure, $m_2$ includes a tertiary amino group, ensuring pH sensitivity and tunable positive charge of the material; and $m_3$ includes a linear alkyl, a linear alkenyl, or

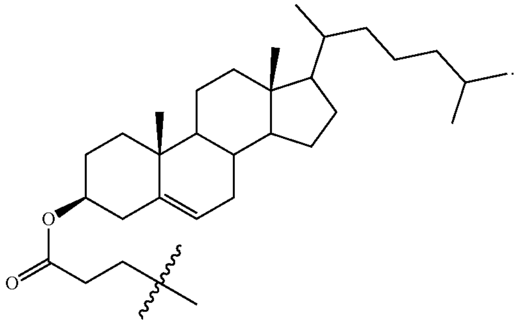 [SMILES: *CCC(=O)O[C@H]1CC[C@@]2(C)C(=CCC3C4CCC(C(C)CCCC(C)C)[C@@]4(C)CCC32)C1]

By controlling its chain length, the hydrophobicity of the material can be adjusted. Through rational design and synthesis, a series of cationic lipid analog materials mentioned above have been prepared. These cationic lipid analog materials can bind with biomacromolecular drugs such as proteins and nucleic acids to form complexes, enabling efficient intracellular delivery of biological macromolecular drugs.

The cationic lipid analog materials of the present disclosure, as carriers for drug delivery, especially for intracellular delivery of biological macromolecular drugs, exhibit high delivery efficiency, low toxicity to cells during the delivery process, and an ability to maintain the biological activity of drugs after delivery into cells. In addition, these cationic lipid analog materials as carrier materials are suitable for various proteins and nucleic acid molecules, making them a universal and efficient carrier for the intracellular delivery of biomacromolecular drugs.

In addition, in formula (I), $m_1$ is selected from the group consisting of an alkyl, phenyl, and a heteroatom-containing aryl each substituted by a substituent α, and the substituent α includes methyl; and preferably, $m_1$ is selected from the group consisting of

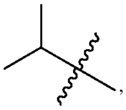,
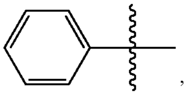, and
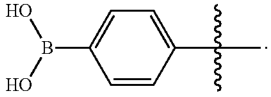.

In addition, in formula (I), $m_2$ is selected from the group consisting of

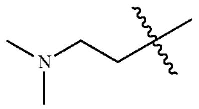,
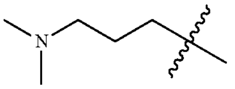,
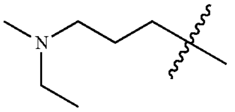,
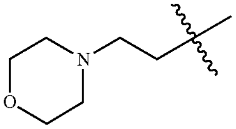,
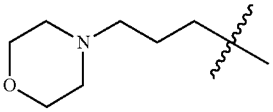,
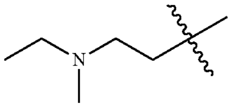,
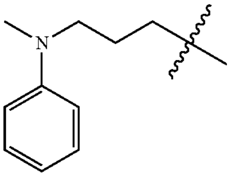, -continued

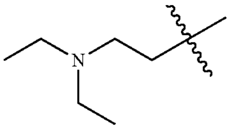,
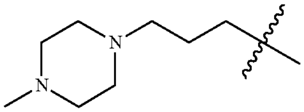,
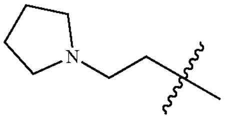, and
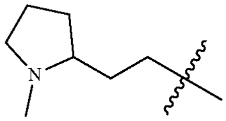;

and preferably, when $m_2$ is selected from the group consisting of

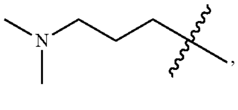,
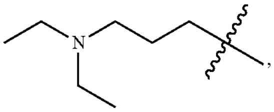, and
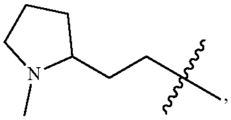, the cationic lipid analog material has high intracellular delivery efficiency for proteins.

In addition, in formula (I), $m_3$ is selected from the group consisting of a linear alkyl with 7 to 19 carbon atoms, a linear alkenyl with 17 carbon atoms, and

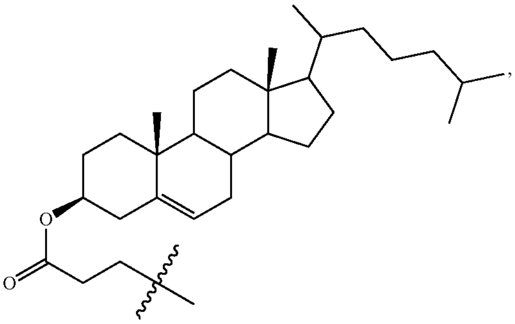 [SMILES: *CCC(=O)O[C@H]1CC[C@@]2(C)C(=CCC3C4CCC(C(C)CCCC(C)C)[C@@]4(C)CCC32)C1], and preferably, $m_3$ is selected from the group consisting of

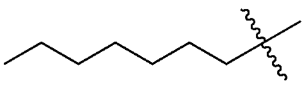,
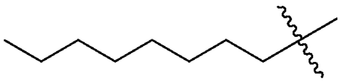,

-continued

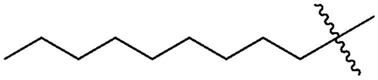

,

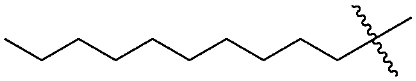

,

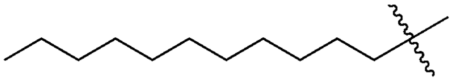

,

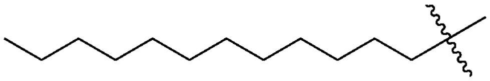

,

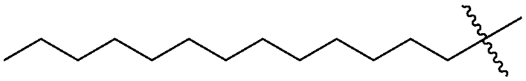

,

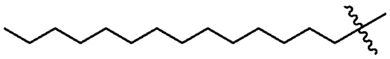

,

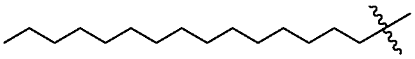

,

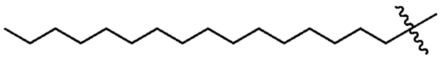

,

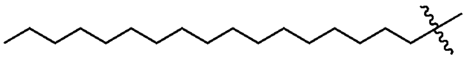

,

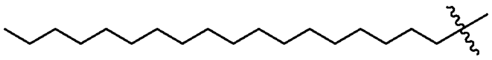

,

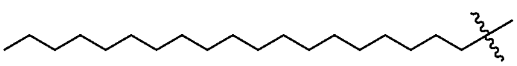

,

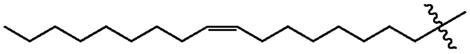

,

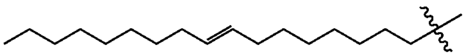

,

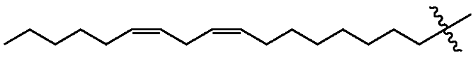

,

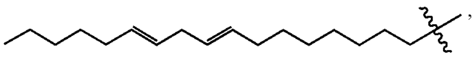

, and

-continued

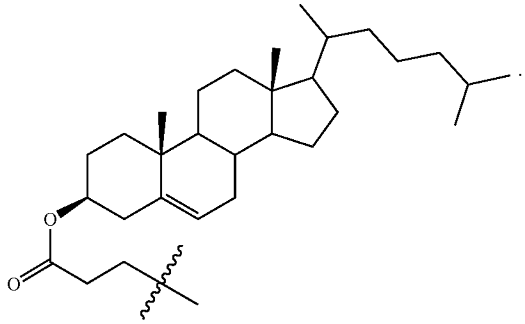

.

In addition, in formula (I), $m_4$ is selected from the group consisting of a linear alkyl with 6 carbon atoms, an ether bond-containing linear alkyl with 4 to 8 carbon atoms, and a N-heterocycle-containing alkyl; and preferably, when $m_4$ is selected from the group consisting of

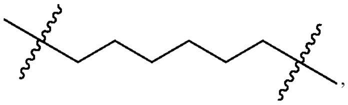

,

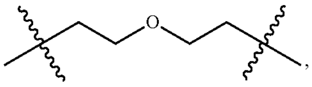

,

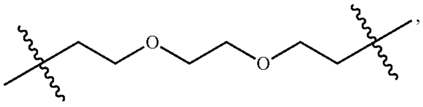

,

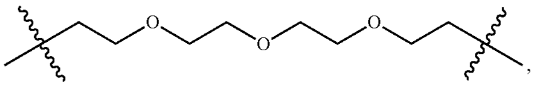

, and

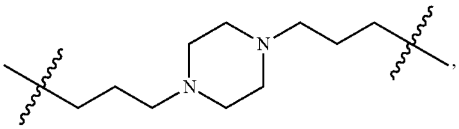

, the cationic lipid analog material has high intracellular delivery efficiency for proteins.

In addition, the cationic lipid analog material has a structure selected from the group consisting of the following 72 structures:

I1R1C12A1
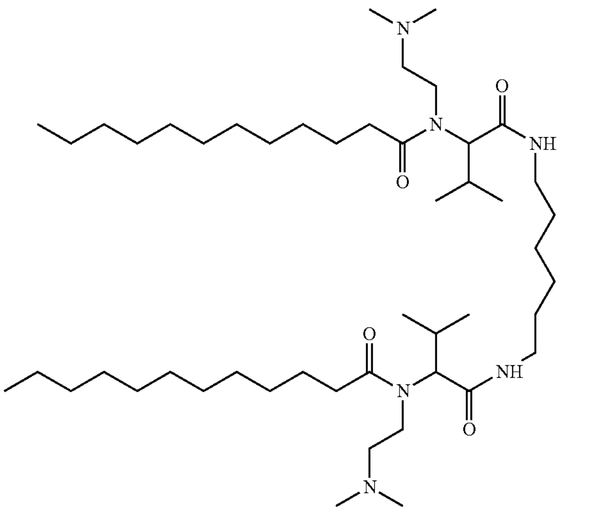
I1R1C14A1
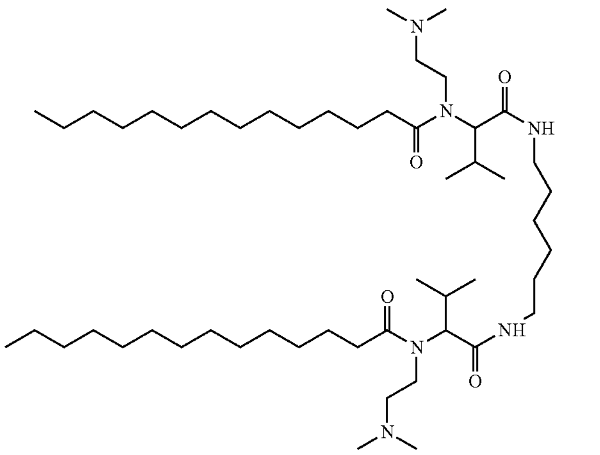
I1R1C16A1
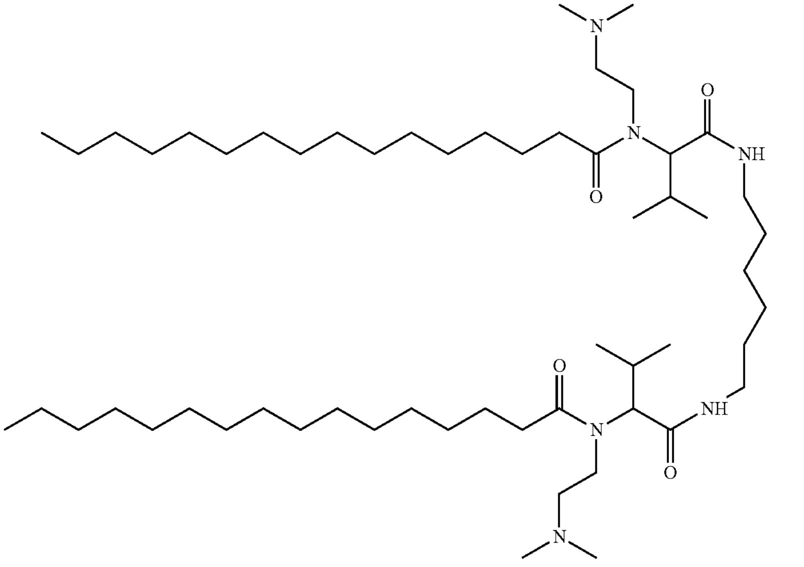
I1R1C18A1
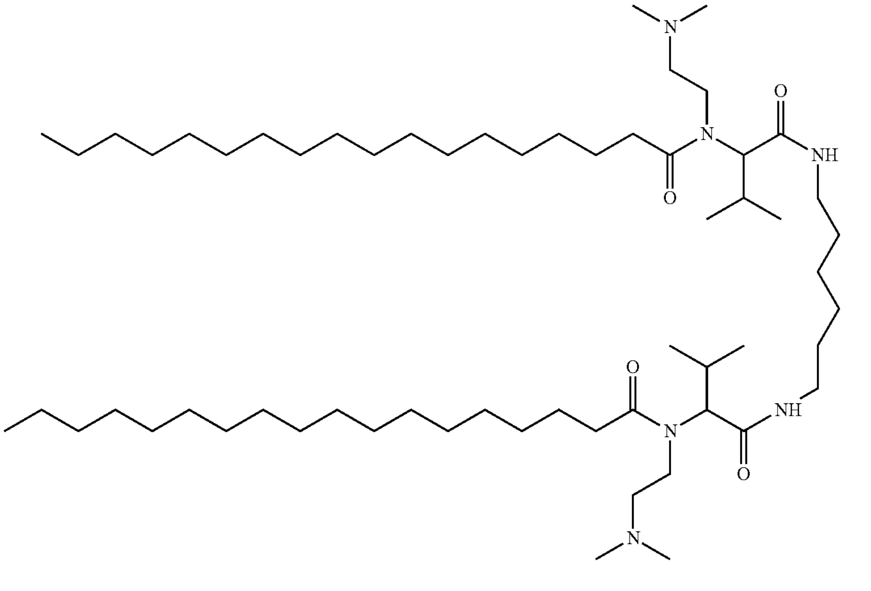

-continued
I1R1C20A1
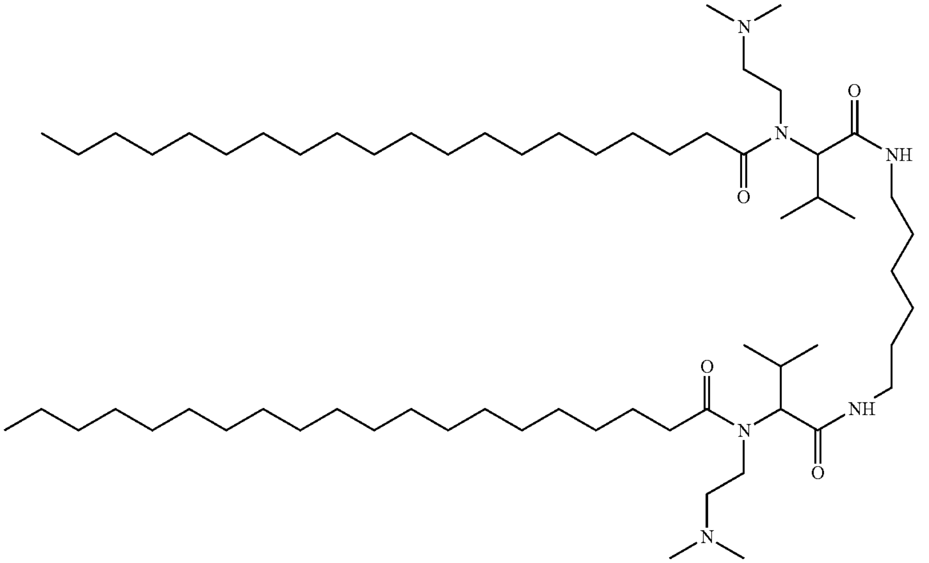
I1R1C18-1A1
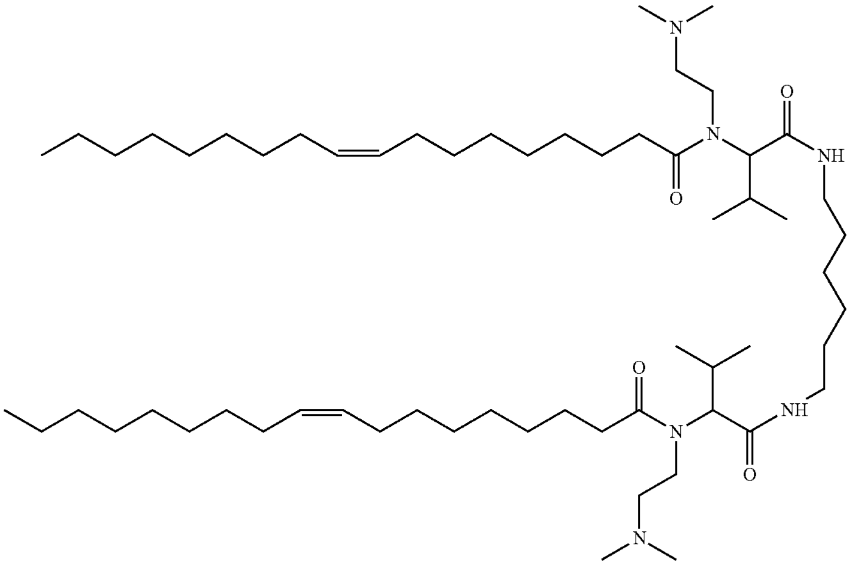

-continued
I1R3C14A1
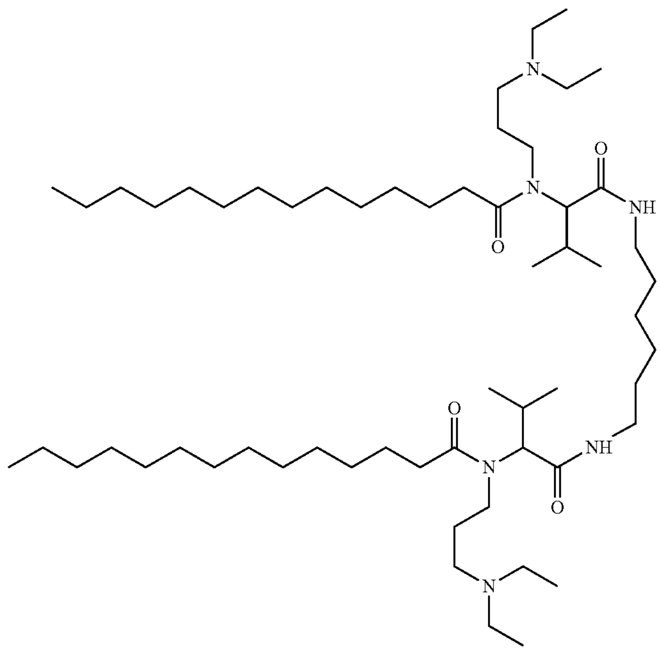
I1R1C18-2A1
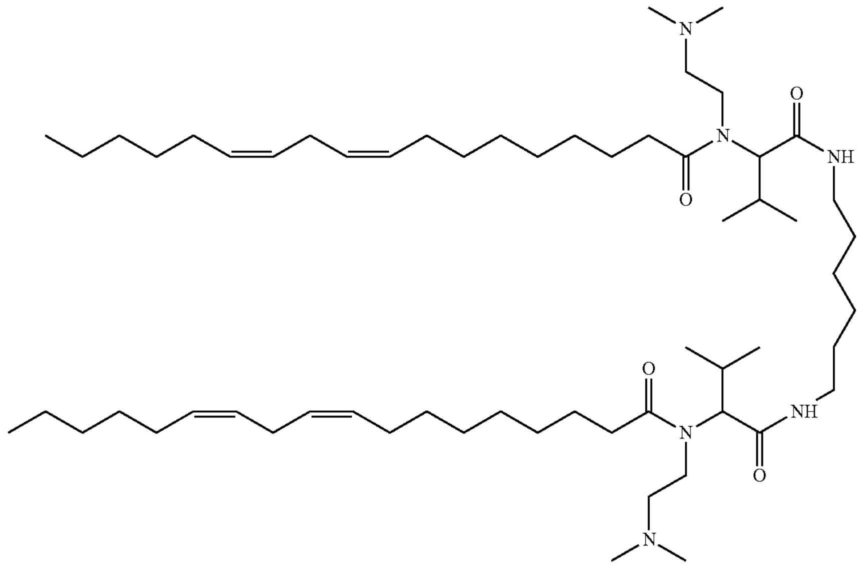

-continued
I1R2C12A1
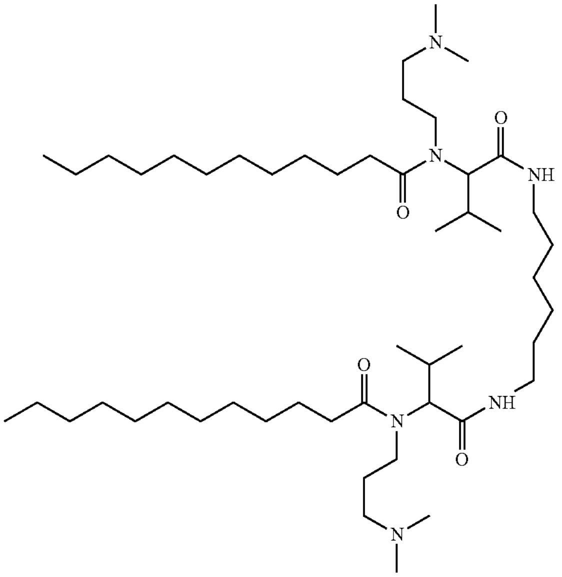
I1R2C14A1
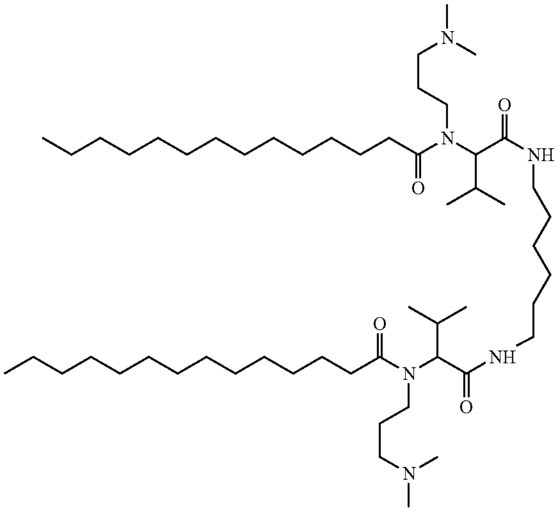
I1R2C16A1
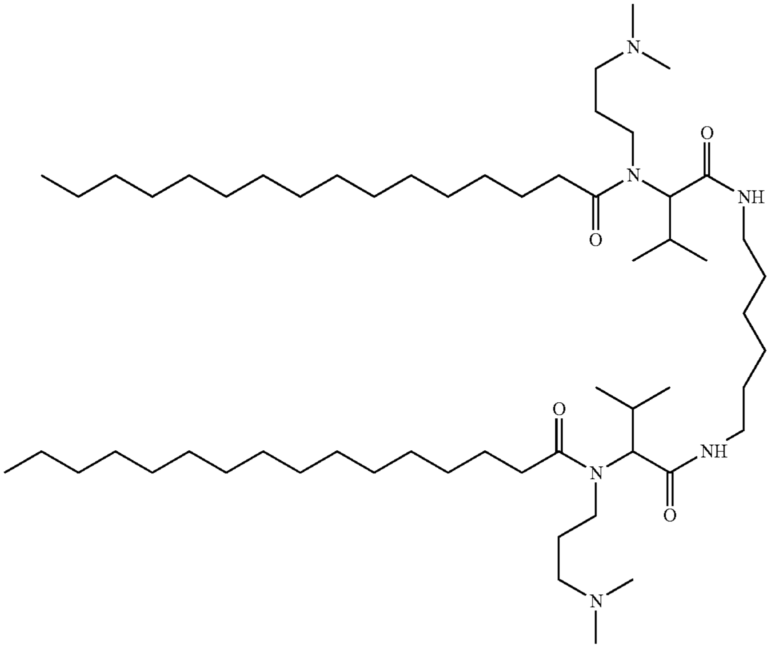

-continued
I1R2C18A1
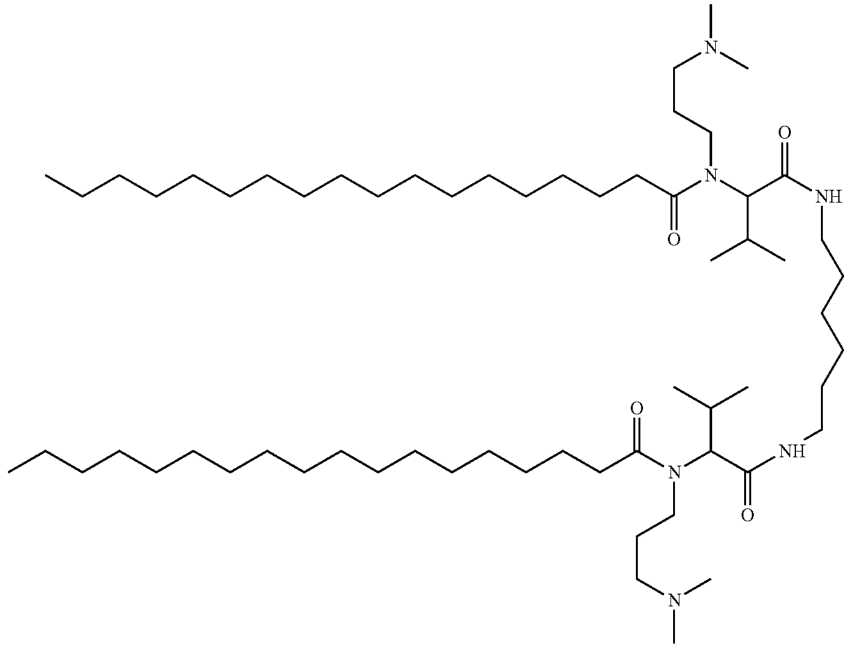
I1R2C20A1
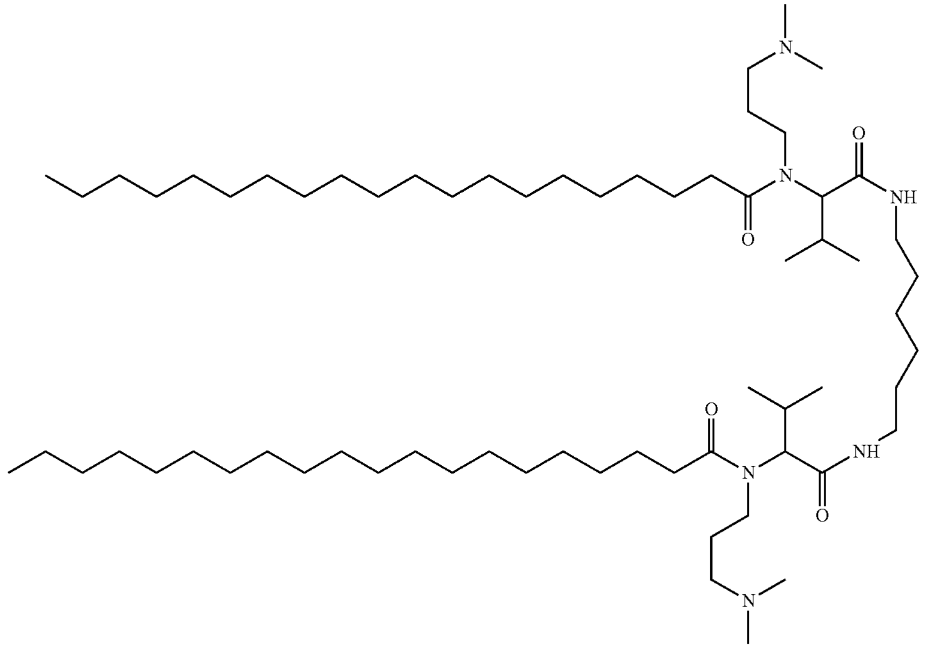

-continued
I1R2C18-1A1
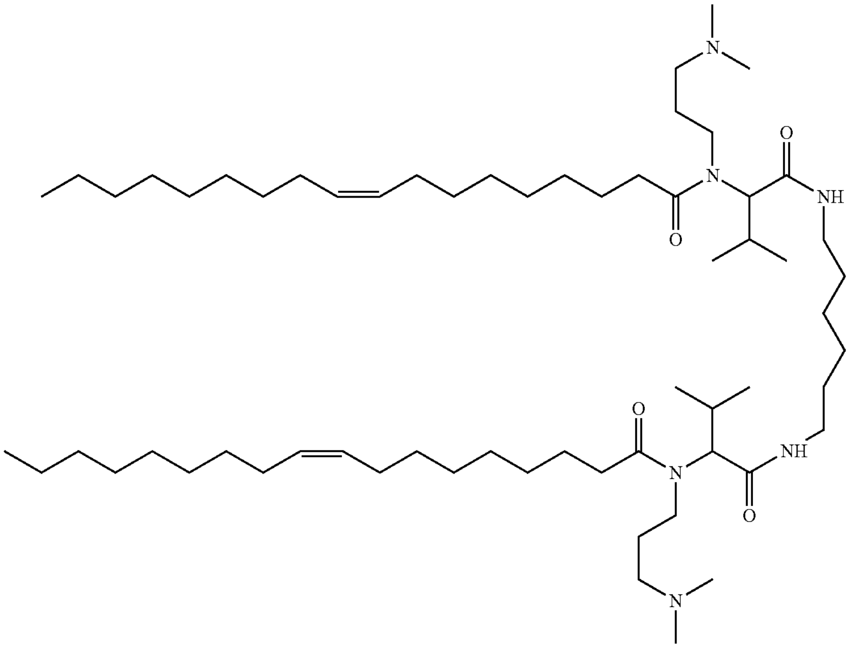
I1R2C18-2A1
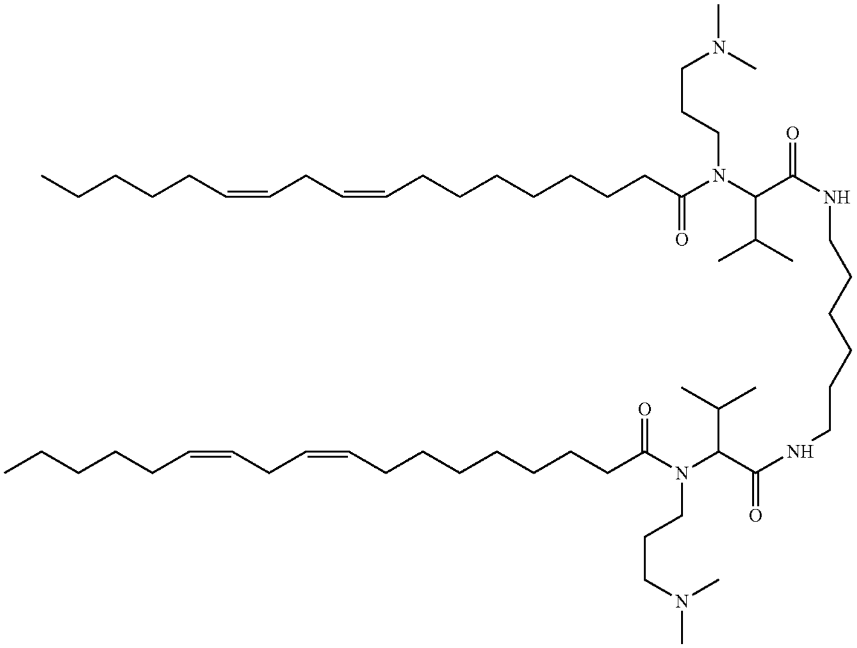

-continued
I1R3C12A1
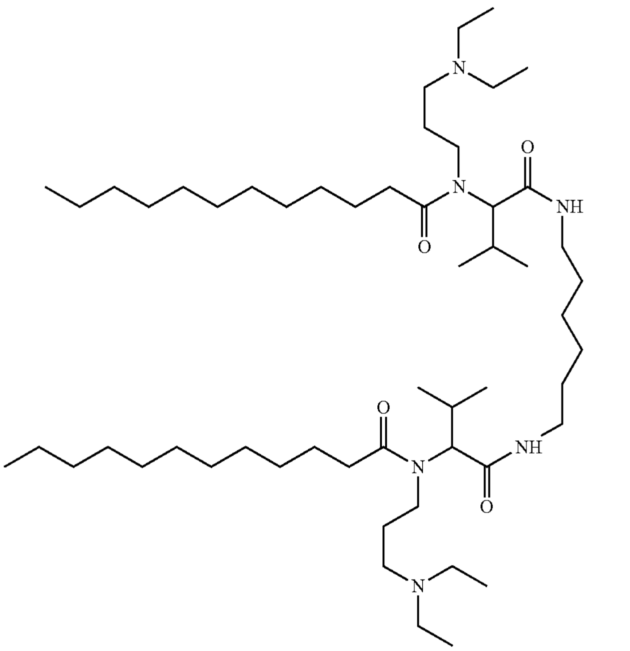
I1R3C16A1
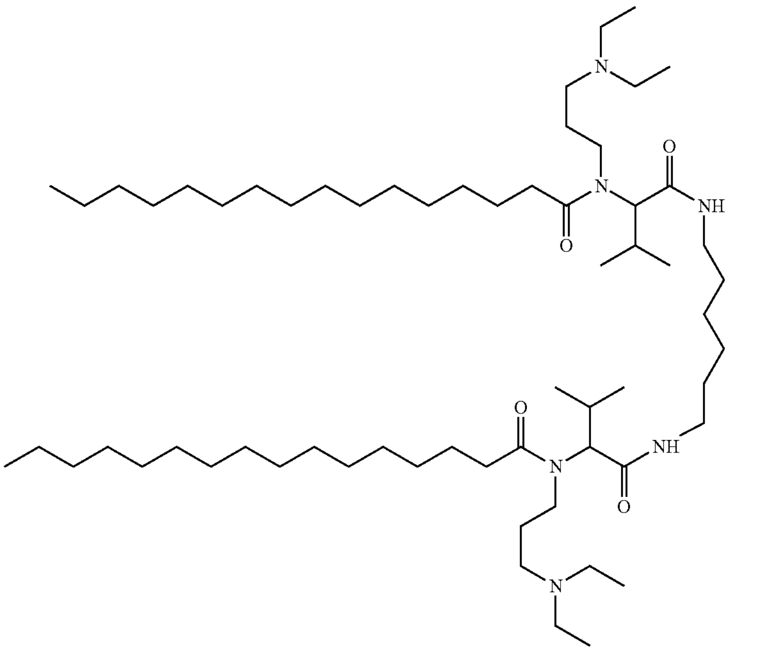

-continued
I1R3C18A1
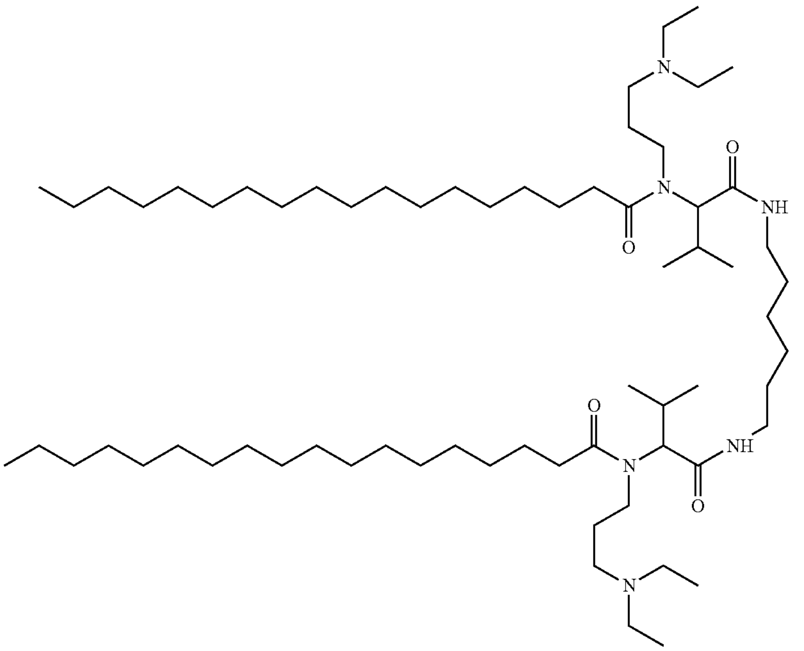
I1R3C20A1
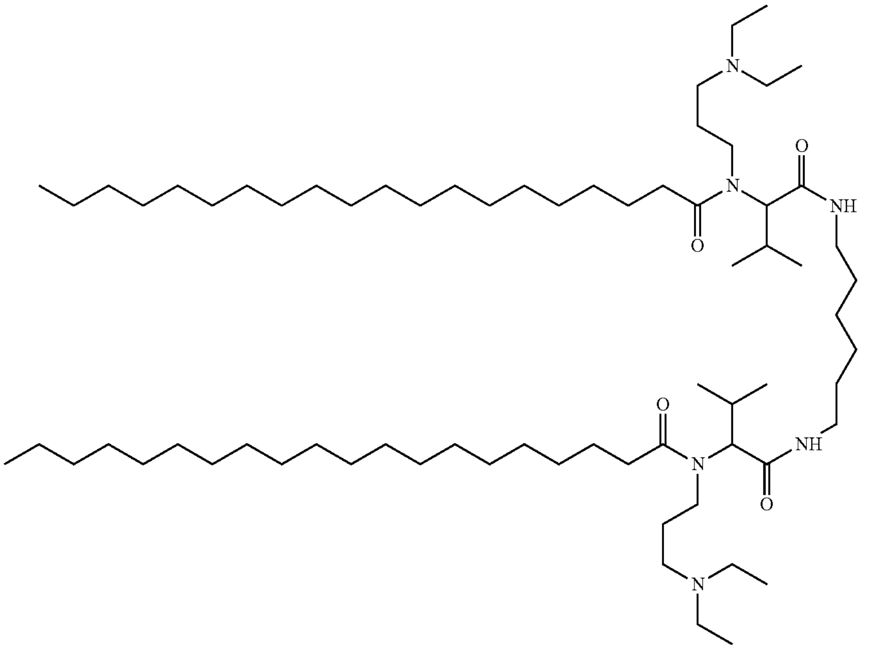

-continued
I1R3C18-1A1
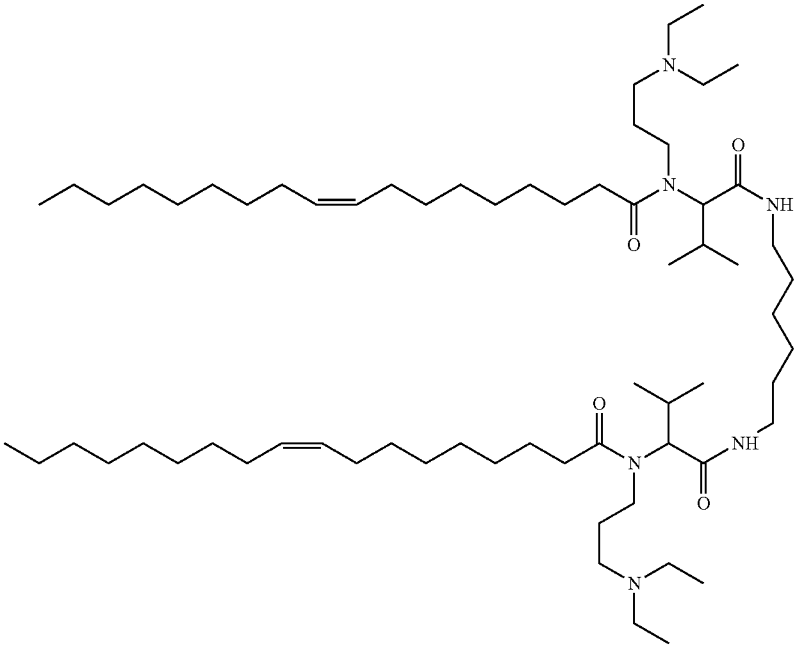
I1R3C18-2A1
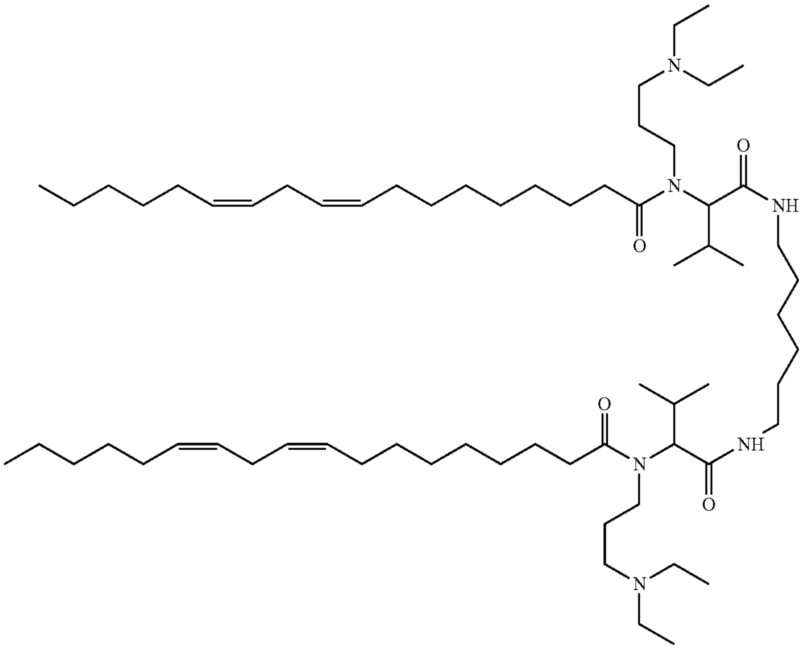

-continued
I1R5C12A1
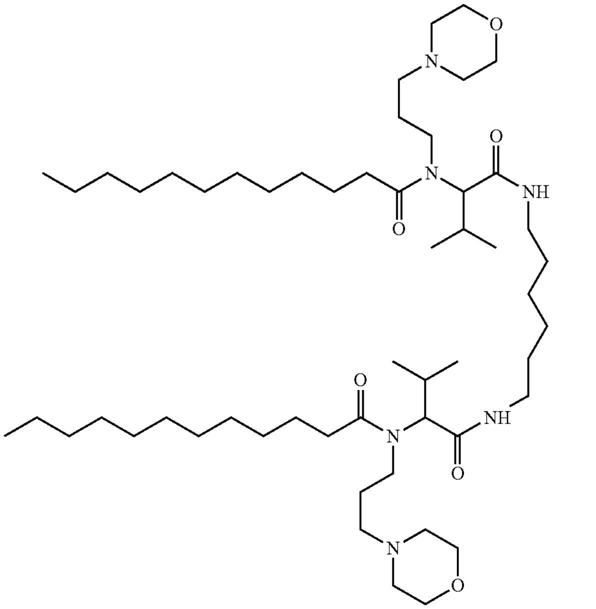
I1R5C14A1
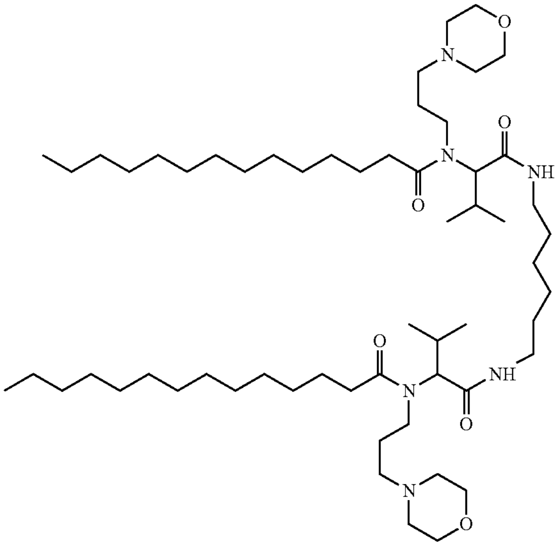
I1R5C16A1
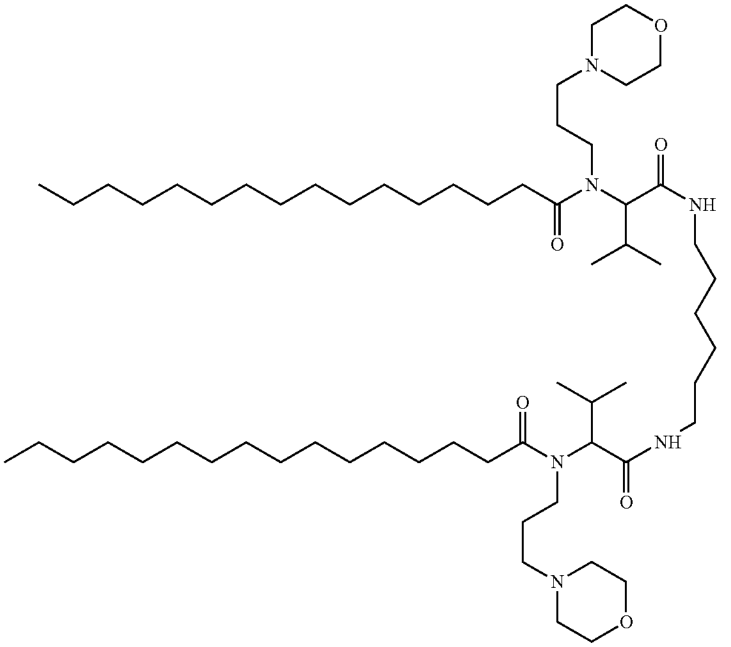

-continued
I1R5C18A1
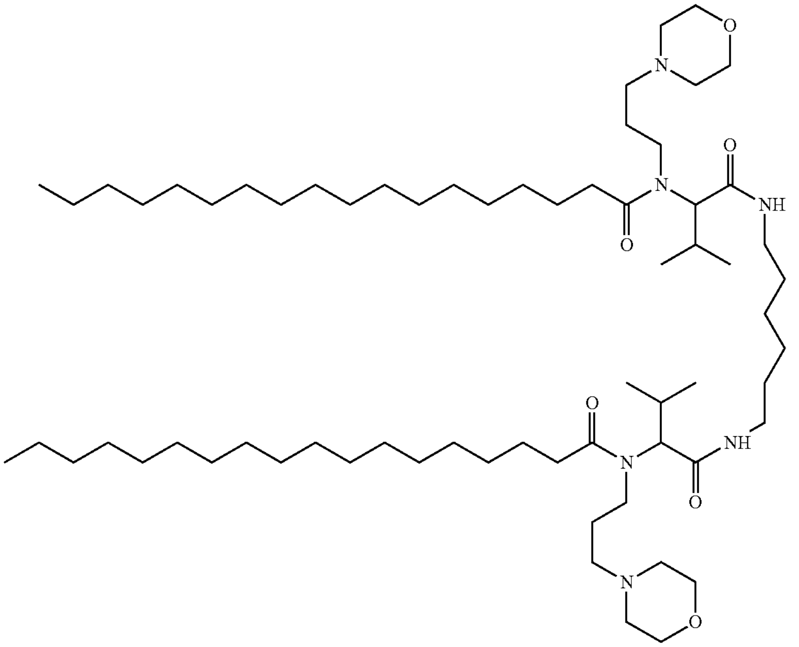
I1R5C20A1
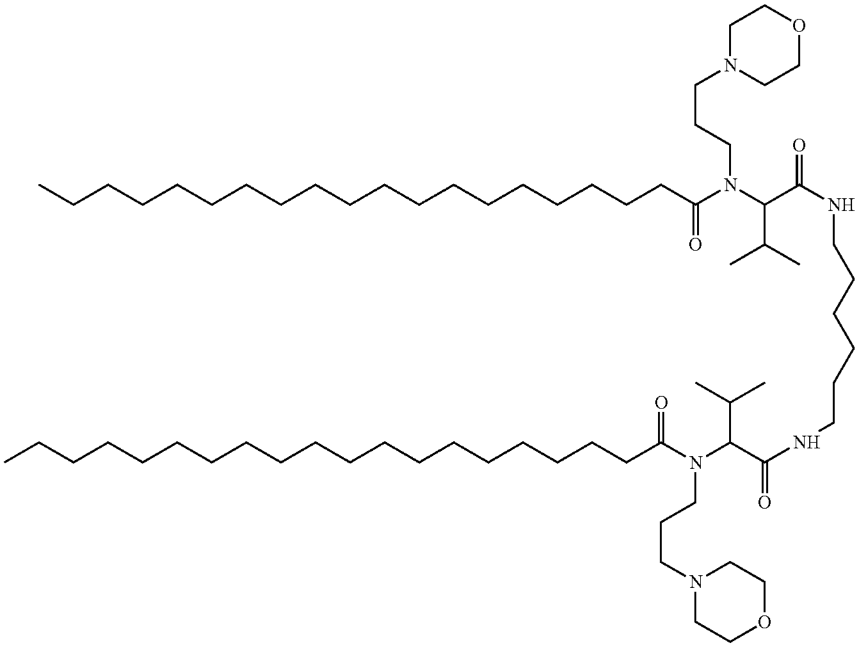

-continued
I1R5C18-1A1
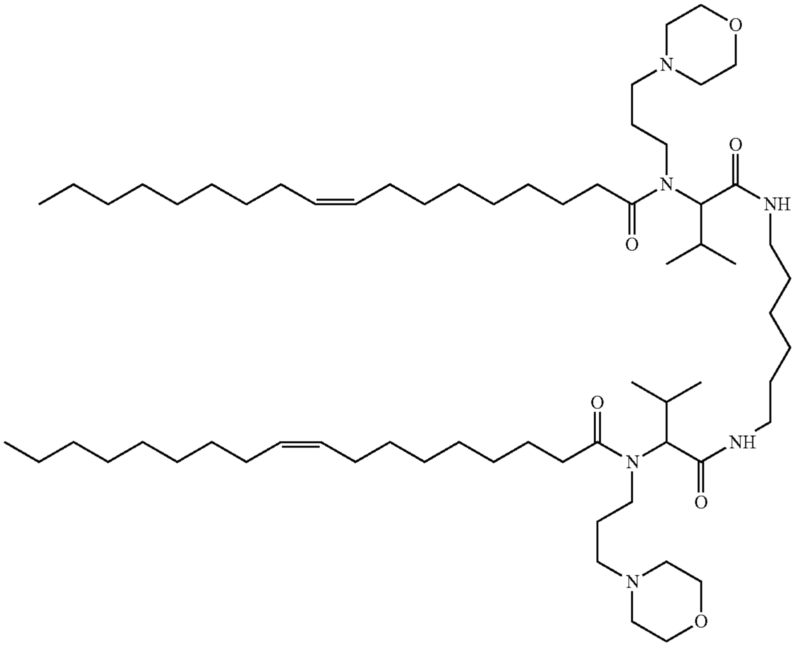
I1R5C18-2A1
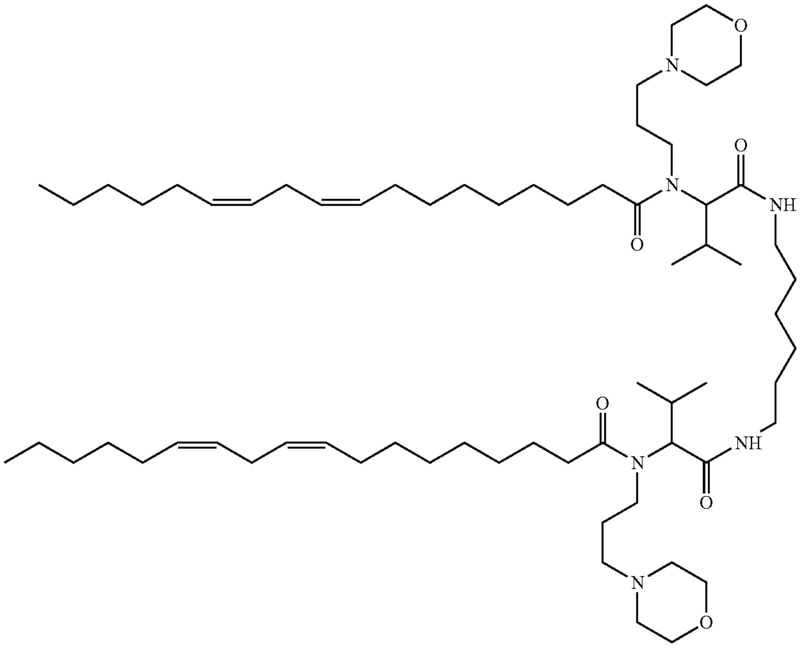

-continued
I1R11C12A1
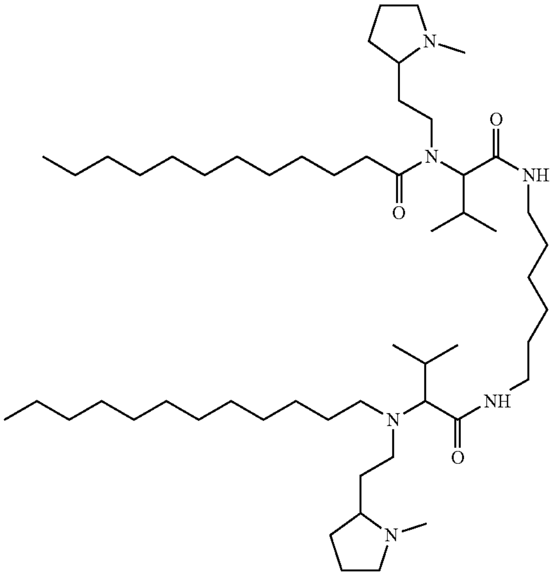
I1R11C14A1
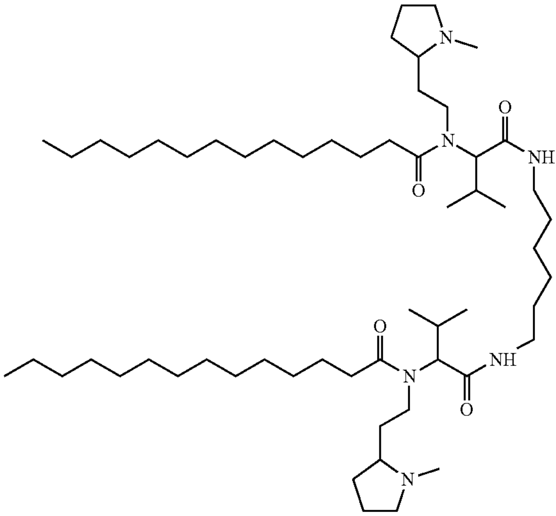
I1R11C16A1
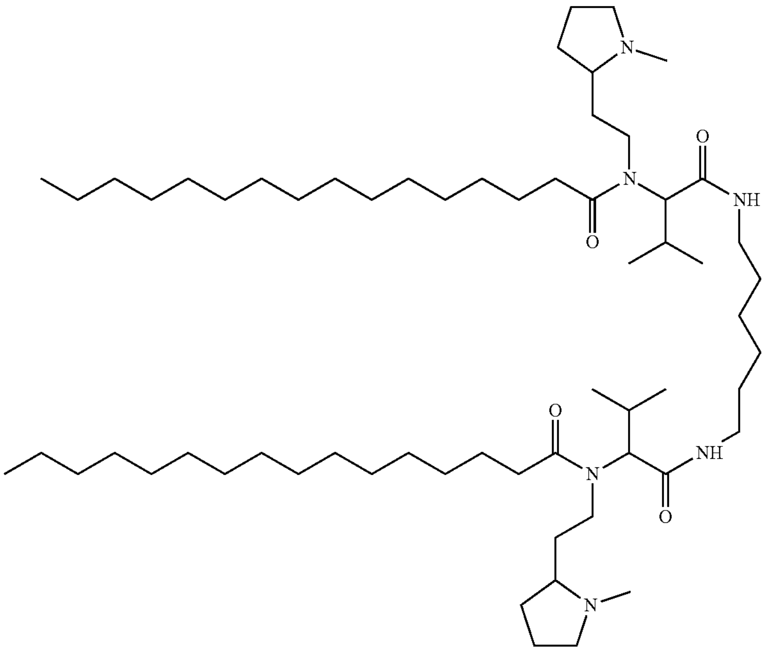

-continued
I1R11C18A1
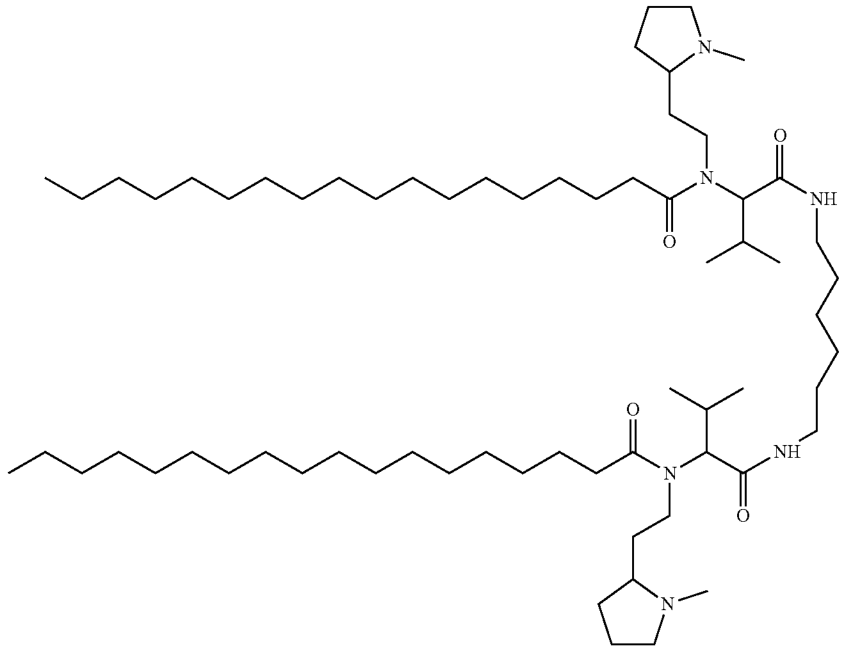
I1R11C20A1
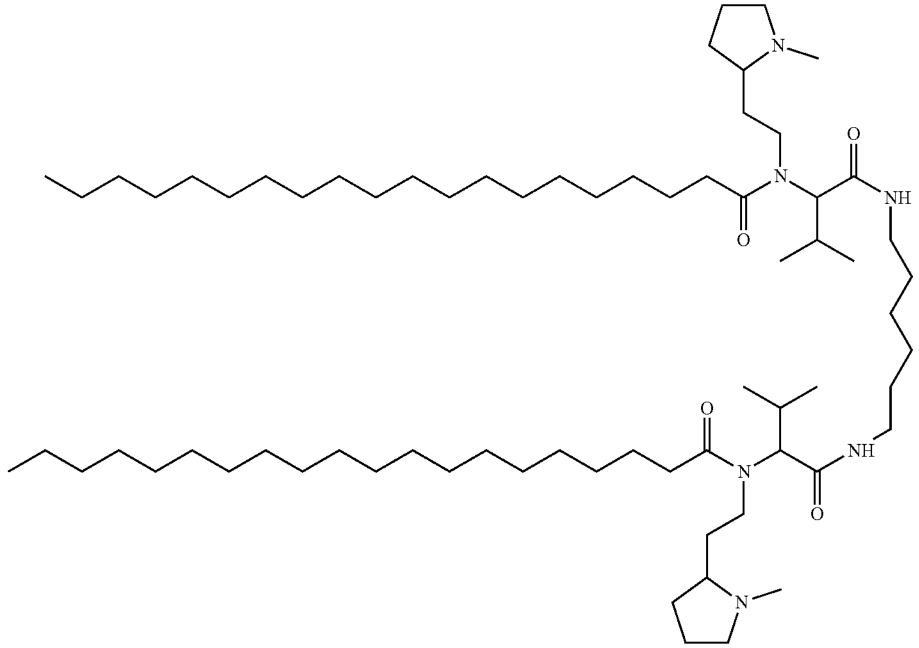

-continued
I1R11C18-1A1
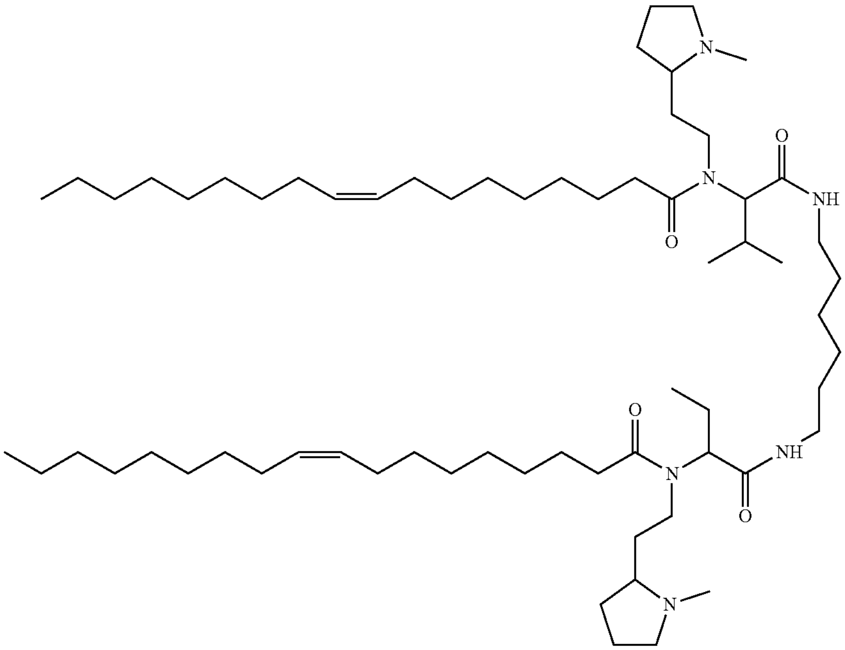
I1R11C18-2A1
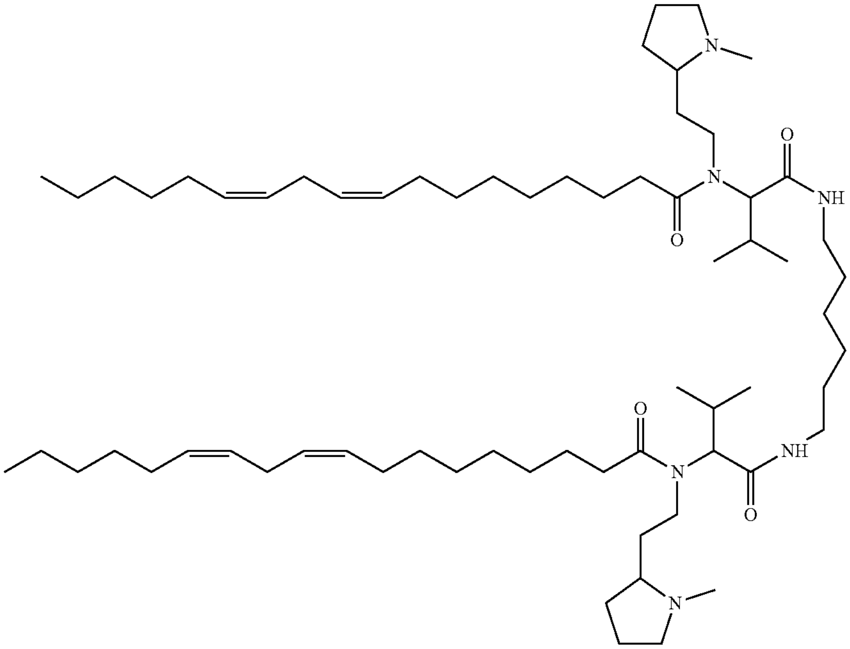

-continued
I2R1C12A1
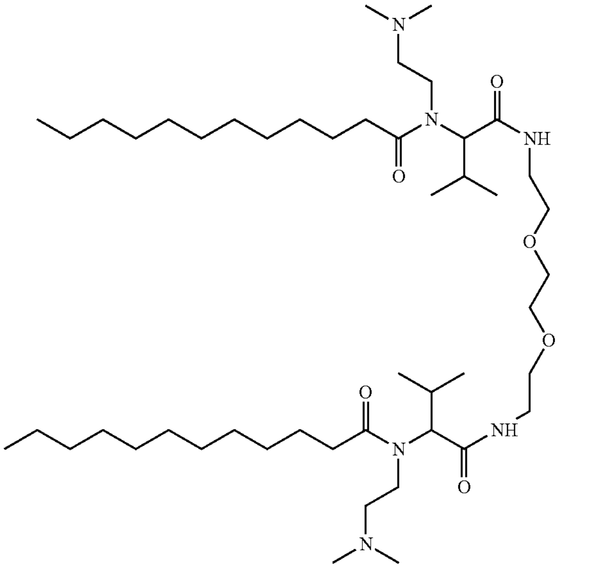
I2R1C14A1
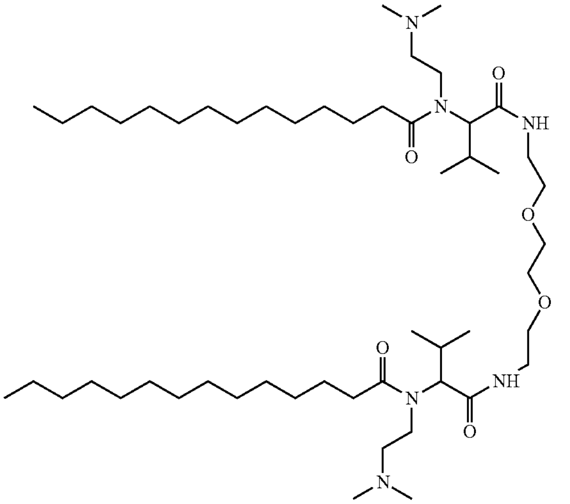
I2R1C16A1
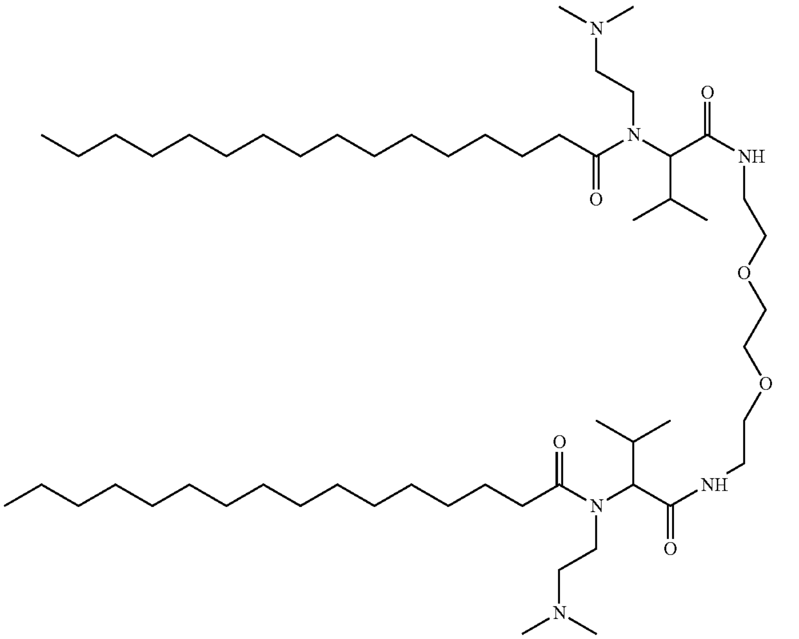

-continued
I2R1C18A1
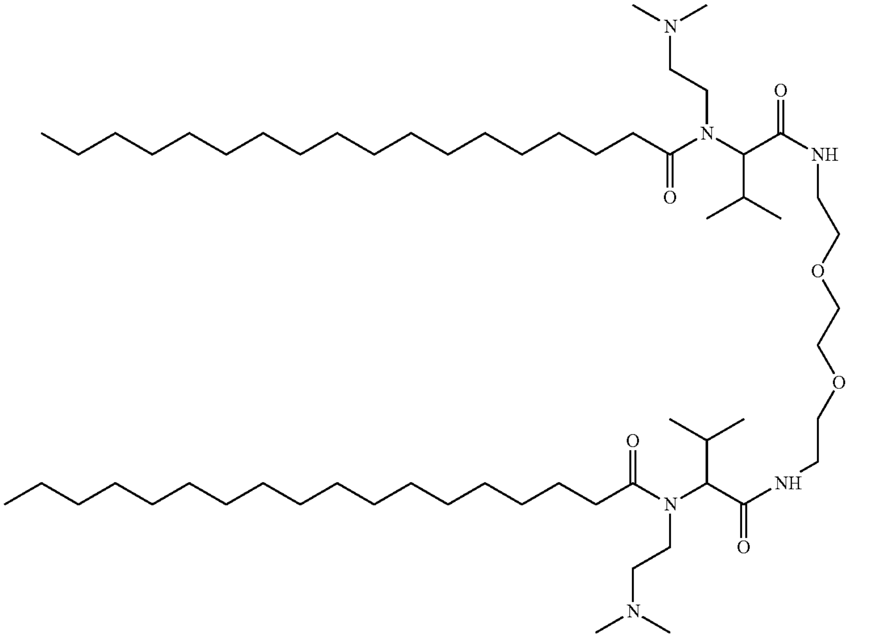
I2R1C20A1
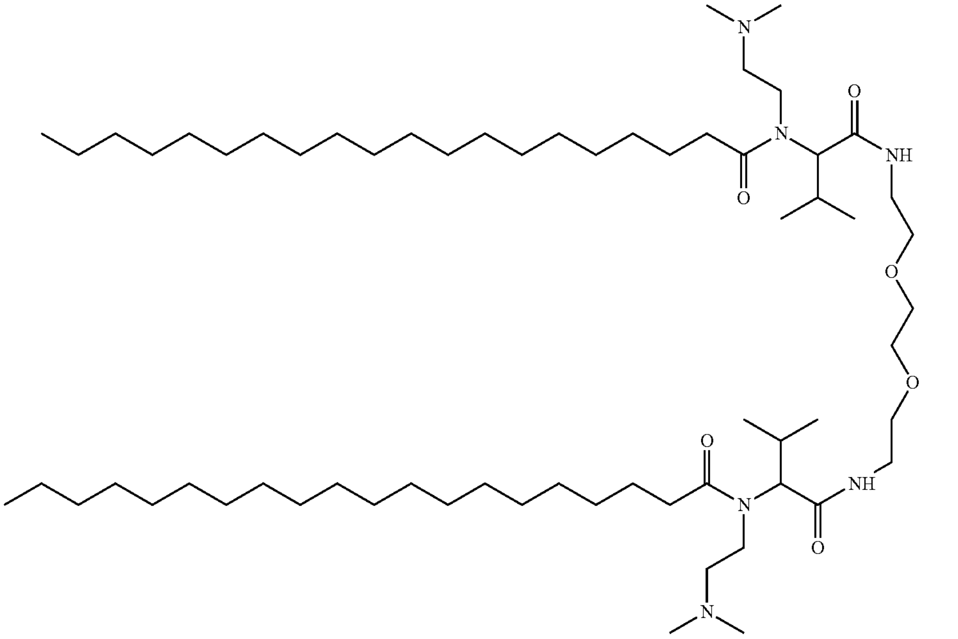

-continued
I2R1C18-1A1
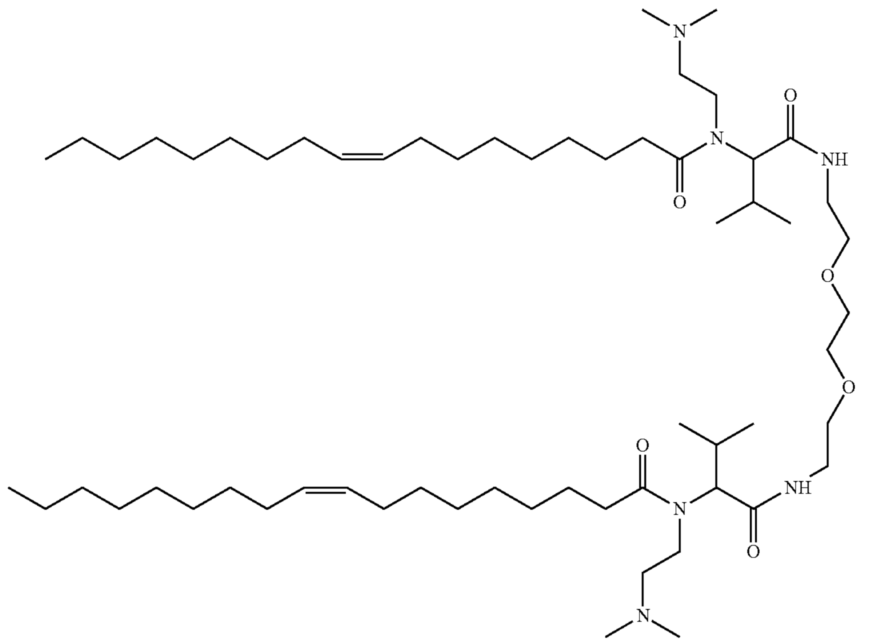
I2R1C18-2A1
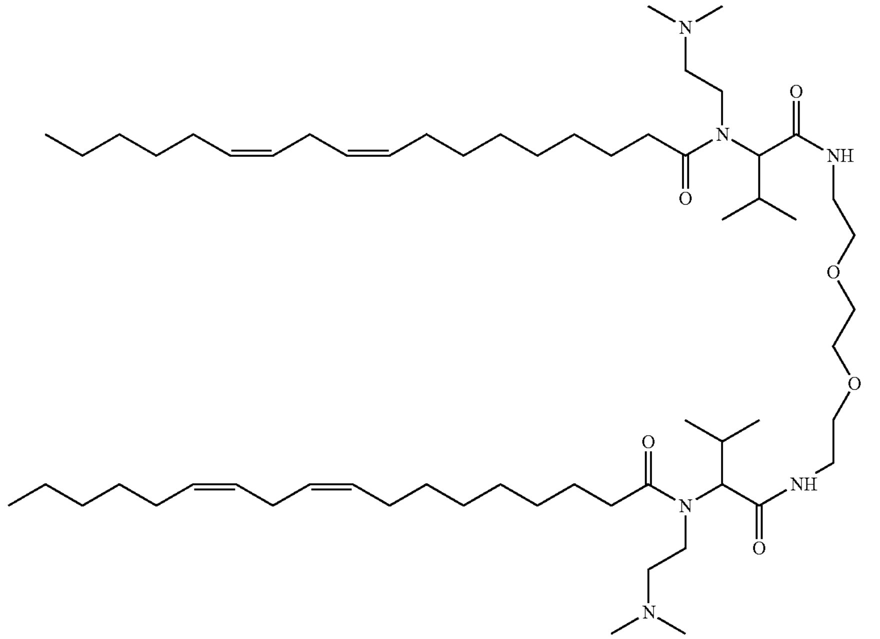

-continued
I2R2C12A1
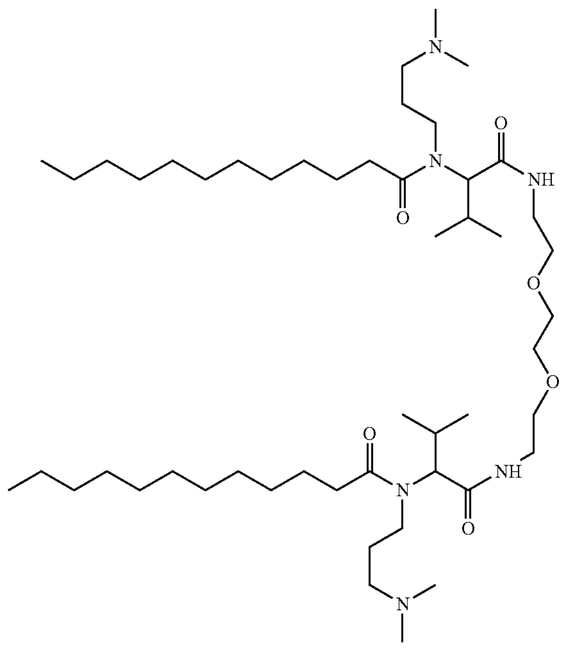
I2R2C14A1
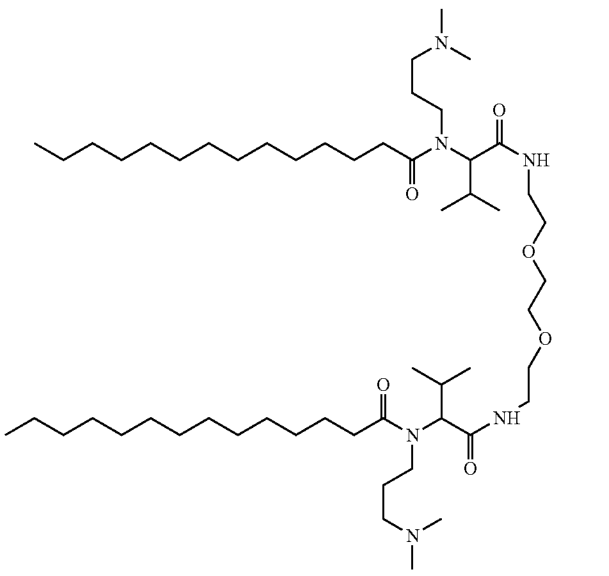
I2R2C16A1
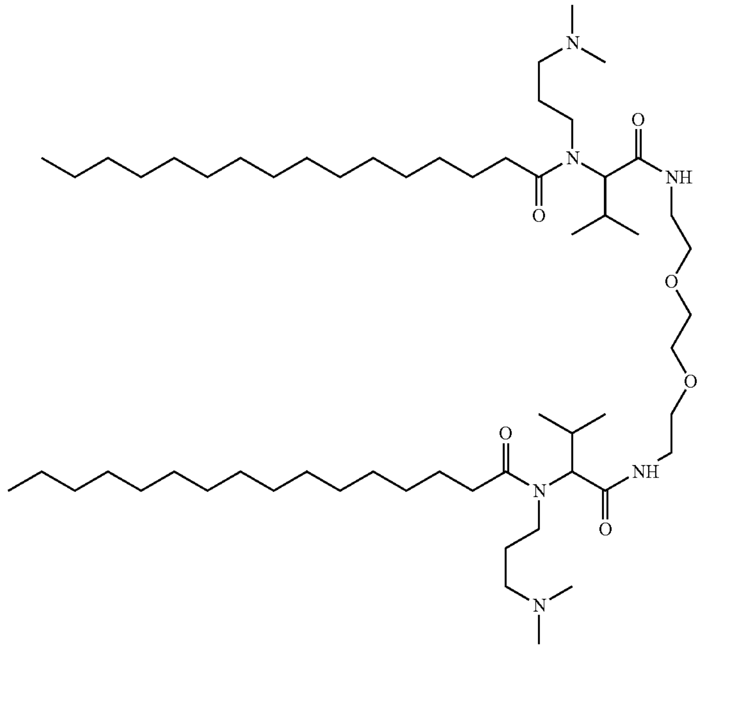

-continued
I2R2C18A1
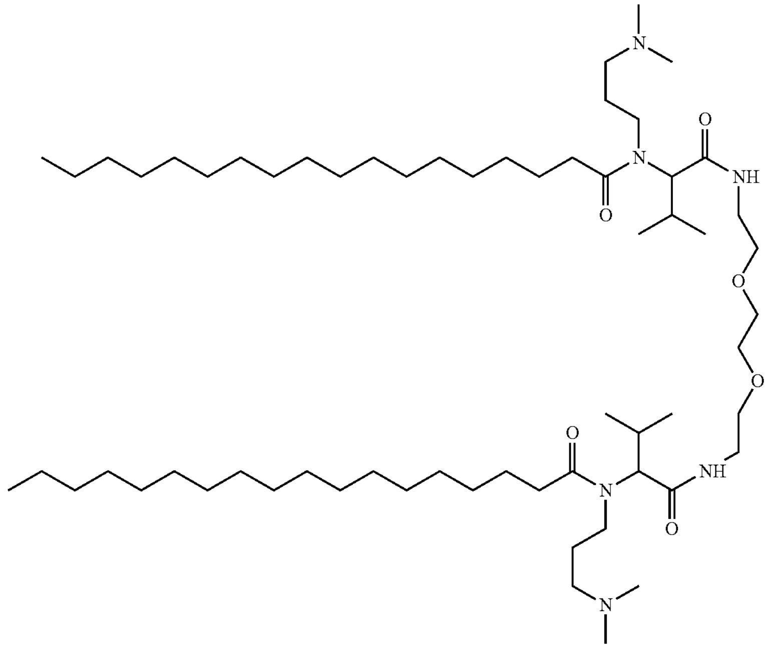
I2R2C20A1
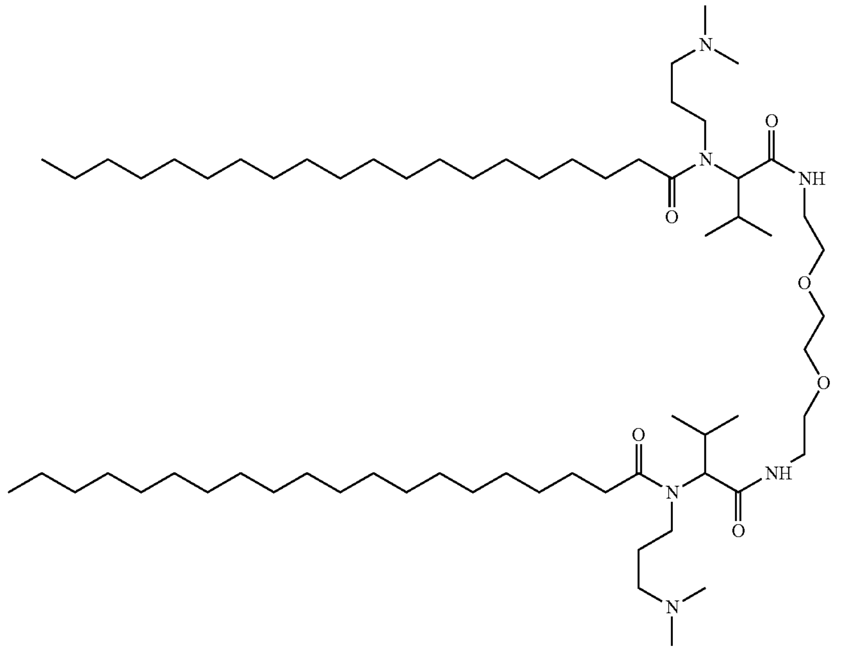

-continued
I2R2C18-1A1
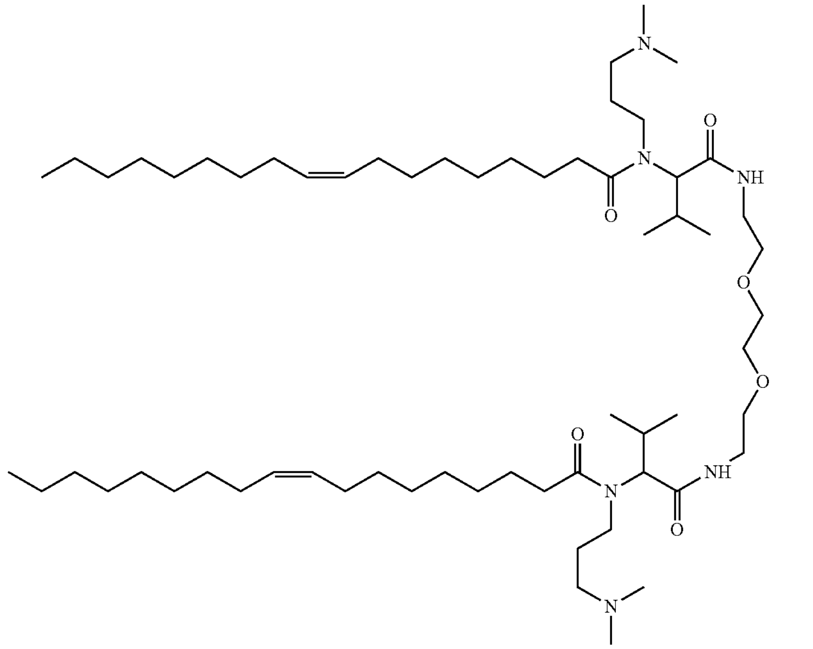
I2R2C18-2A1
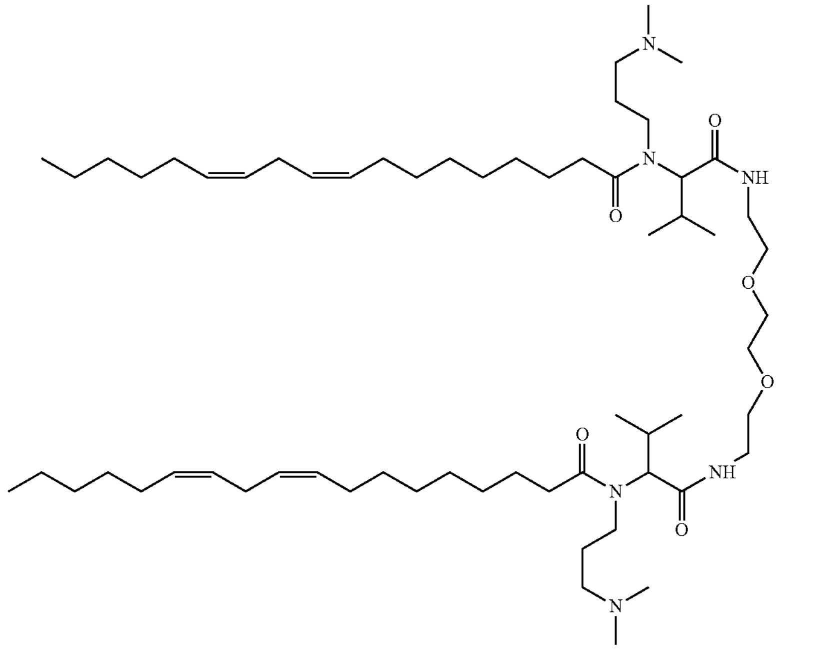

-continued
I2R3C12A1
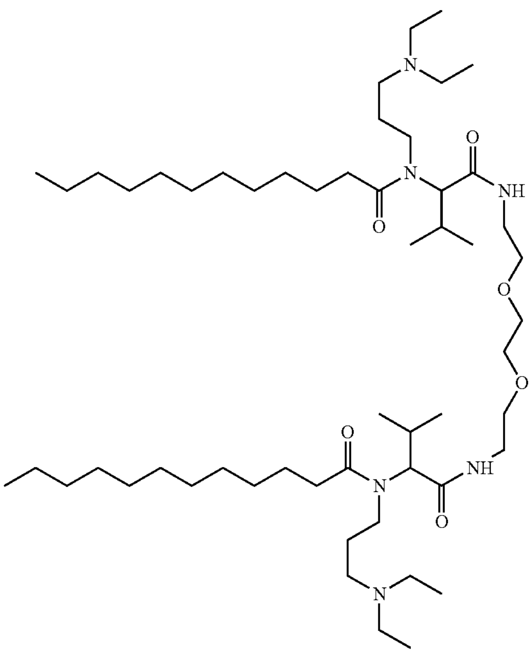
I2R3C14A1
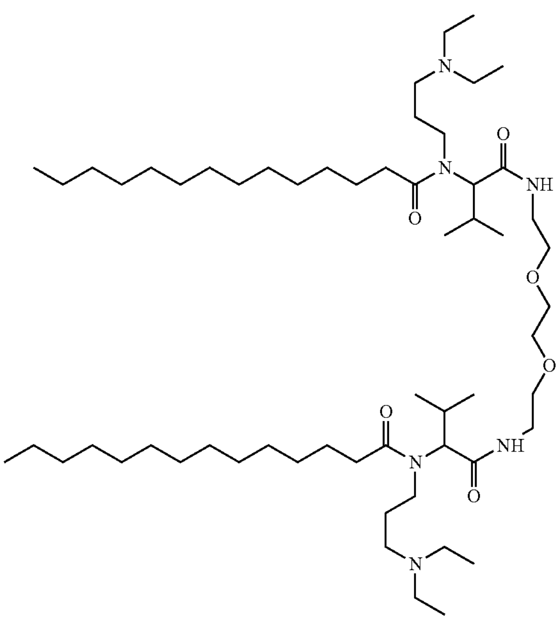
I2R3C18A1
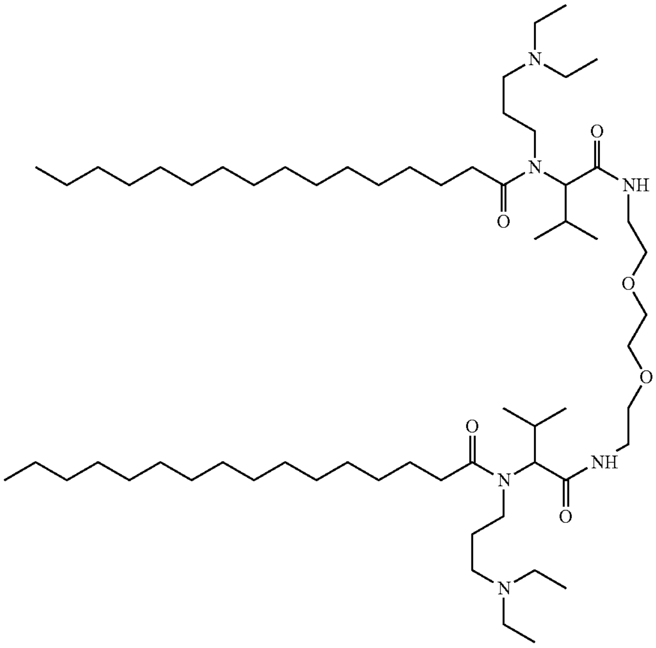

-continued
I2R3C18A1
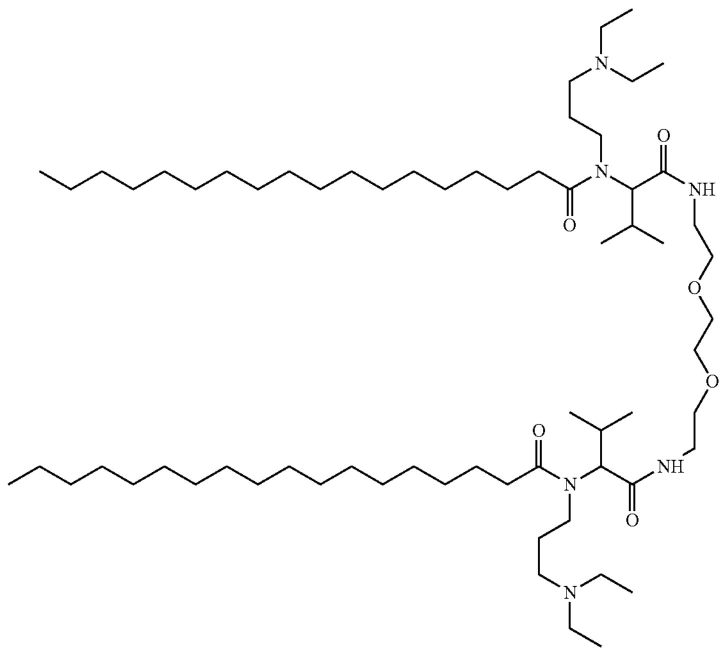
I2R3C20A1
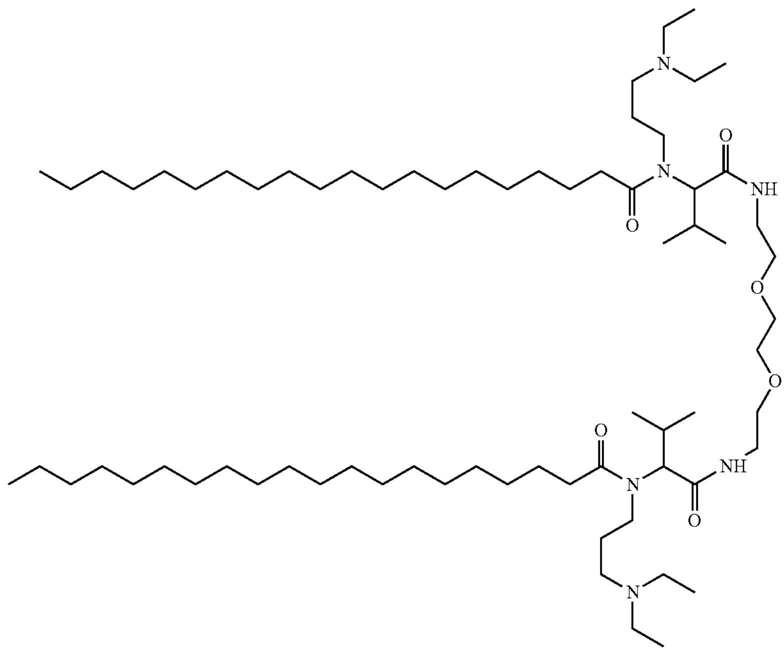

-continued
I2R3C18-1A1
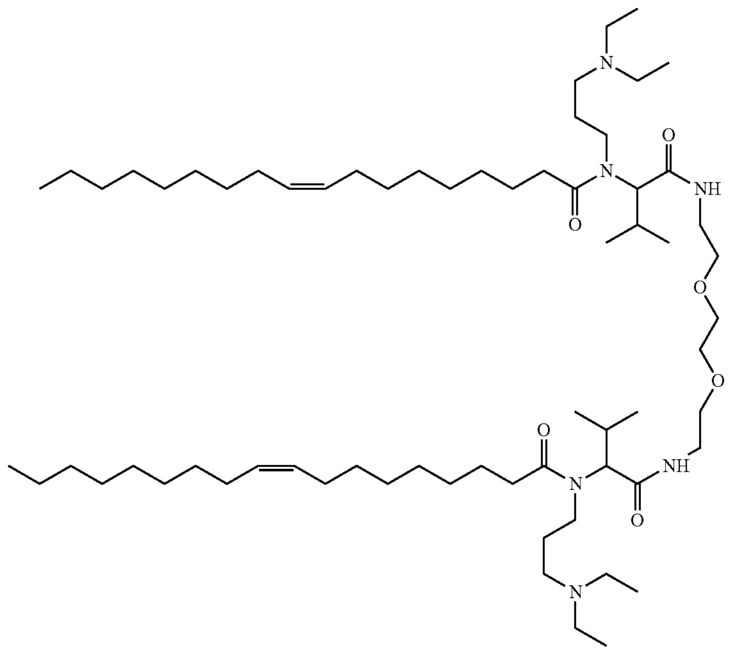
I2R3C18-2A1
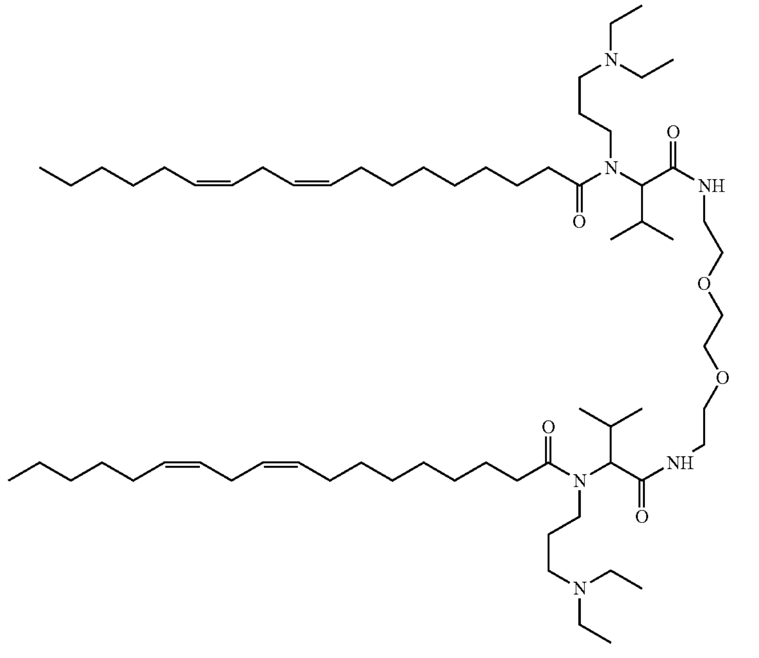

-continued
I2R5C12A1
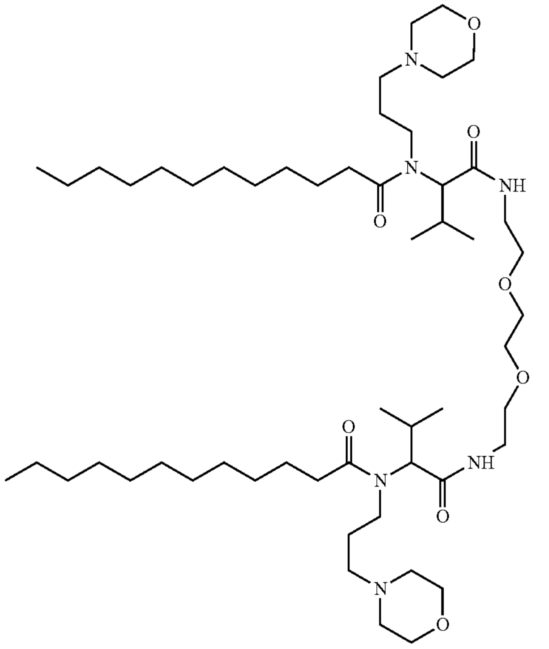
I2R5C14A1
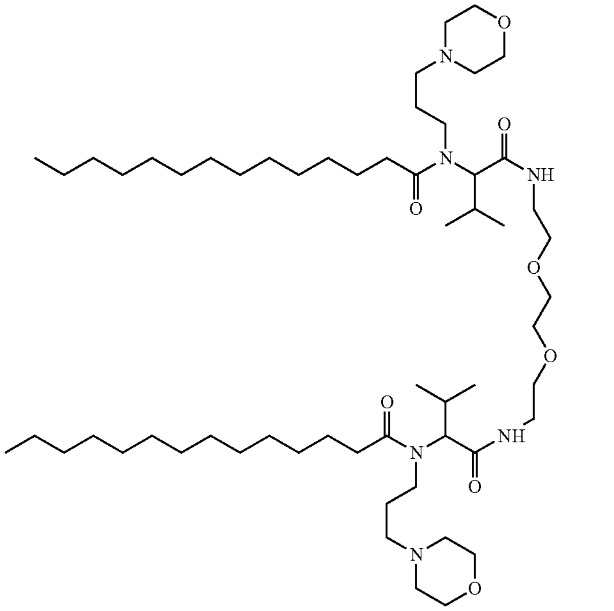
I2R5C16A1
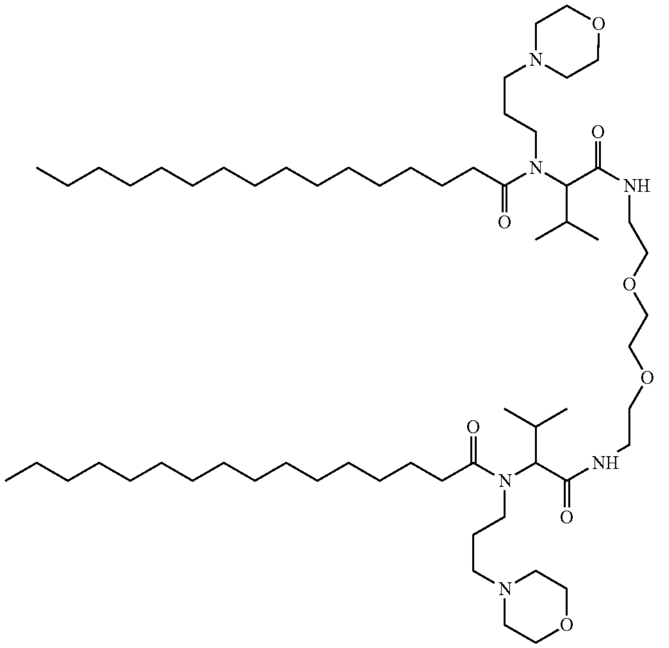

-continued
I2R5C18A1
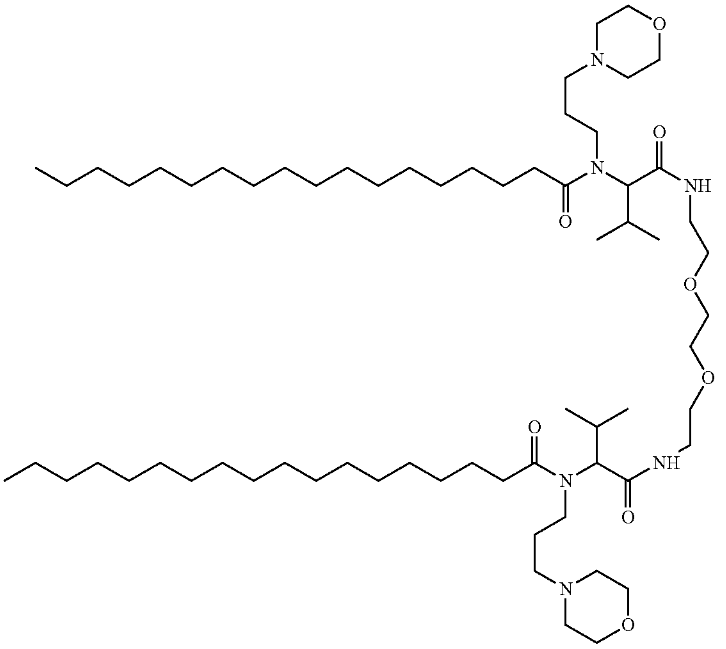
I2R5C20A1
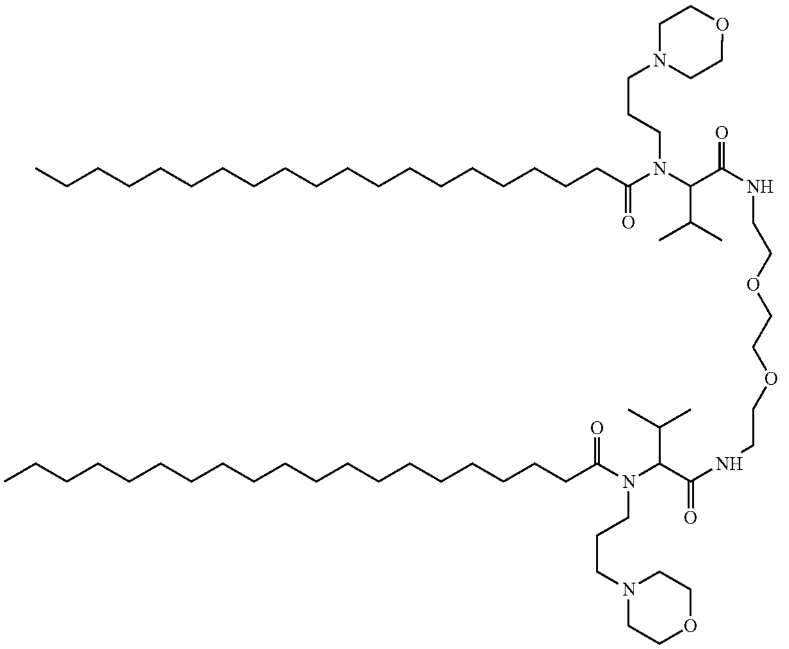

-continued
I2R5C18-1A1
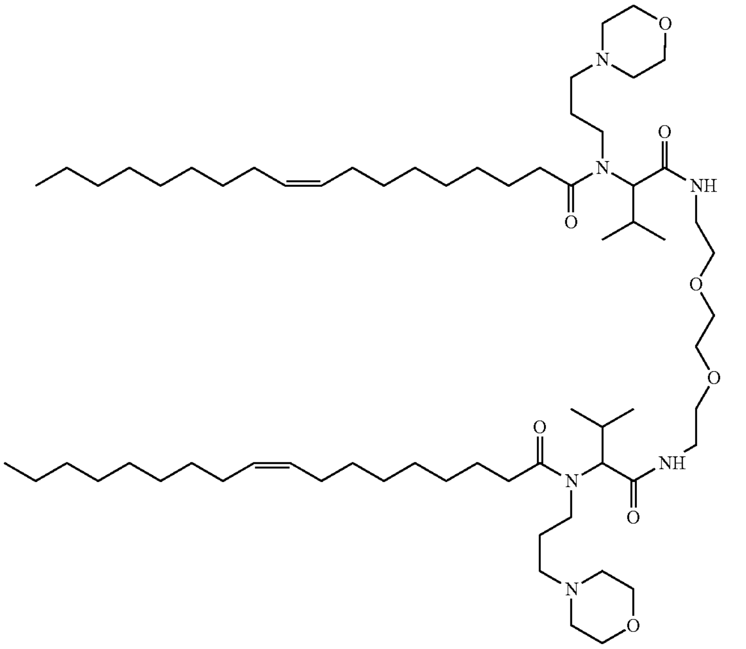
I2R5C18-2A1
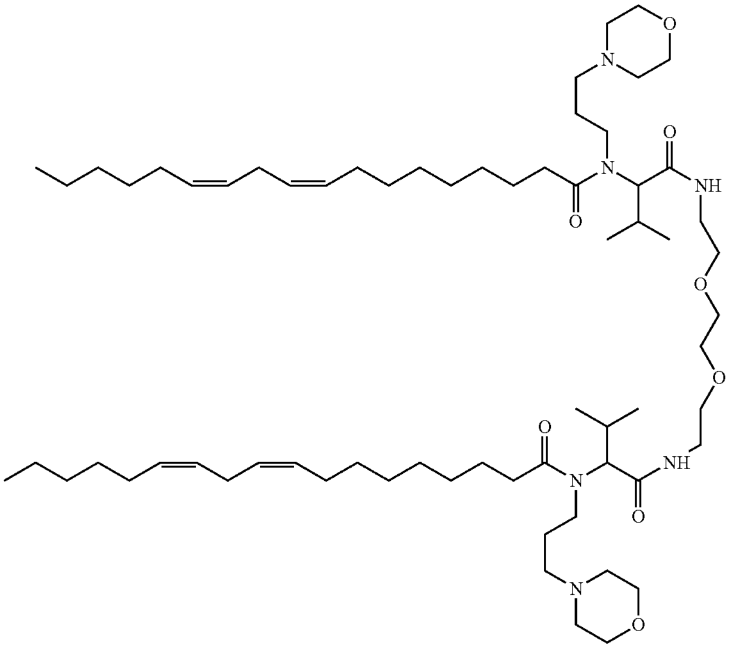

-continued
I2R11C12A1
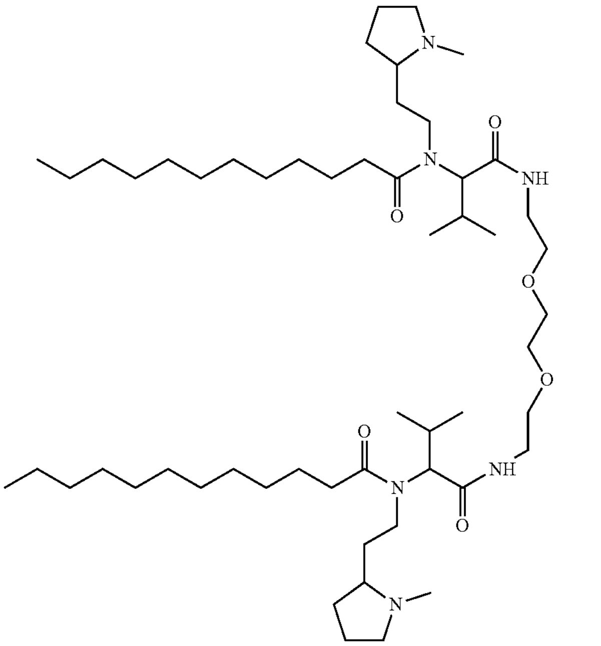
I2R11C14A1
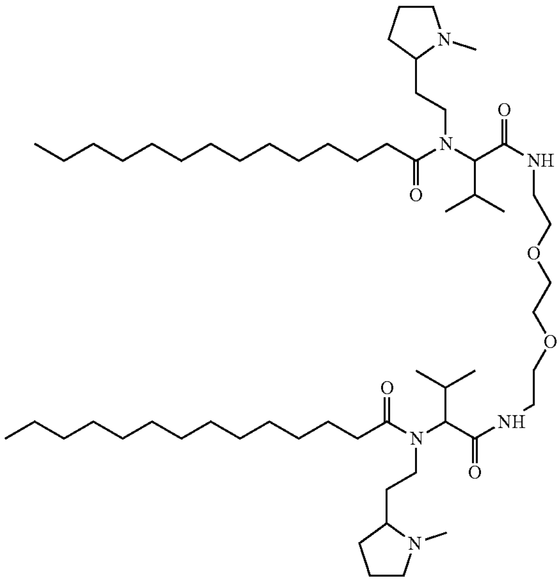
I2R11C16A1
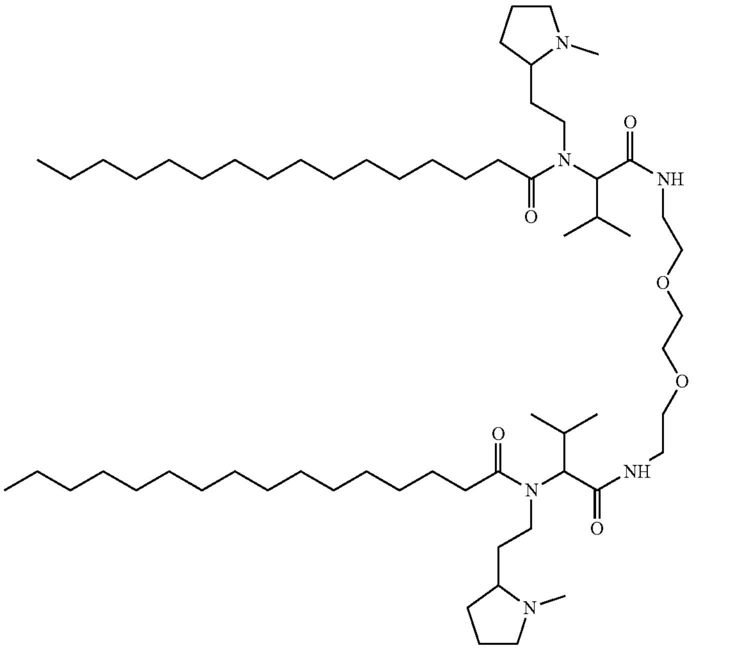

-continued
I2R11C18A1
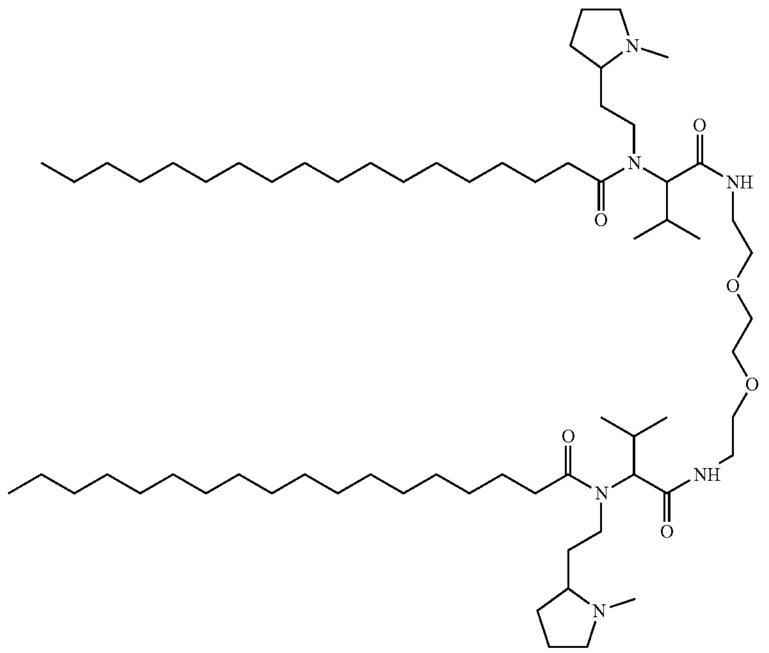
I2R11C20A1
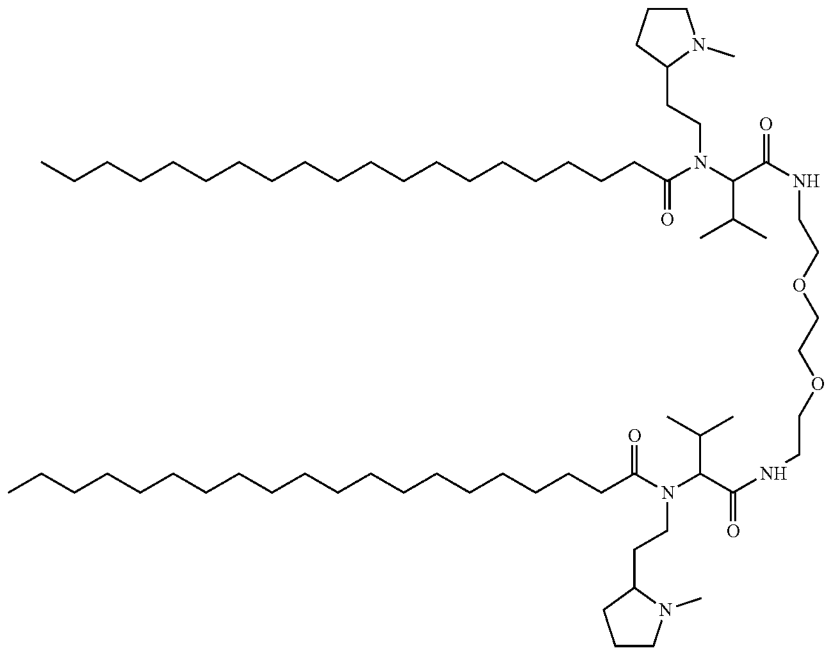

-continued
I2R11C18-1A1
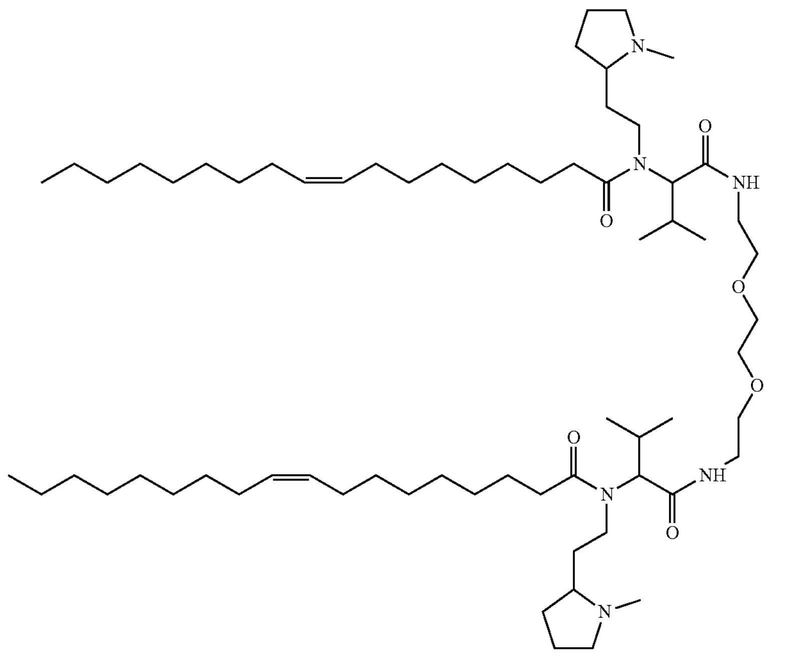
I2R11C18-2A1
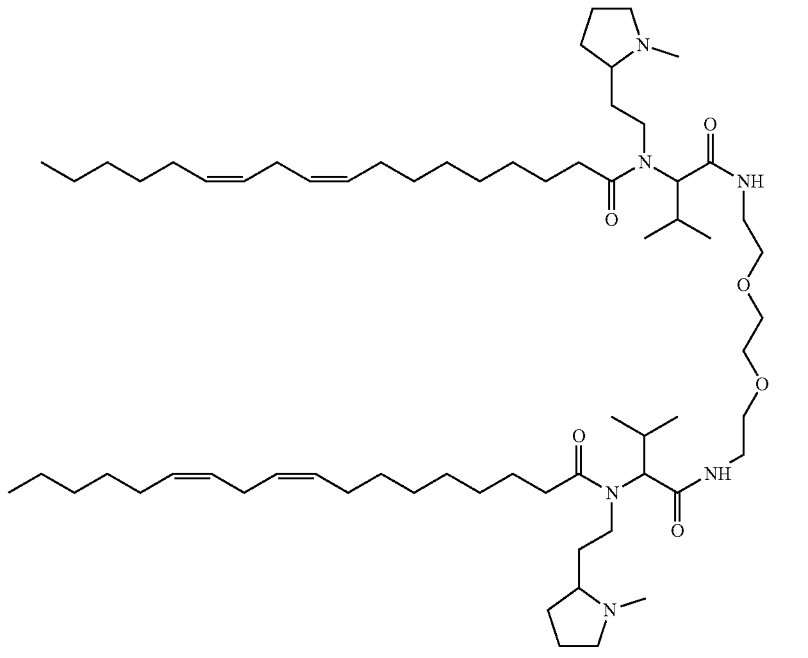

-continued

I2-IR2C18A1

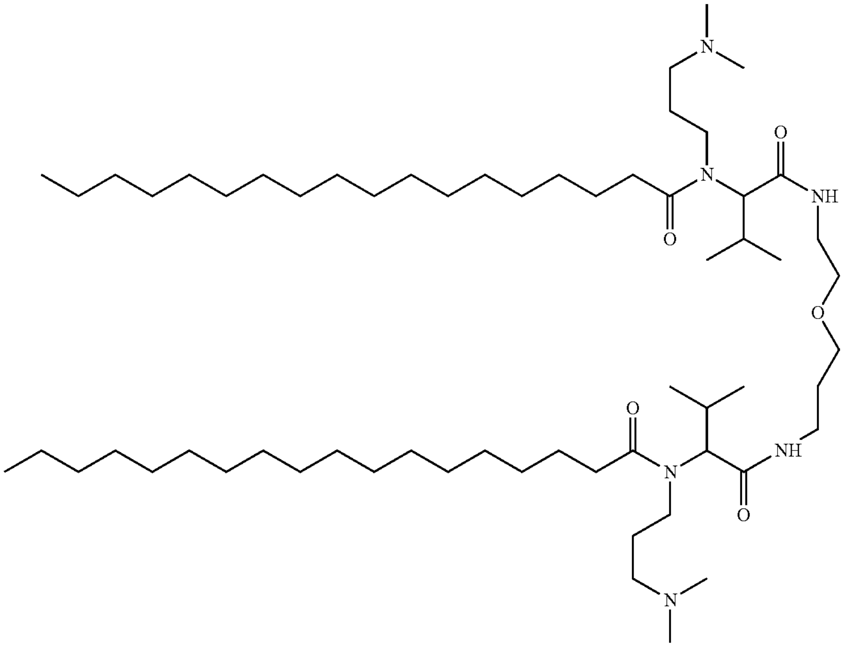

I2-3R2C18A1

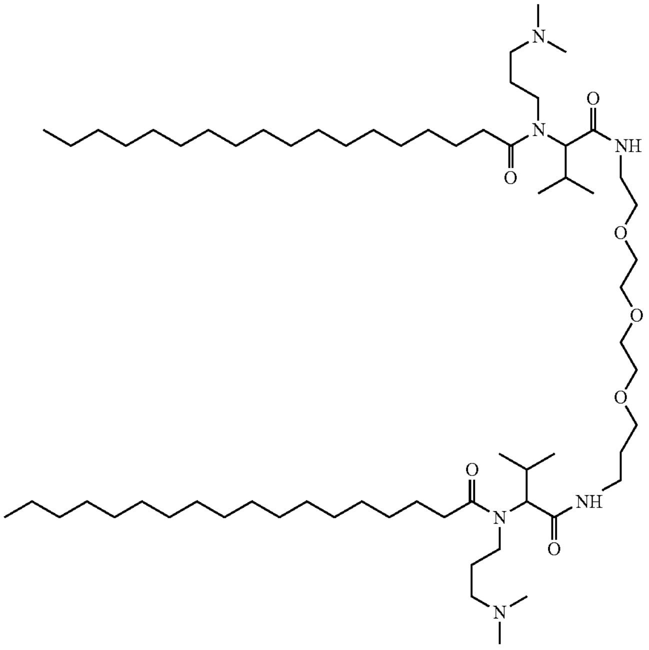

The inventors have found through experiments that the 72 small-molecule cationic lipid analog materials above can co-assemble with protein model drugs to form small and stable nano-complexes. These nano-complexes enable an intracellular delivery of various positively and negatively-charged proteins while maintaining their biological activity, resulting in therapeutic effects. In addition, the 72 small-molecule cationic lipid analog materials can also bind to various nucleic acids to form nanoparticles, achieving efficient intracellular delivery of plasmid DNA, mRNA, and siRNA.

The present disclosure also provides a preparation method of the cationic lipid analog material, specifically including: adding an aldehyde compound and an amine compound to an organic solution; allowing to react for 10 min to 120 min before sequentially adding a carboxylic acid compound and an isocyanide compound; allowing to react at 4° C. to 60° C. for 6 h to 72 h; and separating and purifying a product by column chromatography after completion of reaction to obtain the cationic lipid analog material.

In the present disclosure, the small-molecule cationic lipid analog material is synthesized through a Ugi reaction with the aldehyde compound, the amine compound, the carboxylic acid compound, and the isocyanide compound as raw materials. The reaction condition for the cationic lipid analog material of the present disclosure is mild, and the synthesis process is simple and stable. The small-molecule cationic lipid analog material synthesized has low toxicity and can efficiently deliver various drugs into cells. A synthesized small-molecule cationic lipid analog material has low toxicity.

In addition, in the preparation method of a cationic lipid analog material, a mixture of methanol and dichloromethane (DCM) is used as a mobile phase for the separation with the chromatography column.

In addition, in the preparation method of the cationic lipid analog material, a molar ratio of the aldehyde compound, the amine compound, the carboxylic acid compound, and the isocyanide compound is (0.1--1):(0.1-1):(0.1-1):(0.1-1), and preferably 1:1:1:0.5.

In addition, in the preparation method of the cationic lipid analog material, the aldehyde compound is one selected from the group consisting of compounds A1 to A3:

A1

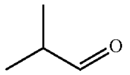

A2

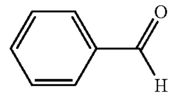

A3

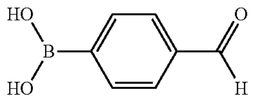

and preferably, the aldehyde compound is compound A1;

the amine compound is one selected from the group consisting of compounds R1 to R11:

R1

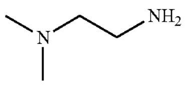

R2

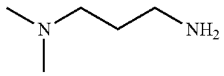

R3

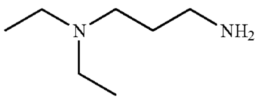

R4

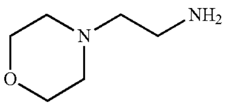

R5

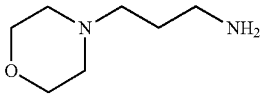

R6

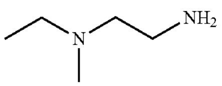

-continued

R7

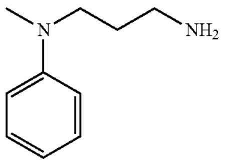

R8

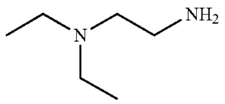

R9

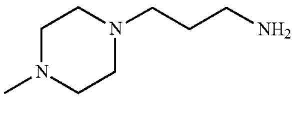

R10

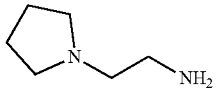

R11

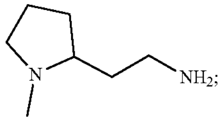

the carboxylic acid compound is one selected from the group consisting of compounds CHS, C18-1, C18-2, and C8 to C20:

C8

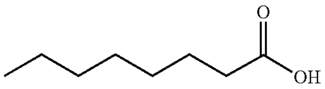

C9

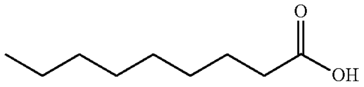

C10

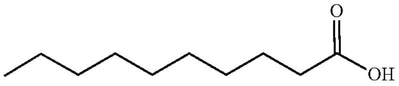

C11

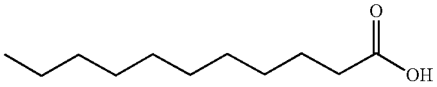

C12

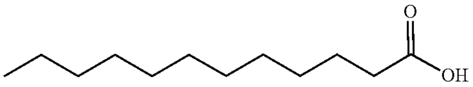

C13

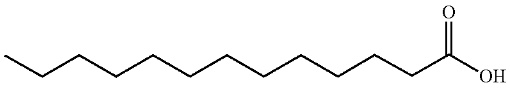

C14

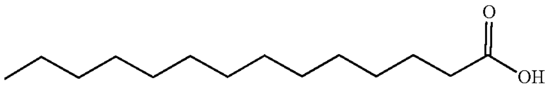

C15

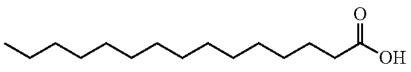

-continued

C16

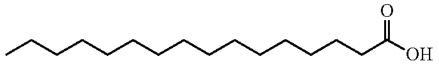

C17

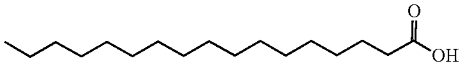

C18

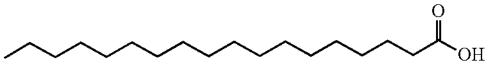

C19

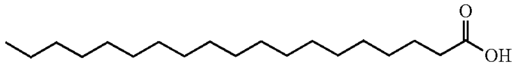

C20

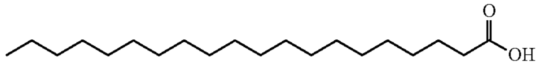

C18-1

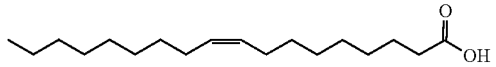

C18-2

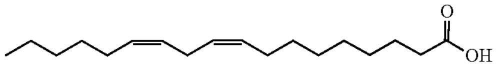

CHS

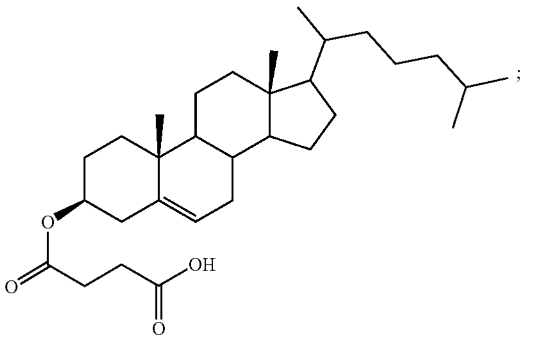

and the isocyanide compound is one selected from the group consisting of compounds I1, I2-1, I2, I2-3, and I3:

I1

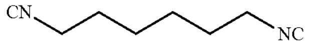

I2-1

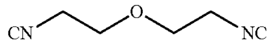

I2

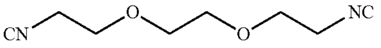

I2-3

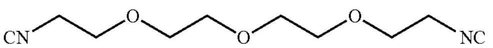

I3

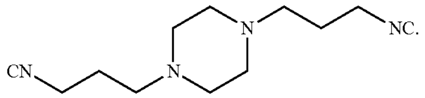

The present disclosure also provides use of the aforementioned cationic lipid analog material as a drug carrier. The small-molecule cationic lipid analog material of the present disclosure can interact with various proteins to produce stable complexes that facilitate cellular uptake. These complexes can effectively cross cell membranes through cell fusion and/or endocytosis while by-passing and/or escaping endosomes, delivering the proteins into cells. The proteins delivered retain their biological activity within the cells. The cationic lipid analog material exhibits no cytotoxicity during delivery and has excellent biocompatibility. In addition, the cationic lipid analog material of the present disclosure can efficiently bind to nucleic acids such as plasmid DNA, mRNA, and siRNA. They can deliver different plasmid DNAs to various cells, with high transfection efficiency, even achieving or exceeding the level of current commercially available transfection reagents. It can be seen that the cationic lipid analog material designed in the present disclosure can be used as an intracellular delivery carrier for a drug, especially a biomacromolecular drug, providing an effective tool for the therapeutic application of biomacromolecular drugs.

The present disclosure also provides a drug delivery system including a carrier and a drug wrapped around the carrier or loaded on the carrier, where the carrier is the cationic lipid analog material described above.

The drug delivery system is not limited to specific types of drugs and includes, but is not limited to, one or two selected from the group consisting of a biological drug and a chemical drug. Specifically, the biological drug includes, but is not limited to, one or more selected from the group consisting of a nucleic acid, a polypeptide, a protein, and a vaccine; and the chemical drug includes, but is not limited to, one or more selected from the group consisting of an antitumor small-molecule drug, fluorescein, and a lymphatic tracer.

In order to further improve the targeting specificity and delivery efficacy of the drug delivery system, the carrier may also directly complex or chemically conjugate a targeted ligand. Specifically, the targeted ligand includes, but is not limited to, an oligonucleotide aptamer, an antibody molecule, an antibody fragment, a naturally occurring receptor surface conjugate, or a polypeptide. The targeted ligand may be prepared or synthesized by one or more chemical modification methods, including, but not limited to, fluorination modification, methoxy modification, amino modification, locked nucleic acid (LNA), glycosylation, amination, or phosphorylation.

Without adversely affecting the present disclosure, the drug delivery system may further include an optional pharmaceutically-acceptable dosage form such as a solution-type liquid formulation, a polymer solution, an emulsion, a suspension, dispersible powders, granules, a tablet, a capsule, or the like. The adjuvant includes, but is not limited to, one or more selected from the group consisting of an excipient, a binder, a diluent, and a disintegrant.

It should be noted that the terms “delivery” or “intracellular delivery” used herein refers to the process of transporting a drug from the outside of a cell to the inside of the cell, confining it within a cytosol or a cell organelle.

The “complexing” of the cationic lipid analog material with a biomacromolecular drug such as a protein and a nucleic acid, and the “complex” formed in this process refer to an interaction between the cationic lipid analog material and the biomacromolecular drug such as a protein and a nucleic acid. The interaction is stable enough to allow the binding of the biomacromolecular drug to the cationic lipid analog material, thereby delivering the biomacromolecular drug into a cell.

The term “nanoparticle” used herein refers to a particle with a particle size of no more than 1 μm.

Compared with the prior art, the present disclosure has the following beneficial effects:

In the present disclosure, the small-molecule cationic lipid analog material is synthesized through a Ugi reaction with the aldehyde compound, the amine compound, the carboxylic acid compound, and the isocyanide compound as raw materials. The preparation method of a cationic lipid analog material in the present disclosure involves mild reaction conditions, a simple process, and excellent stability, and a synthesized small-molecule cationic lipid analog material has excellent biocompatibility and can allow safe and efficient intracellular delivery of various drugs.

DETAILED DESCRIPTION

Figure 1A:
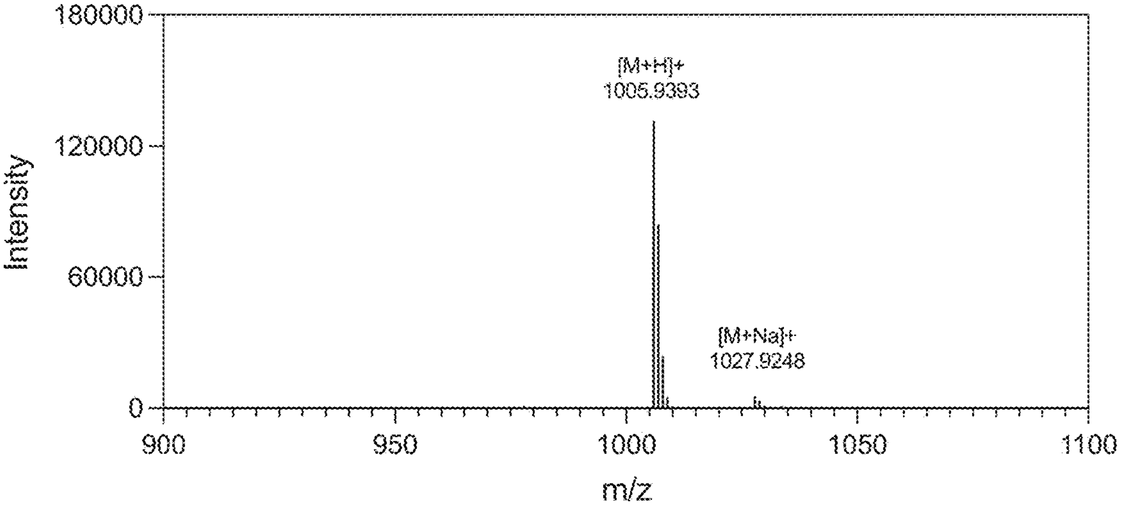
FIG. 1A shows a mass spectrometry (MS) spectrum of cationic lipid analog material I2-1R2C18A1.

In order to well illustrate the objectives, technical solutions, and advantages of the present disclosure, the present disclosure will be further described below in conjunction with specific examples. It should be understood by those skilled in the art that the specific examples described herein are merely intended to explain the present disclosure, rather than to limit the present disclosure.

In the examples, unless otherwise specified, the experimental methods used are conventional, and the materials and reagents used are commercially available.

Example 1 Synthesis and Characterization of Cationic Lipid Analog Materials

A synthesis route of the cationic lipid analog material of the present disclosure was as follows:

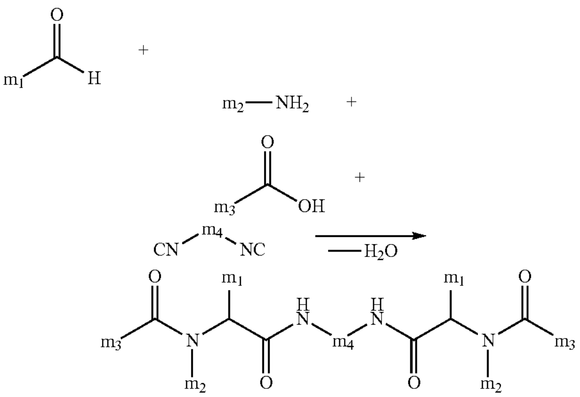

where the amine compound $m_2$-$NH_2$ was one selected from the group consisting of compounds R1 to R11; the carboxylic acid compound

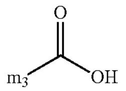

was one selected from the group consisting of compounds C8 to C20 and CHS; the aldehyde compound

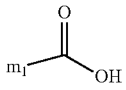

was one selected from the group consisting of compounds A1 to A3; and the isocyanide compound

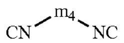

was one selected from the group consisting of compounds I1 to I3:

R1

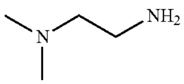

R2

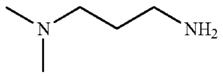

R3

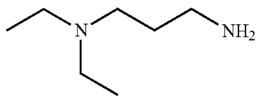

R4

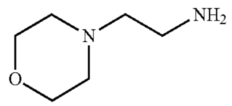

R5

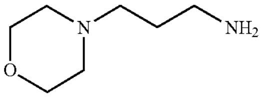

R6

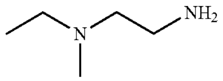

R7

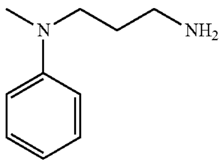

R8

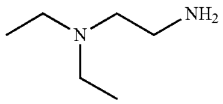

R9

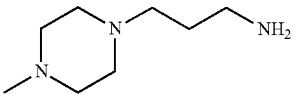

R10

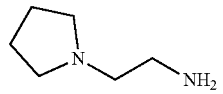

R11

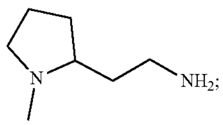

-continued

C8

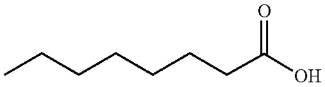

C9

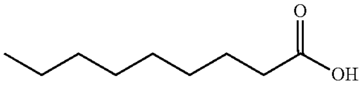

C10

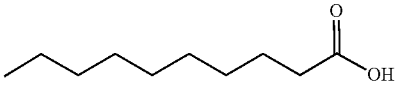

C11

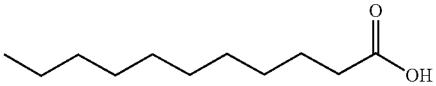

C12

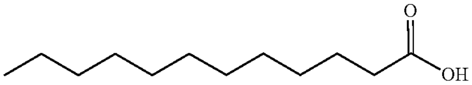

C13

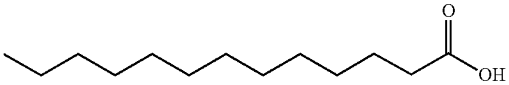

C14

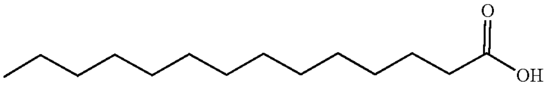

C15

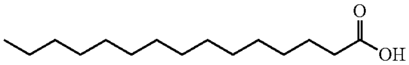

C16

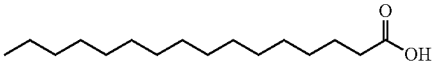

C17

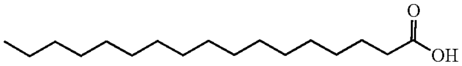

C18

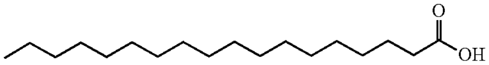

C19

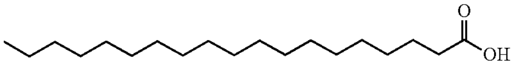

C20

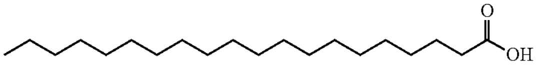

C18-1

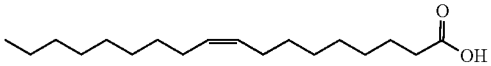

C18-2

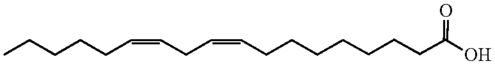

-continued

CHS

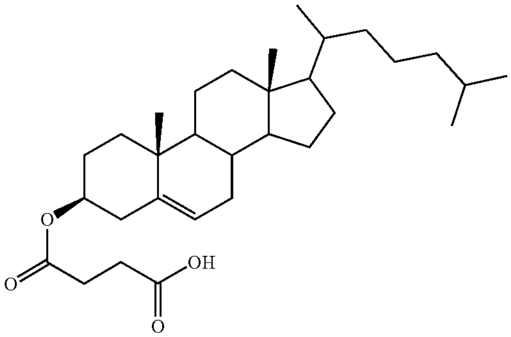

A1

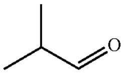

A2

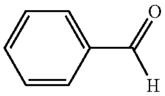

A3

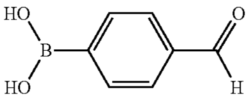

I1

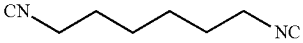

I2-1

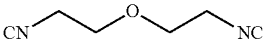

I2

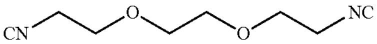

I2-3

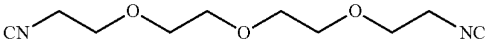

I3

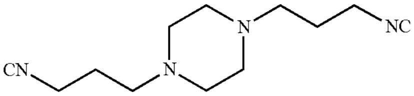

A preparation method of the cationic lipid analog material in this example was specifically as follows: 1 mmol of isobutyl aldehyde (IBA) and 1 mmol of an amine compound were added to 0.5 mL of a methanol solution, and a reaction was conducted for 60 min; 1 mmol of a carboxylic acid compound and 0.5 mmol of an isocyanide compound were added sequentially, and a reaction was conducted at 40° C. for 12 h; and after the reaction was completed, a product was separated and purified by a chromatography column, where a mixture of methanol and DCM was adopted as a mobile phase.

Raw materials used in this example and structures of cationic lipid analog materials synthesized thereby were shown in Table 1.

TABLE 1
| | Isocyanide compound | Amine compound | Carboxylic acid compound | Aldehyde compound | Cationic lipid analog material |
|---|---|---|---|---|---|
| 1 | I1 | R1 | C12 | A1 | I1R1C12A1 |
| | | | | | 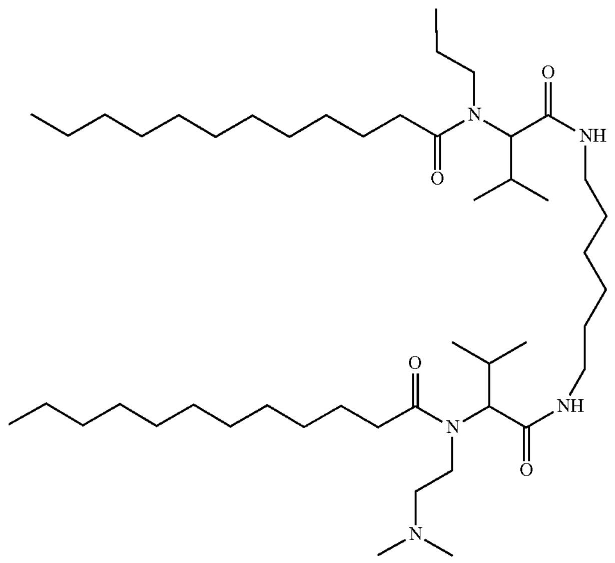 |
| 2 | I1 | R1 | C14 | A1 | I1R1C14A1 |

TABLE 1-continued
| | Isocyanide compound | Amine compound | Carboxylic acid compound | Aldehyde compound | Cationic lipid analog material |
|---|---|---|---|---|---|
| 3 | I1 | R1 | C16 | A1 | 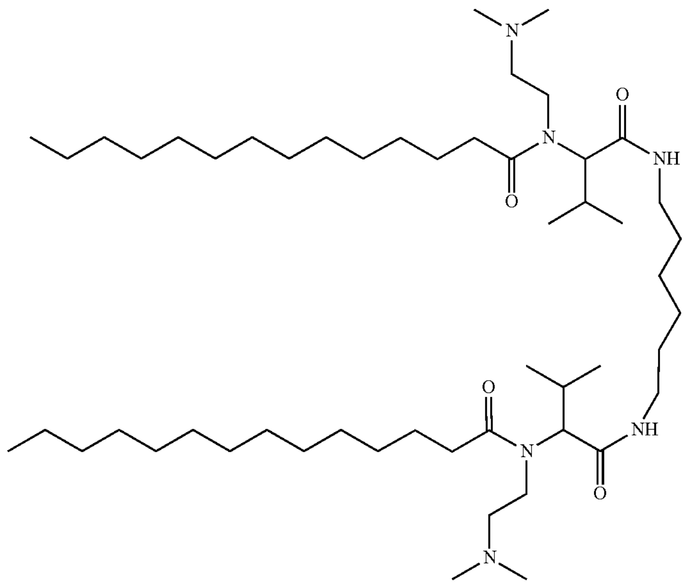 I1R1C16A1 |

TABLE 1-continued
| | Isocyanide compound | Amine compound | Carboxylic acid compound | Aldehyde compound | Cationic lipid analog material |
|---|---|---|---|---|---|
| 4 | I1 | R1 | C18 | A1 | 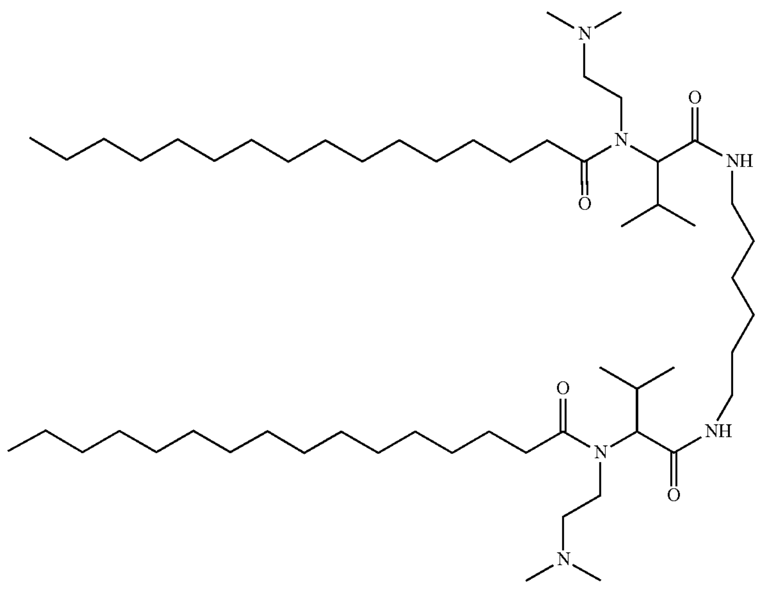 I1R1C18A1 |

TABLE 1-continued
| | Isocyanide compound | Amine compound | Carboxylic acid compound | Aldehyde compound | Cationic lipid analog material |
|---|---|---|---|---|---|
| | | | | | 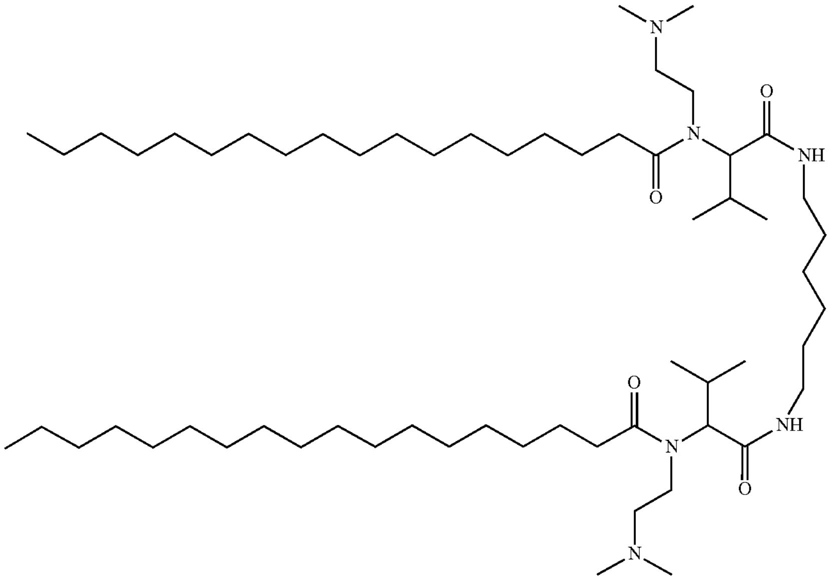 [SMILES: CCCCCCCCCCCCCCCCCC(=O)N(CCN(C)C)C(C(=O)NCCCCCCNC(=O)C(C(C)C)N(CCN(C)C)C(=O)CCCCCCCCCCCCCCCCC)C(C)C] |
| 5 | I1 | R1 | C20 | A1 | I1R1C20A1 |

TABLE 1-continued
| | Isocyanide compound | Amine compound | Carboxylic acid compound | Aldehyde compound | Cationic lipid analog material |
|---|---|---|---|---|---|
| 6 | I1 | R1 | C18-1 | A1 | 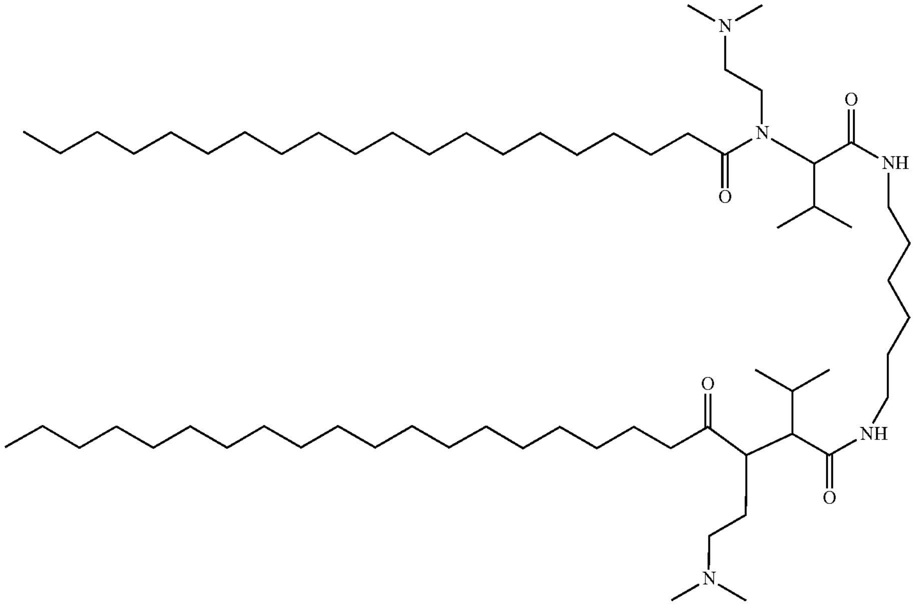 [SMILES: CCCCCCCCCCCCCCCCCCCC(=O)C(CCN(C)C)C(C(=O)NCCCCCCNC(=O)C(C(C)C)N(CCN(C)C)C(=O)CCCCCCCCCCCCCCCCCCC)C(C)C]<br>I1R1C18-1A1 |

TABLE 1-continued
| | Isocyanide compound | Amine compound | Carboxylic acid compound | Aldehyde compound | Cationic lipid analog material |
|---|---|---|---|---|---|
| 7 | I1 | R1 | C18-2 | A1 | 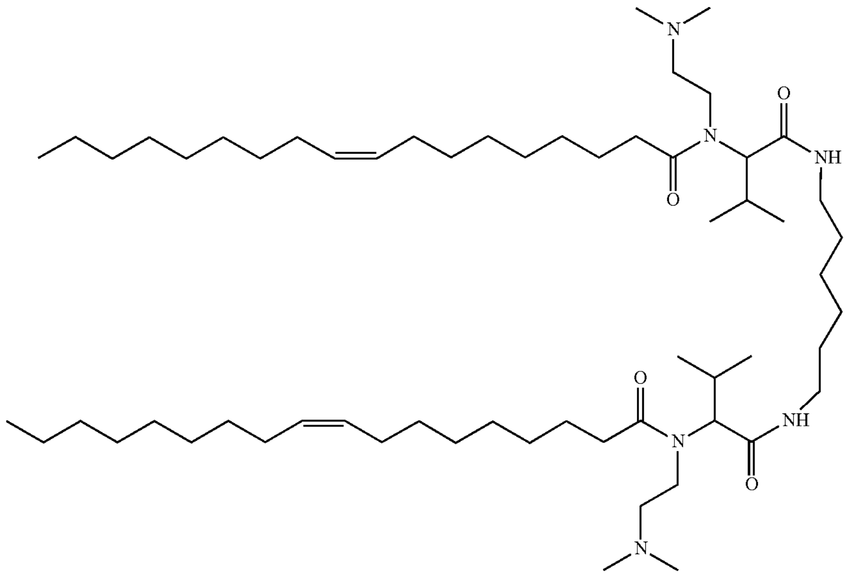 [SMILES: CCCCCCCC/C=C\CCCCCCCC(=O)N(CCN(C)C)C(C(=O)NCCCCCCNC(=O)C(C(C)C)N(CCN(C)C)C(=O)CCCCCCC/C=C\CCCCCCCC)C(C)C] I1R1C18-2A1 |

TABLE 1-continued
| | Isocyanide compound | Amine compound | Carboxylic acid compound | Aldehyde compound | Cationic lipid analog material |
|---|---|---|---|---|---|
| 8 | I1 | R2 | C12 | A1 | 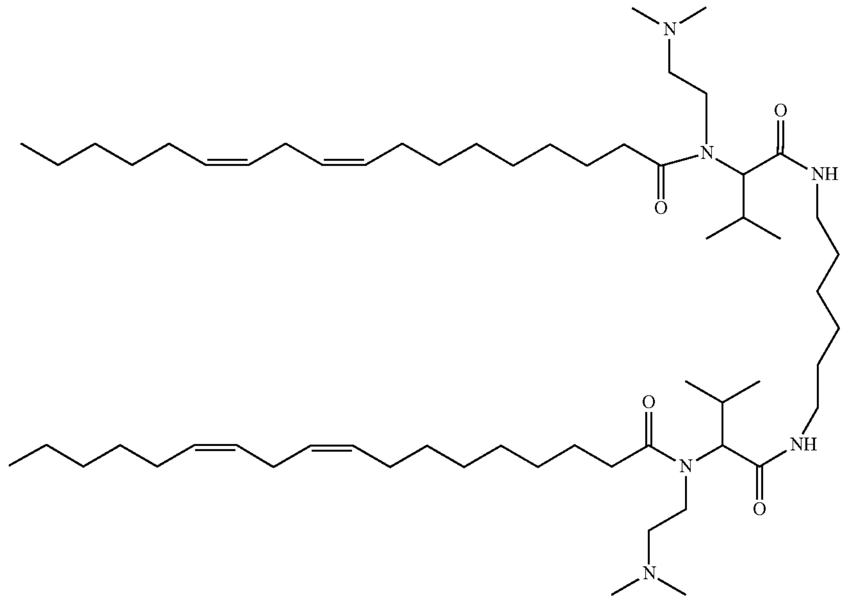 I1R2C12A1 |

TABLE 1-continued
| | Isocyanide compound | Amine compound | Carboxylic acid compound | Aldehyde compound | Cationic lipid analog material |
|---|---|---|---|---|---|
| | | | | | 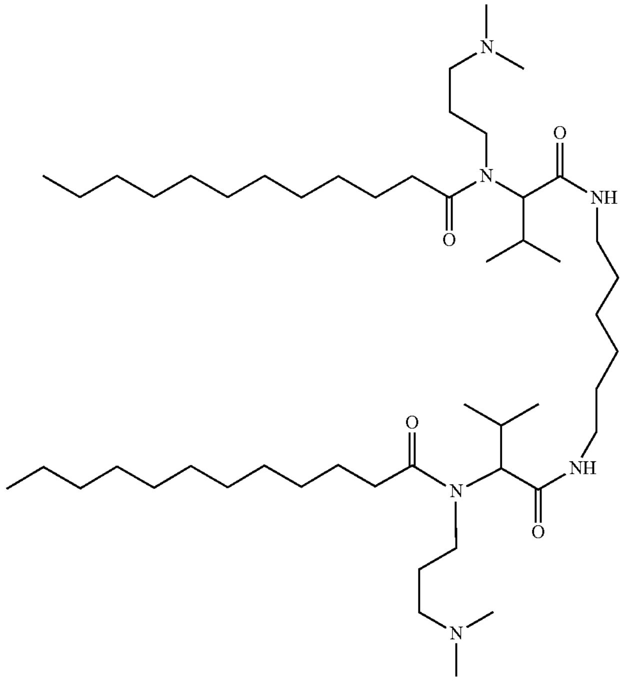 [SMILES: CCCCCCCCCCCC(=O)N(CCCN(C)C)C(C(=O)NCCCCCCNC(=O)C(C(C)C)N(CCCN(C)C)C(=O)CCCCCCCCCCC)C(C)C] |
| 9 | I1 | R2 | C14 | A1 | I1R2C14A1 |

TABLE 1-continued
| | Isocyanide compound | Amine compound | Carboxylic acid compound | Aldehyde compound | Cationic lipid analog material |
|---|---|---|---|---|---|
| 10 | I1 | R2 | C16 | A1 | 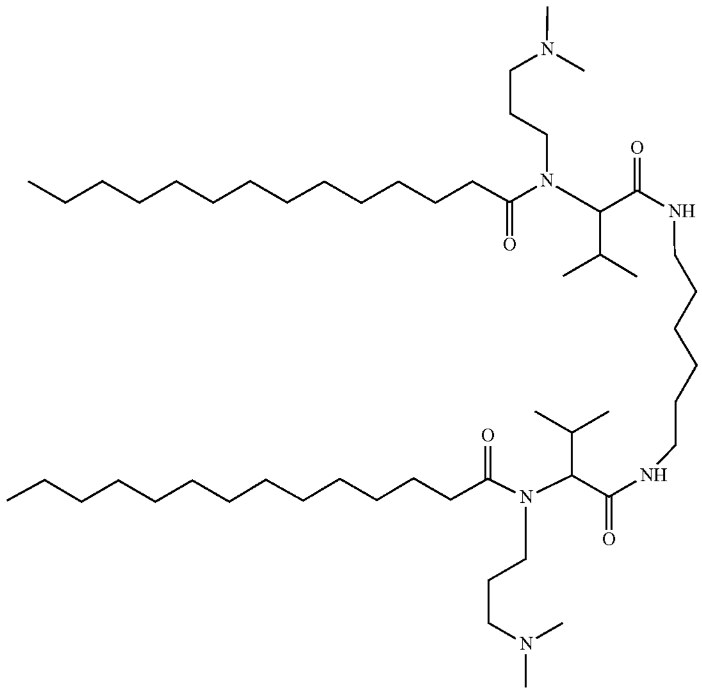 I1R2C16A1 |

TABLE 1-continued
| | Isocyanide compound | Amine compound | Carboxylic acid compound | Aldehyde compound | Cationic lipid analog material |
|---|---|---|---|---|---|
| 11 | I1 | R2 | C18 | A1 | 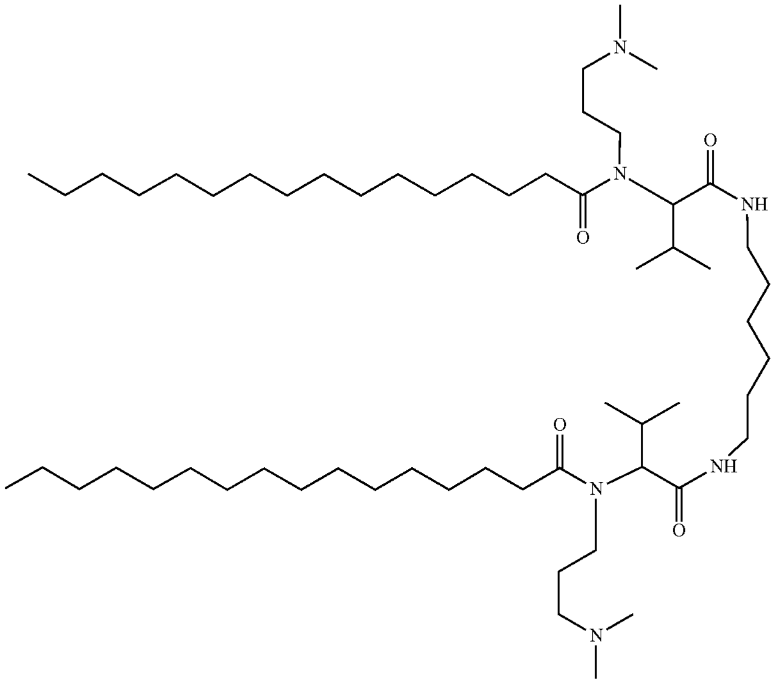 I1R2C18A1 |

TABLE 1-continued
| | Isocyanide compound | Amine compound | Carboxylic acid compound | Aldehyde compound | Cationic lipid analog material |
|---|---|---|---|---|---|
| 12 | I1 | R2 | C20 | A1 | 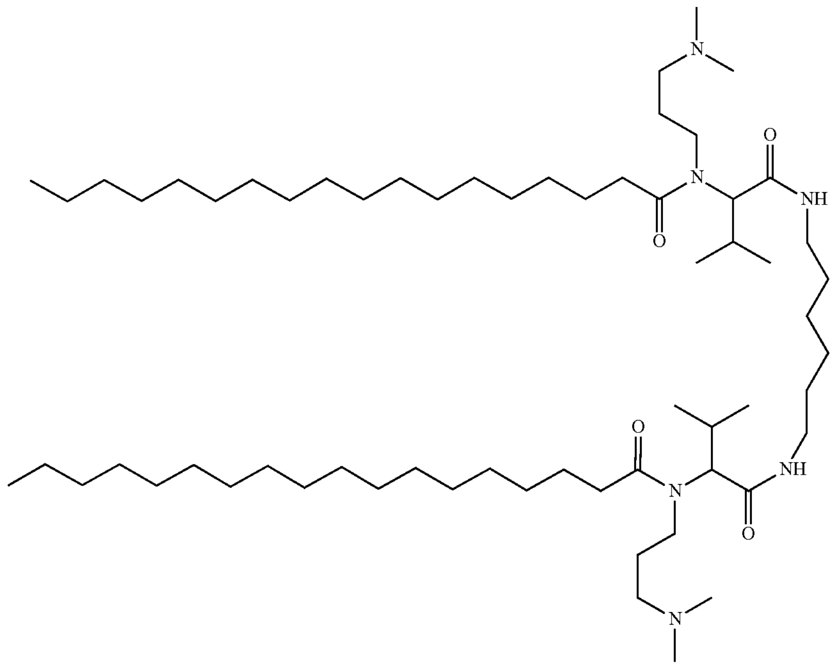 I1R2C20A1 |

TABLE 1-continued
| | Isocyanide compound | Amine compound | Carboxylic acid compound | Aldehyde compound | Cationic lipid analog material |
|---|---|---|---|---|---|
| 13 | I1 | R2 | C18-1 | A1 | 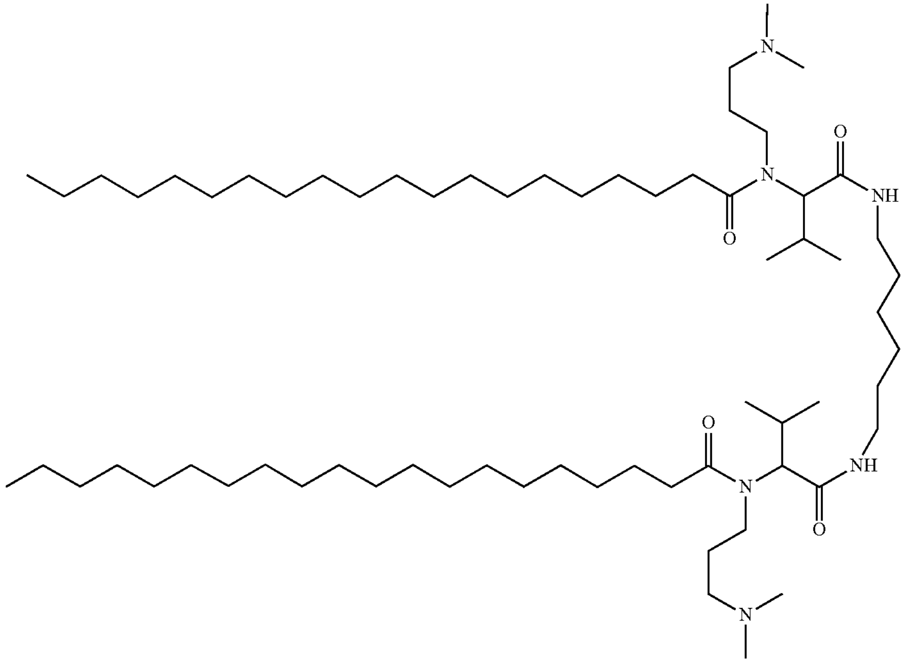 [SMILES: CCCCCCCCCCCCCCCCCCCC(=O)N(CCCN(C)C)C(C(=O)NCCCCCCNC(=O)C(C(C)C)N(CCCN(C)C)C(=O)CCCCCCCCCCCCCCCCCCC)C(C)C] I1R2C18-1A1 |

TABLE 1-continued
| | Isocyanide compound | Amine compound | Carboxylic acid compound | Aldehyde compound | Cationic lipid analog material |
|---|---|---|---|---|---|
| 14 | I1 | R2 | C18-2 | A1 | 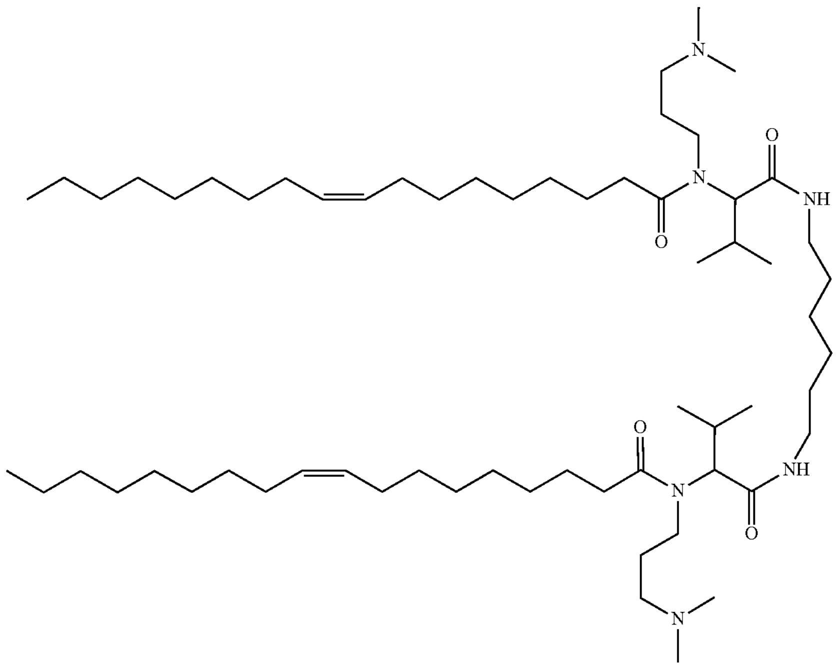 [SMILES: CCCCCCCC/C=C\CCCCCCCC(=O)N(CCCN(C)C)C(C(=O)NCCCCCCNC(=O)C(C(C)C)N(CCCN(C)C)C(=O)CCCCCCC/C=C\CCCCCCCC)C(C)C] I1R2C18-2A1 |

TABLE 1-continued
| | Isocyanide compound | Amine compound | Carboxylic acid compound | Aldehyde compound | Cationic lipid analog material |
|---|---|---|---|---|---|
| 15 | I1 | R3 | C12 | A1 | 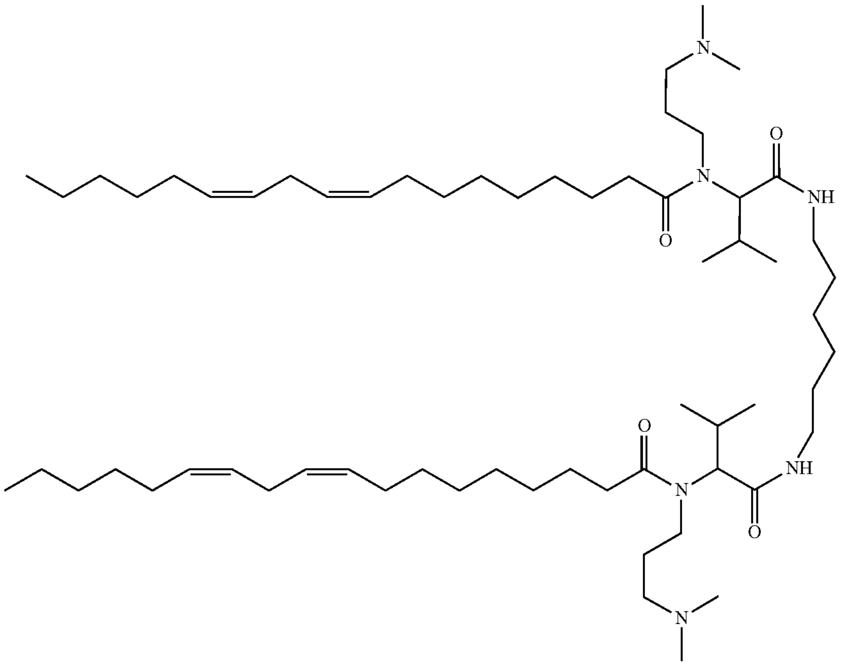 I1R3C12A1 |

TABLE 1-continued
| | Isocyanide compound | Amine compound | Carboxylic acid compound | Aldehyde compound | Cationic lipid analog material |
|---|---|---|---|---|---|
| 16 | I1 | R3 | C14 | A1 | 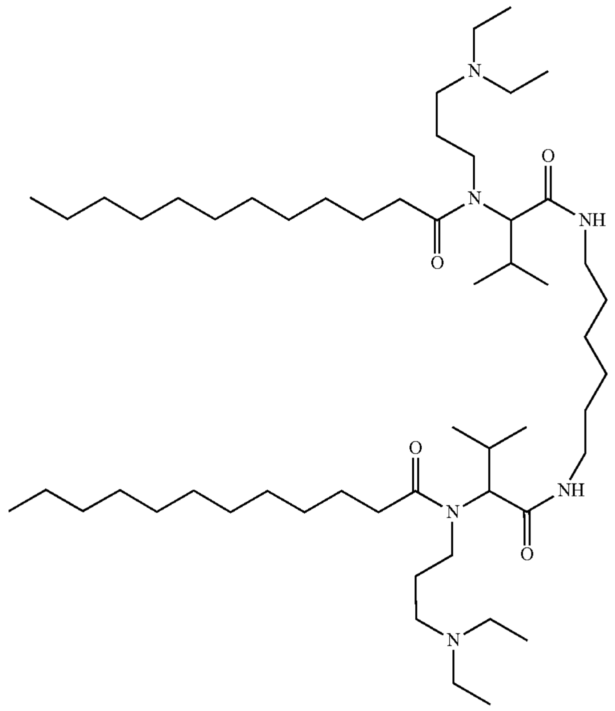 I1R3C14A1 |

TABLE 1-continued
| | Isocyanide compound | Amine compound | Carboxylic acid compound | Aldehyde compound | Cationic lipid analog material |
|---|---|---|---|---|---|
| 17 | I1 | R3 | C16 | A1 | 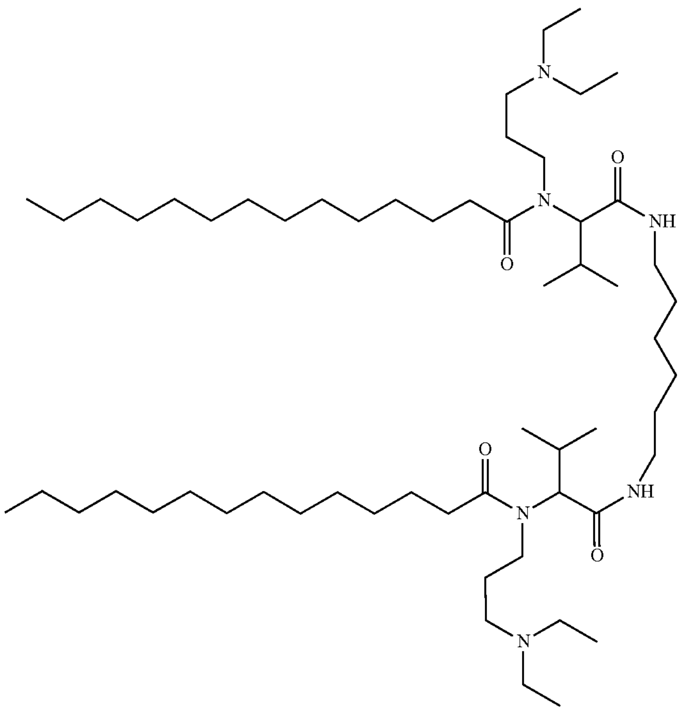 I1R3C16A1 |

TABLE 1-continued
| | Isocyanide compound | Amine compound | Carboxylic acid compound | Aldehyde compound | Cationic lipid analog material |
|---|---|---|---|---|---|
| 18 | I1 | R3 | C18 | A1 | 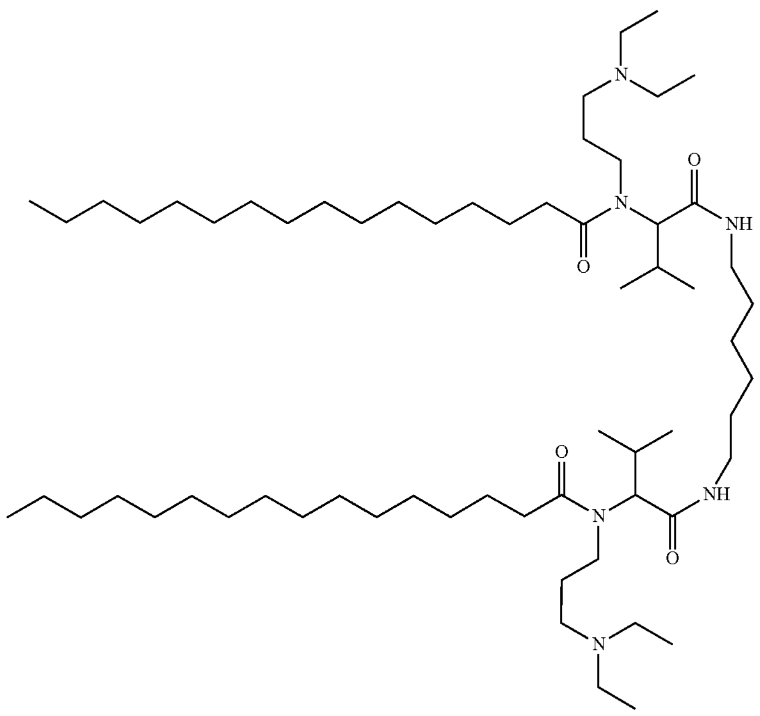 I1R3C18A1 |

TABLE 1-continued
| | Isocyanide compound | Amine compound | Carboxylic acid compound | Aldehyde compound | Cationic lipid analog material |
|---|---|---|---|---|---|
| | | | | | 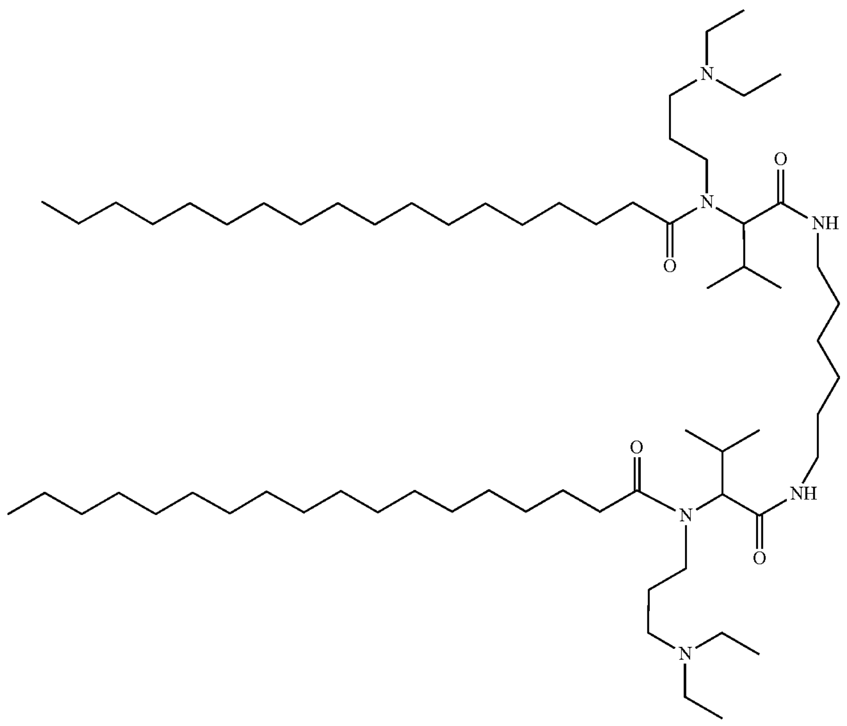 [SMILES: CCCCCCCCCCCCCCCCCC(=O)N(CCCN(CC)CC)C(C(=O)NCCCCCCNC(=O)C(C(C)C)N(CCCN(CC)CC)C(=O)CCCCCCCCCCCCCCCCC)C(C)C] |
| 19 | I1 | R3 | C20 | A1 | I1R3C20A1 |

TABLE 1-continued
| | Isocyanide compound | Amine compound | Carboxylic acid compound | Aldehyde compound | Cationic lipid analog material |
|---|---|---|---|---|---|
| 20 | I1 | R3 | C18-1 | A1 | 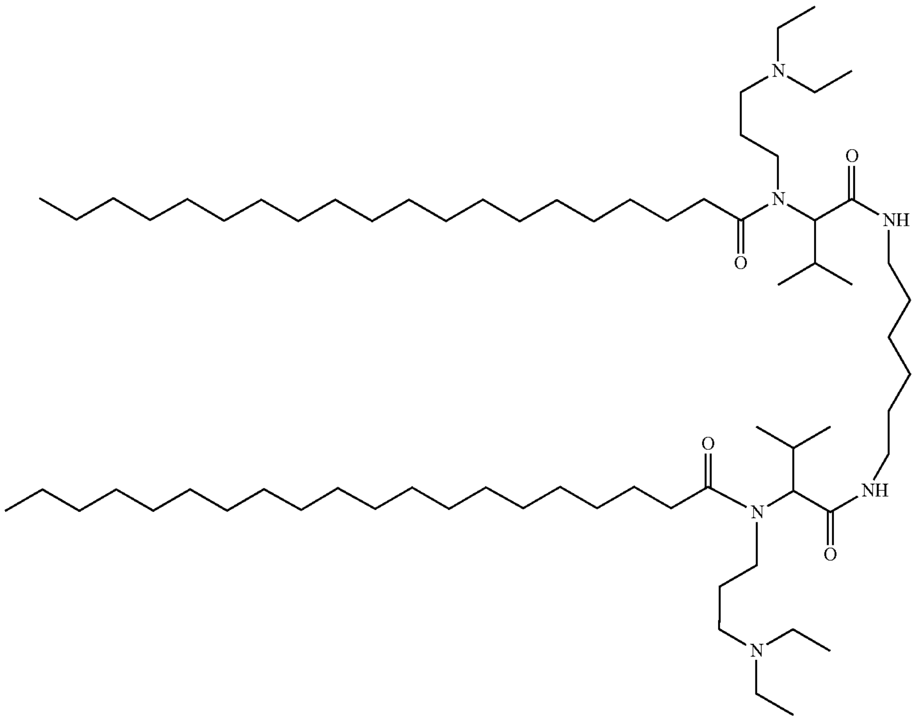 [SMILES: CCCCCCCCCCCCCCCCCCCC(=O)N(CCCN(CC)CC)C(C(=O)NCCCCCCNC(=O)C(C(C)C)N(CCCN(CC)CC)C(=O)CCCCCCCCCCCCCCCCCCC)C(C)C] I1R3C18-1A1 |

TABLE 1-continued
| | Isocyanide compound | Amine compound | Carboxylic acid compound | Aldehyde compound | Cationic lipid analog material |
|---|---|---|---|---|---|
| 21 | I1 | R3 | C18-2 | A1 | 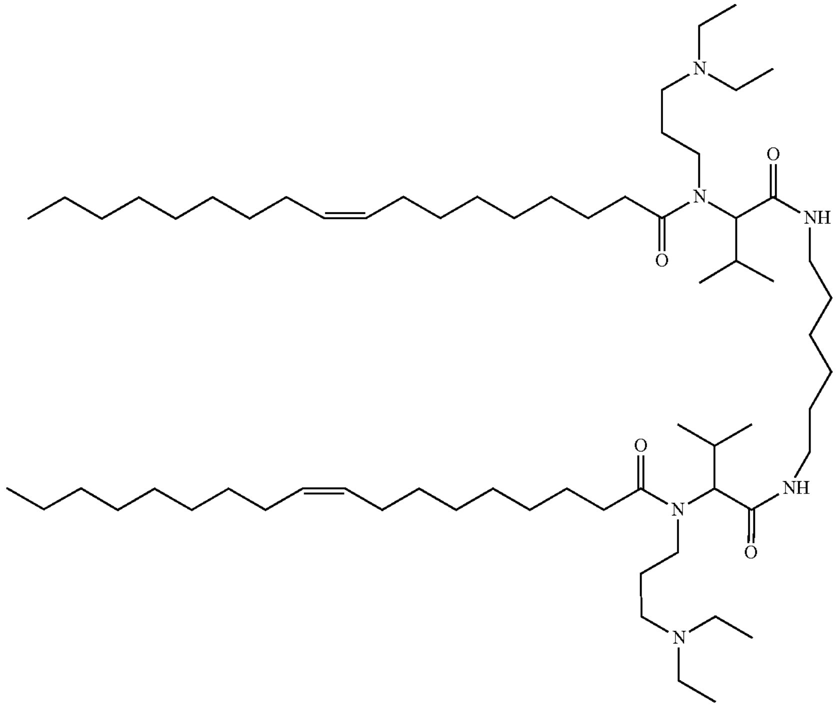 [SMILES: CCCCCCCC/C=C\CCCCCCCC(=O)N(CCCN(CC)CC)C(C(=O)NCCCCCCNC(=O)C(C(C)C)N(CCCN(CC)CC)C(=O)CCCCCCC/C=C\CCCCCCCC)C(C)C] I1R3C18-2A1 |

TABLE 1-continued
| | Isocyanide compound | Amine compound | Carboxylic acid compound | Aldehyde compound | Cationic lipid analog material |
|---|---|---|---|---|---|
| 22 | I1 | R5 | C12 | A1 | 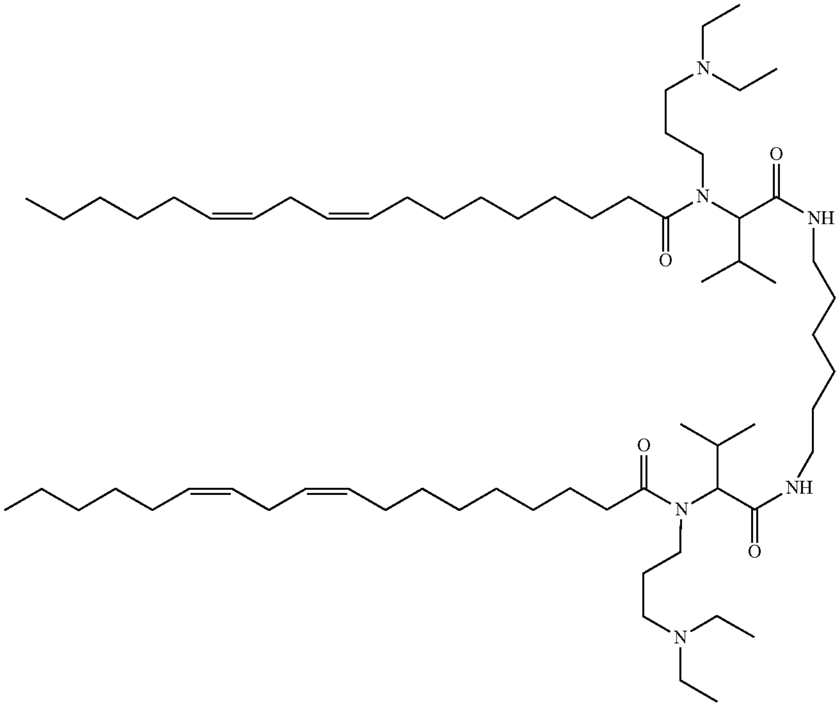 I1R5C12A1 |

TABLE 1-continued
| | Isocyanide compound | Amine compound | Carboxylic acid compound | Aldehyde compound | Cationic lipid analog material |
|---|---|---|---|---|---|
| 23 | I1 | R5 | C14 | A1 | 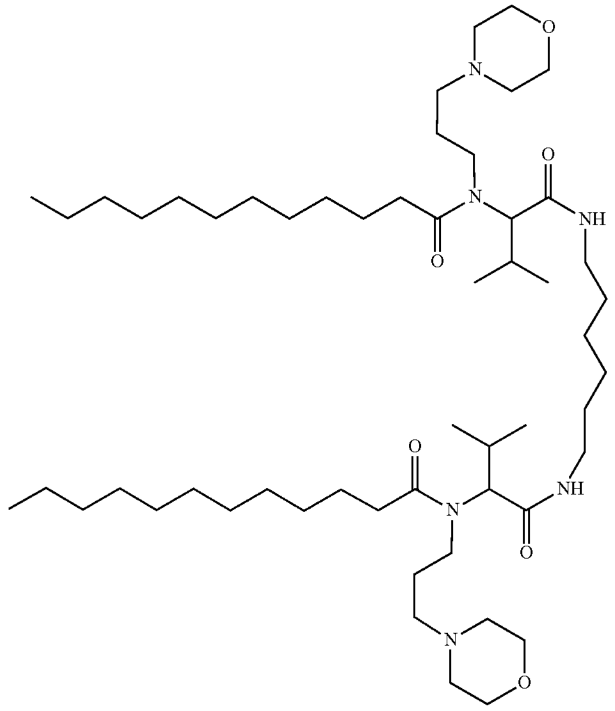 I1R5C14A1 |

TABLE 1-continued
| | Isocyanide compound | Amine compound | Carboxylic acid compound | Aldehyde compound | Cationic lipid analog material |
|---|---|---|---|---|---|
| 24 | I1 | R5 | C16 | A1 | 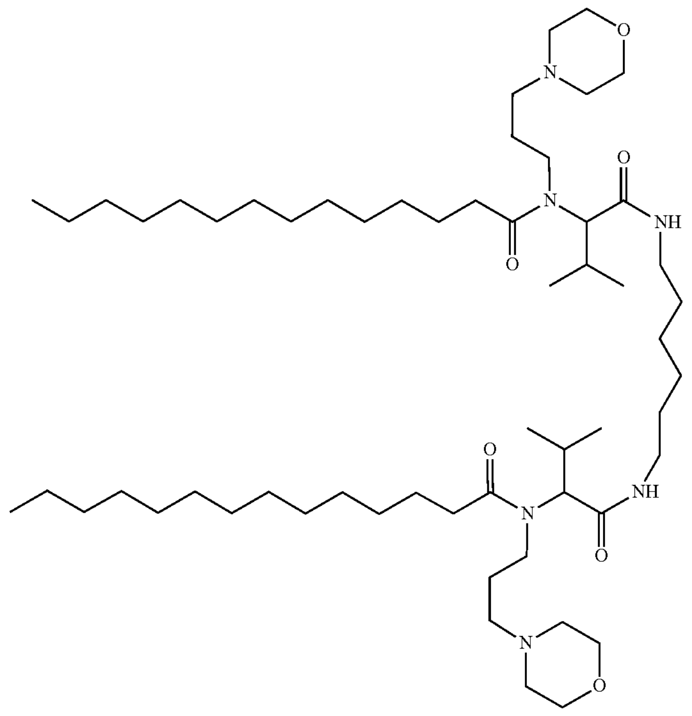 I1R5C16A1 |

TABLE 1-continued
| | Isocyanide compound | Amine compound | Carboxylic acid compound | Aldehyde compound | Cationic lipid analog material |
|---|---|---|---|---|---|
| 25 | I1 | R5 | C18 | A1 | 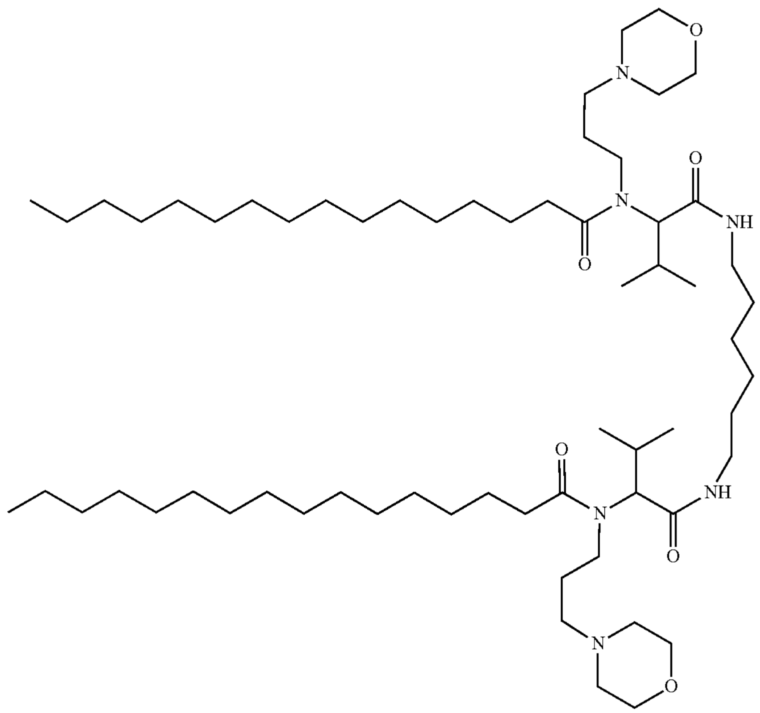 I1R5C18A1 |

TABLE 1-continued
| | Isocyanide compound | Amine compound | Carboxylic acid compound | Aldehyde compound | Cationic lipid analog material |
|---|---|---|---|---|---|
| | | | | | 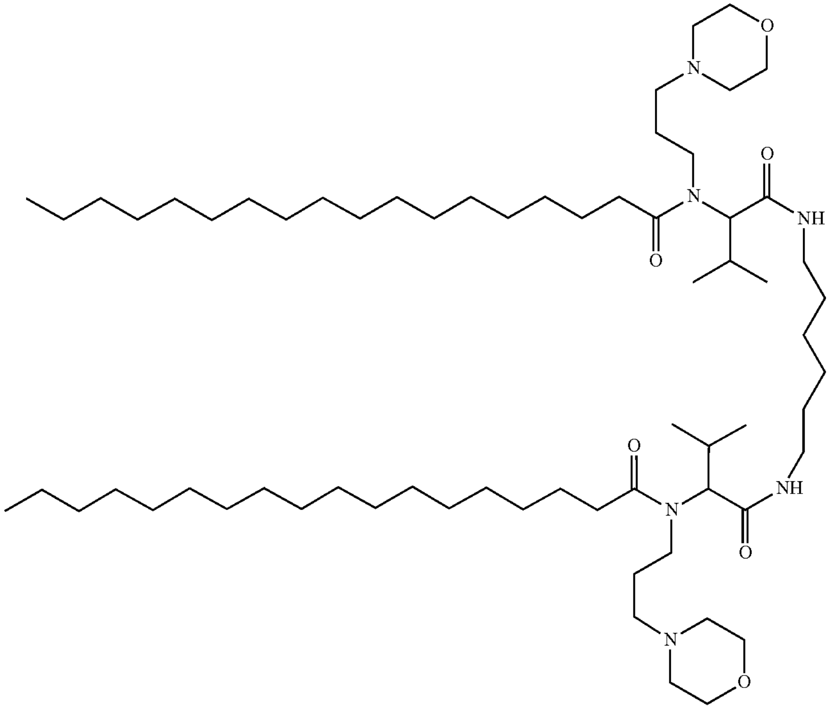 [SMILES: CCCCCCCCCCCCCCCCCC(=O)N(CCCN1CCOCC1)C(C(=O)NCCCCCCNC(=O)C(C(C)C)N(CCCN1CCOCC1)C(=O)CCCCCCCCCCCCCCCCC)C(C)C] |
| 26 | I1 | R5 | C20 | A1 | I1R5C20A1 |

TABLE 1-continued
| | Isocyanide compound | Amine compound | Carboxylic acid compound | Aldehyde compound | Cationic lipid analog material |
|---|---|---|---|---|---|
| 27 | I1 | R5 | C18-1 | A1 | 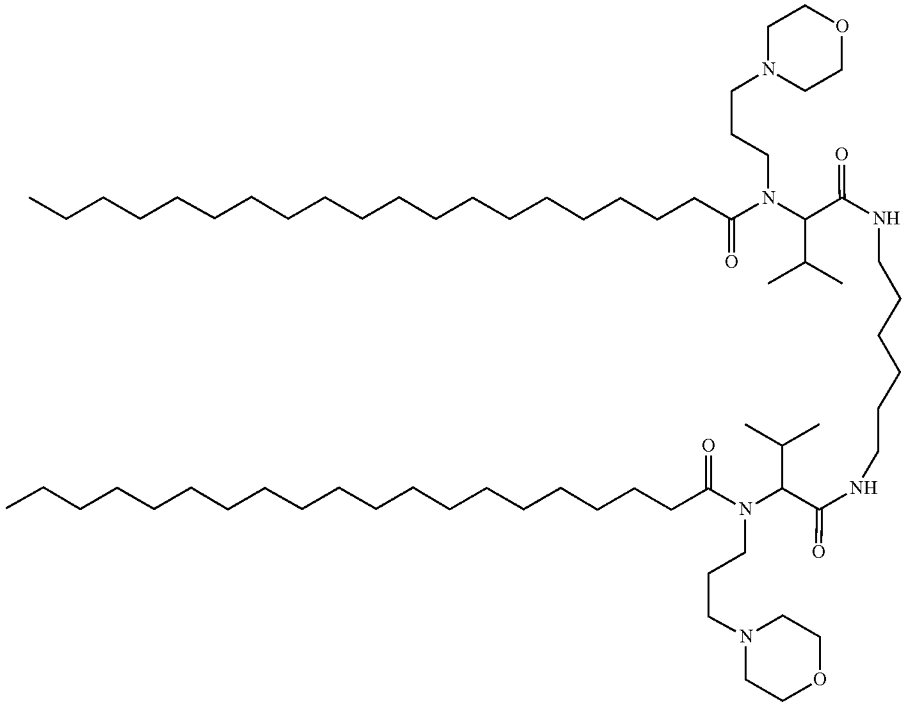 [SMILES: CCCCCCCCCCCCCCCCCCCC(=O)N(CCCN1CCOCC1)C(C(=O)NCCCCCCNC(=O)C(C(C)C)N(CCCN1CCOCC1)C(=O)CCCCCCCCCCCCCCCCCCC)C(C)C] I1R5C18-1A1 |

TABLE 1-continued
| | Isocyanide compound | Amine compound | Carboxylic acid compound | Aldehyde compound | Cationic lipid analog material |
|---|---|---|---|---|---|
| | | | | | 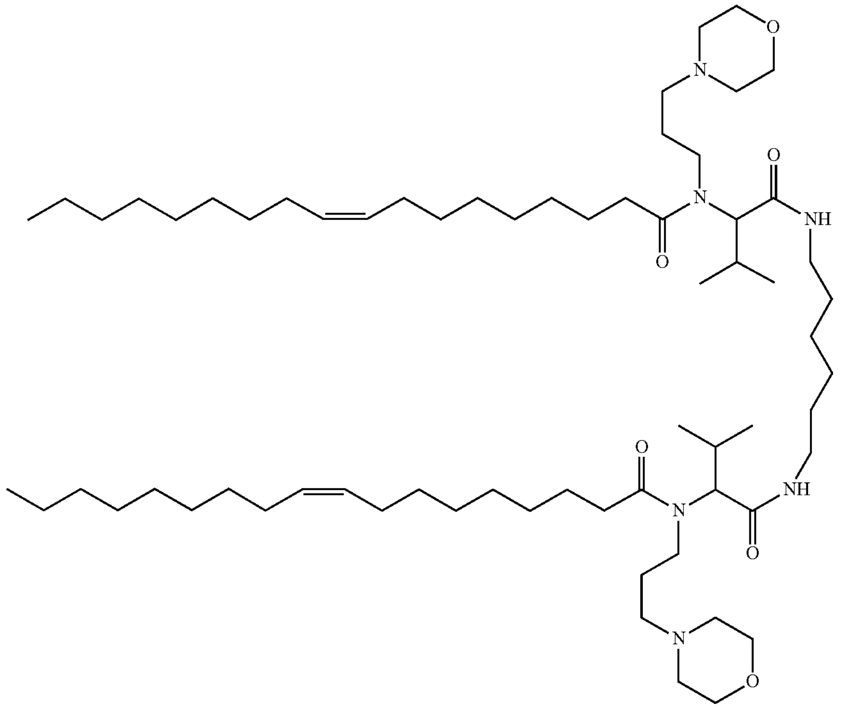 [SMILES: CCCCCCCC/C=C\CCCCCCCC(=O)N(CCCN1CCOCC1)C(C(=O)NCCCCCCNC(=O)C(C(C)C)N(CCCN1CCOCC1)C(=O)CCCCCCC/C=C\CCCCCCCC)C(C)C] |
| 28 | I1 | R5 | C18-2 | A1 | I1R5C18-2A1 |

TABLE 1-continued
| | Isocyanide compound | Amine compound | Carboxylic acid compound | Aldehyde compound | Cationic lipid analog material |
|---|---|---|---|---|---|
| | | | | | 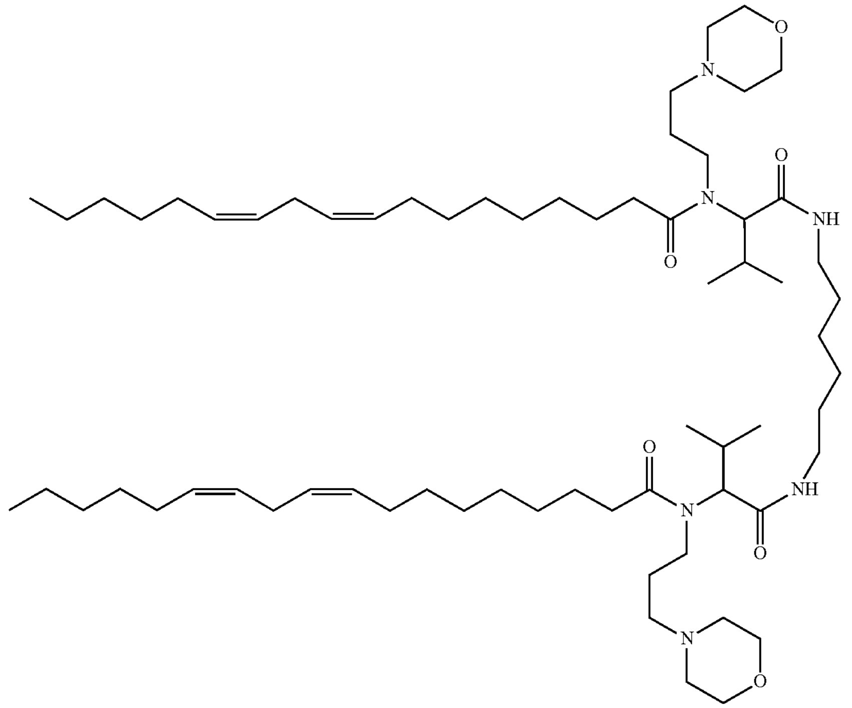 [SMILES: CCCCC/C=C\C/C=C\CCCCCCCC(=O)N(CCCN1CCOCC1)C(C(=O)NCCCCCCNC(=O)C(C(C)C)N(CCCN1CCOCC1)C(=O)CCCCCCC/C=C\C/C=C\CCCCC)C(C)C] |
| 29 | I1 | R11 | C12 | A1 | I1R11C12A1 |

TABLE 1-continued
| | Isocyanide compound | Amine compound | Carboxylic acid compound | Aldehyde compound | Cationic lipid analog material |
|---|---|---|---|---|---|
| 30 | I1 | R11 | C14 | A1 | 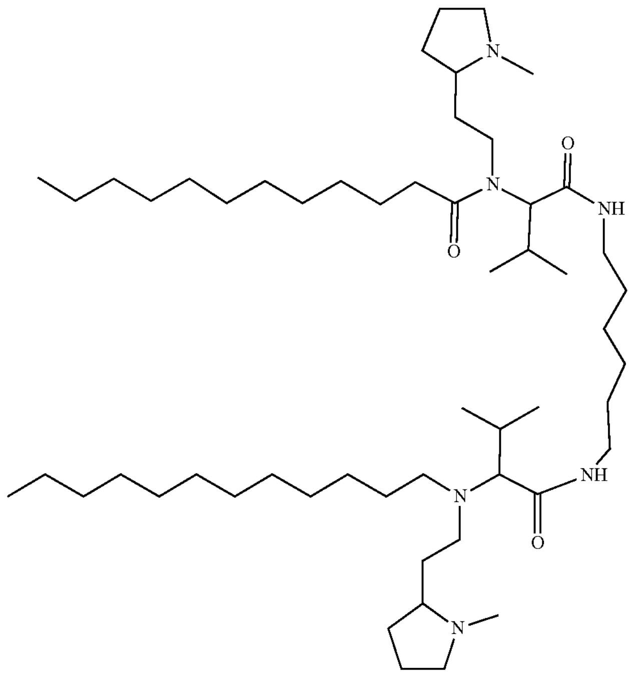 I1R11C14A1 |

TABLE 1-continued
| | Isocyanide compound | Amine compound | Carboxylic acid compound | Aldehyde compound | Cationic lipid analog material |
|---|---|---|---|---|---|
| 31 | I1 | R11 | C16 | A1 | 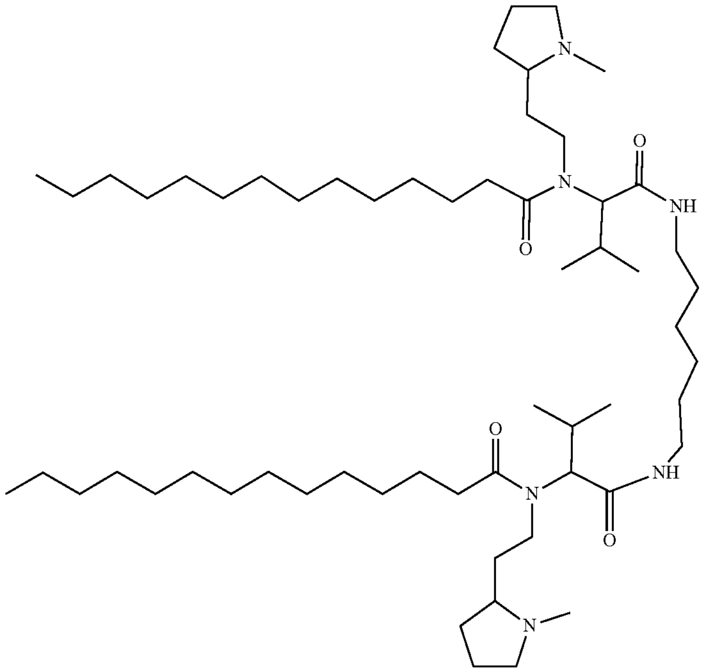 I1R11C16A1 |

TABLE 1-continued
| | Isocyanide compound | Amine compound | Carboxylic acid compound | Aldehyde compound | Cationic lipid analog material |
|---|---|---|---|---|---|
| 32 | I1 | R11 | C18 | A1 | 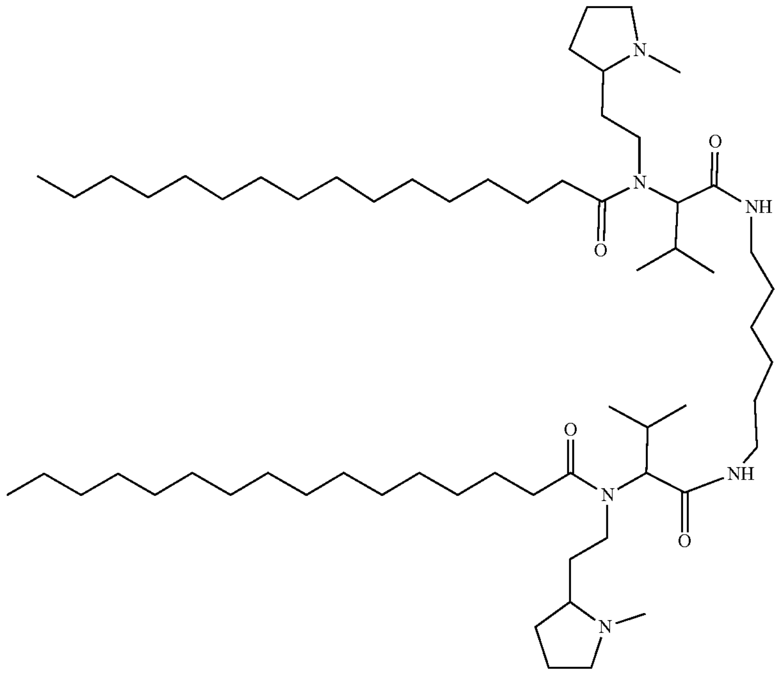 I1R11C18A1 |

TABLE 1-continued
| | Isocyanide compound | Amine compound | Carboxylic acid compound | Aldehyde compound | Cationic lipid analog material |
|---|---|---|---|---|---|
| 33 | I1 | R11 | C20 | A1 | 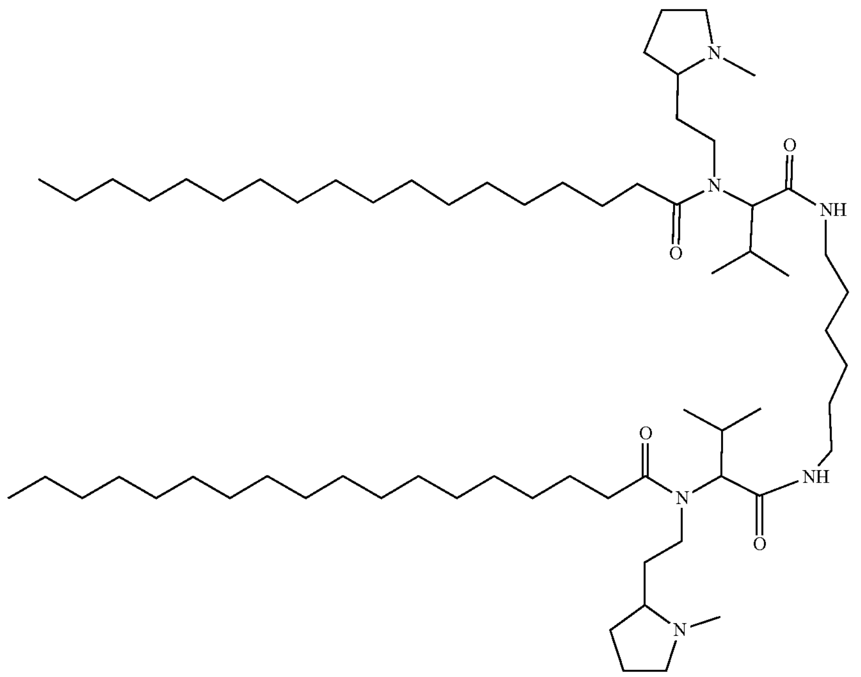 [SMILES: CCCCCCCCCCCCCCCCCC(=O)N(CCC1CCCN1C)C(C(=O)NCCCCCCNC(=O)C(C(C)C)N(CCC1CCCN1C)C(=O)CCCCCCCCCCCCCCCCC)C(C)C]<br>I1R11C20A1 |

TABLE 1-continued
| | Isocyanide compound | Amine compound | Carboxylic acid compound | Aldehyde compound | Cationic lipid analog material |
|---|---|---|---|---|---|
| 34 | I1 | R11 | C18-1 | A1 | 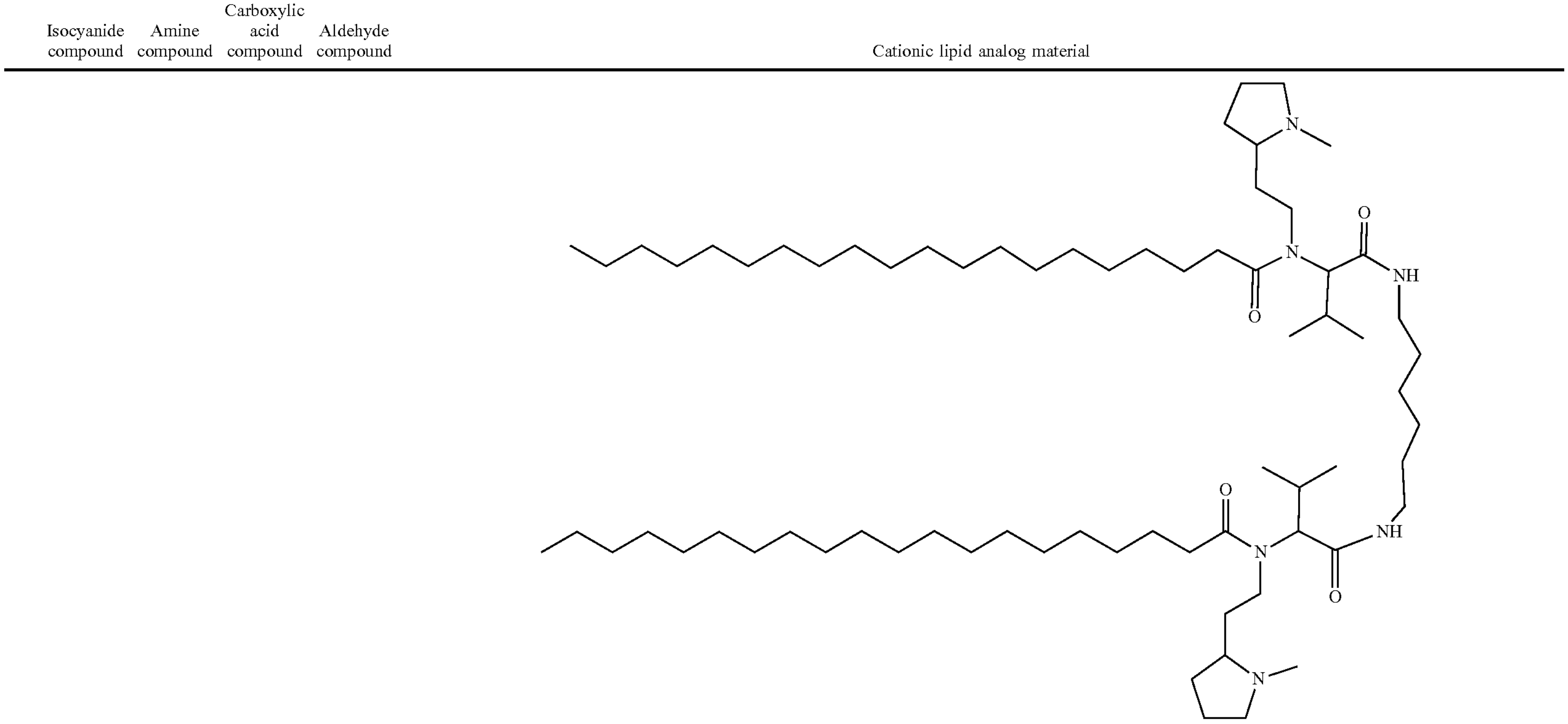<br>I1R11C18-1A1 |

TABLE 1-continued
| | Isocyanide compound | Amine compound | Carboxylic acid compound | Aldehyde compound | Cationic lipid analog material |
|---|---|---|---|---|---|
| 35 | I1 | R11 | C18-2 | A1 | 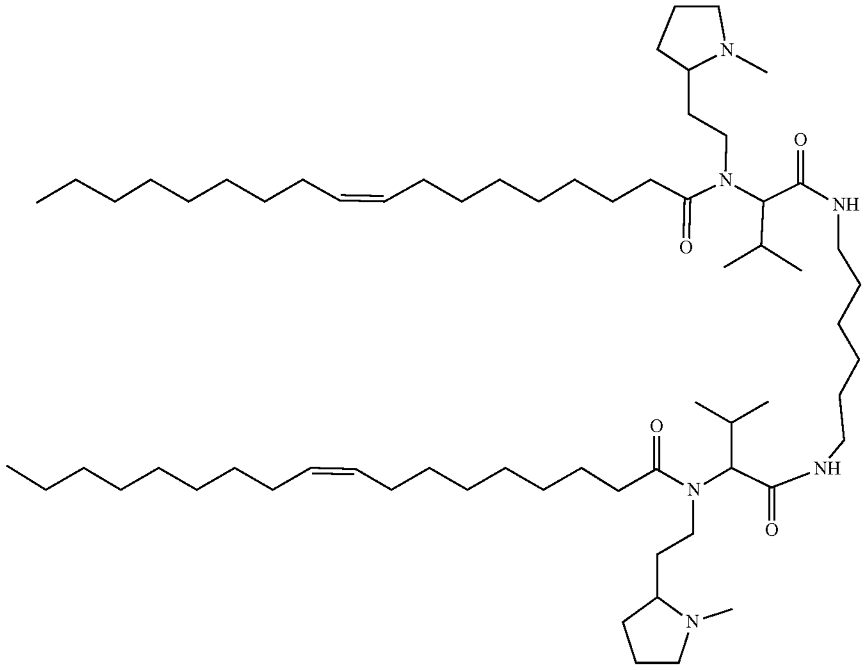 [SMILES: CCCCCCCC/C=C\CCCCCCCC(=O)N(CCC1CCCN1C)C(C(=O)NCCCCCCNC(=O)C(C(C)C)N(CCC1CCCN1C)C(=O)CCCCCCC/C=C\CCCCCCCC)C(C)C] I1R11C18-2A1 |

TABLE 1-continued
| | Isocyanide compound | Amine compound | Carboxylic acid compound | Aldehyde compound | Cationic lipid analog material |
|---|---|---|---|---|---|
| 36 | I2 | R1 | C12 | A1 | 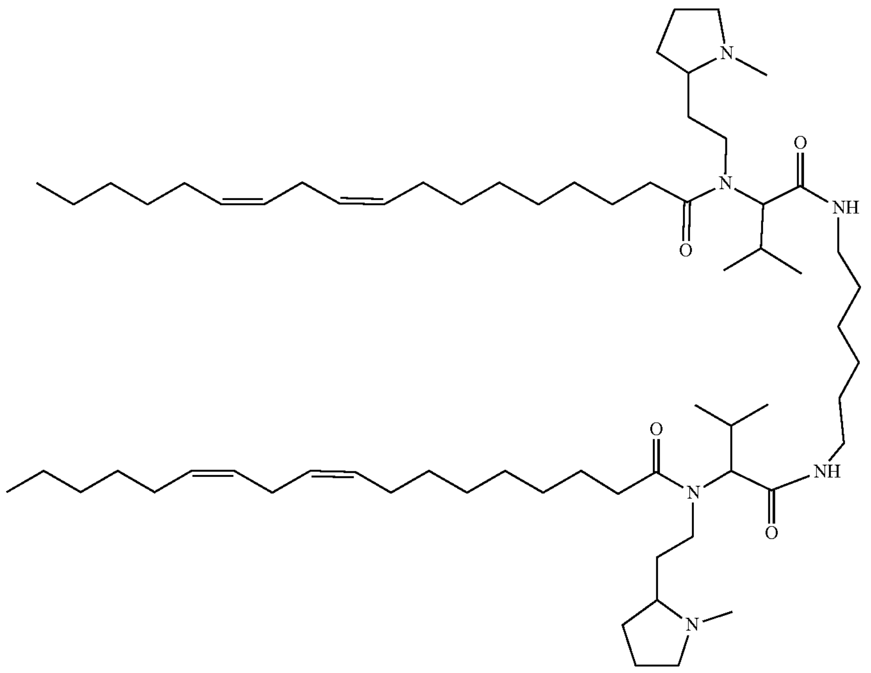 I2R1C12A1 |

TABLE 1-continued
| | Isocyanide compound | Amine compound | Carboxylic acid compound | Aldehyde compound | Cationic lipid analog material |
|---|---|---|---|---|---|
| | | | | | 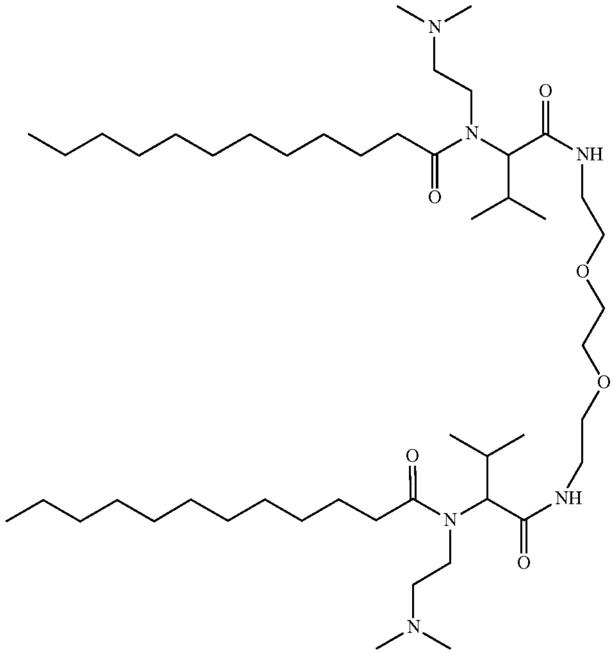 [SMILES: CCCCCCCCCCCC(=O)N(CCN(C)C)C(C(=O)NCCOCCOCCNC(=O)C(C(C)C)N(CCN(C)C)C(=O)CCCCCCCCCCC)C(C)C] |
| 37 | I2 | R1 | C14 | A1 | I2R1C14A1 |

TABLE 1-continued
| | Isocyanide compound | Amine compound | Carboxylic acid compound | Aldehyde compound | Cationic lipid analog material |
|---|---|---|---|---|---|
| | | | | | 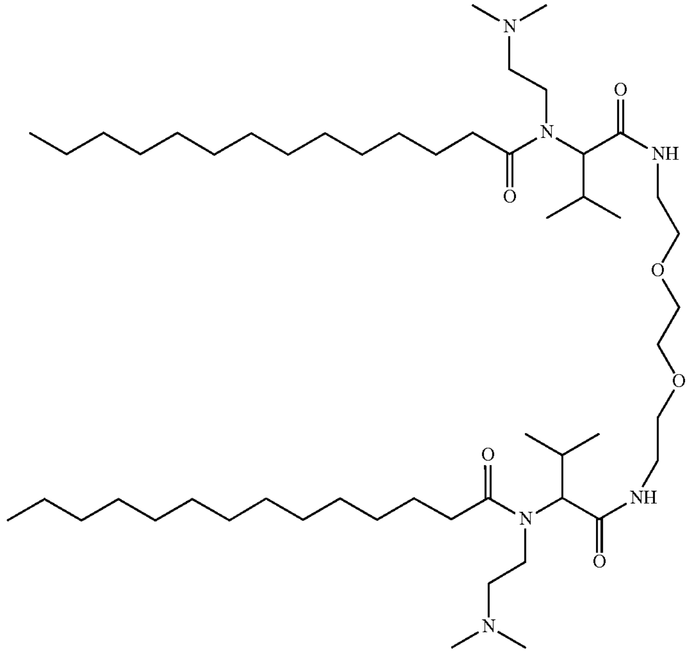 [SMILES: CCCCCCCCCCCCCC(=O)N(CCN(C)C)C(C(=O)NCCOCCOCCNC(=O)C(C(C)C)N(CCN(C)C)C(=O)CCCCCCCCCCCCC)C(C)C] |
| 38 | I2 | R1 | C16 | A1 | I2R1C16A1 |

TABLE 1-continued
| | Isocyanide compound | Amine compound | Carboxylic acid compound | Aldehyde compound | Cationic lipid analog material |
|---|---|---|---|---|---|
| 39 | I2 | R1 | C18 | A1 | 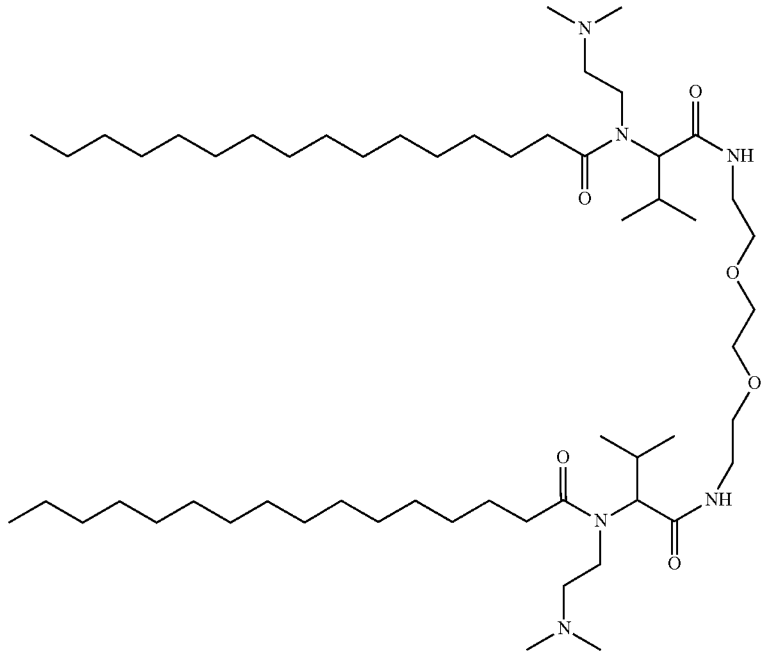 I2R1C18A1 |

TABLE 1-continued
| Isocyanide compound | Amine compound | Carboxylic acid compound | Aldehyde compound | Cationic lipid analog material |
|---|---|---|---|---|
| | | | | 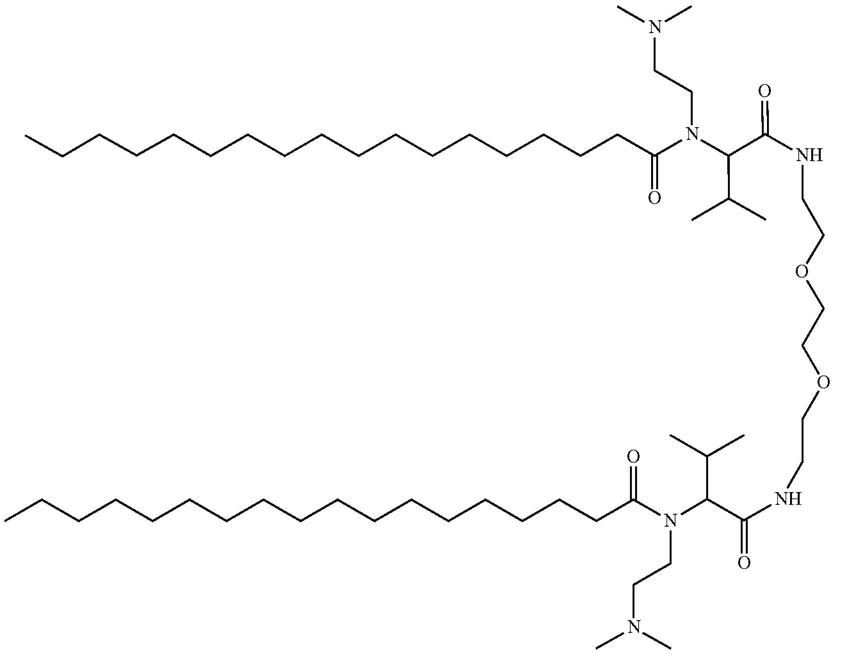 [SMILES: CCCCCCCCCCCCCCCCCC(=O)N(CCN(C)C)C(C(=O)NCCOCCOCCNC(=O)C(C(C)C)N(CCN(C)C)C(=O)CCCCCCCCCCCCCCCCC)C(C)C] |
| 12 | R1 | C20 | A1 | I2R1C20A1 |

TABLE 1-continued
| | Isocyanide compound | Amine compound | Carboxylic acid compound | Aldehyde compound | Cationic lipid analog material |
|---|---|---|---|---|---|
| | | | | | 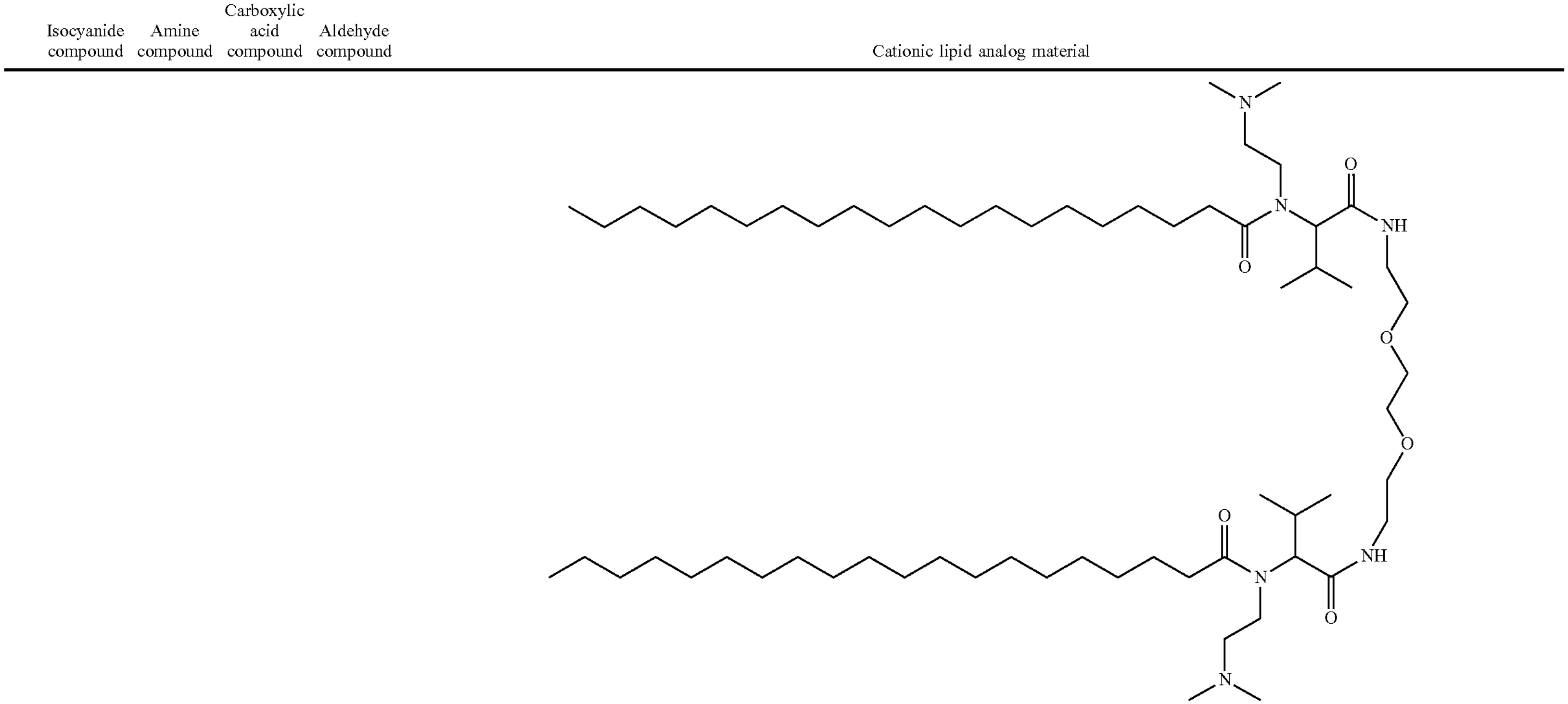 |
| 41 | I2 | R1 | C18-1 | A1 | I2R1C18-1A1 |

TABLE 1-continued
| | Isocyanide compound | Amine compound | Carboxylic acid compound | Aldehyde compound | Cationic lipid analog material |
|---|---|---|---|---|---|
| 42 | I2 | R1 | C18-2 | A1 | 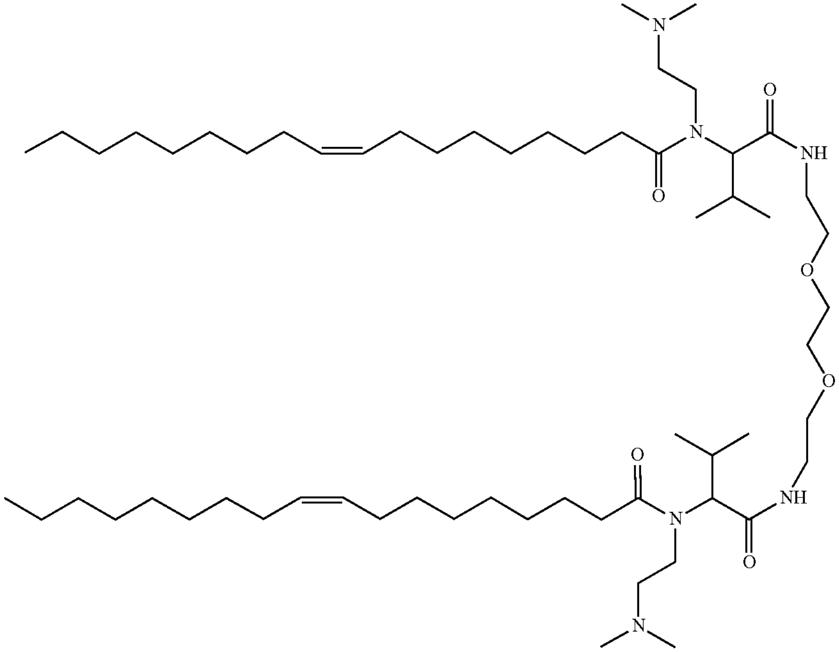 [SMILES: CCCCCCCC/C=C\CCCCCCCC(=O)N(CCN(C)C)C(C(=O)NCCOCCOCCNC(=O)C(C(C)C)N(CCN(C)C)C(=O)CCCCCCC/C=C\CCCCCCCC)C(C)C] I2R1C18-2A1 |

TABLE 1-continued
| | Isocyanide compound | Amine compound | Carboxylic acid compound | Aldehyde compound | Cationic lipid analog material |
|---|---|---|---|---|---|
| | | | | | 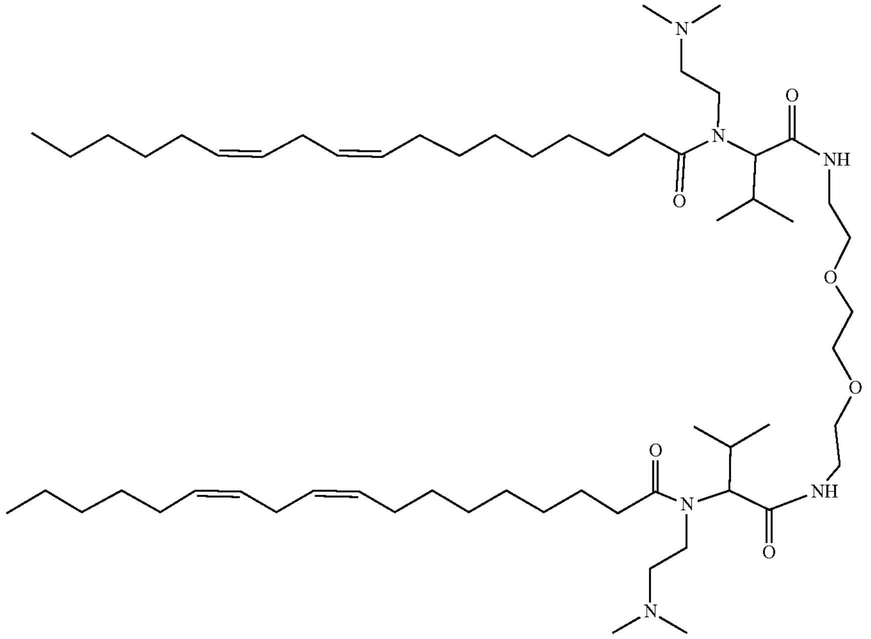 [SMILES: CCCCC/C=C\C/C=C\CCCCCCCC(=O)N(CCN(C)C)C(C(=O)NCCOCCOCCNC(=O)C(C(C)C)N(CCN(C)C)C(=O)CCCCCCC/C=C\C/C=C\CCCCC)C(C)C] |
| 43 | I2 | R2 | C12 | A1 | I2R2C12A1 |

TABLE 1-continued
| | Isocyanide compound | Amine compound | Carboxylic acid compound | Aldehyde compound | Cationic lipid analog material |
|---|---|---|---|---|---|
| 44 | I2 | R2 | C14 | A1 | 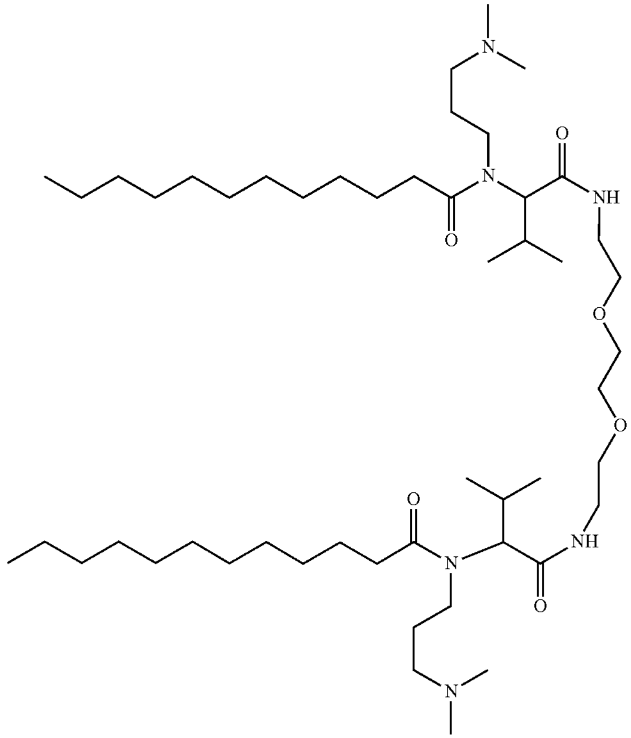 I2R2C14A1 |

TABLE 1-continued
| | Isocyanide compound | Amine compound | Carboxylic acid compound | Aldehyde compound | Cationic lipid analog material |
|---|---|---|---|---|---|
| 45 | I2 | R2 | C16 | A1 | 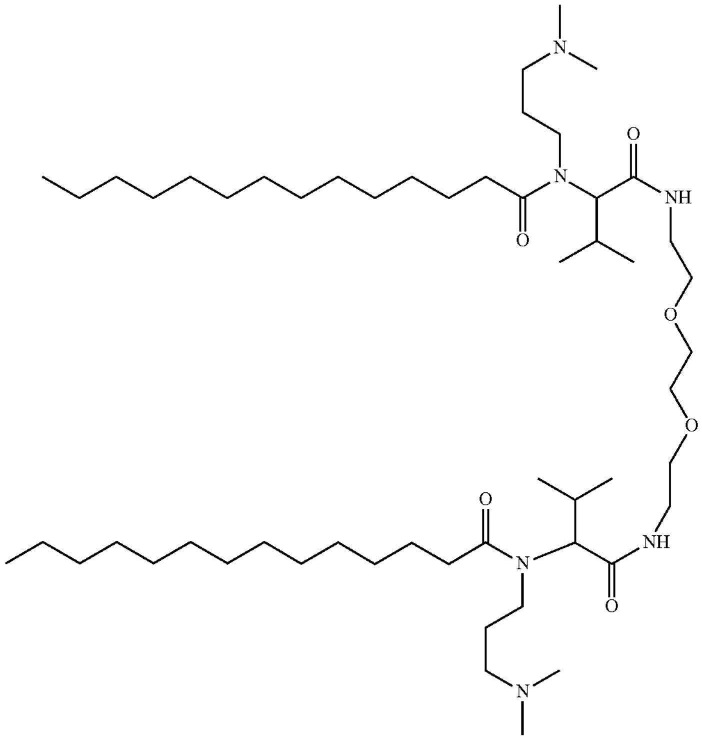 I2R2C16A1 |

TABLE 1-continued
| | Isocyanide compound | Amine compound | Carboxylic acid compound | Aldehyde compound | Cationic lipid analog material |
|---|---|---|---|---|---|
| | | | | | 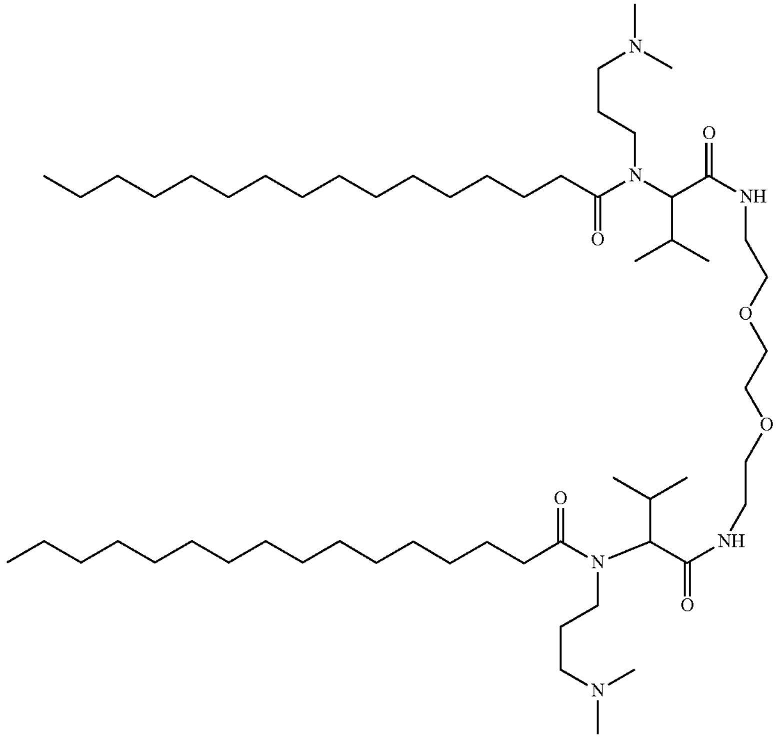 [SMILES: CCCCCCCCCCCCCCCC(=O)N(CCCN(C)C)C(C(=O)NCCOCCOCCNC(=O)C(C(C)C)N(CCCN(C)C)C(=O)CCCCCCCCCCCCCCC)C(C)C] |
| 46 | I2 | R2 | C18 | A1 | I2R2C18A1 |

TABLE 1-continued
| | Isocyanide compound | Amine compound | Carboxylic acid compound | Aldehyde compound | Cationic lipid analog material |
|---|---|---|---|---|---|
| | | | | | 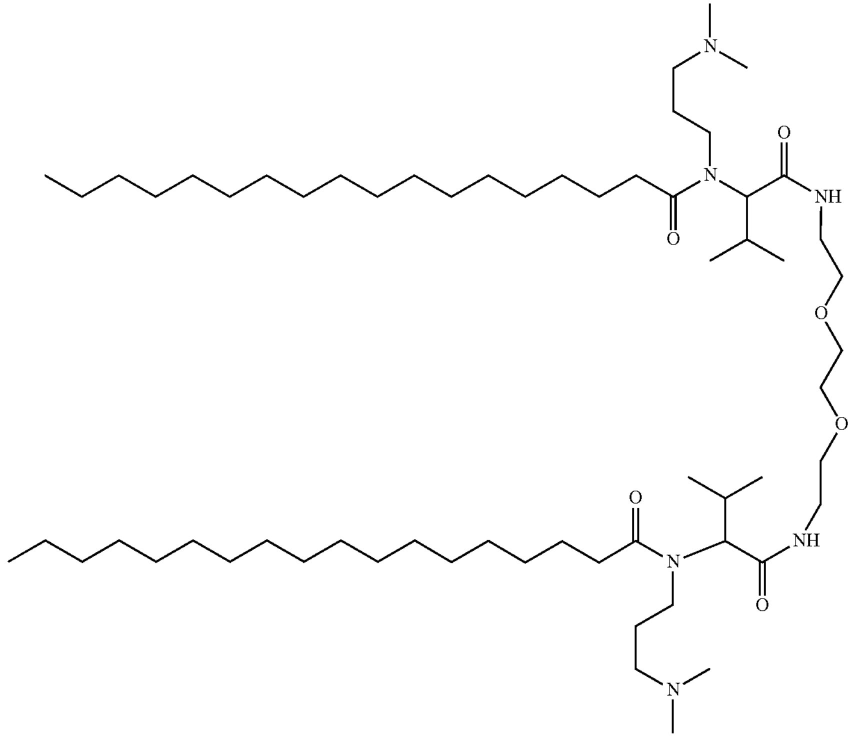 [SMILES: CCCCCCCCCCCCCCCCCC(=O)N(CCCN(C)C)C(C(=O)NCCOCCOCCNC(=O)C(C(C)C)N(CCCN(C)C)C(=O)CCCCCCCCCCCCCCCCC)C(C)C] |
| 47 | I2 | R2 | C20 | A1 | I2R2C20A1 |

TABLE 1-continued
| | Isocyanide compound | Amine compound | Carboxylic acid compound | Aldehyde compound | Cationic lipid analog material |
|---|---|---|---|---|---|
| 48 | I2 | R2 | C18-1 | A1 | 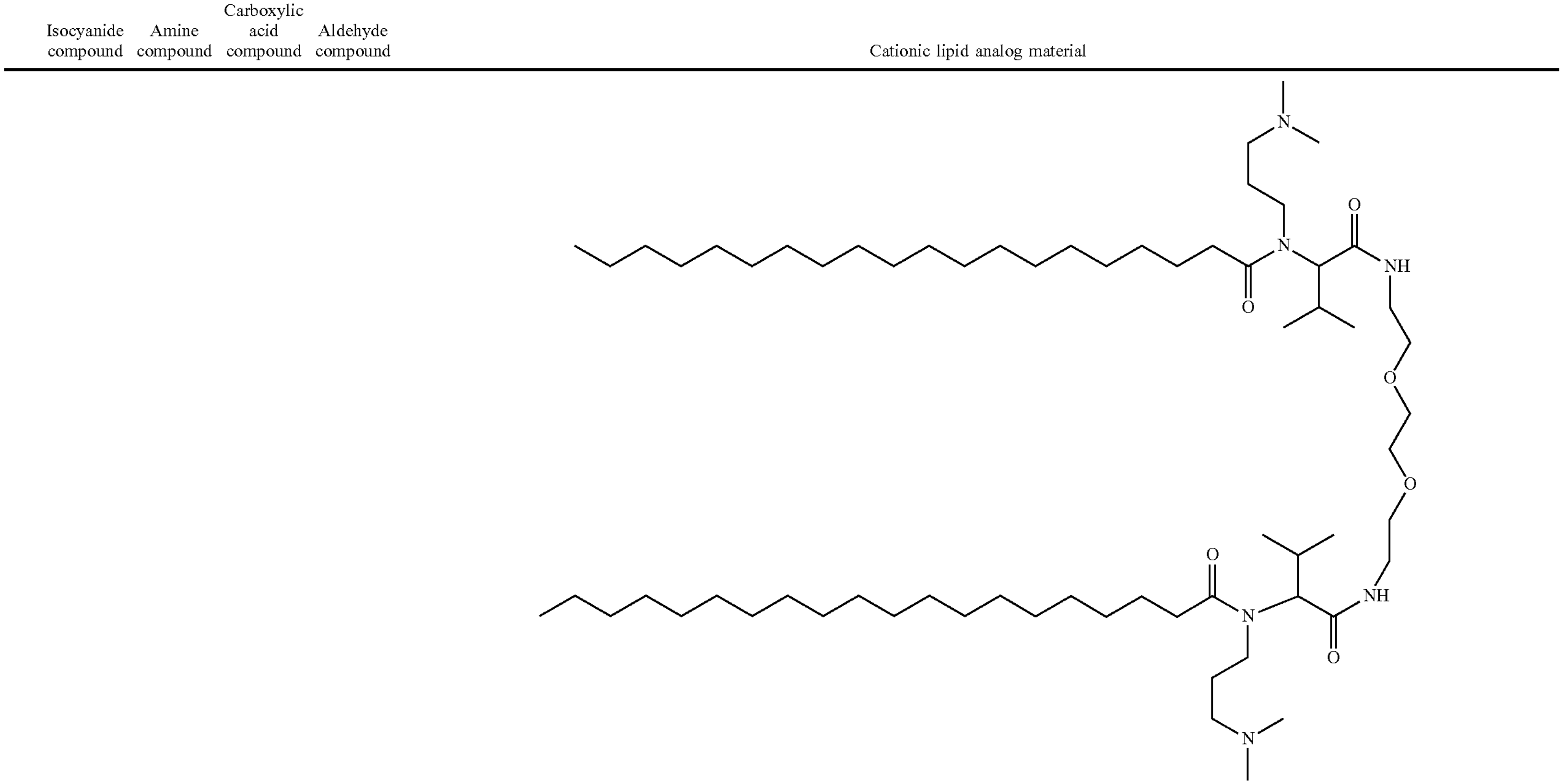 I2R2C18-1A1 |

TABLE 1-continued
| | Isocyanide compound | Amine compound | Carboxylic acid compound | Aldehyde compound | Cationic lipid analog material |
|---|---|---|---|---|---|
| | | | | | 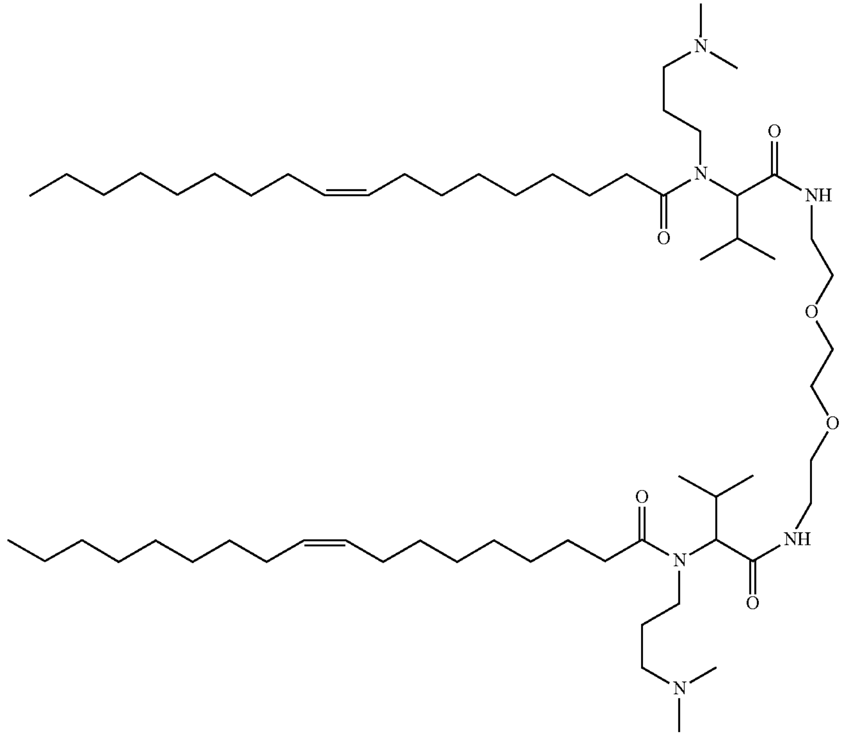 [SMILES: CCCCCCCC/C=C\CCCCCCCC(=O)N(CCCN(C)C)C(C(=O)NCCOCCOCCNC(=O)C(C(C)C)N(CCCN(C)C)C(=O)CCCCCCC/C=C\CCCCCCCC)C(C)C] |
| 49 | I2 | R2 | C18-2 | A1 | I2R2C18-2A1 |

TABLE 1-continued
| | Isocyanide compound | Amine compound | Carboxylic acid compound | Aldehyde compound | Cationic lipid analog material |
|---|---|---|---|---|---|
| | | | | | 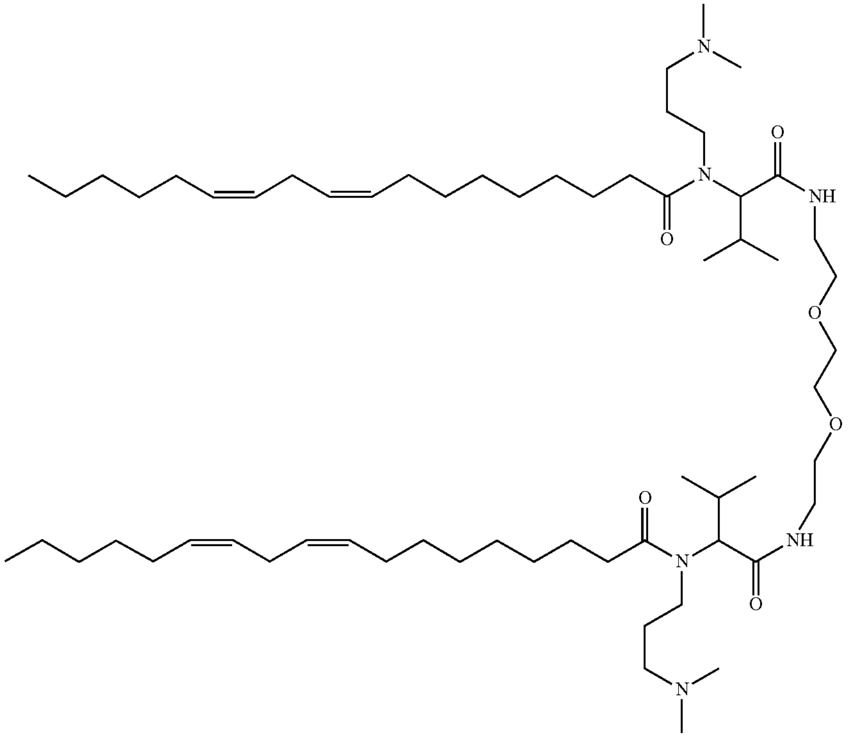 [SMILES: CCCCC/C=C\C/C=C\CCCCCCCC(=O)N(CCCN(C)C)C(C(=O)NCCOCCOCCNC(=O)C(C(C)C)N(CCCN(C)C)C(=O)CCCCCCC/C=C\C/C=C\CCCCC)C(C)C] |
| 50 | I2 | R3 | C12 | A1 | I2R3C12A1 |

TABLE 1-continued
| | Isocyanide compound | Amine compound | Carboxylic acid compound | Aldehyde compound | Cationic lipid analog material |
|---|---|---|---|---|---|
| 51 | I2 | R3 | C14 | A1 | 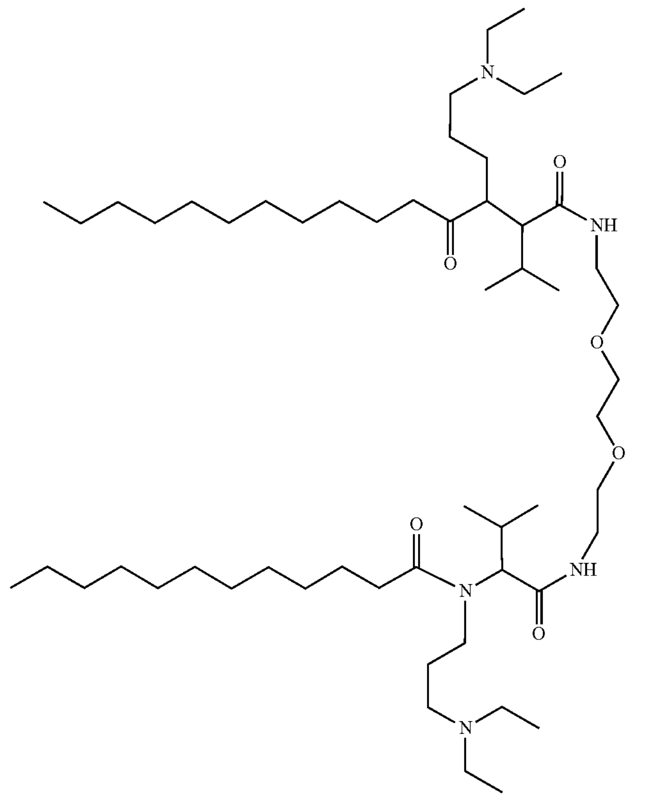 I2R3C14A1 |

TABLE 1-continued
| | Isocyanide compound | Amine compound | Carboxylic acid compound | Aldehyde compound | Cationic lipid analog material |
|---|---|---|---|---|---|
| | | | | | 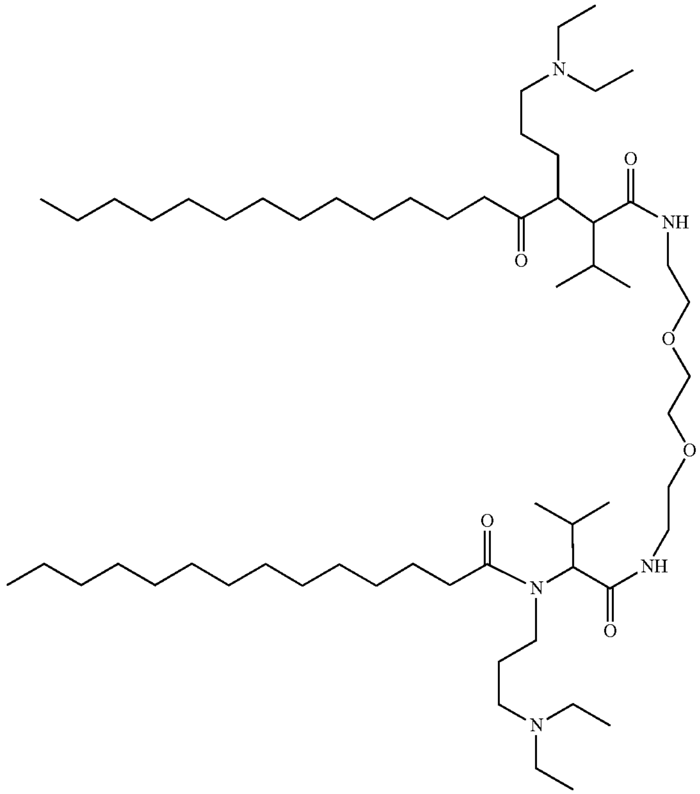 [SMILES: CCCCCCCCCCCCCC(=O)C(CCCN(CC)CC)C(C(=O)NCCOCCOCCNC(=O)C(C(C)C)N(CCCN(CC)CC)C(=O)CCCCCCCCCCCCC)C(C)C] |
| 52 | I2 | R3 | C16 | A1 | I2R3C16A1 |

TABLE 1-continued
| | Isocyanide compound | Amine compound | Carboxylic acid compound | Aldehyde compound | Cationic lipid analog material |
|---|---|---|---|---|---|
| 53 | I2 | R3 | C18 | A1 | 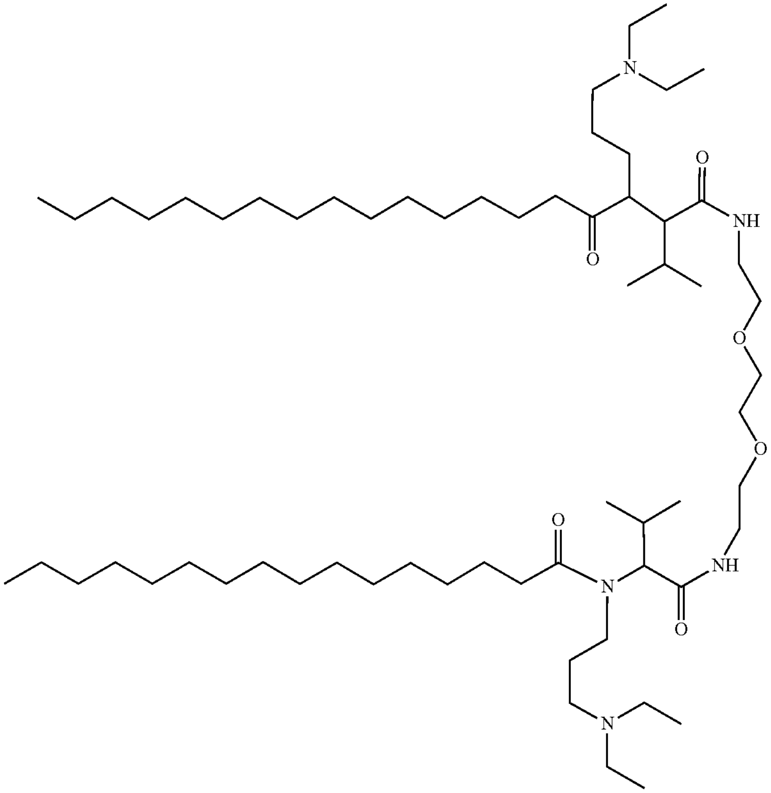 I2R3C18A1 |

TABLE 1-continued
| | Isocyanide compound | Amine compound | Carboxylic acid compound | Aldehyde compound | Cationic lipid analog material |
|---|---|---|---|---|---|
| 54 | I2 | R3 | C20 | A1 | 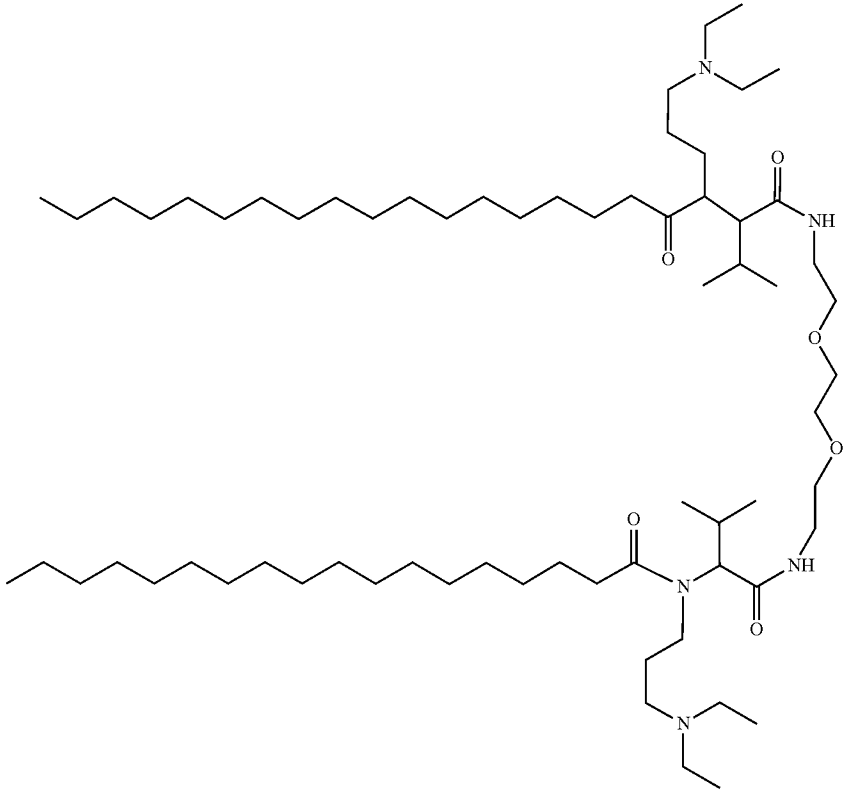 I2R3C20A1 |

TABLE 1-continued
| | Isocyanide compound | Amine compound | Carboxylic acid compound | Aldehyde compound | Cationic lipid analog material |
|---|---|---|---|---|---|
| 55 | I2 | R3 | C18-1 | A1 | 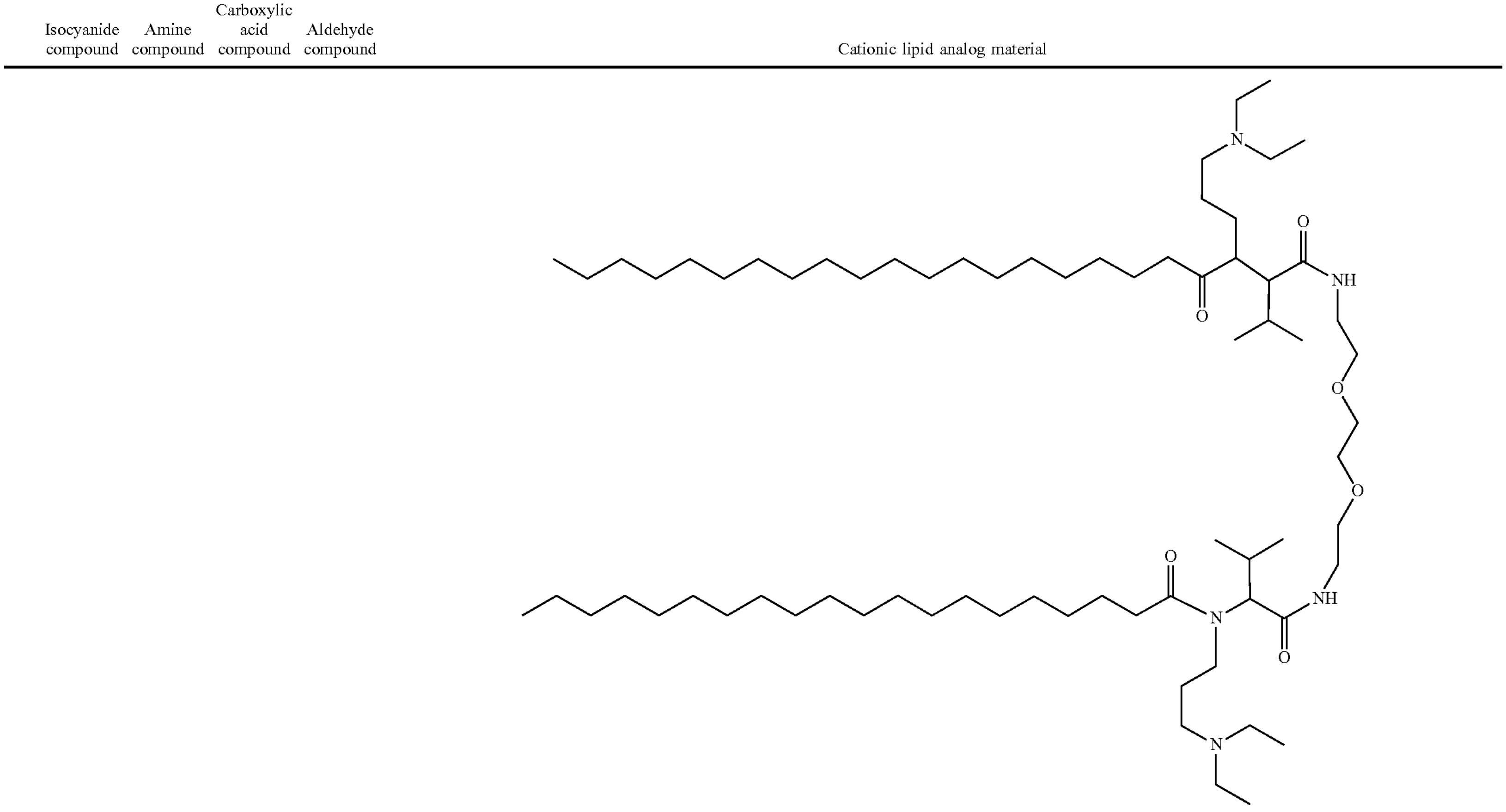 I2R3C18-1A1 |

TABLE 1-continued
| | Isocyanide compound | Amine compound | Carboxylic acid compound | Aldehyde compound | Cationic lipid analog material |
|---|---|---|---|---|---|
| | | | | | 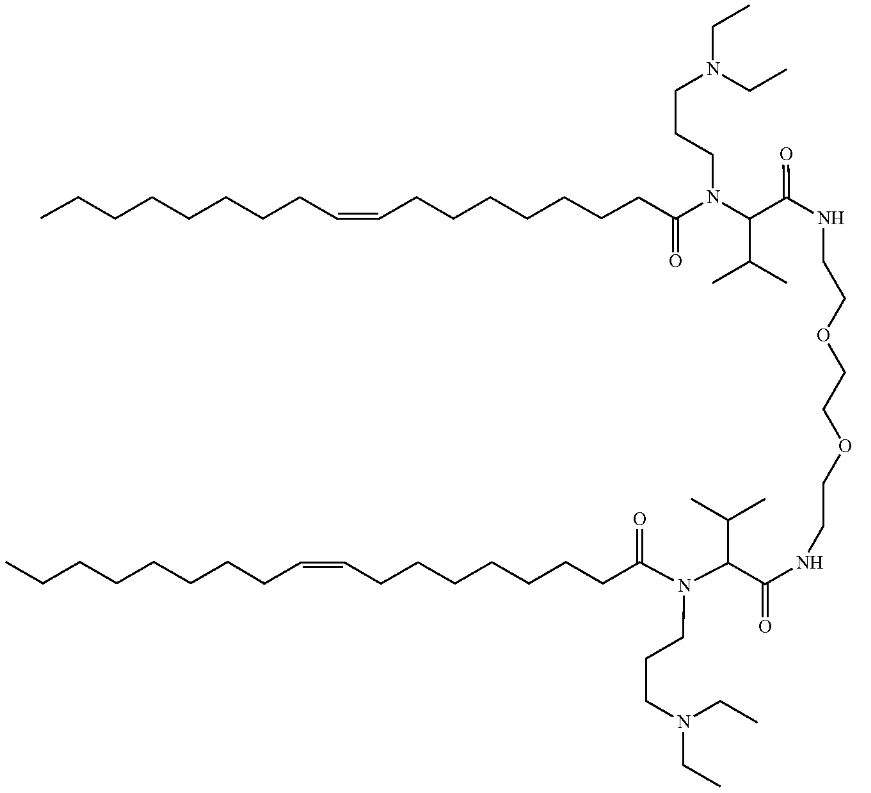 [SMILES: CCCCCCCC/C=C\CCCCCCCC(=O)N(CCCN(CC)CC)C(C(=O)NCCOCCOCCNC(=O)C(C(C)C)N(CCCN(CC)CC)C(=O)CCCCCCC/C=C\CCCCCCCC)C(C)C] |
| 56 | I2 | R3 | C18-2 | A1 | I2R3C18-2A1 |

TABLE 1-continued
| | Isocyanide compound | Amine compound | Carboxylic acid compound | Aldehyde compound | Cationic lipid analog material |
|---|---|---|---|---|---|
| 57 | I2 | R5 | C12 | A1 | 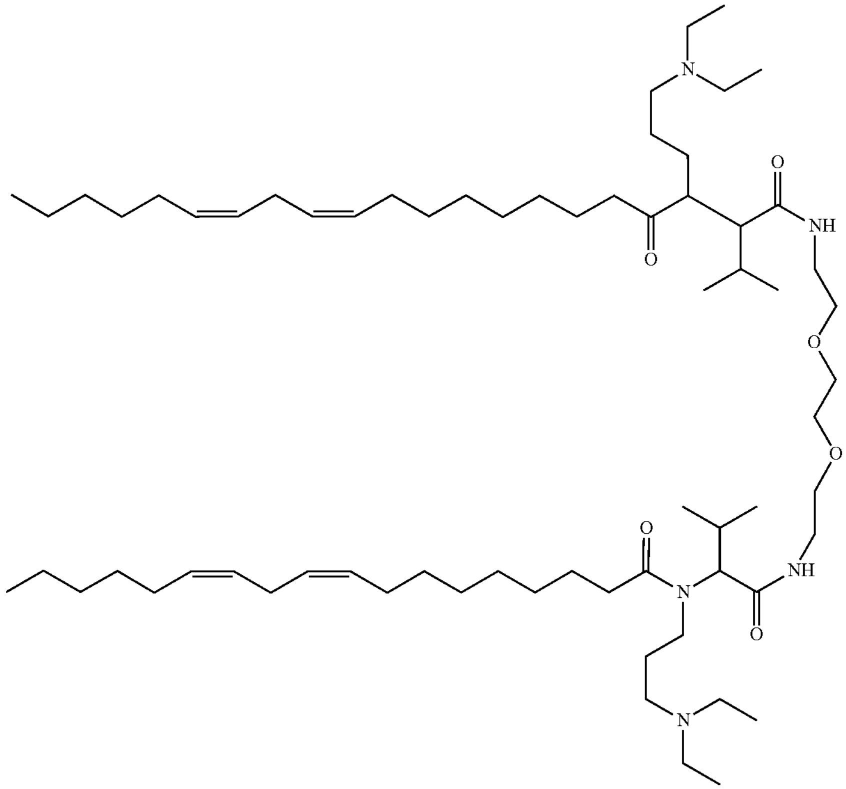 I2R5C12A1 |

TABLE 1-continued
| | Isocyanide compound | Amine compound | Carboxylic acid compound | Aldehyde compound | Cationic lipid analog material |
|---|---|---|---|---|---|
| | | | | | 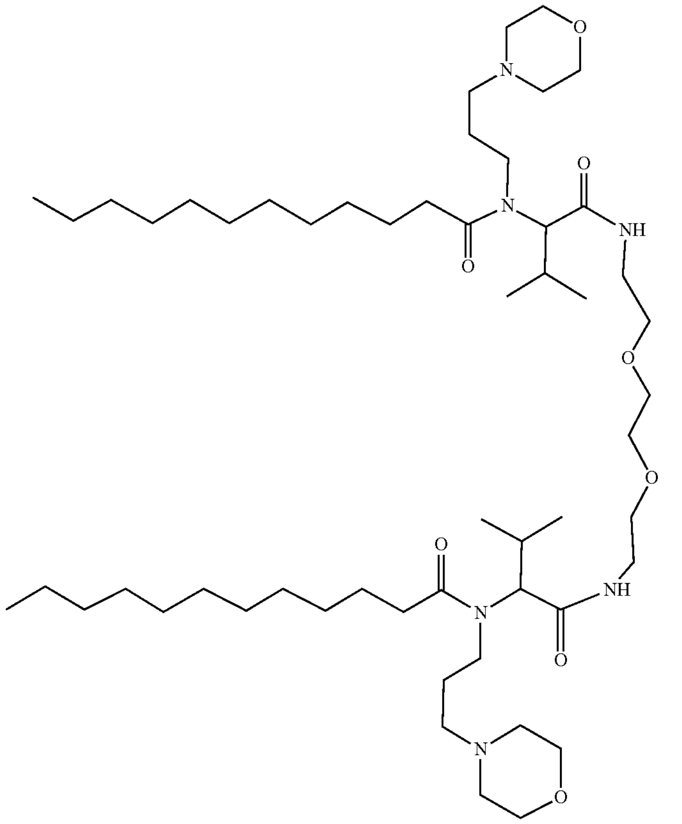 [SMILES: CCCCCCCCCCCC(=O)N(CCCN1CCOCC1)C(C(=O)NCCOCCOCCNC(=O)C(C(C)C)N(CCCN1CCOCC1)C(=O)CCCCCCCCCCC)C(C)C] |
| 58 | I2 | R5 | C14 | A1 | I2R5C14A1 |

TABLE 1-continued
| | Isocyanide compound | Amine compound | Carboxylic acid compound | Aldehyde compound | Cationic lipid analog material |
|---|---|---|---|---|---|
| | | | | | 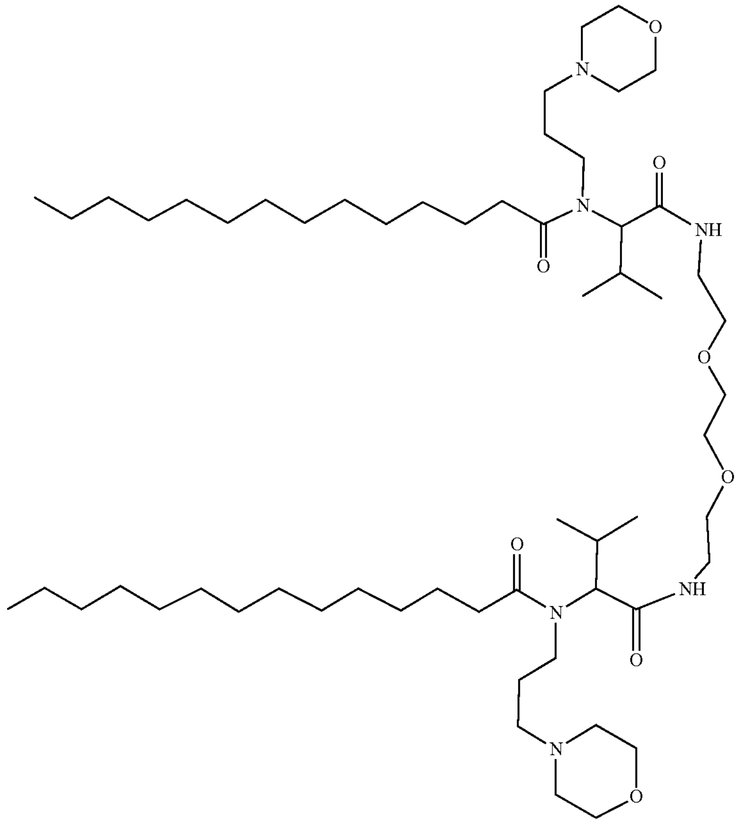 [SMILES: CCCCCCCCCCCCCC(=O)N(CCCN1CCOCC1)C(C(=O)NCCOCCOCCNC(=O)C(C(C)C)N(CCCN1CCOCC1)C(=O)CCCCCCCCCCCCC)C(C)C] |
| 59 | I2 | R5 | C16 | A1 | I2R5C16A1 |

TABLE 1-continued
| | Isocyanide compound | Amine compound | Carboxylic acid compound | Aldehyde compound | Cationic lipid analog material |
|---|---|---|---|---|---|
| 60 | I2 | R5 | C18 | A1 | 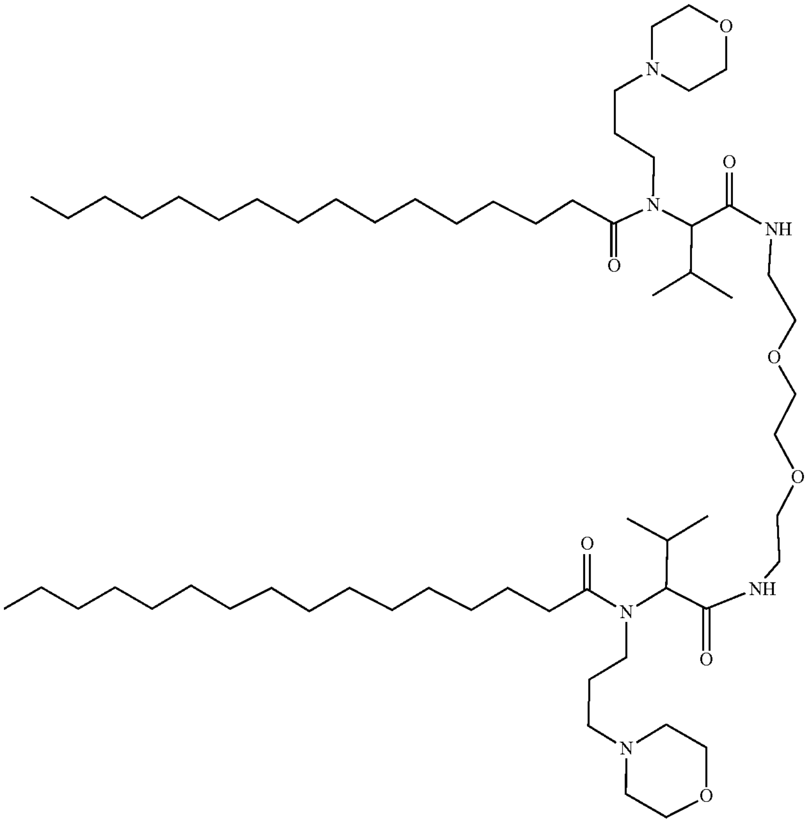 I2R5C18A1 |

TABLE 1-continued
| | Isocyanide compound | Amine compound | Carboxylic acid compound | Aldehyde compound | Cationic lipid analog material |
|---|---|---|---|---|---|
| 61 | I2 | R5 | C20 | A1 | 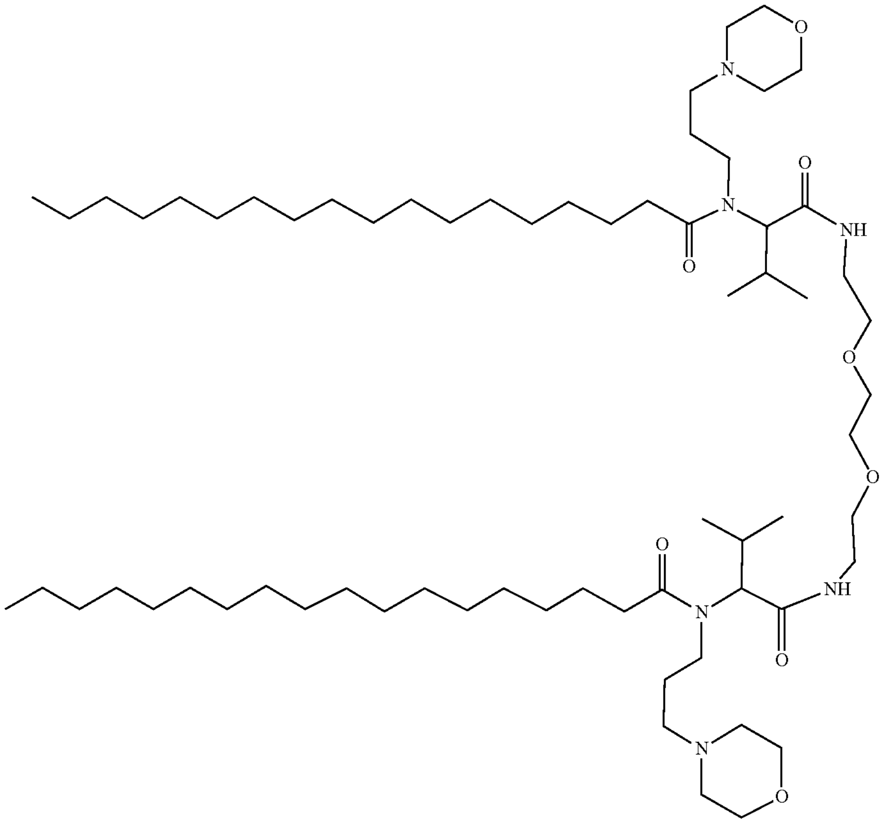 [SMILES: CCCCCCCCCCCCCCCCCC(=O)N(CCCN1CCOCC1)C(C(=O)NCCOCCOCCNC(=O)C(C(C)C)N(CCCN1CCOCC1)C(=O)CCCCCCCCCCCCCCCCC)C(C)C]<br>I2R5C20A1 |

TABLE 1-continued
| | Isocyanide compound | Amine compound | Carboxylic acid compound | Aldehyde compound | Cationic lipid analog material |
|---|---|---|---|---|---|
| 62 | I2 | R5 | C18-1 | A1 | 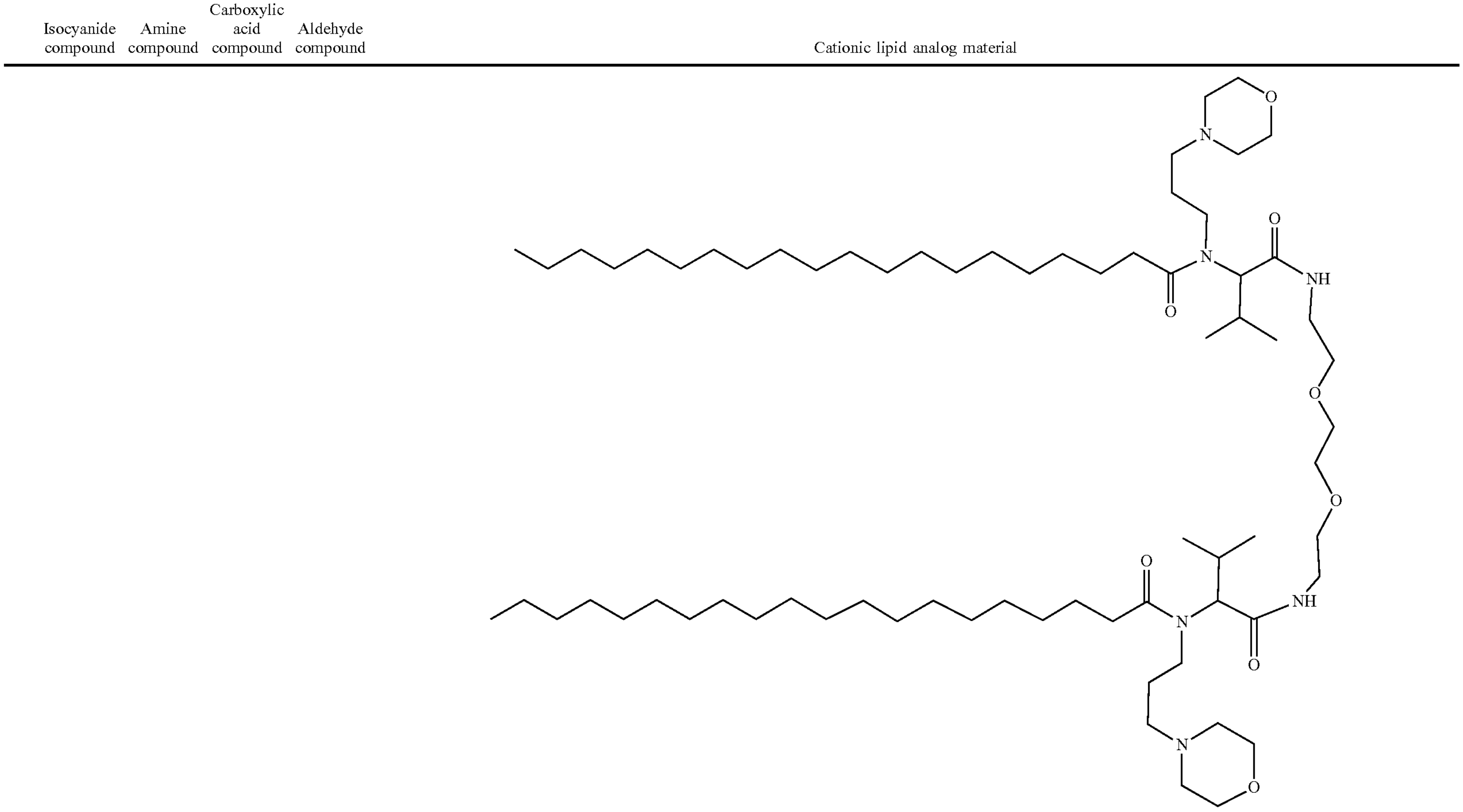 I2R5C18-1A1 |

TABLE 1-continued
| | Isocyanide compound | Amine compound | Carboxylic acid compound | Aldehyde compound | Cationic lipid analog material |
|---|---|---|---|---|---|
| 63 | 12 | R5 | C18-2 | A1 | 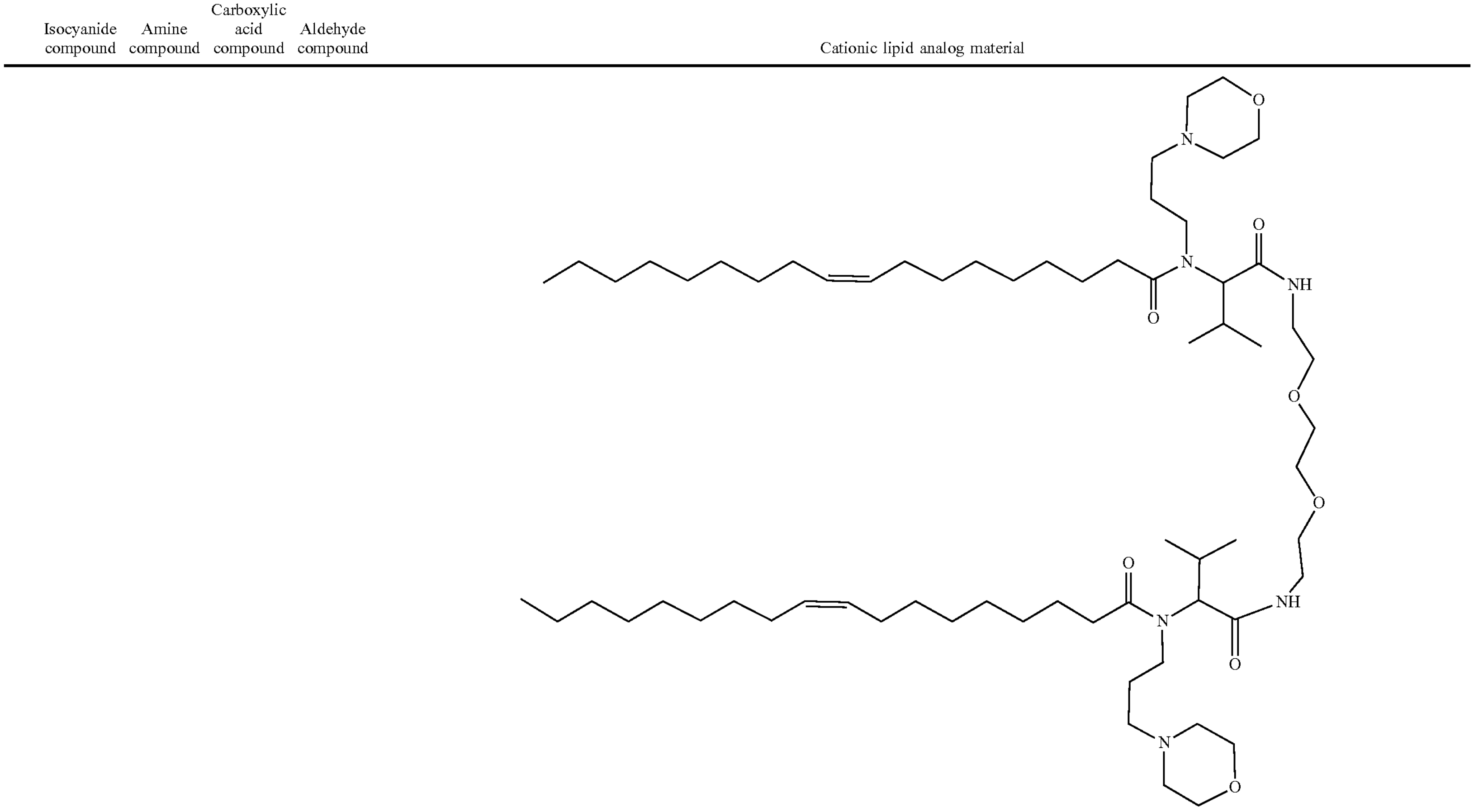 I2R5C18-2A1 |

TABLE 1-continued
| | Isocyanide compound | Amine compound | Carboxylic acid compound | Aldehyde compound | Cationic lipid analog material |
|---|---|---|---|---|---|
| 64 | I2 | R11 | C12 | A1 | 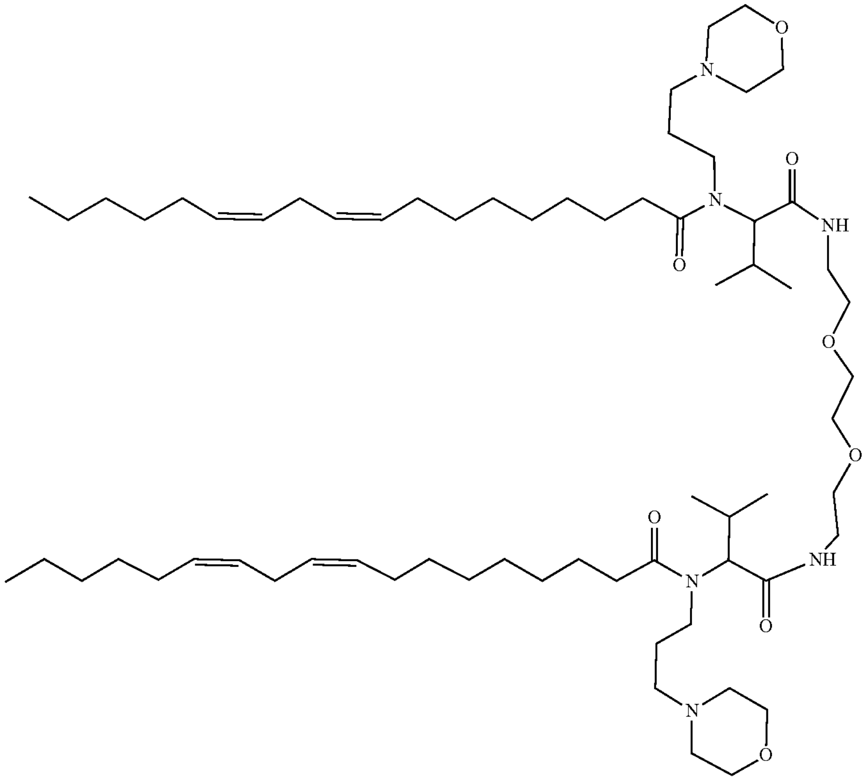 I2R11C12A1 |

TABLE 1-continued
| | Isocyanide compound | Amine compound | Carboxylic acid compound | Aldehyde compound | Cationic lipid analog material |
|---|---|---|---|---|---|
| 65 | I2 | R11 | C14 | A1 | 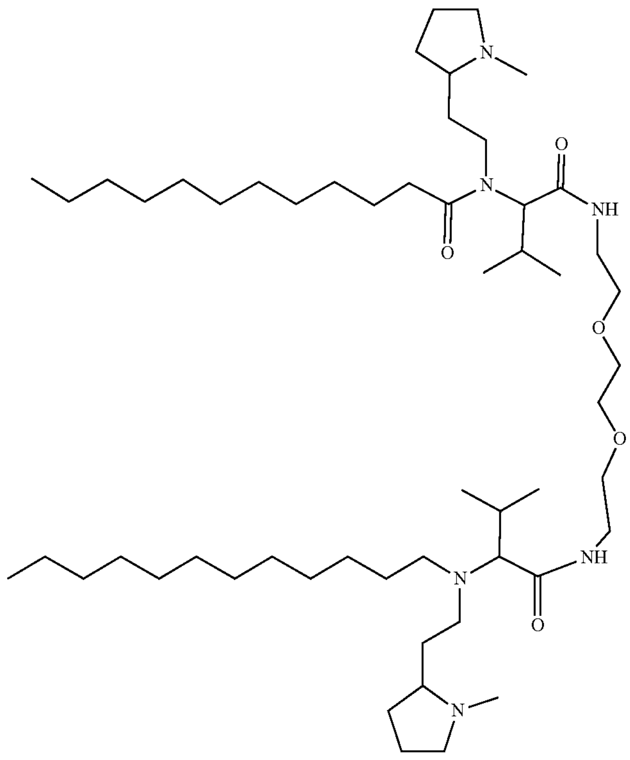 I2R11C14A1 |

TABLE 1-continued
| | Isocyanide compound | Amine compound | Carboxylic acid compound | Aldehyde compound | Cationic lipid analog material |
|---|---|---|---|---|---|
| 66 | I2 | R11 | C16 | A1 | 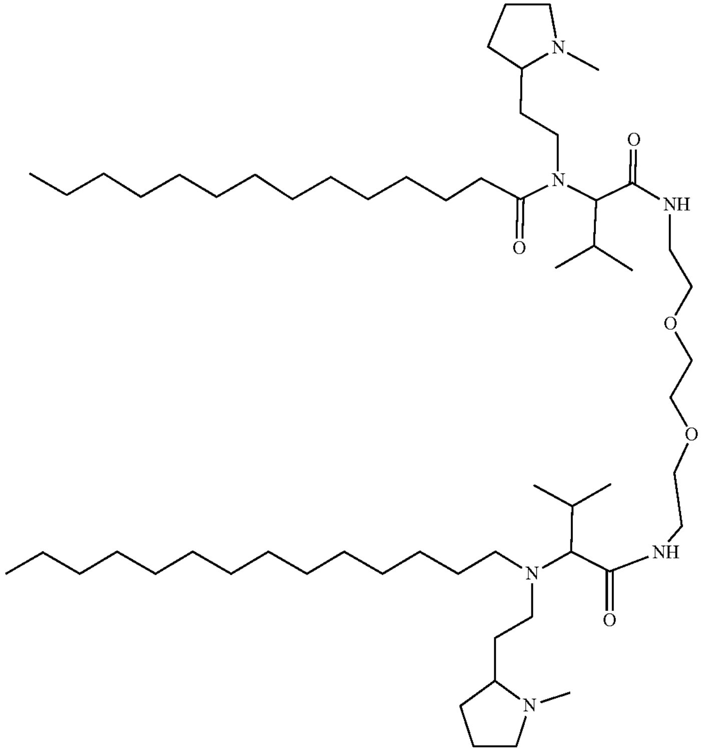 I2R11C16A1 |

TABLE 1-continued
| | Isocyanide compound | Amine compound | Carboxylic acid compound | Aldehyde compound | Cationic lipid analog material |
|---|---|---|---|---|---|
| 67 | I2 | R11 | C18 | A1 | 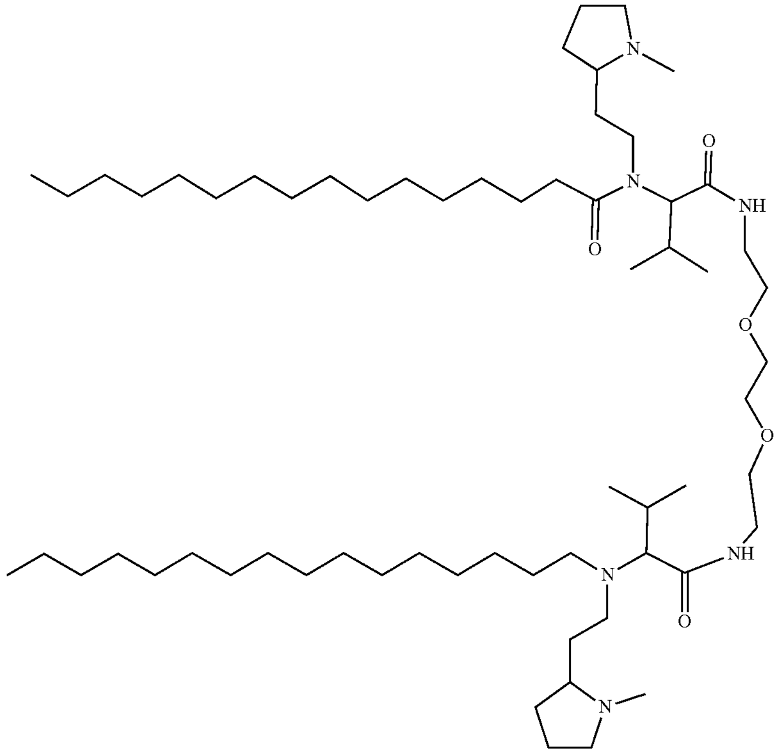 [SMILES: CCCCCCCCCCCCCCCCN(CCC1CCCN1C)C(C(=O)NCCOCCOCCNC(=O)C(C(C)C)N(CCC1CCCN1C)C(=O)CCCCCCCCCCCCCCC)C(C)C]<br>I2R11C18A1 |

TABLE 1-continued
| | Isocyanide compound | Amine compound | Carboxylic acid compound | Aldehyde compound | Cationic lipid analog material |
|---|---|---|---|---|---|
| | | | | | 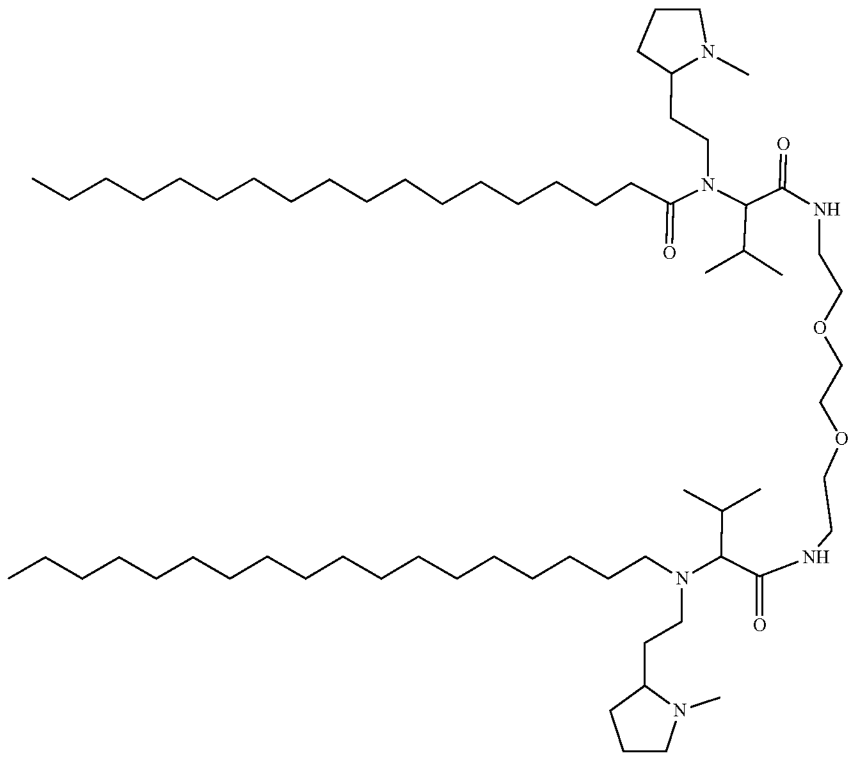 [SMILES: CCCCCCCCCCCCCCCCCCN(CCC1CCCN1C)C(C(=O)NCCOCCOCCNC(=O)C(C(C)C)N(CCC1CCCN1C)C(=O)CCCCCCCCCCCCCCCCC)C(C)C] |
| 68 | I2 | R11 | C20 | A1 | I2R11C20A1 |

TABLE 1-continued
| | Isocyanide compound | Amine compound | Carboxylic acid compound | Aldehyde compound | Cationic lipid analog material |
|---|---|---|---|---|---|
| | | | | | 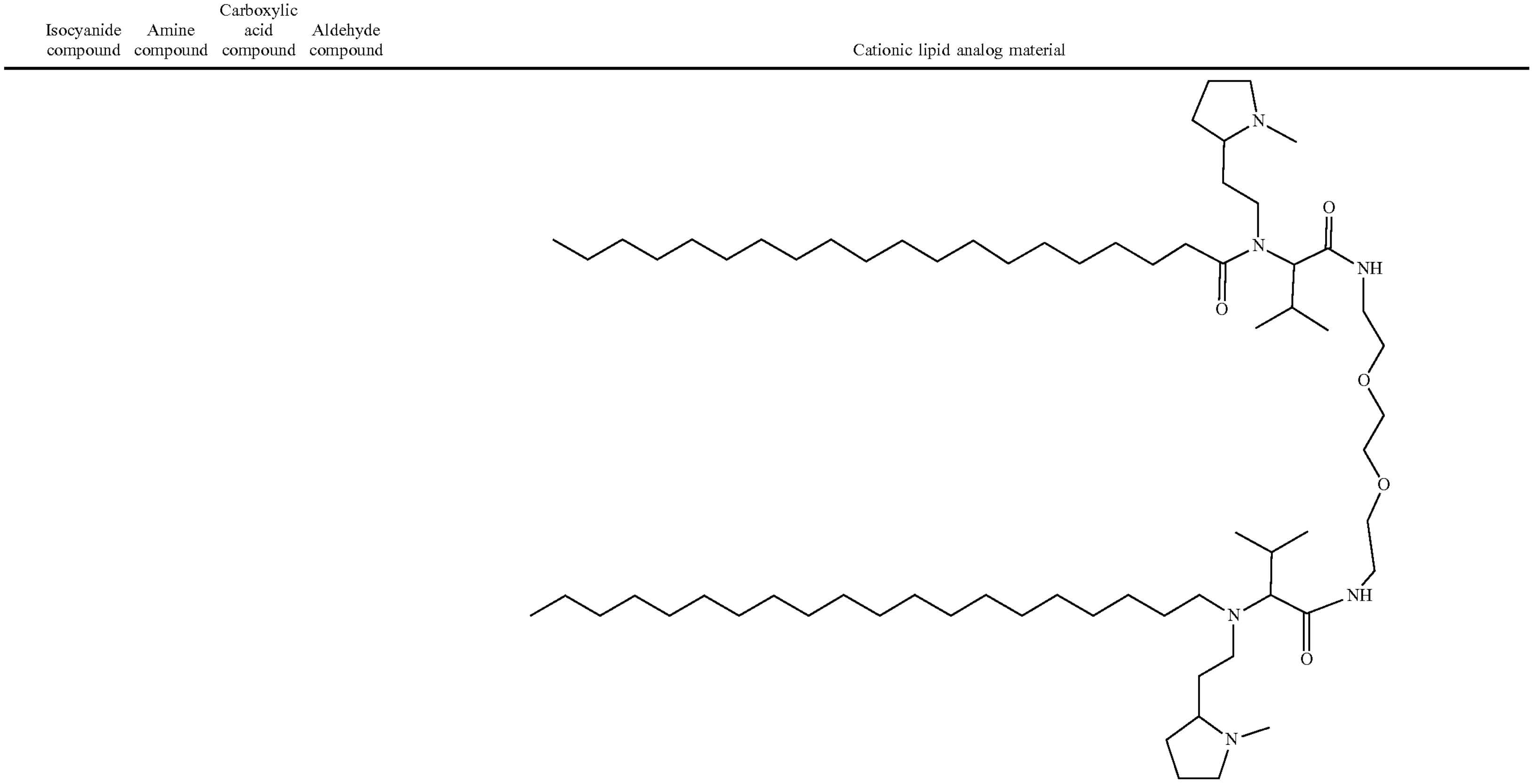 |
| 69 | I2 | R11 | C18-1 | A1 | I2R11C18-1A1 |

TABLE 1-continued
| | Isocyanide compound | Amine compound | Carboxylic acid compound | Aldehyde compound | Cationic lipid analog material |
|---|---|---|---|---|---|
| 70 | I2 | R11 | C18-2 | A1 | 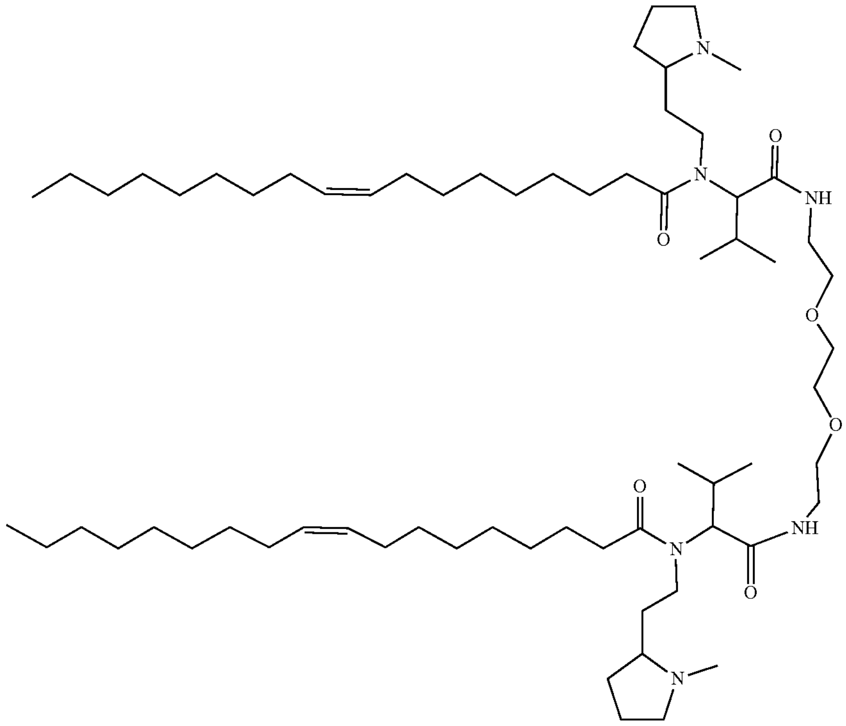 [SMILES: CCCCCCCC/C=C\CCCCCCCC(=O)N(CCC1CCCN1C)C(C(=O)NCCOCCOCCNC(=O)C(C(C)C)N(CCC1CCCN1C)C(=O)CCCCCCC/C=C\CCCCCCCC)C(C)C] I2R11C18-2A1 |

TABLE 1-continued
| | Isocyanide compound | Amine compound | Carboxylic acid compound | Aldehyde compound | Cationic lipid analog material |
|---|---|---|---|---|---|
| 71 | 12-1 | R2 | C18 | A1 | 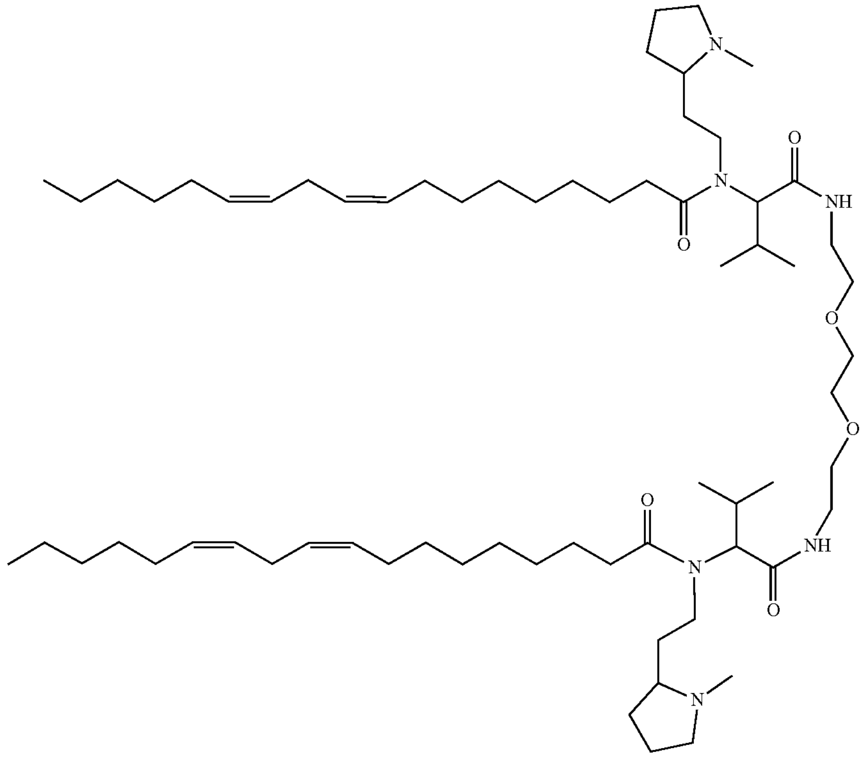 [SMILES: CCCCC/C=C\C/C=C\CCCCCCCC(=O)N(CCC1CCCN1C)C(C(=O)NCCOCCOCCNC(=O)C(C(C)C)N(CCC1CCCN1C)C(=O)CCCCCCC/C=C\C/C=C\CCCCC)C(C)C] 12-1R2C18A1 |

TABLE 1-continued
| | Isocyanide compound | Amine compound | Carboxylic acid compound | Aldehyde compound | Cationic lipid analog material |
|---|---|---|---|---|---|
| 72 | 12-3 | R2 | C18 | A1 | 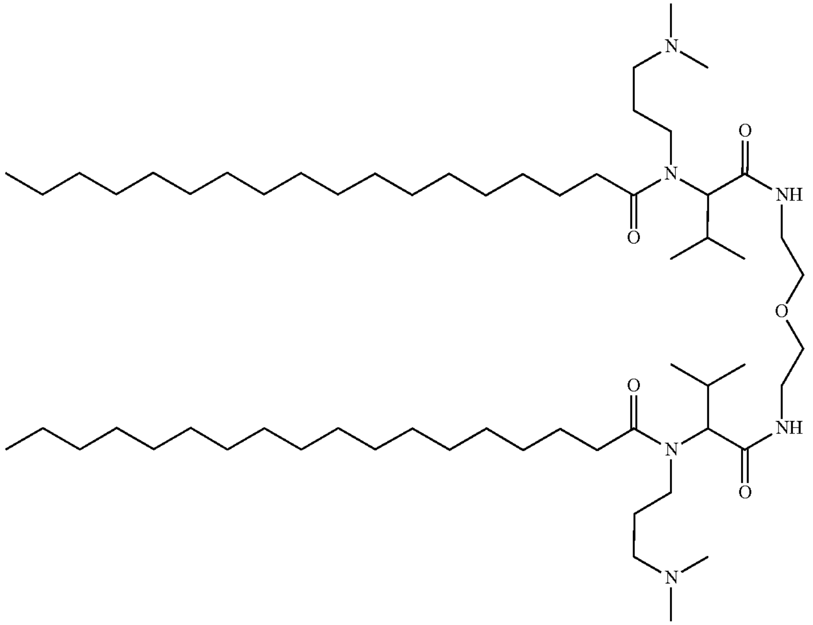 [SMILES: CCCCCCCCCCCCCCCCCC(=O)N(CCCN(C)C)C(C(=O)NCCOCCNC(=O)C(C(C)C)N(CCCN(C)C)C(=O)CCCCCCCCCCCCCCCCC)C(C)C] I2-3R2C18A1 |

TABLE 1-continued
| Isocyanide compound | Amine compound | Carboxylic acid compound | Aldehyde compound | Cationic lipid analog material |
|---|---|---|---|---|
| | | | | 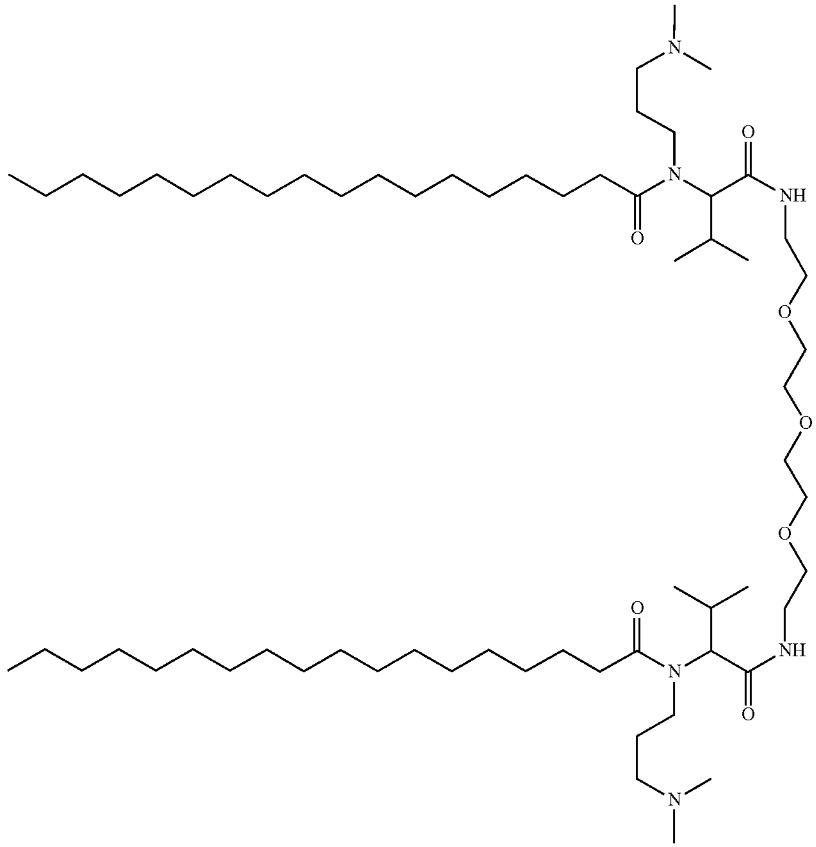 [SMILES: CCCCCCCCCCCCCCCCCC(=O)N(CCCN(C)C)C(C(=O)NCCOCCOCCOCCNC(=O)C(C(C)C)N(CCCN(C)C)C(=O)CCCCCCCCCCCCCCCCC)C(C)C] |

Figure 1B:
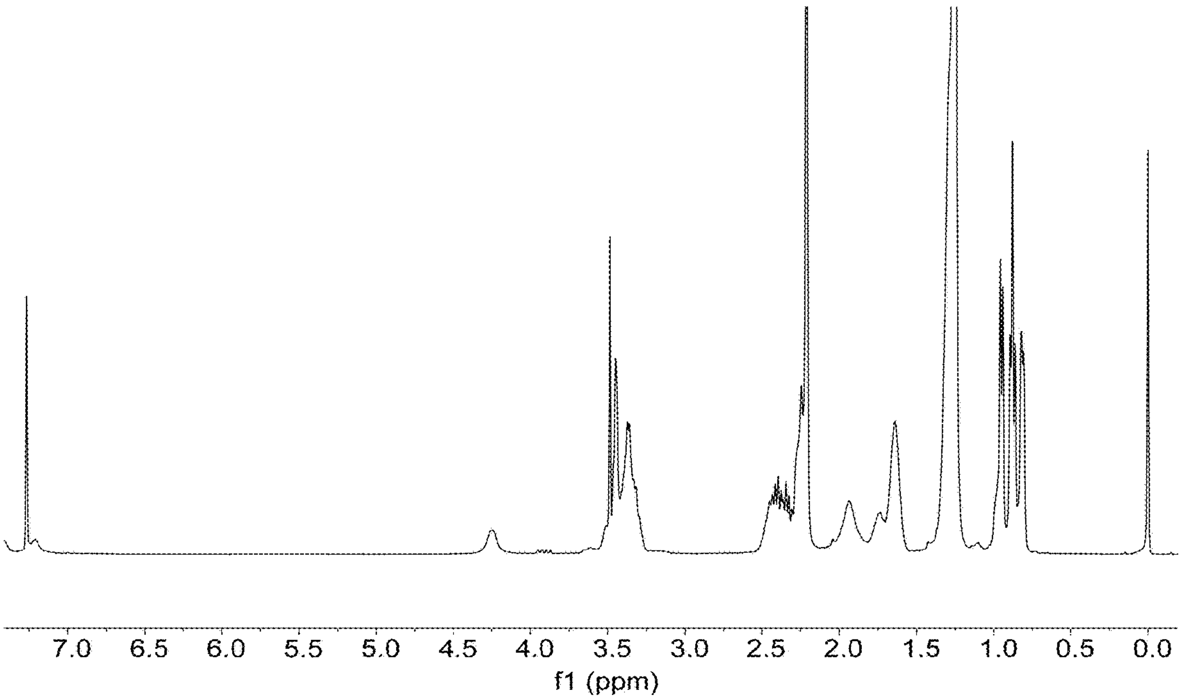
FIG. 1B shows a proton nuclear magnetic resonance ($^1$H NMR) spectrum of cationic lipid analog material I2-1R2C18A1.
Figure 2A:
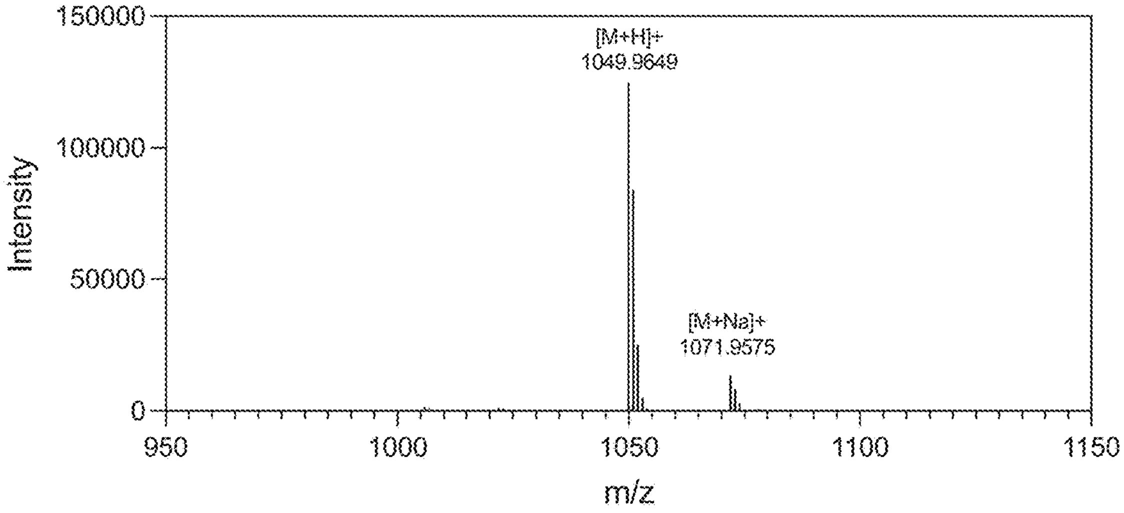
FIG. 2A shows an MS spectrum of cationic lipid analog material I2R2C18A1.
Figure 2B:
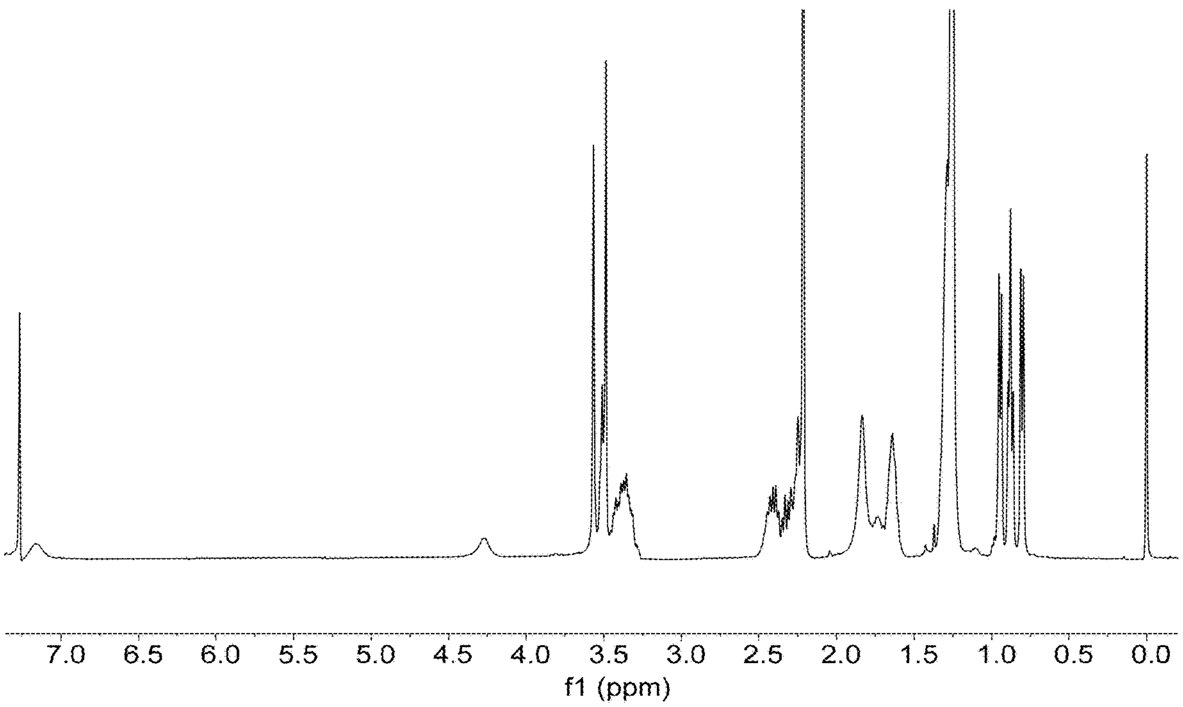
FIG. 2B shows a $^1$H NMR spectrum of cationic lipid analog material I2R2C18A1.
Figure 3A:
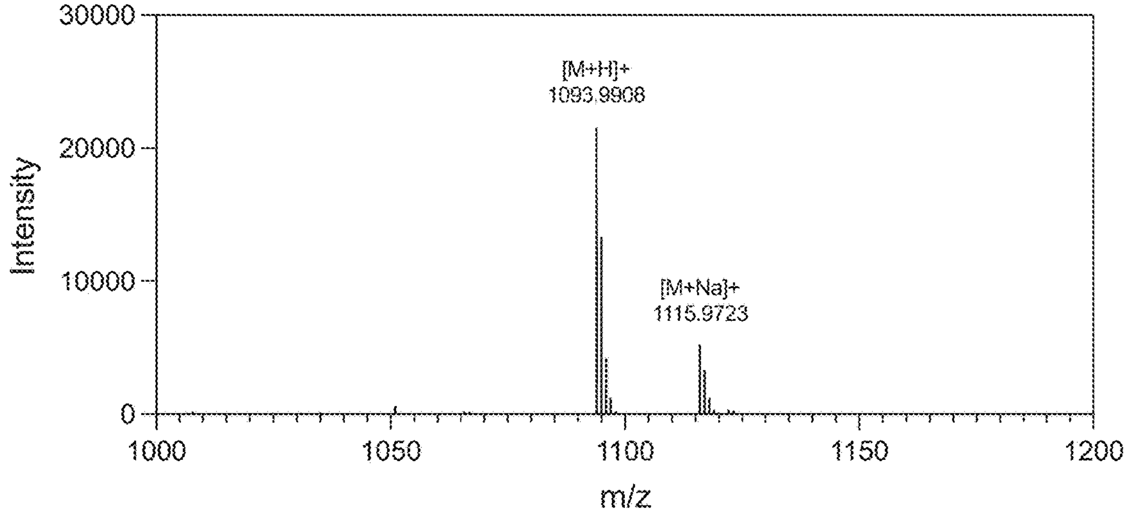
FIG. 3A shows an MS spectrum of cationic lipid analog material I2-3R2C18A1.
Figure 3B:
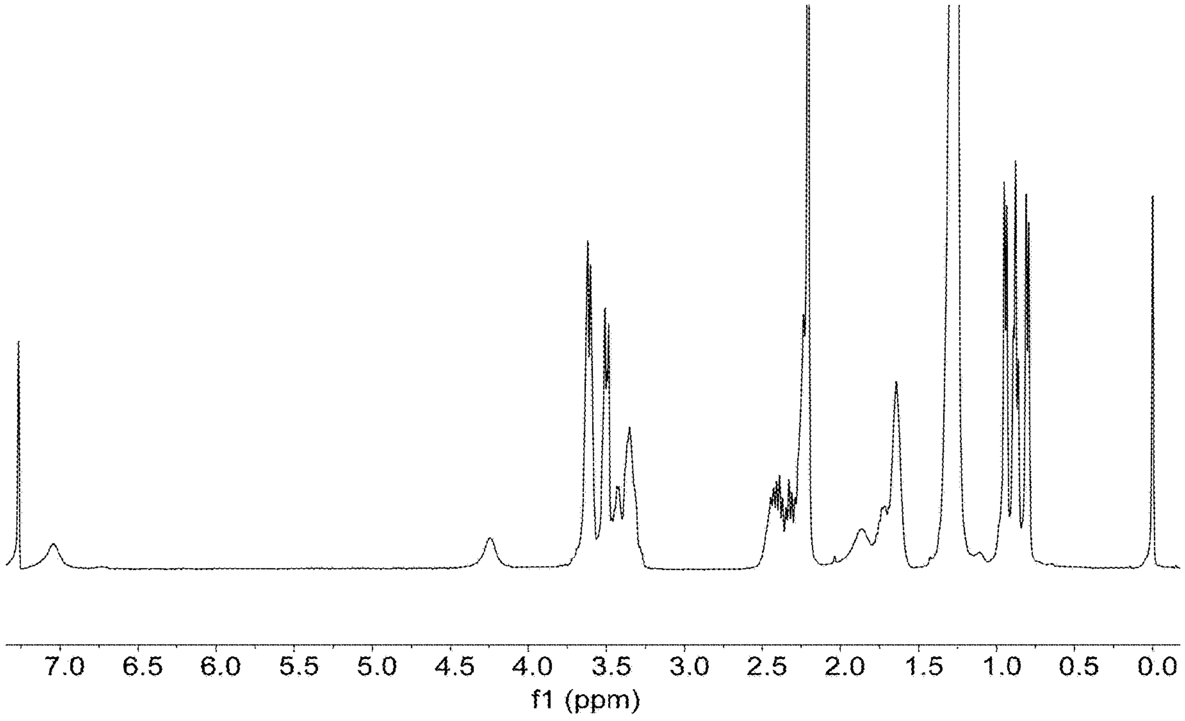
FIG. 3B shows a $^1$H NMR spectrum of cationic lipid analog material I2-3R2C18A1.

Cationic lipid analog materials I2-1R2C18A1, I2R2C18A1, and I2-3R2C18A1 were selected as representative materials, and structures of these materials were characterized. MS and $^{1}H$ NMR spectra of I2-1R2C18A1 were shown in FIGS. 1A and 1B; MS and $^{1}H$ NMR spectra of I2R2C18A1 were shown in FIGS. 2A and 2B; and MS and $^{1}H$ NMR spectra of I2-3R2C18A1 were shown in FIGS. 3A and 3B. $^{1}H$ NMR and MS results were consistent with the expected structures of the cationic lipid analog materials.

Example 2

In this example, BSA-FITC was used as a protein model to investigate the intracellular protein delivery of a cationic lipid analog material.

A specific experimental method was as follows: HeLa cells were inoculated in a 24-well plate and cultured in an incubator for 12 h in advance; different cationic lipid analog materials (0.25 μg/well to 8 μg/well) each were mixed with BSA-FITC (2 μg/well) in 50 μl of a N-2-hydroxyethylpiperazine-N-2-ethane sulfonic acid (HEPES) buffer, and resulting mixtures each were diluted with 450 μl of a serum-free Dulbecco's Modified Eagle Medium (DMEM) to obtain protein/cationic lipid analog complex solutions; a medium for the HeLa cells in the plate was removed, then the HeLa cells were washed once with phosphate buffered saline (PBS), and the protein/cationic lipid analog complex solutions each were added; and the cells were further cultured for 4 h, and then a fluorescence intensity and a positive cell rate in each well were analyzed by flow cytometry (FCM). In this experiment, the commercial protein delivery reagent PULSin® was adopted as a positive control.

Figure 4:
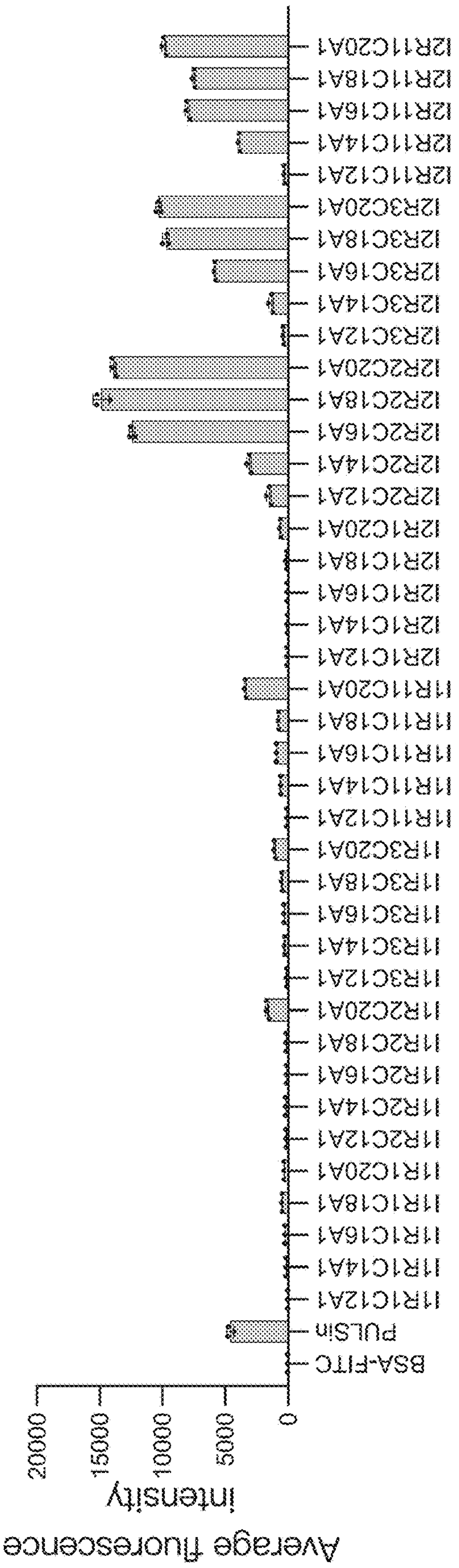
FIG. 4 shows average fluorescence intensities of fluorescently-labeled proteins in HeLa cells in which fluorescein isothiocyanate-labeled bovine serum albumin (BSA-FITC) is delivered by different cationic lipid analog materials, where a dosage of I1R1C12A1, I2R1C14A1, and I2R3C16A1 is 1 μg/well; a dosage of I1R2C14A1, I1R2C16A1, I1R2C18A1, I1R3C18A1, I1R11C18A1, I2R1C12A1, I2R1C20A1, I2R2C16A1, I2R3C18A1, I2R11C14A1, I2R11C16A1, and I2R11C18A1 is 2 μg/well; a dosage of I1R3C14A1, I1R3C16A1, I1R3C20A1, I1R11C14A1, I1R11C16A1, I1R11C20A1, I2R2C18A1, I2R2C20A1, I2R3C20A1, and I2R11C20A1 is 4 μg/well; a dosage of I1R1C14A1, I1R1C16A1, I1R1C18A1, I1R1C20A1, I1R2C12A1, I1R2C20A1, I1R3C12A1, I1R5C12A1, I1R5C14A1, I1R5C16A1, I1R5C18A1, I1R5C20A1, I1R11C12A1, I2R1C16A1, I2R1C18A1, I2R2C12A1, I2R2C14A1, I2R3C12A1, I2R3C14A1, I2R5C12A1, I2R5C14A1, I2R5C16A1, I2R5C18A1, I2R5C20A1, and I2R11C12A1 is 8 μg/well; and a dosage of BSA-FITC is 2 μg/well.
Figure 5:
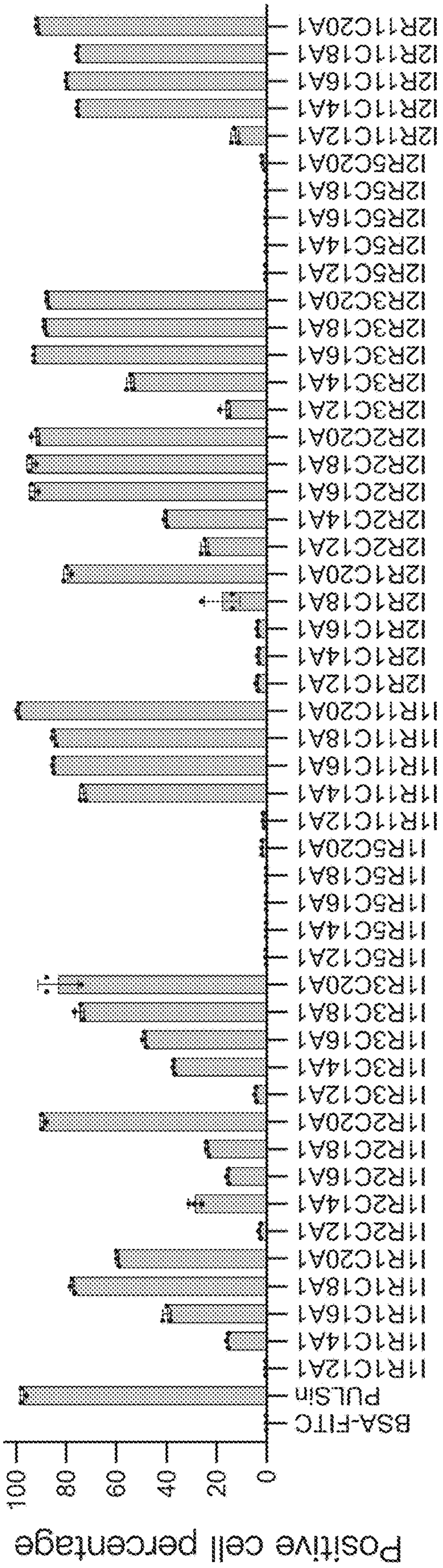
FIG. 5 shows percentages of HeLa cells positive for the fluorescently-labeled proteins after delivery of BSA-FITC using different cationic lipid analog materials, where the experimental conditions are consistent with those described in FIG. 4.

It can be seen from the results in FIG. 4 and FIG. 5 that the cationic lipid analog material of the present disclosure has an intracellular delivery effect for BSA-FITC to some degree; and in particular, when the isocyanide compound is I2 and the amine compound is selected from the group consisting of R2, R3, and R11, most of the synthesized cationic lipid analog materials have significantly-better delivery efficiency than the commercial protein delivery reagent PULSin®.

Figure 6:
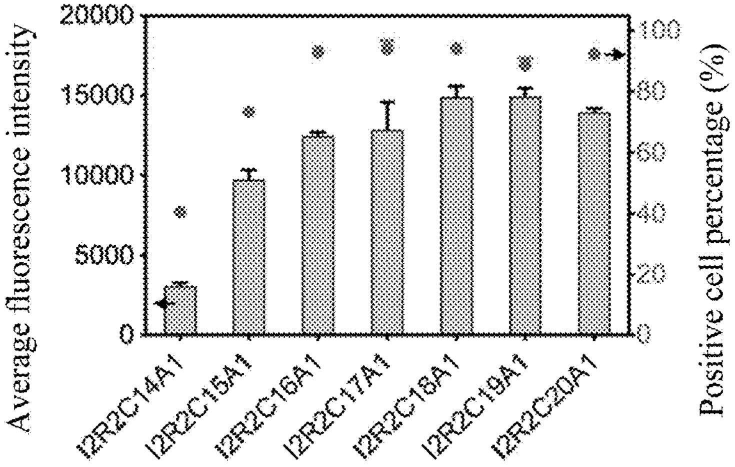
FIG. 6 shows average fluorescence intensities of fluorescently-labeled proteins in HeLa cells after delivery of BSA-FITC using cationic lipid analog materials with different alkyl chain lengths, where the dosage of a cationic lipid analog material is 4 μg/well and a dosage of BSA-FITC is 2 μg/well.

In this experiment, with I2R2C14A1, I2R2C15A1, I2R2C16A1, I2R2C17A1, I2R2C18A1, I2R2C19A1, and I2R2C20A1 as representatives, average fluorescence intensities of cellular proteins of the cationic lipid analog materials with different alkyl chain lengths were compared. It can be seen from the results in FIG. 6 that, in the present disclosure, an alkyl chain length of a carboxylic acid compound can be increased to adjust the hydrophobicity of a cationic lipid analog material; and an intracellular protein delivery efficiency of a cationic lipid analog material is also increased with the increase of an alkyl chain length, and reaches a platform value when an alkyl chain of the carboxylic acid compound includes 18 carbon atoms.

Figure 7A:
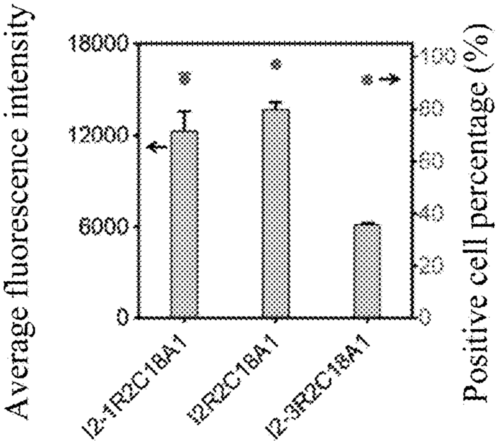
FIG. 7A shows BSA-FITC intracellular delivery efficiencies corresponding to I2-1R2C18A1, I2R2C18A1, and I2-3R2C18A1.
Figure 7B:
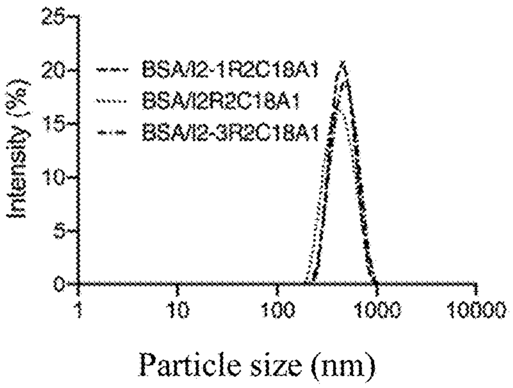
FIG. 7B shows particle size distributions of corresponding complexes.

In this experiment, with I2-1R2C18A1, I2R2C18A1, and I2-3R2C18A1 as representatives, particle sizes of corresponding protein/cationic lipid analog complexes were determined. It can be seen from the results in FIGS. 7A and 7B that I2-1R2C18A1, I2R2C18A1, and I2-3R2C18A1 all have excellent intracellular delivery efficiencies for proteins (a dosage of a cationic lipid analog was 4 μg/well and a dosage of BSA-FITC was 2 μg/well), and can bind to BSA to produce a complex with a small size and a homogeneous distribution, where the complex has a particle size of about 500 nm.

Example 3 Protein Delivery Effects of I2-1R2C18A1 in Different Types of Cells

In this experiment, I2-1R2C18A1 was selected as a representative cationic lipid analog material, and protein delivery effects of the cationic lipid analog material in different types of cells were investigated.

In this experiment, a BSA-FITC/I2-1R2C18A1 complex solution was prepared with reference to the method in Example 2, where a dosage of I2-1R2C18A1 was 4 μg/well and a dosage of BSA-FITC was 4 μg/well; and the BSA-FITC/I2-1R2C18A1 complex solution was added to each of human renal epithelial cells (HRECs) (HEK-293T), human pancreatic cancer cells (BxPC3), mouse macrophages (RAW 264.7), mouse dendritic cells (DCs) (DC 2.4), human umbilical vein endothelial cells (HUVECs), and mouse mesenchymal stem cells (MSCs), then these cells each were cultured for 4 h, and then an FITC fluorescence signal in cells was observed by LSCM.

Figure 8:
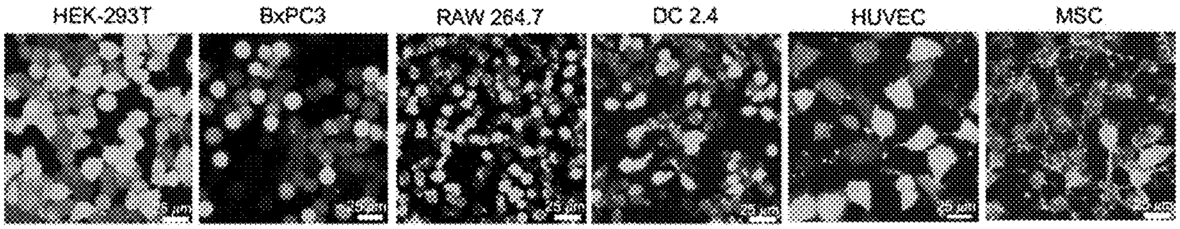
FIG. 8 shows laser scanning confocal microscopy (LSCM) images of different types of cells in which BSA-FITC is delivered by I2-1R2C18A1.

It can be seen from the results in FIG. 8 that BSA-FITC can be transfected by I2-1R2C18A1 into epithelial cells: HRECs (HEK-293T); cancer cells: human pancreatic cancer cells (BxPC3); immune cells: mouse macrophages (RAW 264.7) and mouse DCs (DC 2.4); endothelial cells: HUVECs; and stem cells: mouse MSCs. It can be seen that I2-1R2C18A1 exhibits excellent protein delivery effects in different types of cells.

Example 4 Cytotoxicity Test of Cationic Lipid Analog Materials and Complexes of these Materials with a Protein In this experiment, I2R2C16A1, I2R2C17A1, I2R2C18A1, I2R2C19A1, and I2R2C20A1 with high protein delivery efficiencies were selected as representative cationic lipid analog materials, and the toxicity of protein/cationic lipid analogs for HeLa cells was detected by an MTT experiment. A specific experimental method was as follows: HeLa cells were inoculated in a 96-well plate and cultured in an incubator for 12 h, then a medium was removed, and a cationic lipid analog material or a BSA-FITC/cationic lipid analog complex (a mass ratio of the cationic lipid analog material to the BSA-FITC was 2:1) was added at 1 μg/well; the cells were further cultured for 4 h, then the material was washed away, and DMEM was added; and the cells were further cultured for 20 h, and finally cell viability was detected by MTT.

Figure 9:
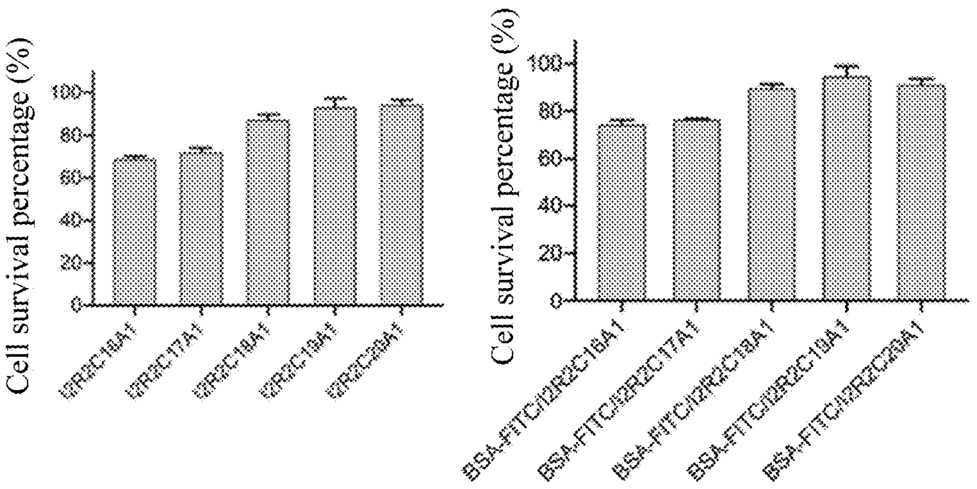
FIG. 9 shows cytotoxicity results of I2R2C16A1, I2R2C17A1, I2R2C18A1, I2R2C19A1, and I2R2C20A1 and complexes of these materials with BSA-FITC.

It can be seen from the results in FIG. 9 that the cationic lipid analog material of the present disclosure and a complex of the material with a protein have excellent biocompatibility.

Example 5 Intracellular Delivery Effects of a Cationic Lipid Analog Material for Different Proteins In this experiment, intracellular delivery effects of the cationic lipid analog material for phycoerythrin (R-PE), SOD, ovalbumin, GFP, cytochrome C, and lysozyme were investigated. In this experiment, a protein/cationic lipid analog complex solution was prepared with reference to the method in Example 2, and a delivery effect of the complex solution in HeLa cells was investigated.

Figure 10:
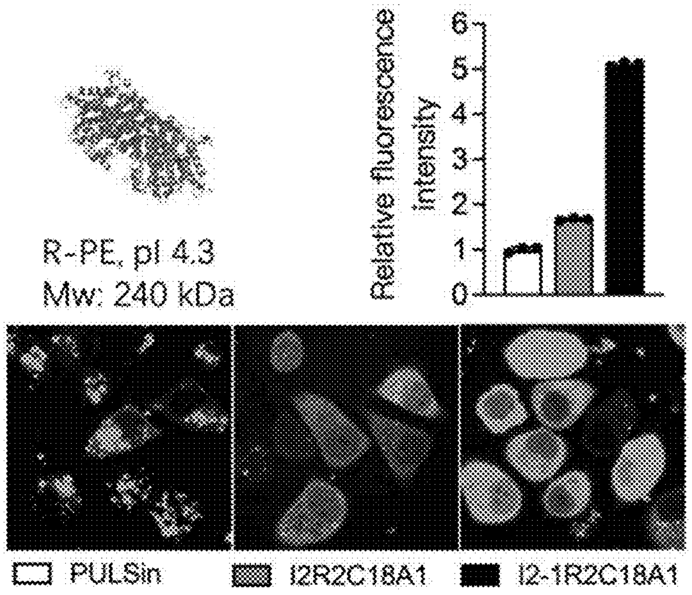
FIG. 10 shows intracellular delivery efficiencies of I2R2C18A1, I2-1R2C18A1, and a positive control PULSin® for negatively-charged phycoerythrin (R-PE)
Figure 11:
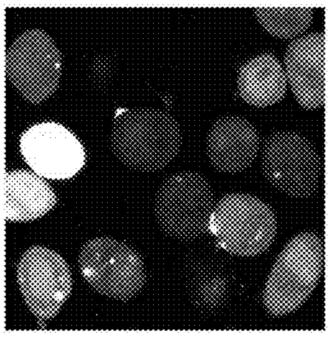
FIG. 11 shows an intracellular delivery efficiency of I2-1R2C18A1 for negatively-charged superoxide dismutase (SOD)
Figure 12:
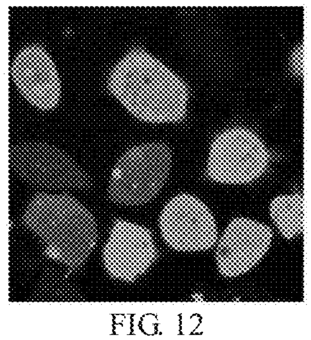
FIG. 12 shows an intracellular delivery efficiency of I2-1R2C18A1 for negatively-charged ovalbumin.
Figure 13:
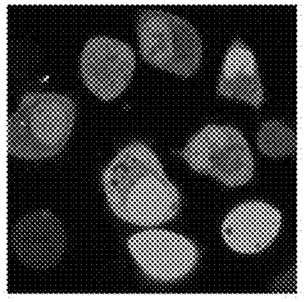
FIG. 13 shows an intracellular delivery efficiency of I2-1R2C18A1 for negatively-charged green fluorescent protein (GFP)
Figure 14:
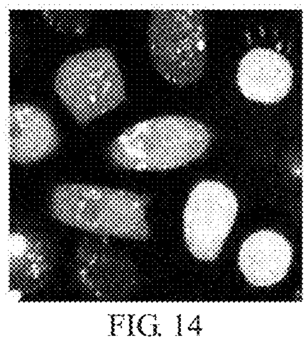
FIG. 14 shows an intracellular delivery efficiency of I2-1R2C18A1 for positively-charged cytochrome C.
Figure 15:
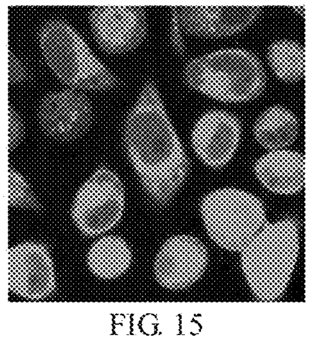
FIG. 15 shows an intracellular delivery efficiency of I2-1R2C18A1 for a positively-charged lysozyme.

Delivery effects of I2R2C18A1, I2-1R2C18A1, and a positive control PULSin® for negatively-charged phycoerythrin were shown in FIG. 10; a delivery effect of I2-1R2C18A1 for negatively-charged SOD was shown in FIG. 11; a delivery effect of I2-1R2C18A1 for negatively-charged ovalbumin was shown in FIG. 12; a delivery effect of I2-1R2C18A1 for negatively-charged GFP was shown in FIG. 13; a delivery effect of I2-1R2C18A1 for positively-charged cytochrome C was shown in FIG. 14; and a delivery effect of I2-1R2C18A1 for positively-charged lysozyme was shown in FIG. 15. It can be seen from the above results that the cationic lipid analog material of the present disclosure can efficiently deliver proteins of different molecular weights and different charged properties into cells, such as BSA, phycoerythrin, SOD, ovalbumin, GFP, cytochrome C, and lysozyme, indicating that the cationic lipid analog material of the present disclosure has universal applicability in terms of intracellular delivery of protein drugs.

Example 6 Delivery of β-Gal by I2-1R2C18A1 and Detection of Activity of β-Gal in Cells HeLa cells were cultured with β-Gal, β-Gal/PULSin, or β-Gal/I2-1R2C18A1 for 4 h and then washed with PBS, and then the activity of β-Gal in cells was detected with a β-Gal in situ assay kit according to instructions. In this experiment, a commercial protein transfection reagent PULSin® was adopted as a positive control.

Figure 16:
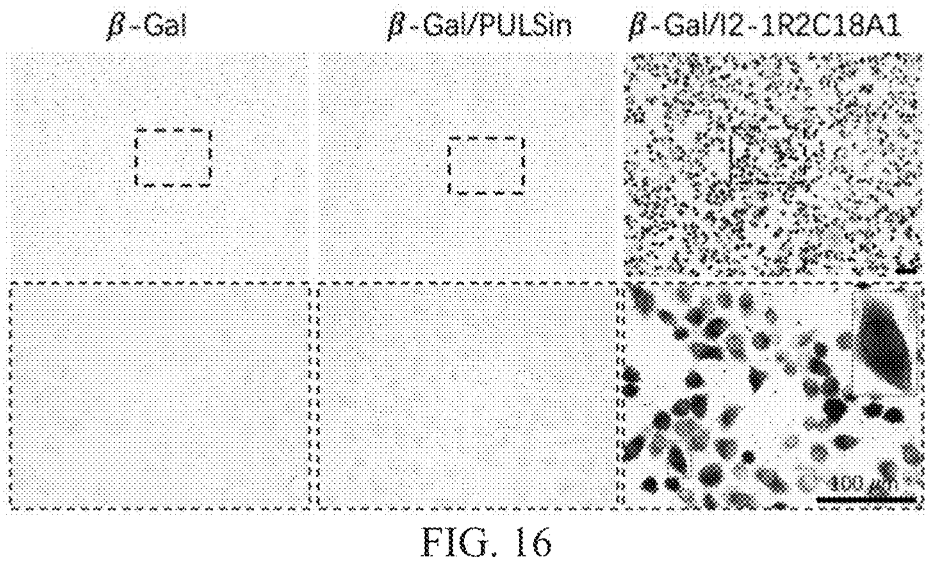
FIG. 16 shows activity results of β-galactosidase (β-Gal) in HeLa cells in which β-Gal is delivered, where a dosage of a cationic lipid analog material is 4 μg/well and a dosage of β-Gal is 4 μg/well; each of the lower pictures bounded by rectangular dotted lines is an enlarged view of a part of the corresponding upper picture.

Maintaining the biological activity of a bioactive molecule is an important principle in the delivery of the bioactive molecule. It can be seen from the results in FIG. 16 that I2-1R2C18A1 can efficiently deliver β-Gal into cells while retaining its biological activity. The effectiveness of I2-1R2C18A1 is significantly better than that of the commercially available protein delivery reagent PULSin®.

Example 7 Delivery of Saporin Into HeLa Cells by I2-1R2C18A1 and Detection of Cell Viability HeLa cells were incubated with saporin or saporin/I2-1R2C18A1 for 4 h, then the material was replaced by a complete medium, the cells were further cultured for 20 h, and then cell viability was detected by an MTT method.

Figure 17:
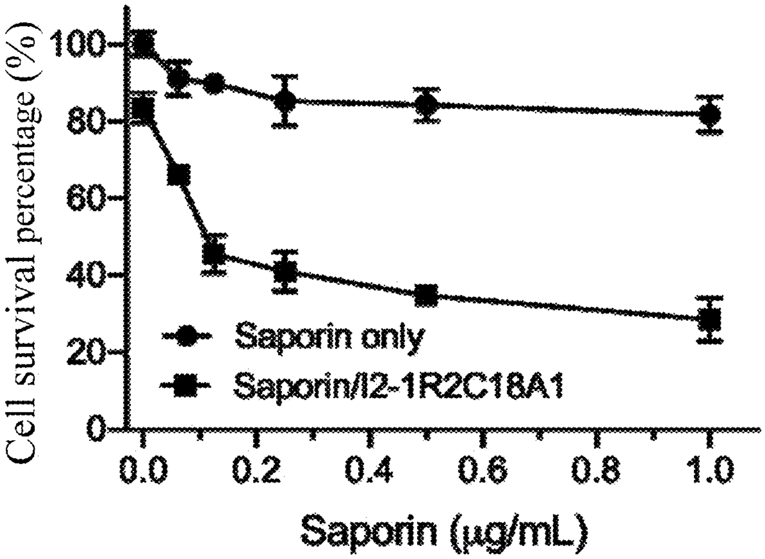
FIG. 17 shows cell viability results of HeLa cells in which saporin is delivered by I2-1R2C18A1, where a dosage of a cationic lipid analog material is 3 μg/well.

It can be seen from the results in FIG. 17 that saporin itself exhibits minimal toxicity for cells; and I2-1R2C18A1 can effectively deliver saporin into cells due to its high protein delivery efficiency, and saporin delivered into the cells has a therapeutic function and can effectively kill tumor cells.

Example 8 Transfection Experiment of GFP-Expressing Plasmid DNA

In this experiment, with GFP-expressing plasmid DNA as a reporter gene, a gene transfection efficiency of a cationic lipid analog material in HeLa cells was detected. A specific method was as follows:

HeLa cells were inoculated in a 24-well plate and cultured in an incubator for 12 h; each of different cationic lipid analog materials—(0.25 μg/well to 8 μg/well) was mixed with GFP-expressing plasmid DNA (0.5 μg/well) in 40 μL of a sodium acetate buffer (25 mM, pH and resulting mixtures each were allowed to stand for 10 min and then diluted with 460 μL of a Opti-MEM medium to obtain plasmid DNA-loaded cationic lipid analog complex particle solutions; a medium for the HeLa cells in the plate was removed, then the HeLa cells were washed once with PBS, and the complex particle solutions each were added; and the cells were further cultured for 24 h, and then a plasmid DNA transfection efficiency in cells was analyzed by FCM. A commercial gene transfection reagent Lipofectamine 2000 was adopted as a positive control.

Figure 18:
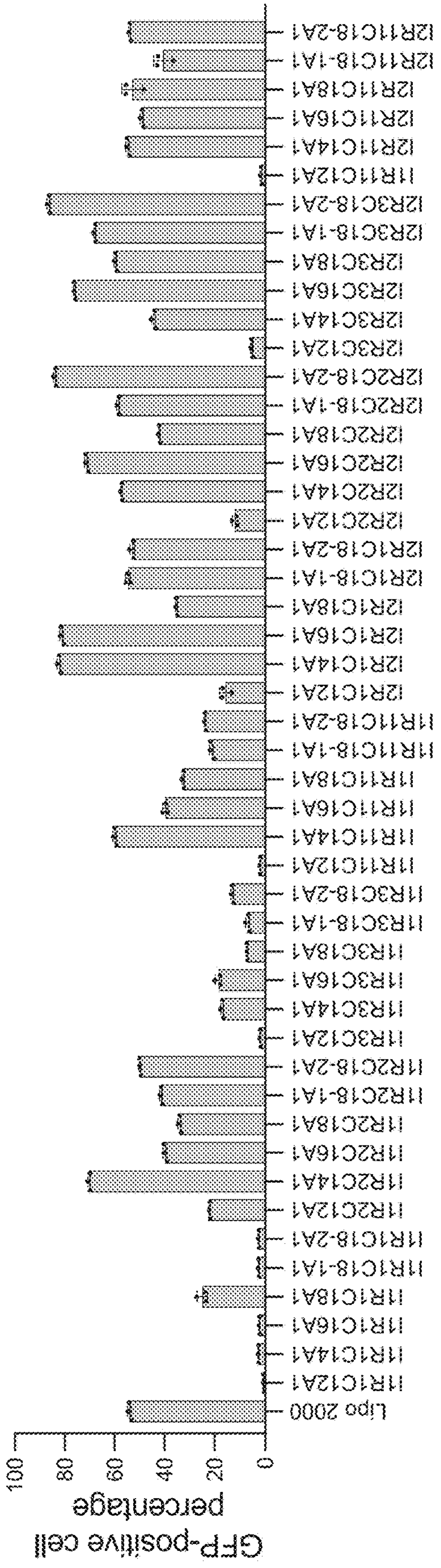
FIG. 18 shows positive rates of GFP-expressing plasmid DNA after transfection by different cationic lipid analog materials, where a dosage of I2R11C14A1 and I2R11C18-2A1 is 0.5 μg/well; a dosage of I1R2C14A1, I2R1C16A1, I2R1C18A1, I2R1C18-1A1, I2R1C18-2A1, I2R2C18-2A1, I2R3C14A1, I2R3C16A1, and I2R3C18-2A1 is 1 μg/well; a dosage of I1R2C16A1, I1R2C18-1A1, I1R2C18-2A1, I1R3C14A1, I1R3C16A1, I1R3C18-2A1, I1R11C14A1, I1R11C16A1, I1R11C18A1, I1R11C18-1A1, I1R11C18-2A1, I2R1C14A1, I2R2C14A1, I2R2C16A1, I2R2C18-1A1, I2R3C18A1, I2R3C18-1A1, and I2R11C16A1 is 2 μg/well; a dosage of I1R1C16A1, I1R2C18A1, I1R3C12A1, I1R3C18A1, I1R3C18-1A1, I1R11C12A1, I2R2C18A1, I2R11C12A1, I2R11C18A1, and I2R11C18-1A1 is 4 μg/well; and a dosage of I1R1C12A1, I1R1C14A1, I1R1C18A1, I1R1C18-1A1, I1R1C18-2A1, I1R2C12A1, I1R5C12A1, I1R5C14A1, I1R5C16A1, I1R5C18A1, I1R5C18-1A1, I1R5C18-2A1, I2R1C12A1, I2R2C12A1, I2R3C12A1, I2R5C12A1, I2R5C14A1, I2R5C16A1, I2R5C18A1, I2R5C18-1A1, and I2R5C18-2A1 is 8 μg/well.

It can be seen from the results in FIG. 18 that the cationic lipid analog material of the present disclosure can transfect GFP-expressing plasmid DNA into HeLa cells with high gene transfection efficiency, and in particular, a transfection efficiency of I1R2C14A1, I1R2C18-2A1, I1R11C14A1, I2R1C14A1, I2R1C16A1, I2R1C18-1A1, I2R1C18-2A1, I2R2C14A1, I2R2C16A1, I2R2C18-1A1, I2R2C18-2A1, I2R3C16A1, I2R3C18A1, I2R3C18-1A1, I2R3C18-2A1, I2R11C14A1, I2R11C16A1, I2R11C18A1, I2R11C18-1A1, and I2R11C18-2A1 can be equivalent to or higher than a transfection efficiency of the commercial transfection reagent Lipofectamine 2000.

Example 9 Transfection Experiment of Luciferase (Luminescence)-Expressing Plasmid DNA In this example, with luciferase-expressing plasmid DNA as a reporter gene, a gene transfection efficiency of a cationic lipid analog material in HeLa cells was detected. A specific operation method was as follows: HeLa cells were inoculated in a 96-well plate and cultured in an incubator for 12 h; each of different cationic lipid analog materials was mixed with luciferase-expressing plasmid DNA (0.5 μg) in 40 μL of a sodium acetate buffer (25 mM, pH 5.2), and resulting mixtures each were allowed to stand for 10 min and then diluted with 460 μL of a Opti-MEM medium to obtain plasmid DNA-loaded cationic lipid analog complex particle solutions; a medium for the HeLa cells in the plate was removed, then the HeLa cells were washed once with PBS, and the complex particle solutions each were added in a volume of 125 μL; the cells were further cultured for 24 h, then a resulting culture supernatant was discarded, and the cells were fully lysed; and a substrate was added at 50 μl/well, and an expression level of luciferase was detected by a multi-mode microplate reader.

Figure 19:
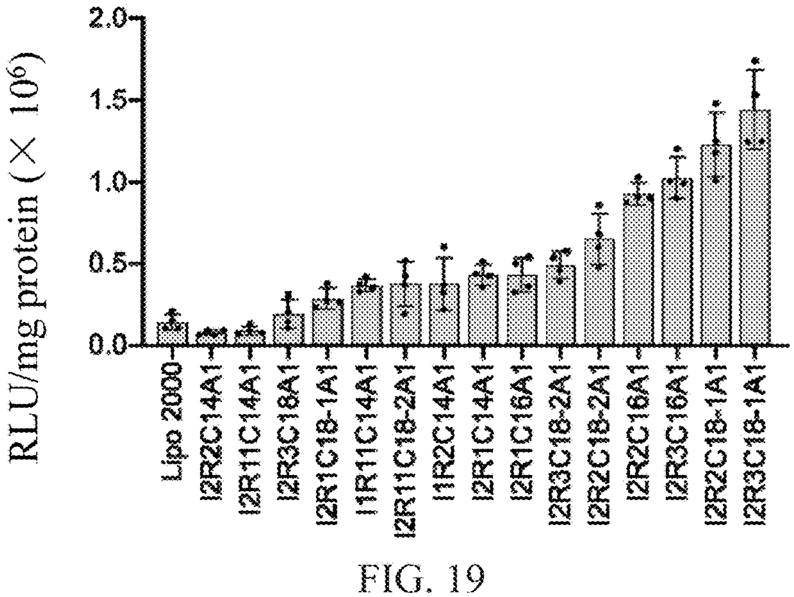
FIG. 19 shows detection results of luciferase expression in HeLa cells transfected with luciferase-expressing plasmid DNA by different cationic lipid analog materials.

It can be seen from the results in FIG. 19 that a transfection efficiency of I2R3C18A1, I2R1C18-1A1, I1R11C14A1, I2R11C18-2A1, I1R2C14A1, I2R1C14A1, I2R1C16A1, I2R3C18-2A1, I2R2C18-2A1, I2R2C16A1, I2R3C16A1, I2R2C18-1A1, and I2R3C18-1A1 can be equivalent to or higher than a transfection efficiency of the commercial transfection reagent Lipofectamine 2000.

Example 10 Transfection Effects of I2R3C18-1A1 for GFP-Expressing Plasmid DNA in Different Types of Cells In this experiment, with I2R3C18-1A1 as a representative cationic lipid analog material and GFP-expressing plasmid DNA as a reporter gene, transfection effects of the cationic lipid analog material at different amounts (0.5 μg/well to 3 μg/well) for plasmid DNA (0.5 μg/well) in different types of cells were investigated. A commercial gene transfection reagent Lipofectamine 2000 was adopted as a positive control. In this experiment, a GFP-expressing plasmid DNA-loaded I2R3C18-1A1 particle complex solution was prepared with reference to the method in Example 8 and added to each of DC2.4, RAW 264.7, A549, BxPC3, and HeLa cells, these cells were cultured for 24 h, and then a transfection efficiency of plasmid DNA in cells was observed by LSCM.

Figure 20:
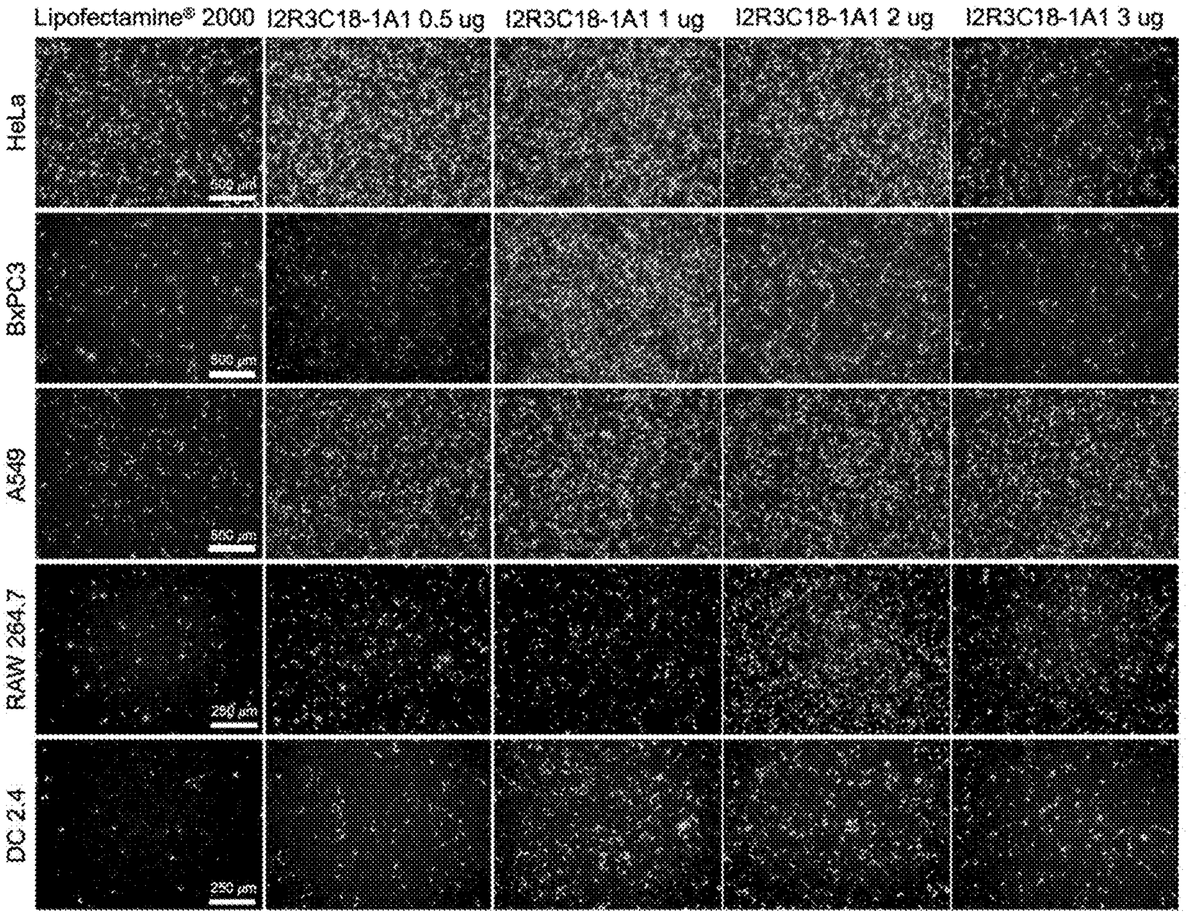
FIG. 20 shows LSCM images of different types of cells transfected with GFP-expressing plasmid DNA by I2R3C18-1A1 with different doses.

It can be seen from the results in FIG. 20 that the I2R3C18-1A1 material can transfect GFP-expressing plasmid DNA into tumor cells and immune cells.

Example 11 Transfection Experiment of Enhanced Green Fluorescent Protein (eGFP)-Expressing mRNA In this experiment, with eGFP-mRNA as model mRNA, an mRNA transfection efficiency of a cationic lipid analog material in DC 2.4 cells was detected. A specific operation method was as follows:

DC 2.4 cells were inoculated in a 48-well plate and cultured in an incubator for 12 h; each of different cationic lipid analog materials (0.25 μg/well to 2 μg/well) was mixed with eGFP-expressing mRNA (0.2 μg/well) in 20 μL of a sodium acetate buffer (25 mM, pH 5.2), and resulting mixtures each were allowed to stand for 10 min and then diluted with 230 μL of a Opti-MEM medium to obtain mRNA-loaded complex particle solutions; a medium for the DC 2.4 cells in the plate was removed, then the DC 2.4 cells were washed once with PBS, and the complex particle solutions each were added; and the cells were cultured for 24 h, an mRNA transfection efficiency in cells was observed by FCM and LSCM. A commercial gene transfection reagent Lipofectamine 2000 was adopted as a positive control.

Figure 21:
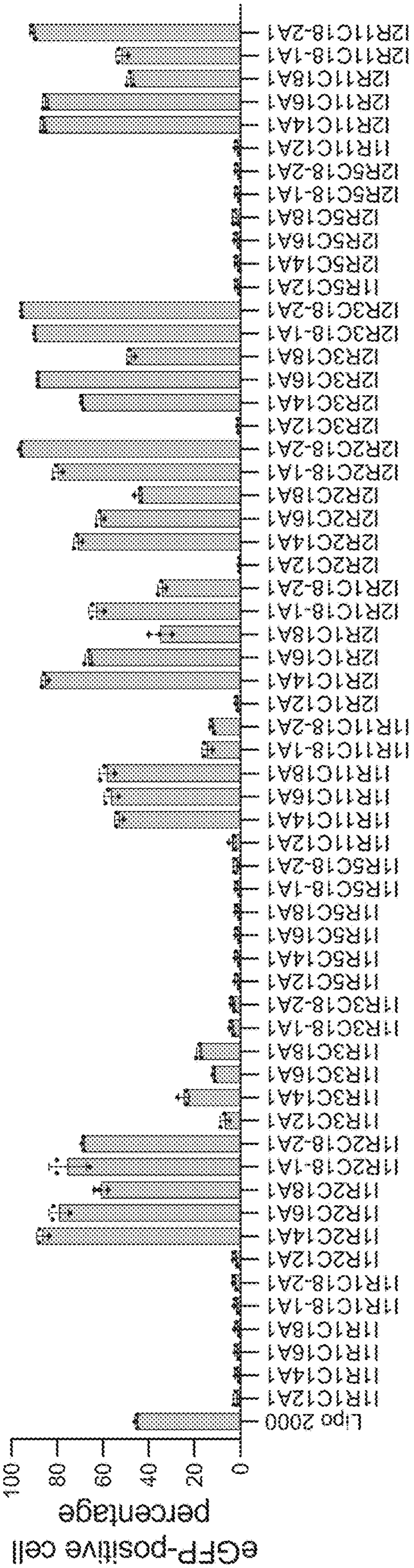
FIG. 21 shows positive rates of eGFP-mRNA transfected by different cationic lipid analog materials, where a dosage of I1R2C14A1, I1R2C18-1A1, I1R2C18-2A1, I1R11C14A1, I2R2C14A1, I2R2C18-1A1, I2R2C18-2A1, I2R3C16A1, I2R3C18A1, I2R3C18-1A1, I2R3C18-2A1, I2R11C14A1, I2R11C16A1, I2R11C18-1A1, and I2R11C18-2A1 is 1 μg/well; and a dosage of I1R1C12A1, I1R1C14A1, I1R1C16A1, I1R1C18A1, I1R1C18-1A1, I1R1C18-2A1, I1R2C12A1, I1R2C16A1, I1R2C18A1, I1R3C12A1, I1R3C14A1, I1R3C16A1, I1R3C18A1, I1R3C18-1A1, I1R3C18-2A1, I1R5C12A1, I1R5C14A1, I1R5C16A1, I1R5C18A1, I1R5C18-1A1, I1R5C18-2A1, I1R11C12A1, I1R11C16A1, I1R11C18A1, I1R11C18-1A1, I1R11C18-2A1, I2R1C12A1, I2R1C14A1, I2R1C16A1, I2R1C18A1, I2R1C18-1A1, I2R1C18-2A1, I2R2C12A1, I2R2C16A1, I2R2C18A1, I2R3C12A1, I2R3C14A1, I2R5C12A1, I2R5C14A1, I2R5C16A1, I2R5C18A1, I2R5C18-1A1, I2R5C18-2A1, I2R11C12A1, and I2R11C18A1 is 2 μg/well.
Figure 22:
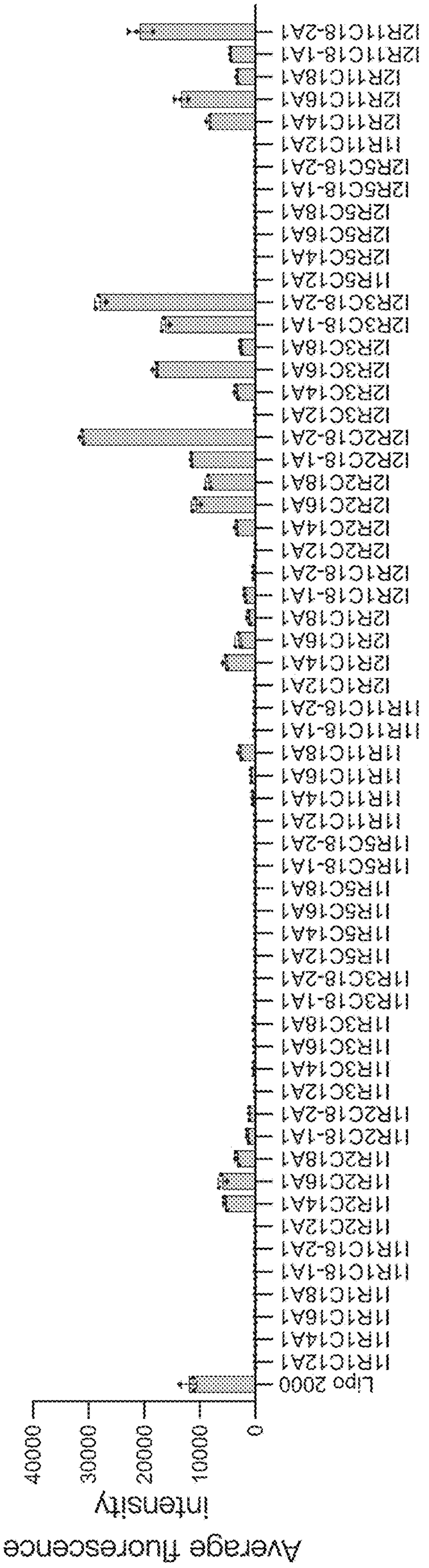
FIG. 22 shows average fluorescence intensities of eGFP-mRNA transfected by different cationic lipid analog materials, where experimental conditions are consistent with those in FIG. 21.
Figure 23:
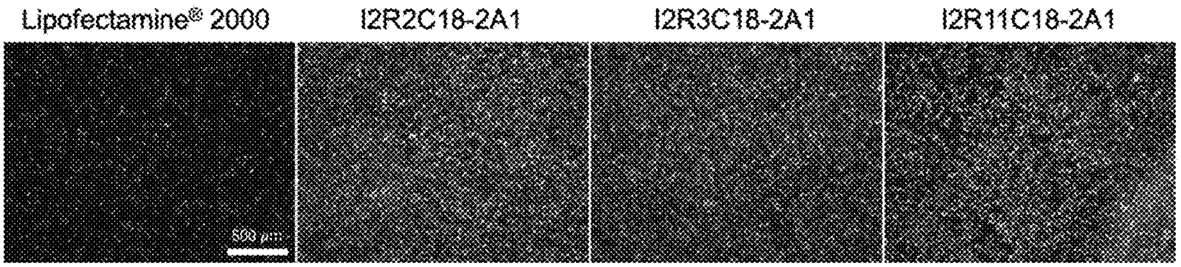
FIG. 23 shows LSCM images of DC2.4 cells transfected with eGFP-mRNA by I2R2C18-2A1, I2R3C18-2A1, I2R11C18-2A1, and a commercial transfection reagent Lipofectamine 2000 as a positive control.

It can be seen from the results in FIG. 21 to FIG. 23 that the cationic lipid analog material of the present disclosure can transfect eGFP-expressing mRNA into DC 2.4 cells, and in particular, an mRNA transfection efficiency of I1R2C14A1, I1R2C16A1, I1R2C18A1, I1R2C18-1A1, I1R2C18-2A1, I1R11C14A1, I1R11C16A1, I1R11C18A1, I2R1C14A1, I2R1C16A1, I2R1C18-1A1, I2R2C14A1, I2R2C16A1, I2R2C18A1, I2R2C18-1A1, I2R2C18-2A1, I2R3C14A1, I2R3C16A1, I2R3C18A1, I2R3C18-1A1, I2R3C18-2A1, I2R11C14A1, I2R11C16A1, I2R11C18A1, I2R11C18-1A1, and I2R11C18-2A1 can be equivalent to or higher than an mRNA transfection efficiency of the commercial transfection reagent Lipofectamine 2000.

Example 12 Transfection Experiment of Small Interfering Ribonucleic Acid (siRNA)

In this experiment, with I2R2C18-1A1, I2R3C18-1A1, I2R2C18-2A1, and I2R3C18-2A1 as representative cationic lipid analog materials, A549 cells (A549-Luc) stably expressing the luciferase reporter gene as model cells, and a siRNA sequence specifically targeting the luciferase reporter gene as model siRNA, siRNA transfection and delivery effects of the cationic lipid analog materials were investigated. A specific operation method was as follows:

Luciferase-expressing A549 cells (A549-Luc) were inoculated in a 96-well plate and cultured in an incubator for 12 h; each of different materials (0.5 μg/well to 3 μg/well) was mixed with siRNA in 40 μL of a sodium acetate buffer (25 mM, pH 5.2), and resulting mixtures each were allowed to stand for 10 min and then diluted with 460 μL of a Opti-MEM medium to obtain siRNA-loaded complex particle solutions (final siRNA concentration: 100 nM); a medium for the A549-Luc cells in the plate was removed, then the A549-Luc cells were washed once with PBS, and the complex particle solutions each were added in a volume of 125 μL; the cells were further cultured for 48 h, then a resulting culture supernatant was discarded, and the cells were fully lysed; and a substrate was added at 50 μl/well, and an expression level of luciferase was detected by a multi-mode microplate reader.

Figure 24:
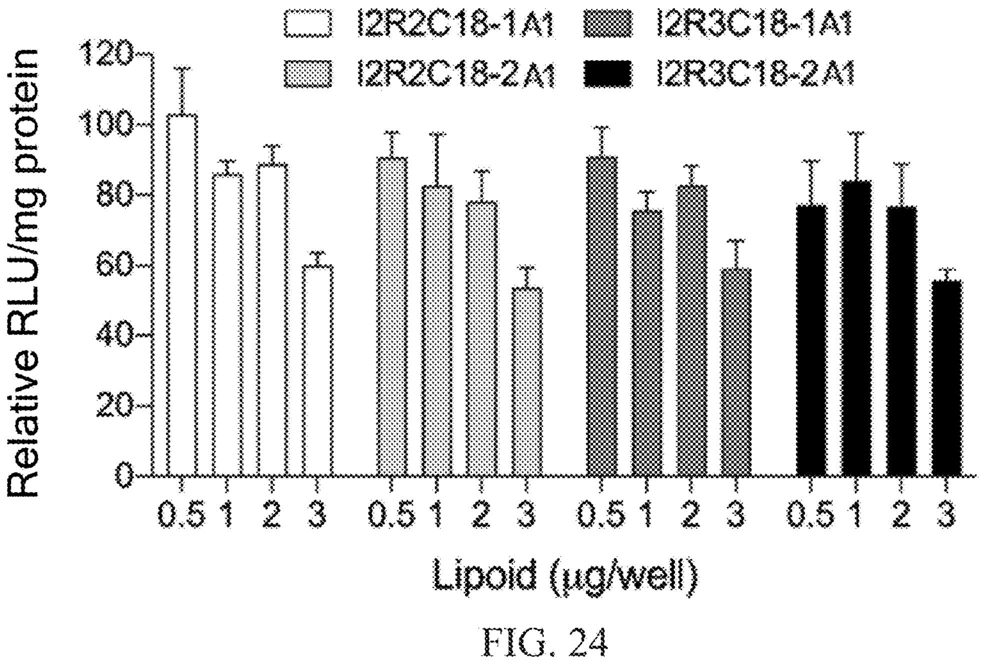
FIG. 24 shows gene silencing results of siRNA transfected by I2R2C18-1A1, I2R3C18-1A1, I2R2C18-2A1, and I2R3C18-2A1 at different doses.

It can be seen from the results in FIG. 24 that I2R2C18-1A1, I2R3C18-1A1, I2R2C18-2A1, and I2R3C18-2A1 can transfect siRNA into cells to specifically silence the expression of the luciferase reporter gene, and the gene silencing efficiency increases with the increase of an amount of the cationic lipid analog material.

In addition, the inventors have found in previous research that, when the IBA in Example 1 is replaced by

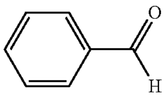 and 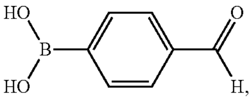, cationic lipid analog materials prepared correspondingly also have low cytotoxicity, and when BSA-FITC is adopted as a protein model, these cationic lipid analog materials also exhibit a specified intracellular delivery effects for the protein in HeLa cells; or when GFP-expressing plasmid DNA or luciferase (luminescence)-expressing plasmid DNA is adopted as a reporter gene, the cationic lipid analog materials exhibit a specific gene transfection efficiency in HeLa cells. Therefore, it can be speculated that these cationic lipid analog materials can also be used as delivery carriers for biomacromolecular drugs such as proteins and nucleic acids.

Finally, it should be noted that the above examples are provided merely to describe the technical solutions of the present disclosure, rather than to limit the protection scope of the present disclosure. Although the present disclosure is described in detail with reference to preferred examples, a person of ordinary skill in the art should understand that modifications or equivalent replacements may be made to the technical solutions of the present disclosure without departing from the spirit and scope of the technical solutions of the present disclosure.

The invention claimed is:

1. An ionizable cationic lipid analog material with a structure shown in formula (I):

I

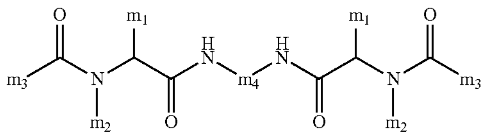

wherein $m_1$ is independently selected from the group consisting of a linear alkyl, a branched alkyl, phenyl, and a heteroatom-containing aryl;

$m_2$ is

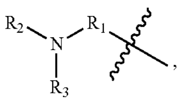, $R_1$ is an alkyl, $R_2$ is an alkyl, $R_3$ is an alkyl or phenyl, or $R_2$ and $R_3$ are connected as a cyclic group or a heterocyclic group;

$m_3$ is independently selected from the group consisting of a linear alkyl, a linear alkenyl, and

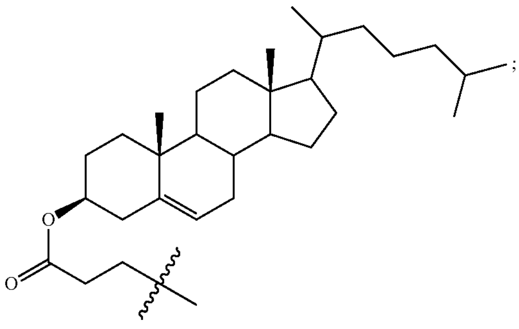 [SMILES: *CCC(=O)O[C@H]1CC[C@@]2(C)C(=CCC3C4CCC(C(C)CCCC(C)C)[C@@]4(C)CCC32)C1 ; ";"];

and $m_4$ is independently selected from the group consisting of a linear alkyl, an ether bond-containing linear alkyl, and a N-heterocycle-containing alkyl.

2. The ionizable cationic lipid analog material according to claim 1, wherein $m_1$ is selected from the group consisting of an alkyl, phenyl, and a heteroatom-containing aryl, each substituted by a substituent α, and the substituent α comprises methyl.

3. The ionizable cationic lipid analog material according to claim 1, wherein $m_1$ is selected from the group consisting of

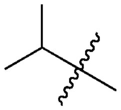, 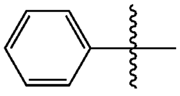, and

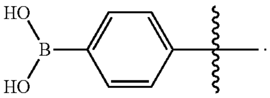.

4. The ionizable cationic lipid analog material according to claim 1, wherein $m_2$ is selected from the group consisting of

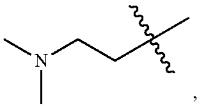, 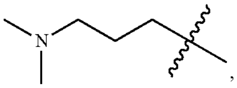,

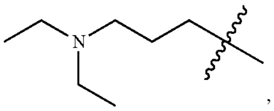, 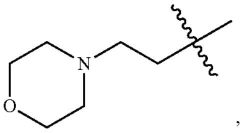,

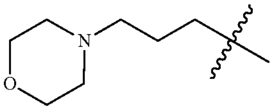, 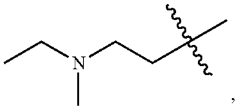,

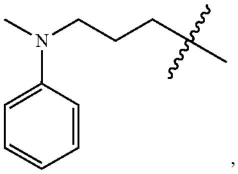, 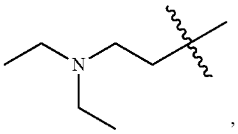,

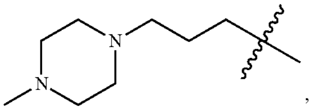,

-continued

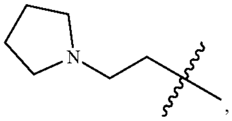, and 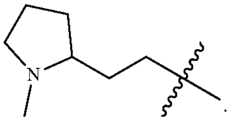.

5. The ionizable cationic lipid analog material according to claim 1, wherein $m_3$ is selected from the group consisting of a linear alkyl with 7 to 19 carbon atoms, a linear alkenyl with 17 carbon atoms, and

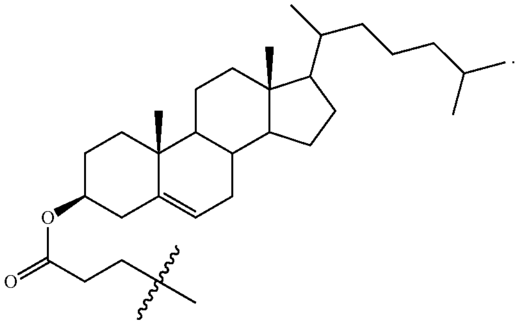 [SMILES: *CCC(=O)O[C@H]1CC[C@@]2(C)C(=CCC3C4CCC(C(C)CCCC(C)C)[C@@]4(C)CCC32)C1 ; "."].

6. The ionizable cationic lipid analog material according to claim 5, wherein $m_3$ is selected from the group consisting of

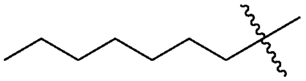,

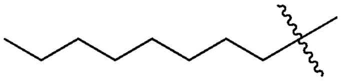,

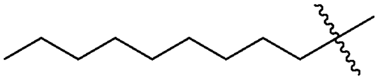,

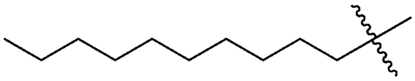,

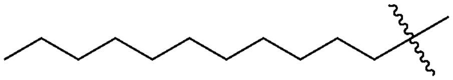,

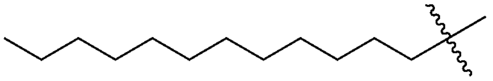,

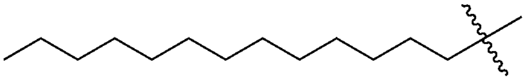,

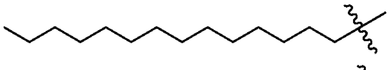,

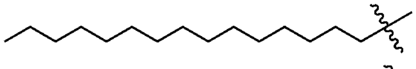,

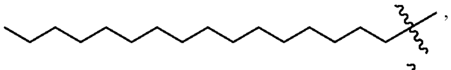,

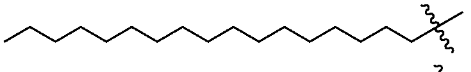,

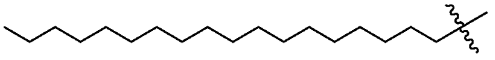,

-continued

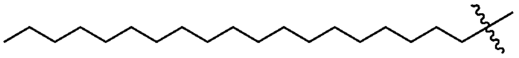
,
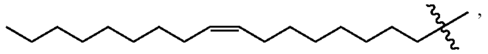
,
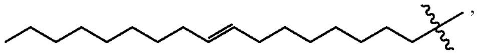
,
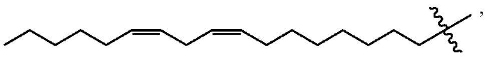
,
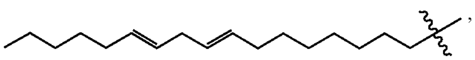
, and
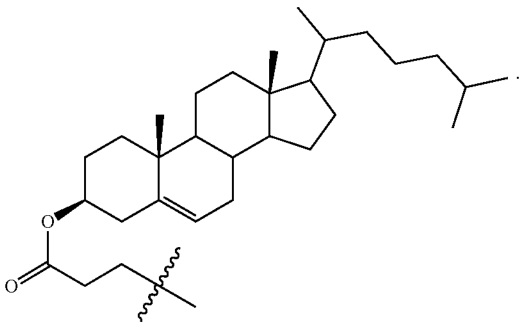
.

7. The ionizable cationic lipid analog material according to claim 1, wherein $m_4$ is selected from the group consisting of a linear alkyl with 6 carbon atoms, an ether bond-containing linear alkyl with 4 to 8 carbon atoms, and a N-heterocycle-containing alkyl.

8. The ionizable cationic lipid analog material according to claim 7, wherein $m_4$ is selected from the group consisting of

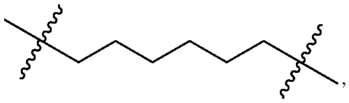
,
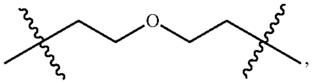
,
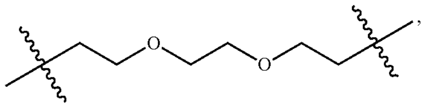
,
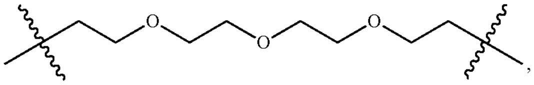
, and
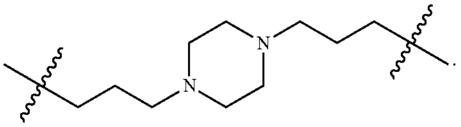
.

9. The ionizable cationic lipid analog material according to claim 1, wherein the ionizable cationic lipid analog material has a structure selected from the group consisting of the following 72 structures:

I1R1C12A1

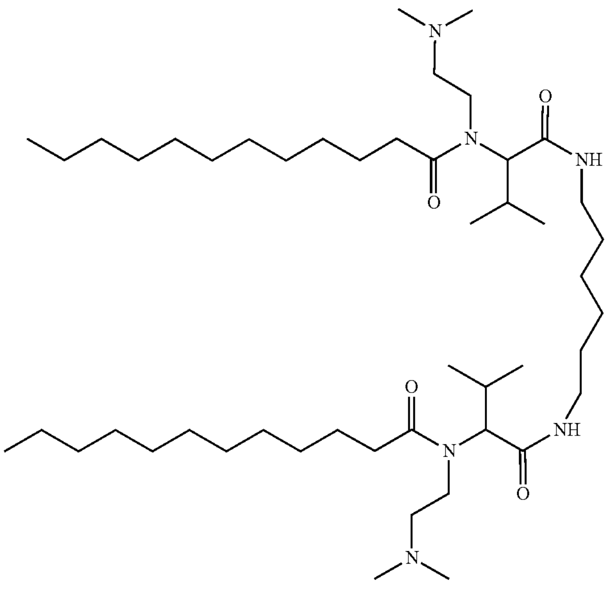

-continued
I1R1C14A1
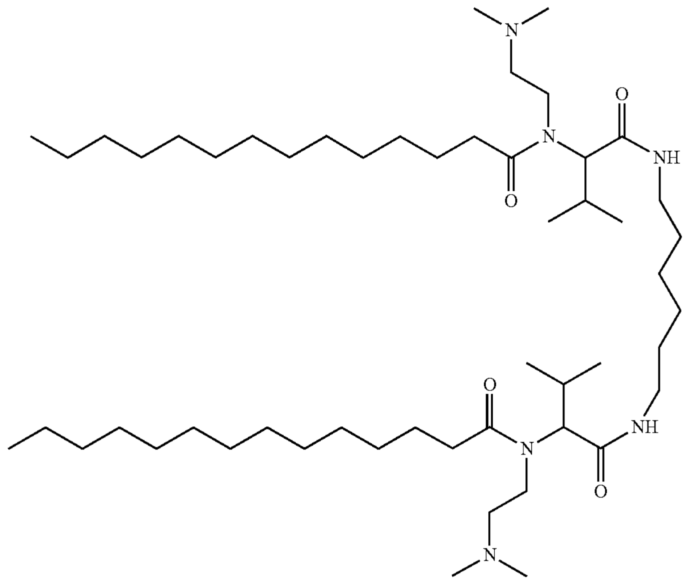
I1R1C16A1
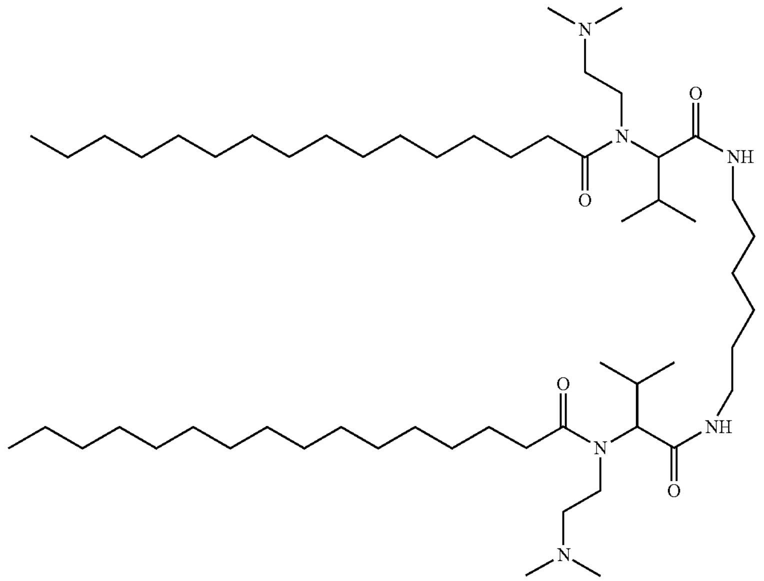

-continued
I1R1C18A1
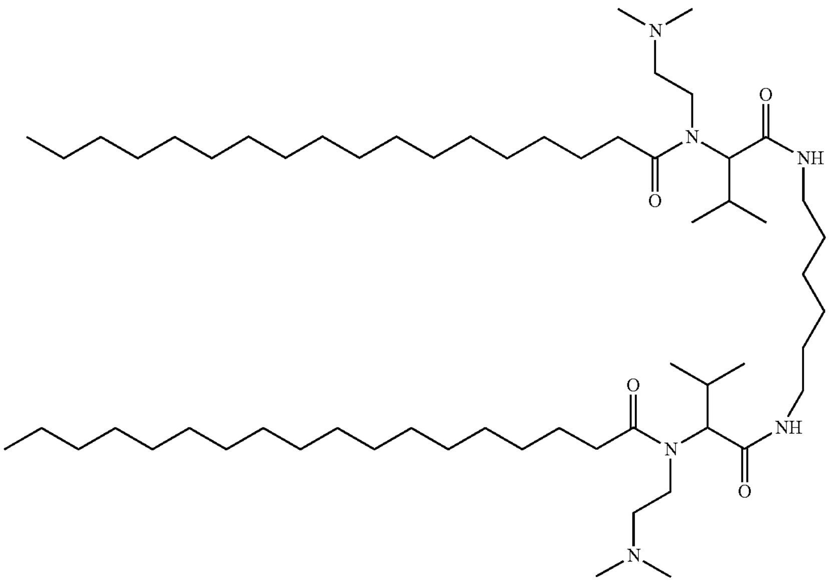
I1R1C20A1
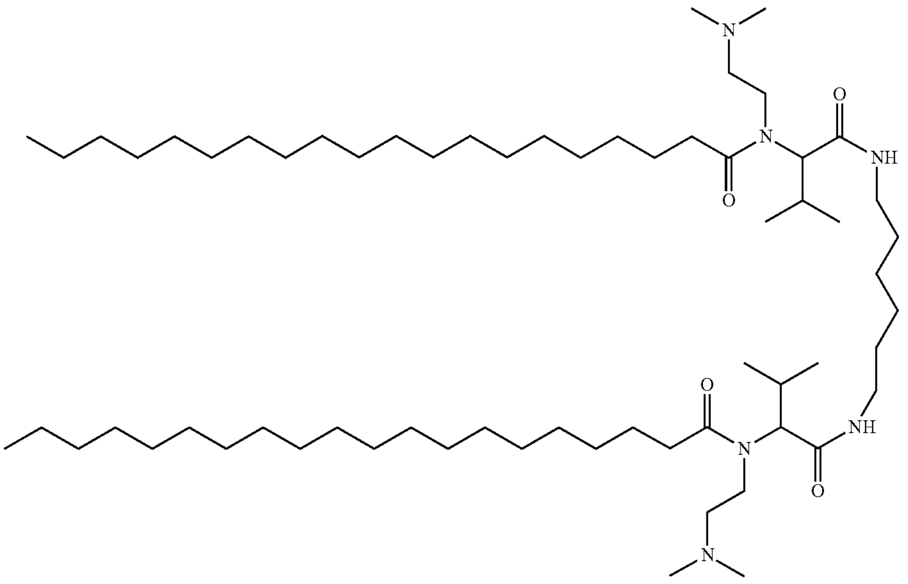

-continued
I1R1C18-1A1
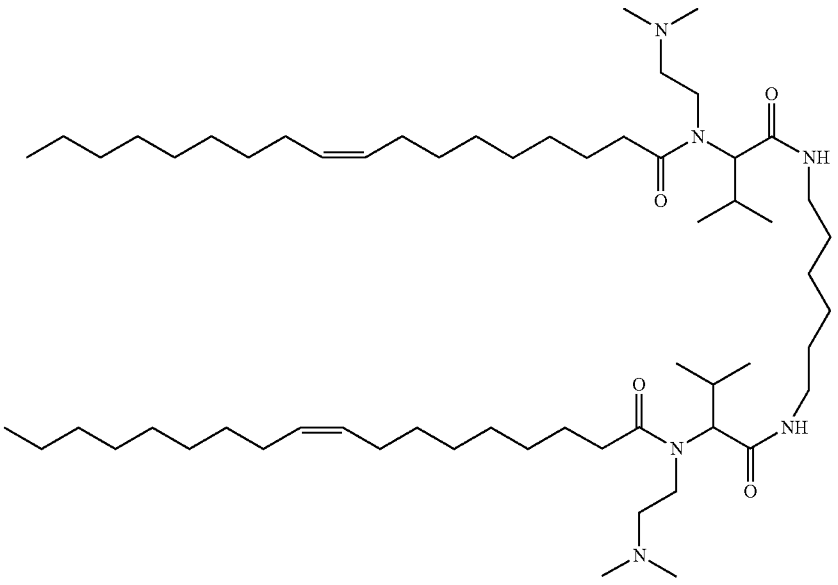
I1R3C14A1
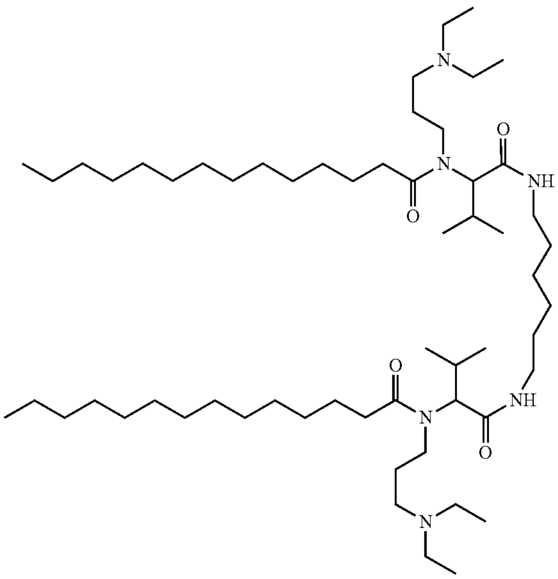

-continued
I1R1C18-2A1
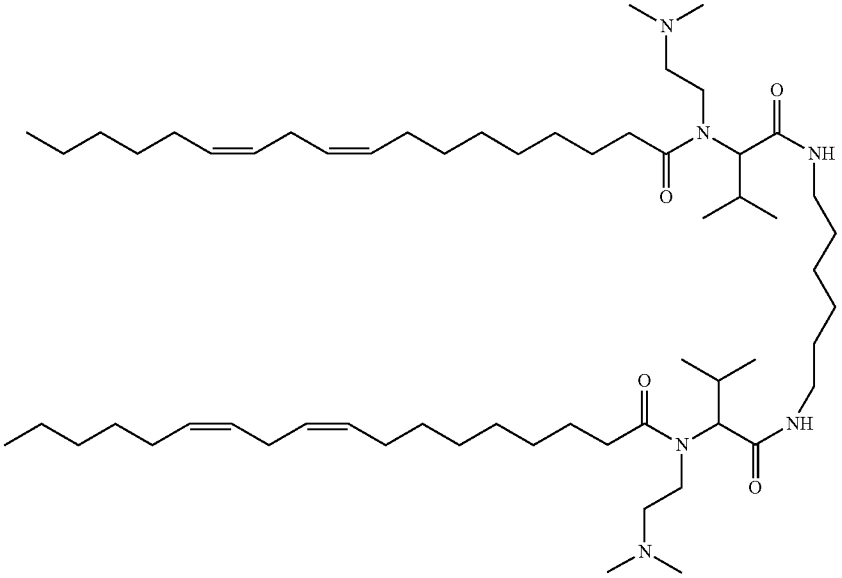
I1R2C12A1
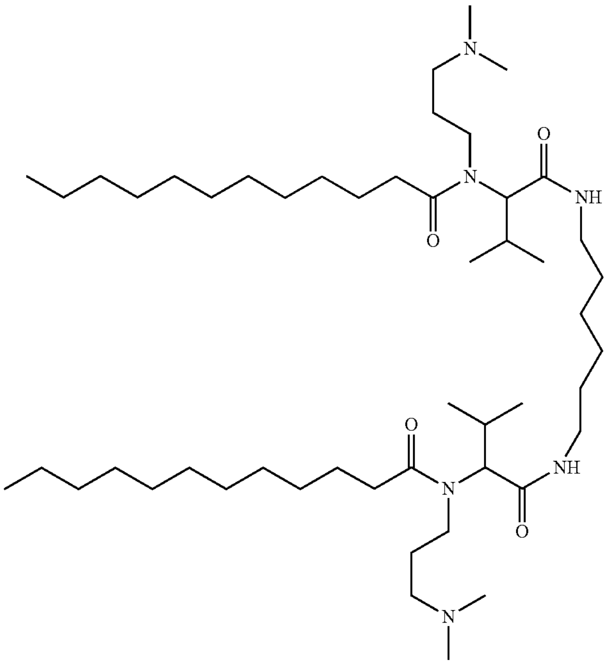

-continued
I1R2C14A1
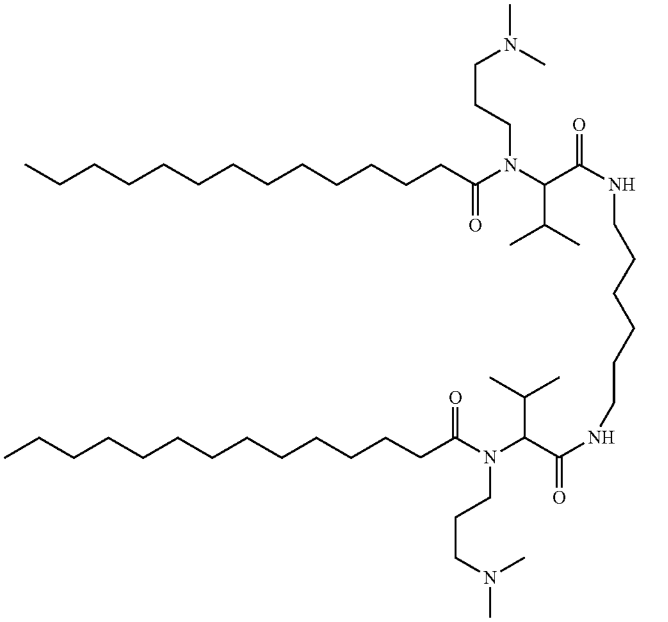
I1R2C16A1
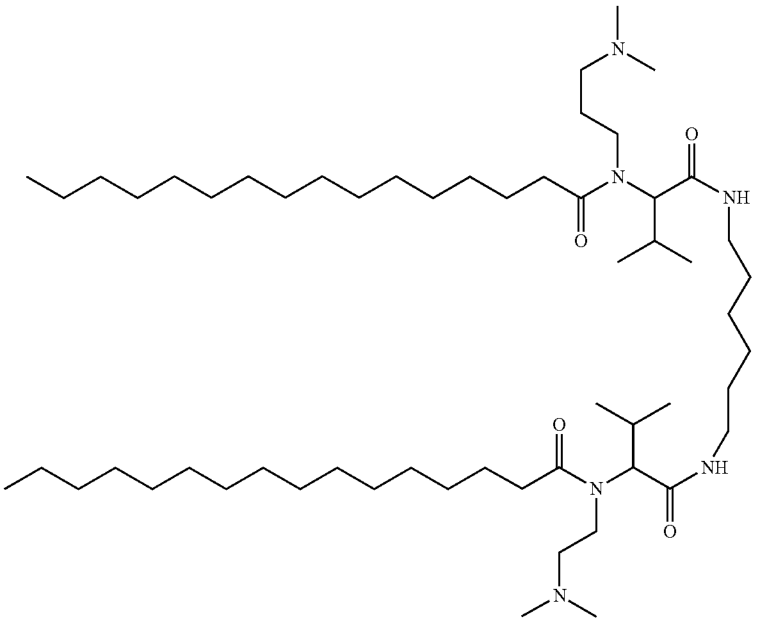

-continued
I1R2C18A1
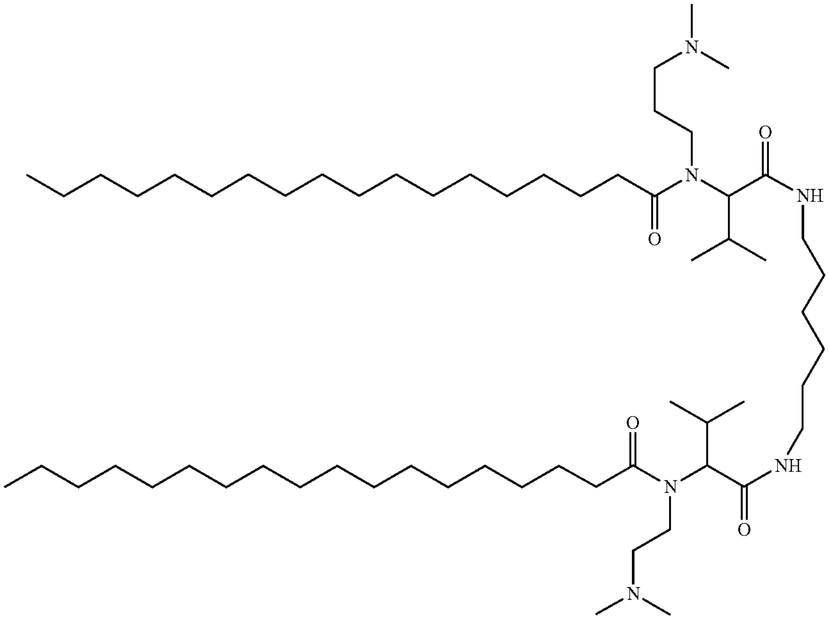
I1R2C20A1
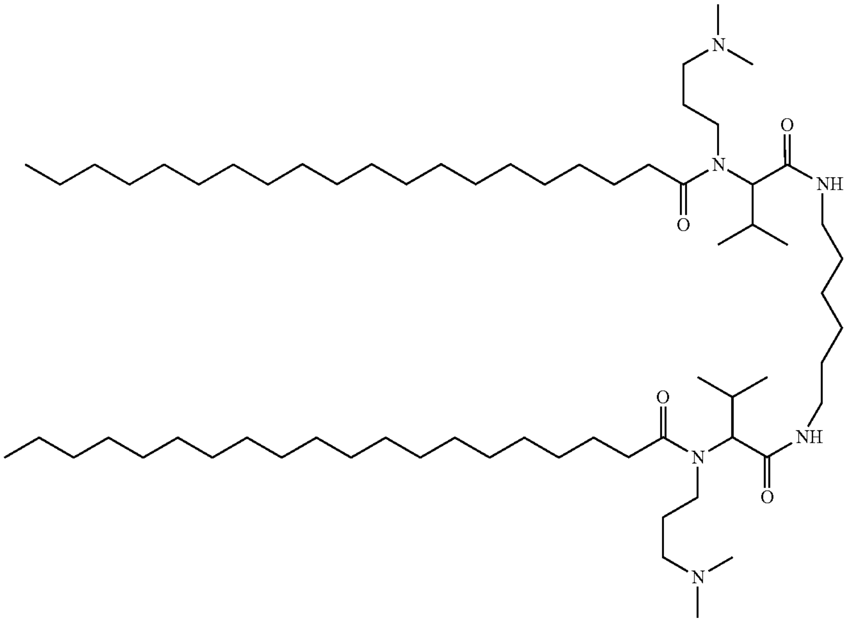

-continued
I1R2C18-1A1
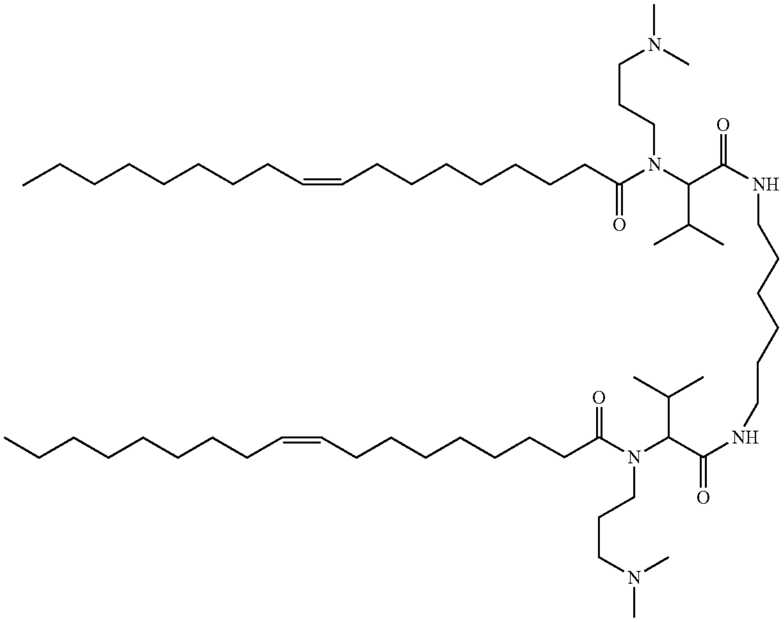
I1R2C18-2A1
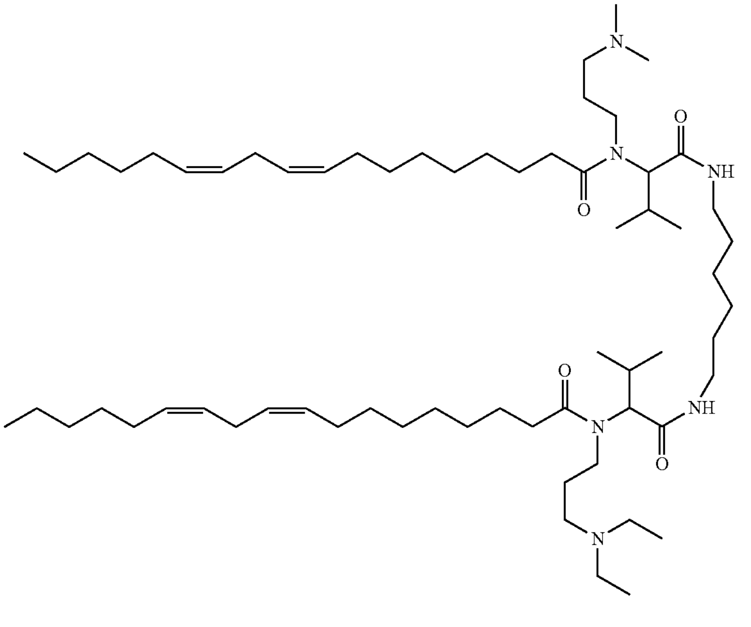

-continued
I1R3C12A1
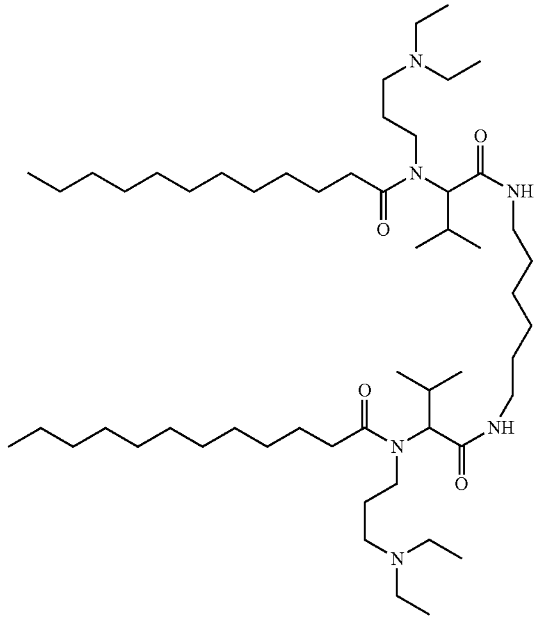
I1R3C16A1
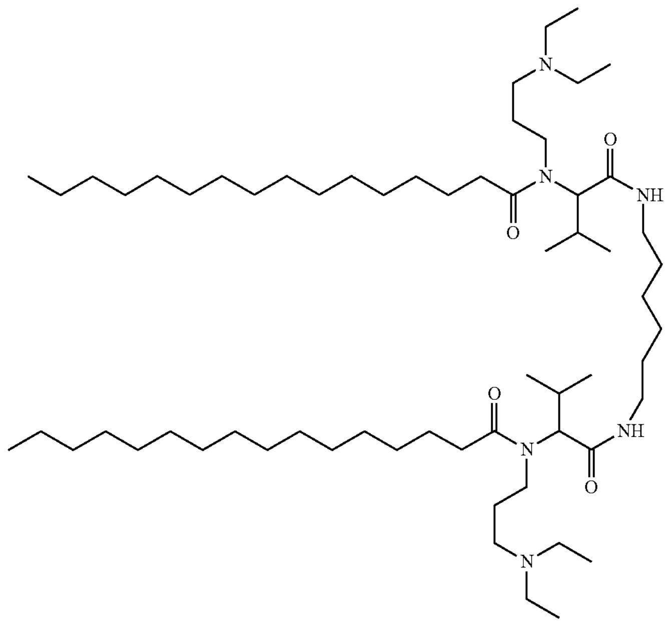

-continued
I1R3C18A1
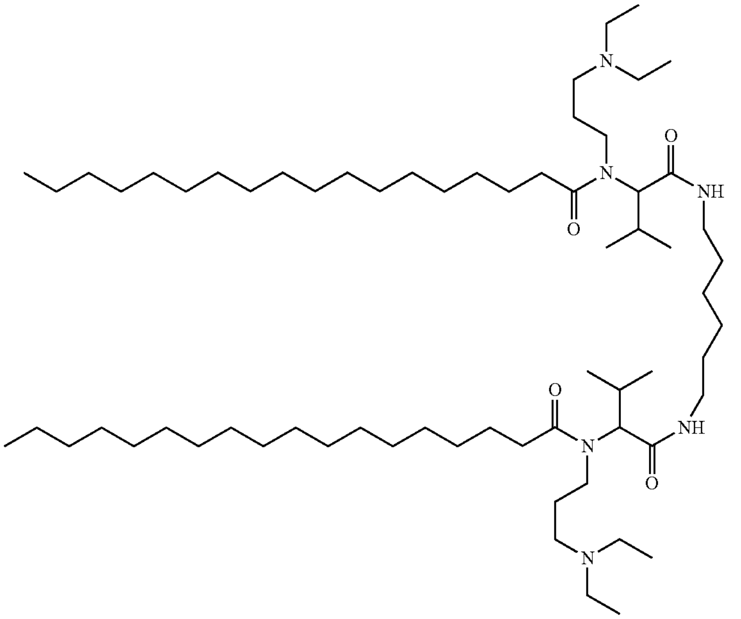
I1R3C20A1
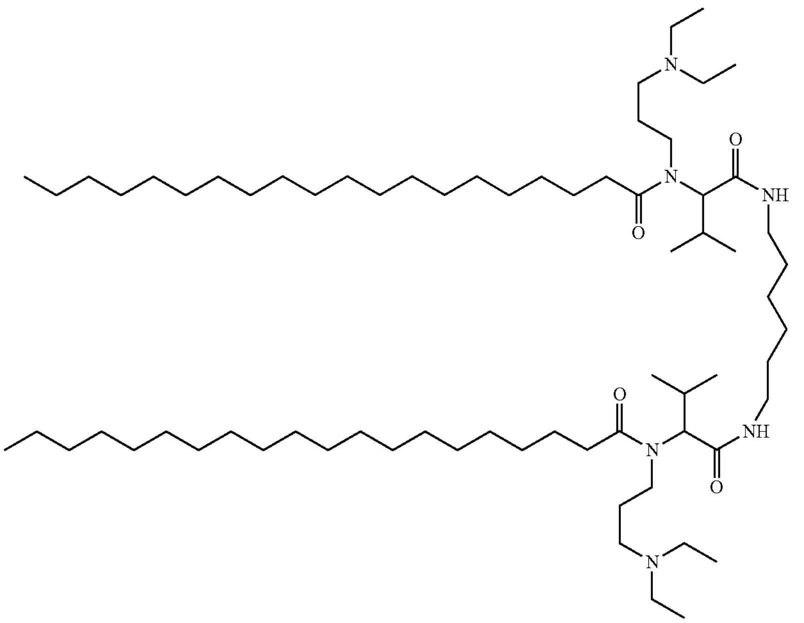

-continued
I1R3C18-1A1
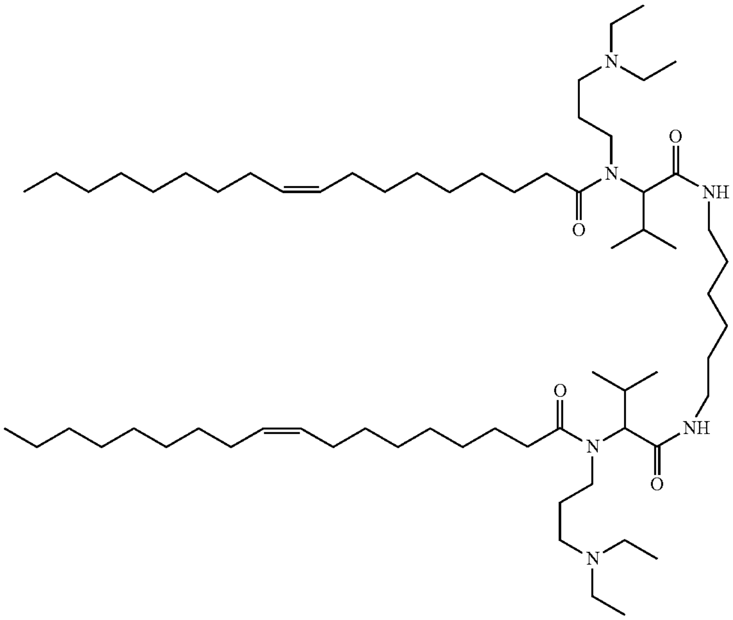
I1R3C18-2A1
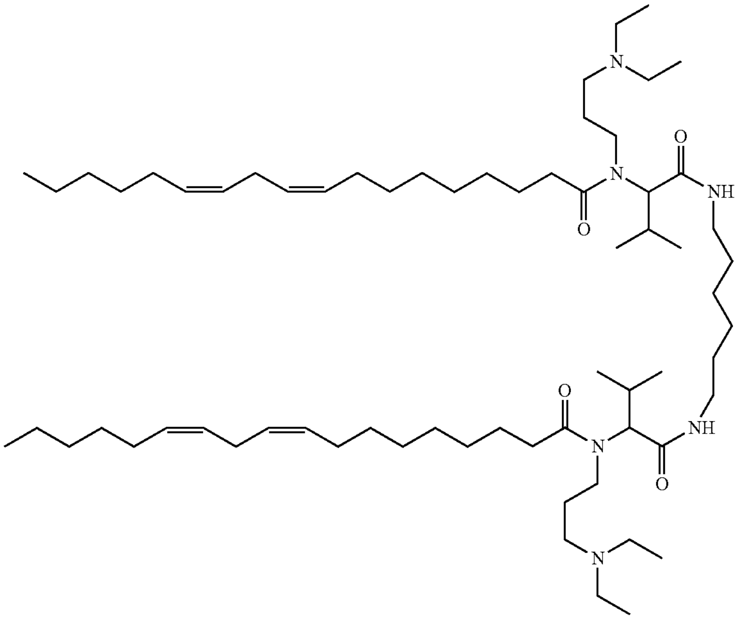

-continued
I1R5C12A1
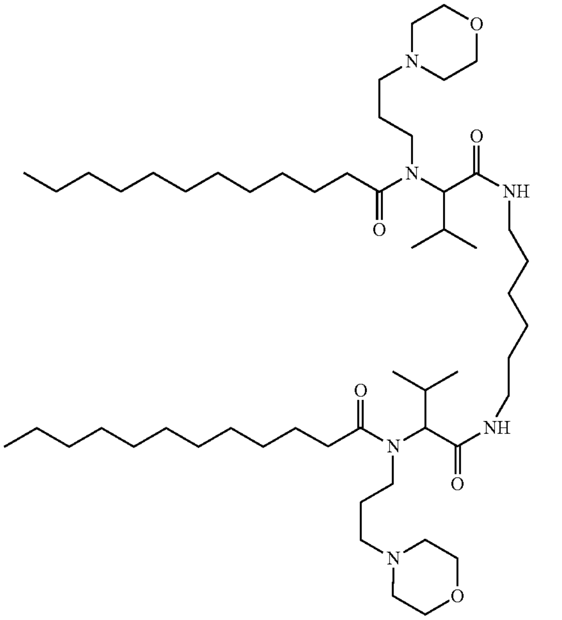
I1R5C14A1
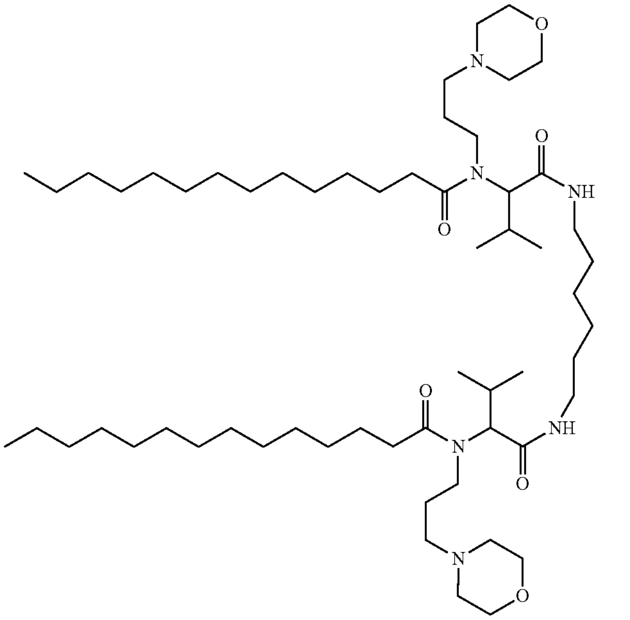

-continued
I1R5C16A1
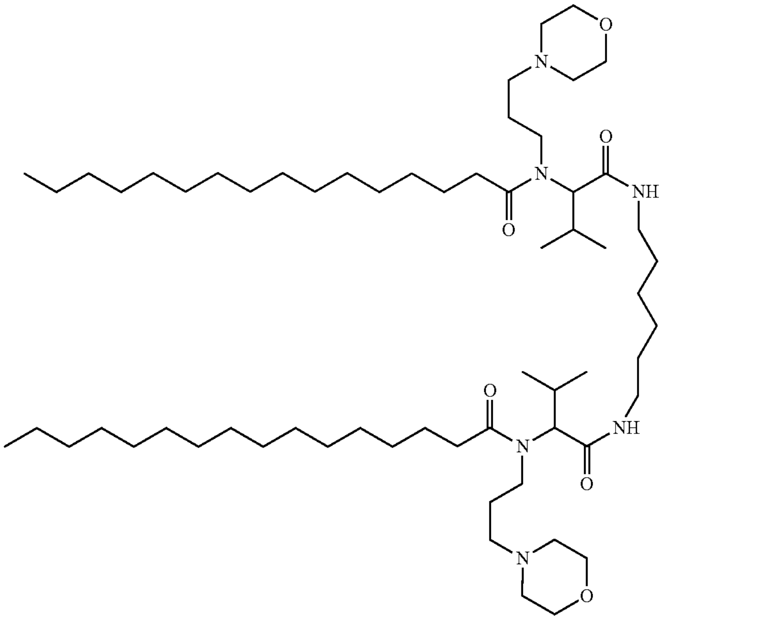
I1R5C18A1
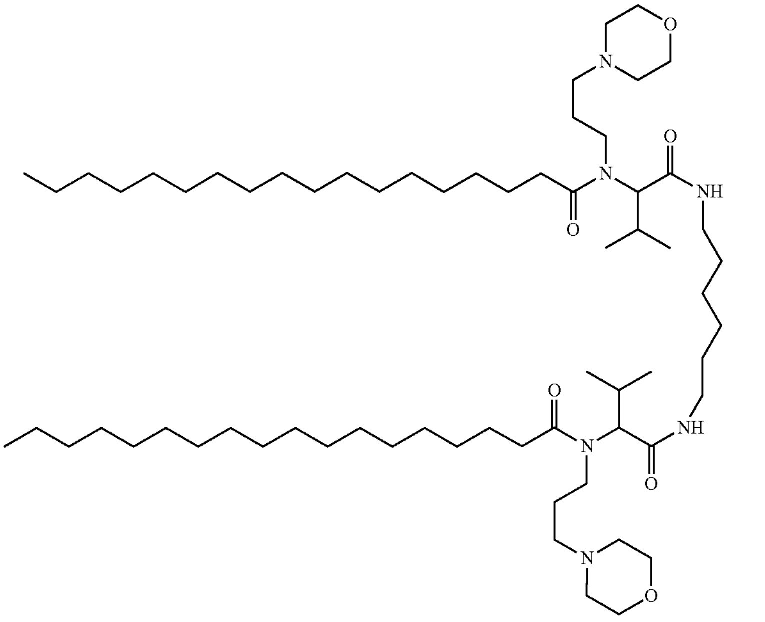

-continued
I1R5C20A1
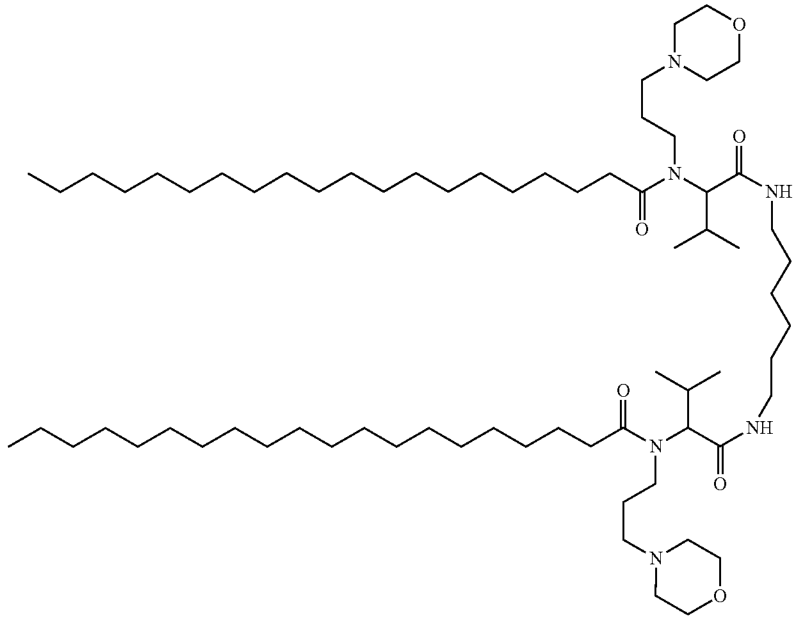
I1R5C18-1A1
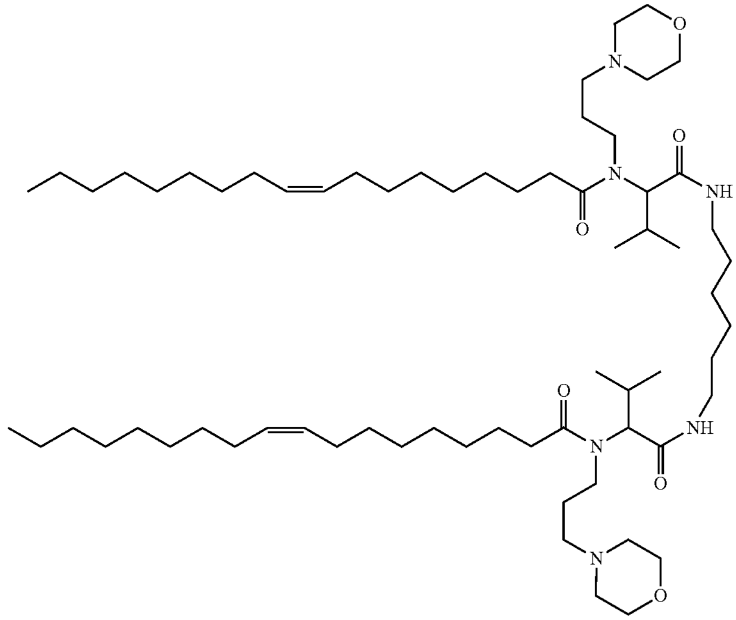

-continued
I1R5C18-2A1
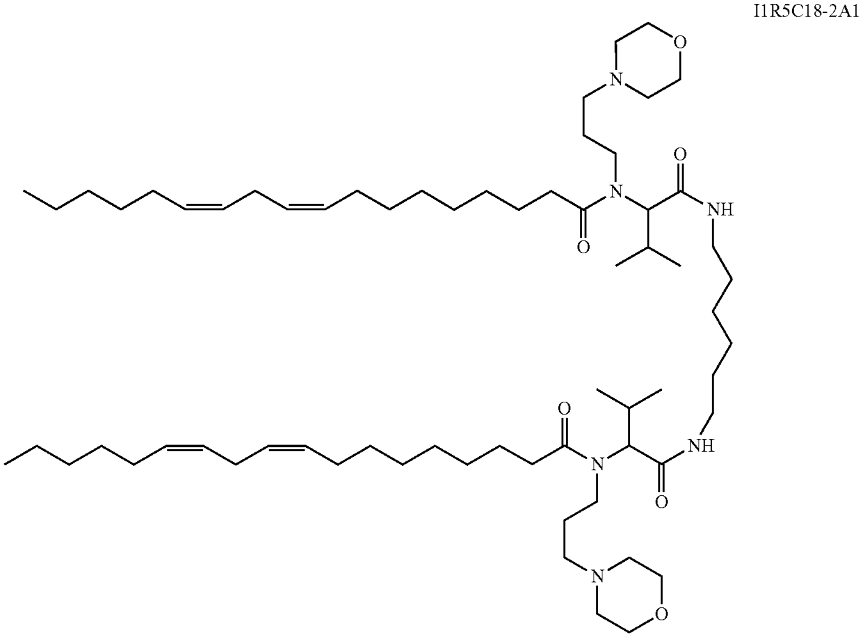
I1R11C12A1
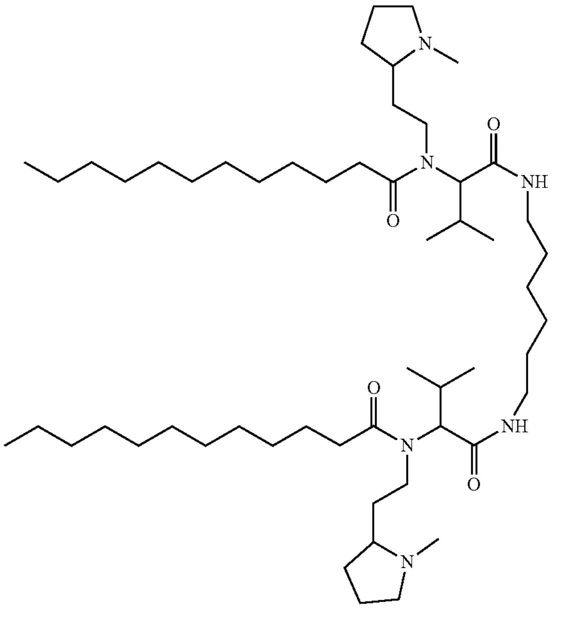

-continued
I1R11C14A1
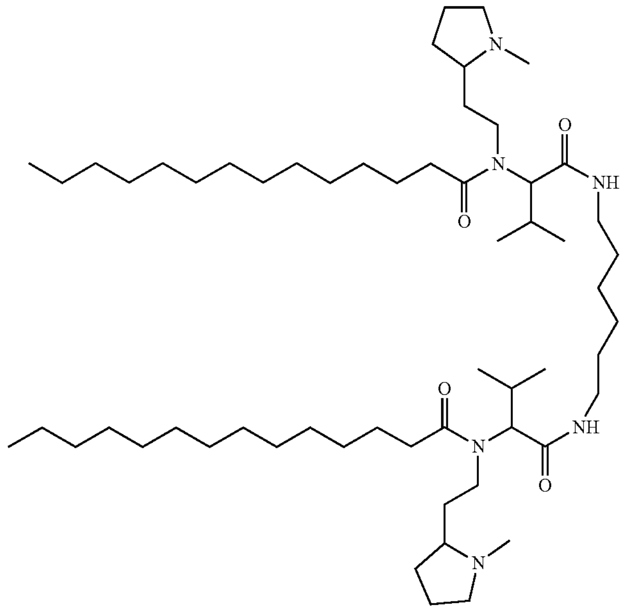
I1R11C16A1
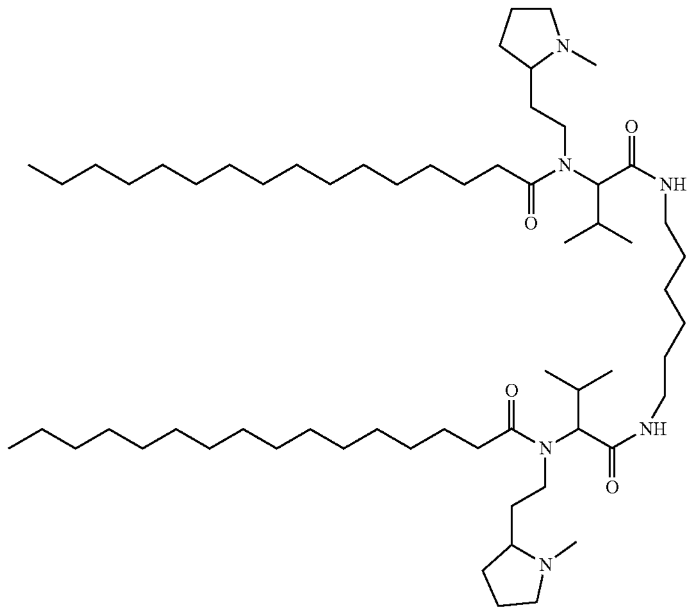

-continued
I1R11C18A1
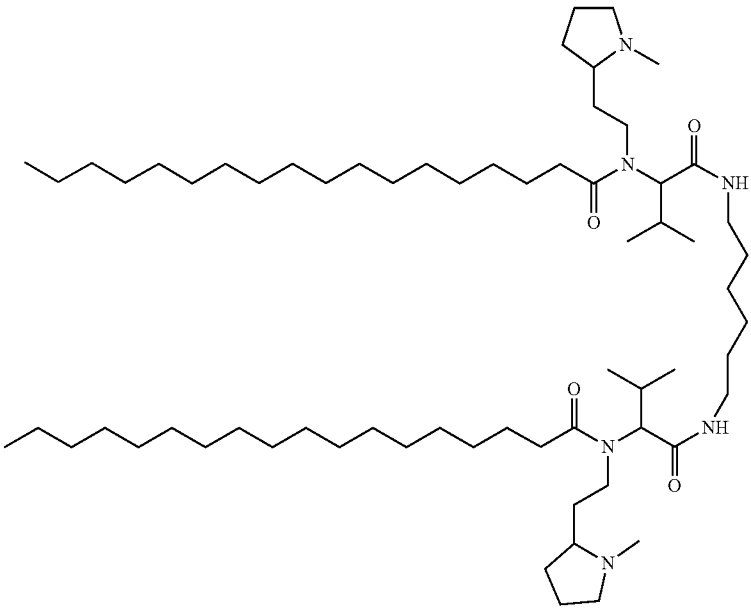
I1R11C20A1
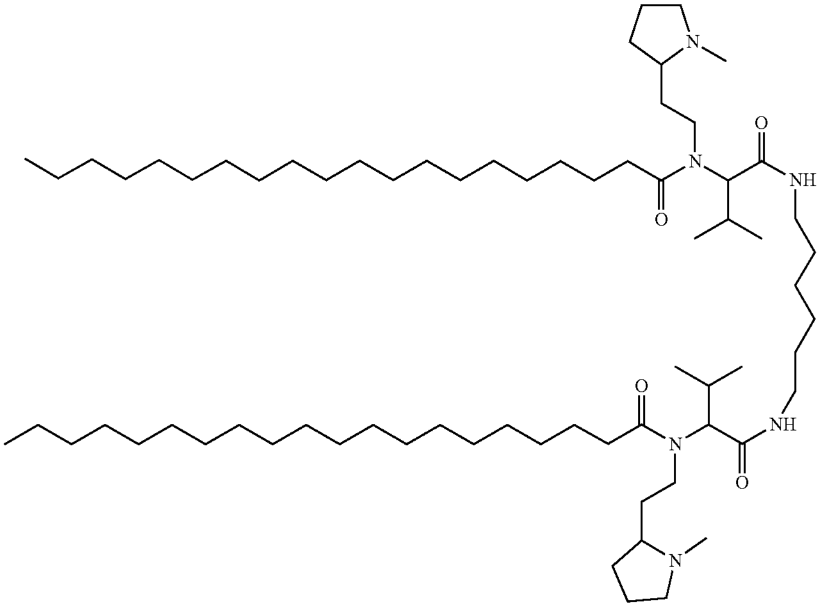

-continued
I1R11C18-1A1
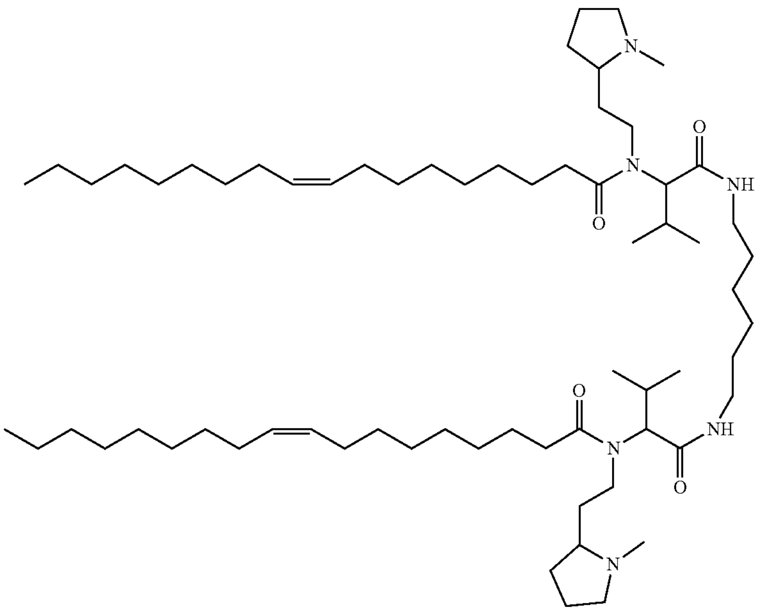
I1R11C18-2A1
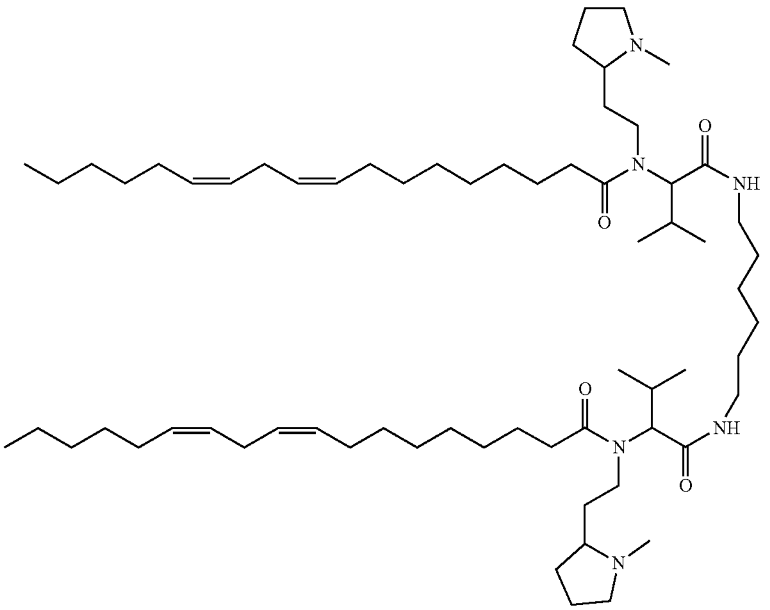

-continued
I2R1C12A1
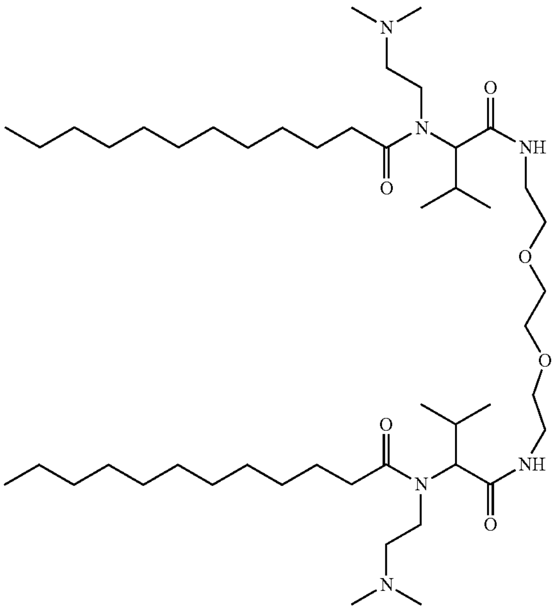
I2R1C14A1
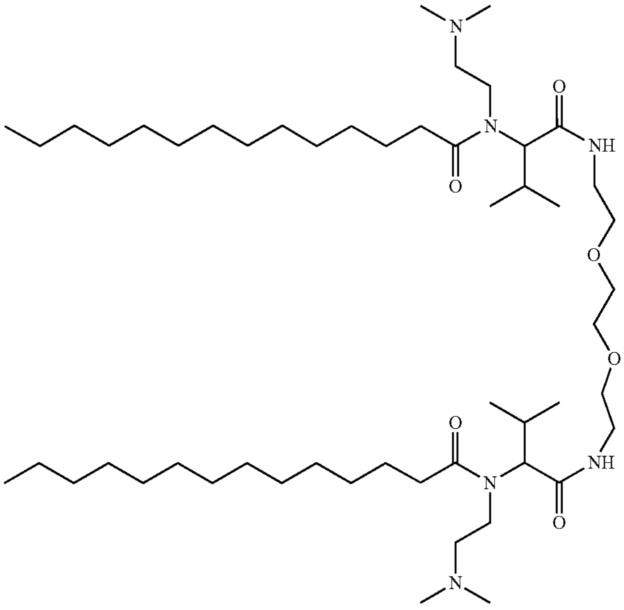

-continued
I2R1C16A1
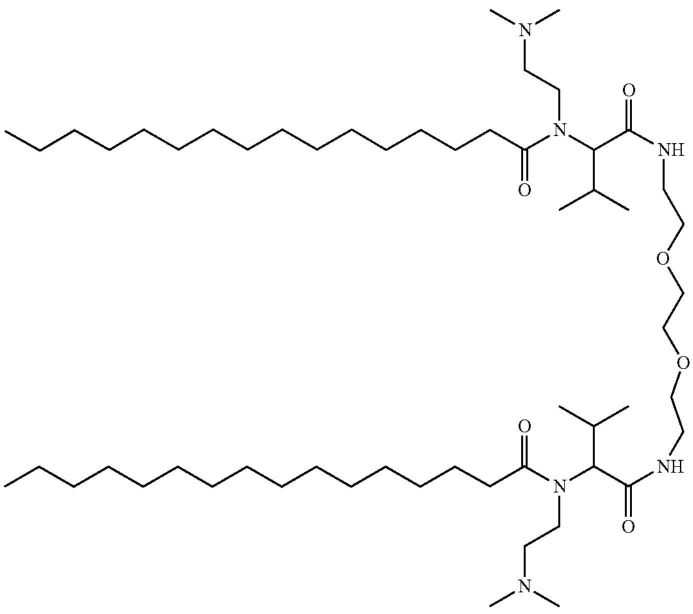
I2R1C18A1
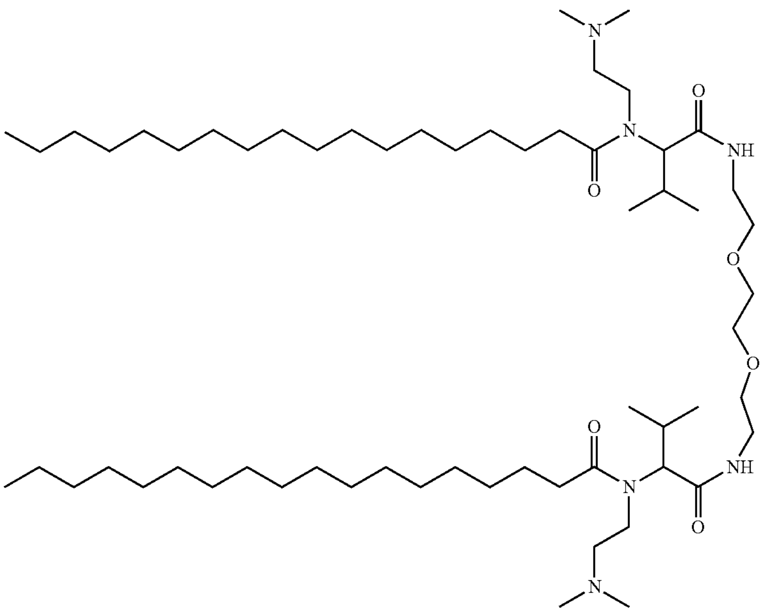

-continued
I2R1C20A1
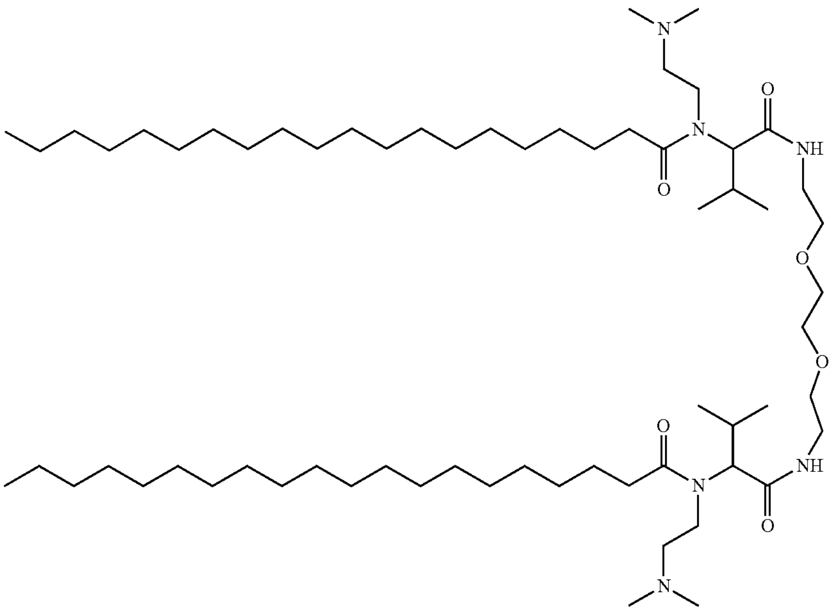
I2R1C18-1A1
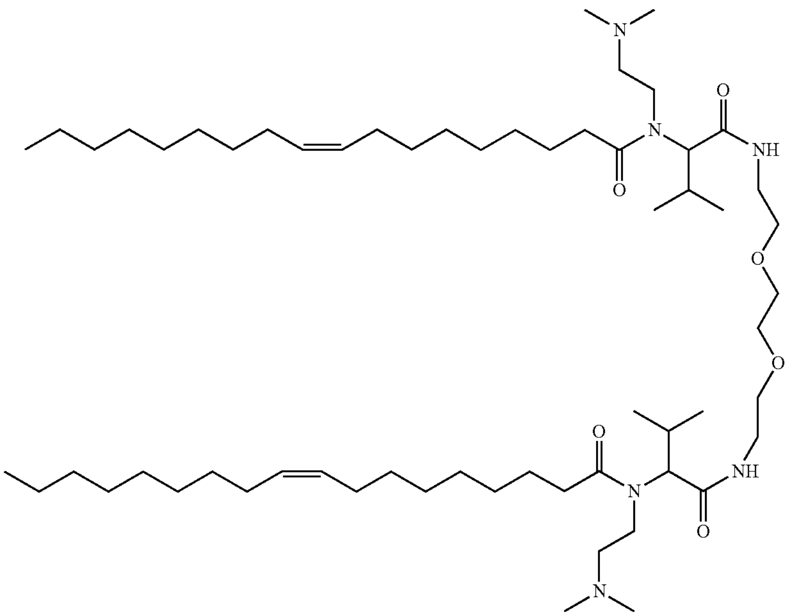

-continued
I2R1C18-2A1
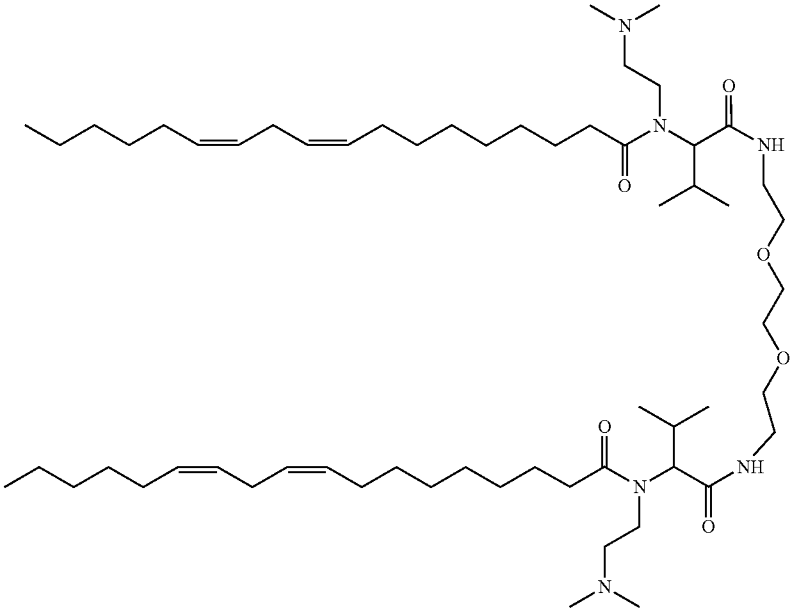
I2R2C12A1
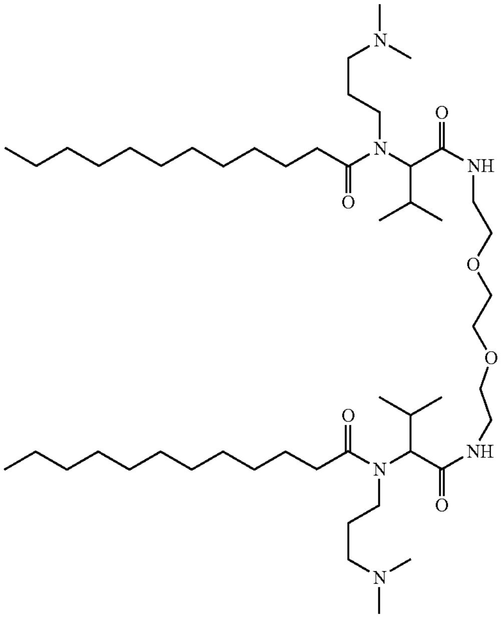

-continued
I2R2C14A1
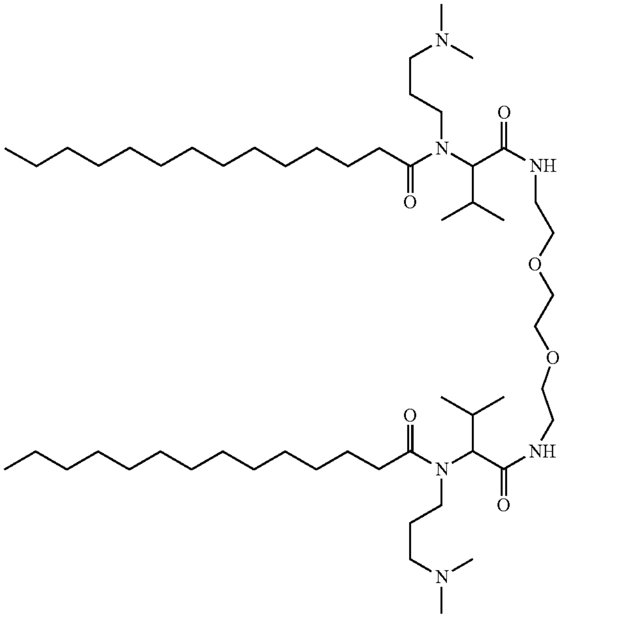
I2R2C16A1
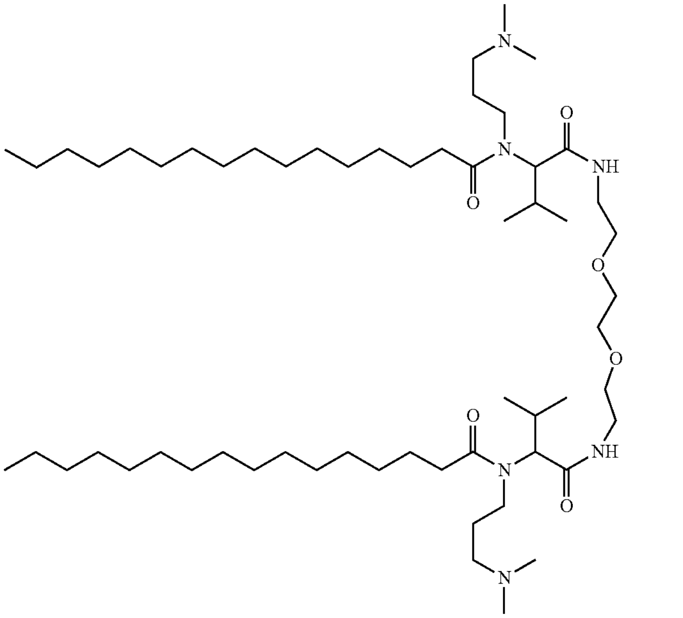

-continued
I2R2C18A1
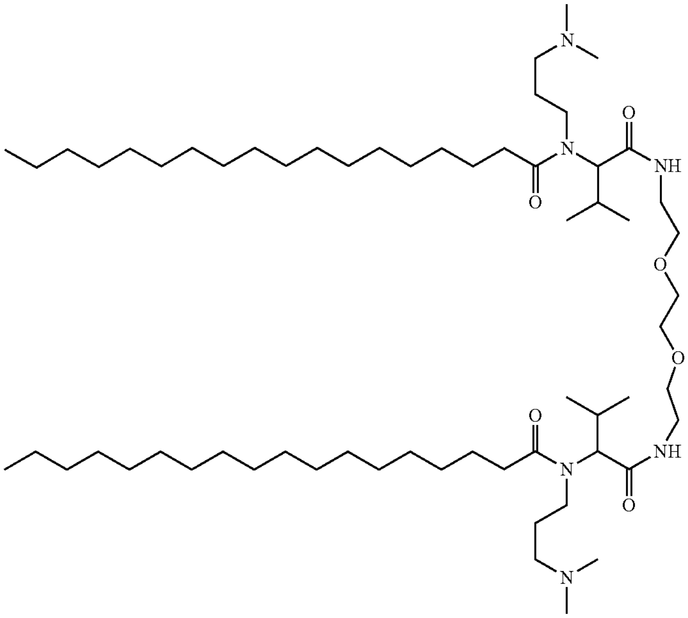
I2R2C20A1
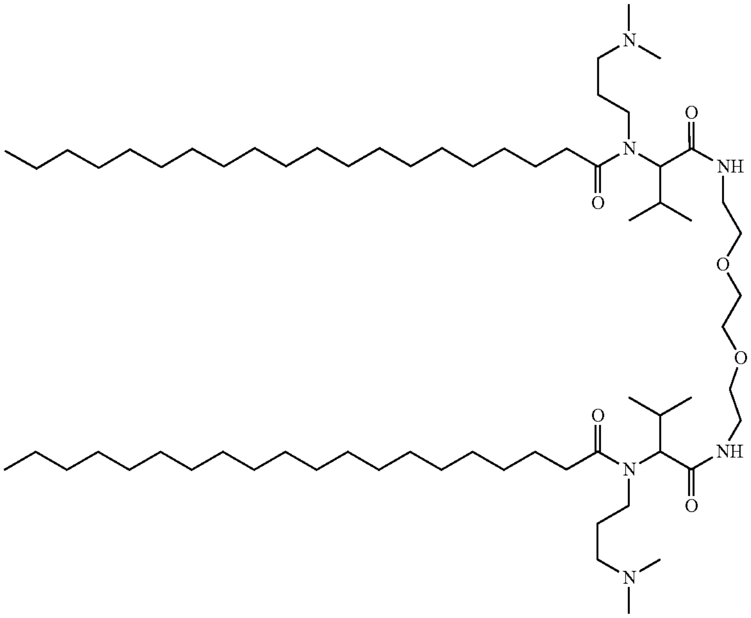

-continued
I2R2C18-1A1
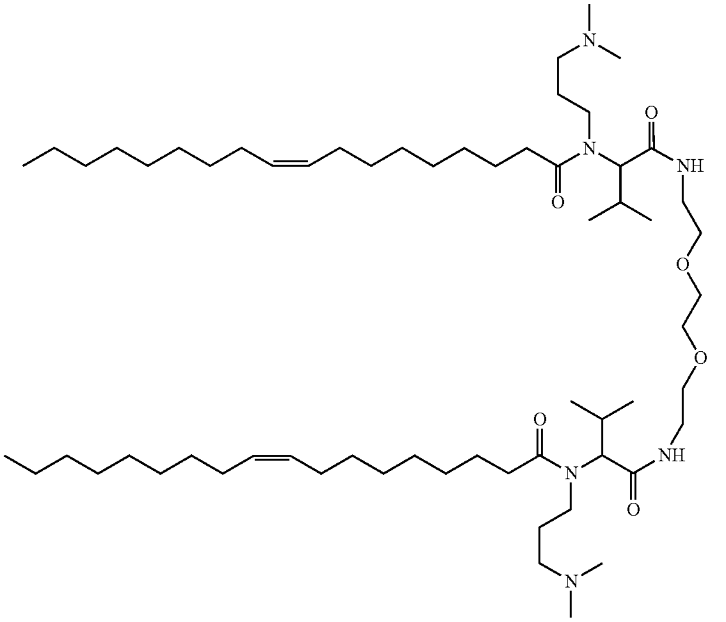
I2R2C18-2A1
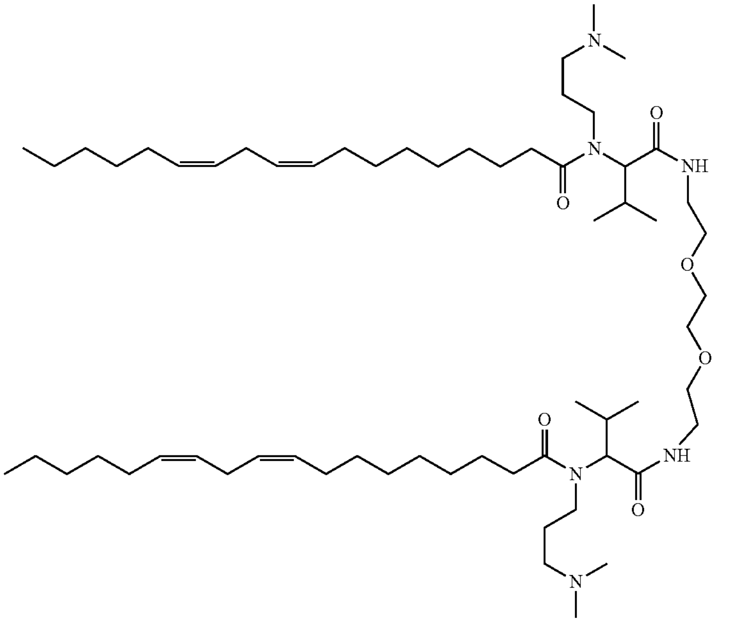

-continued
I2R3C12A1
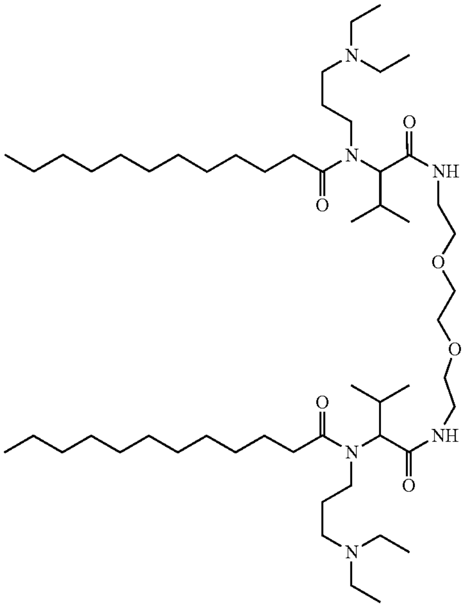
I2R3C14A1
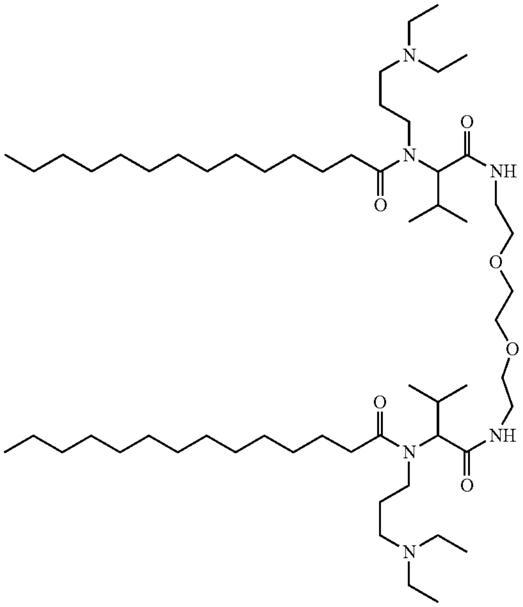

-continued
I1R3C16A1
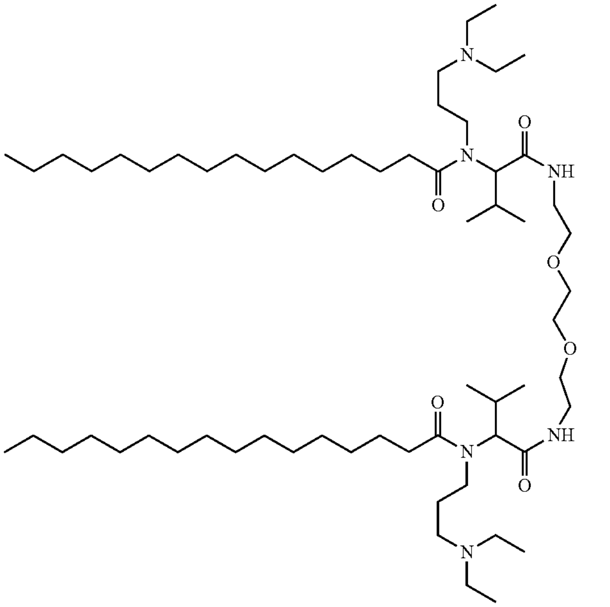
I1R3C18A1
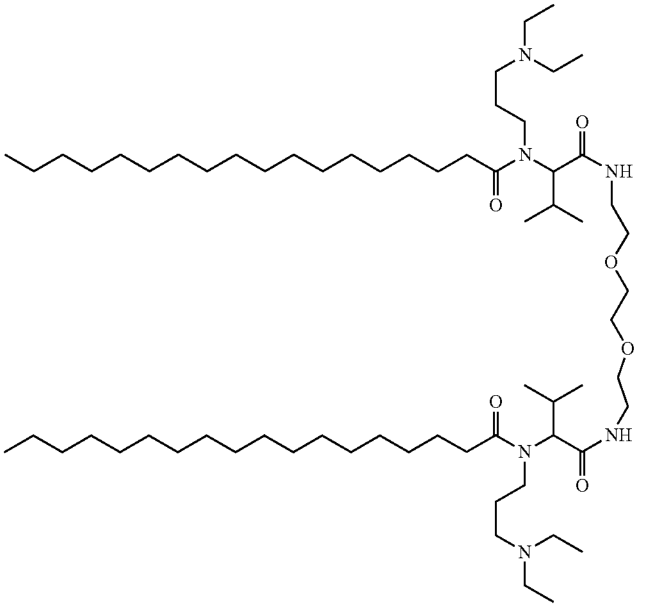

-continued
I1R3C20A1
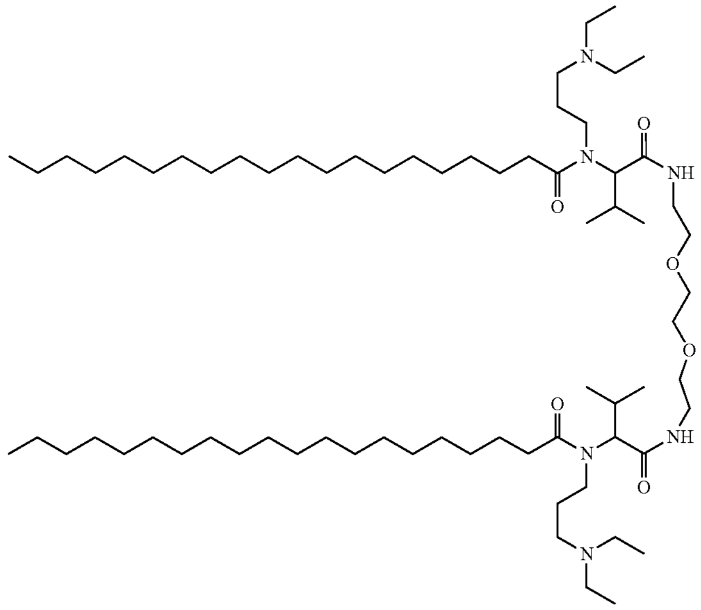
I2R3C18-1A1
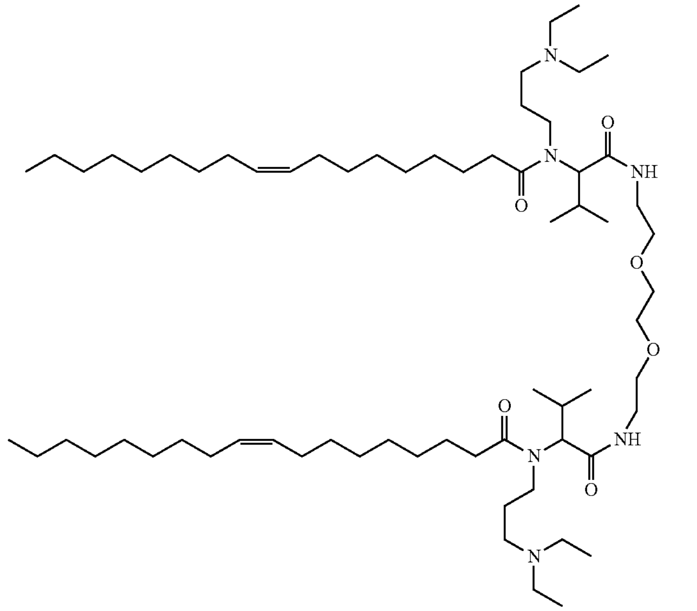

-continued
I2R3C18-2A1
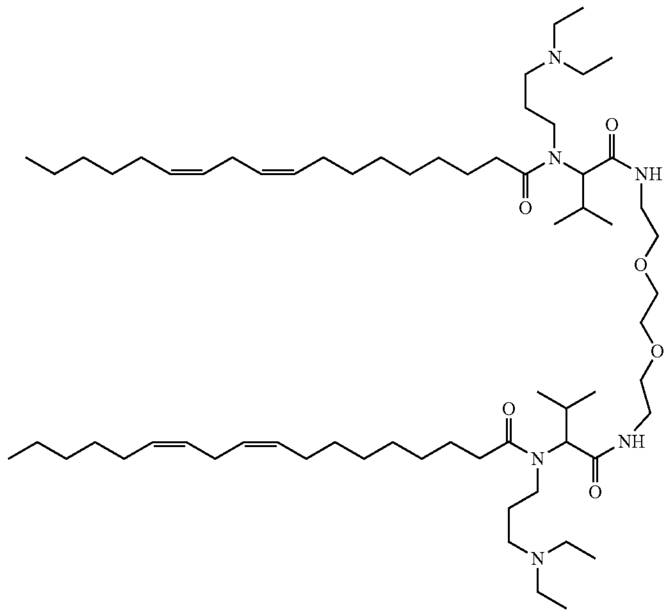
I2R5C12A1
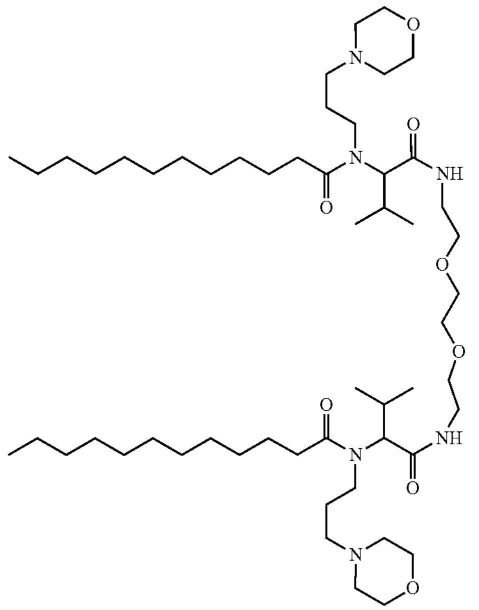

-continued
I2R5C14A1
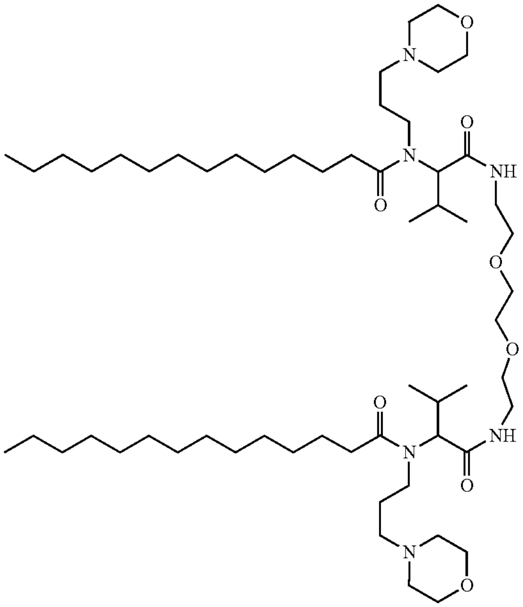
I2R5C16A1
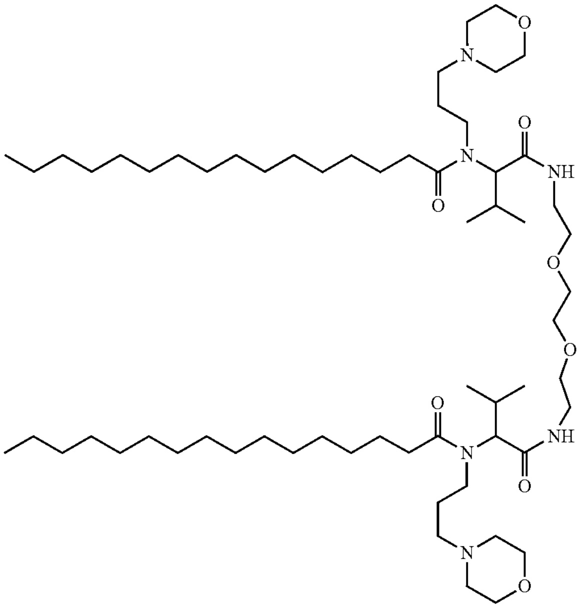

-continued
I2R5C18A1
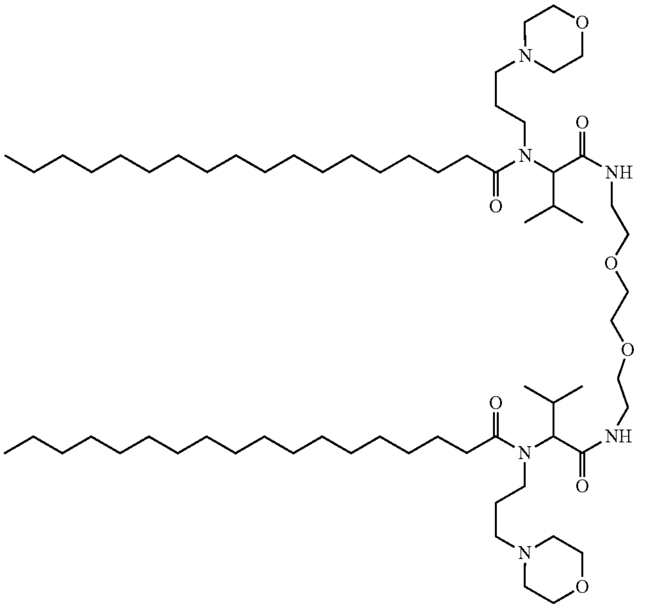
I2R5C20A1
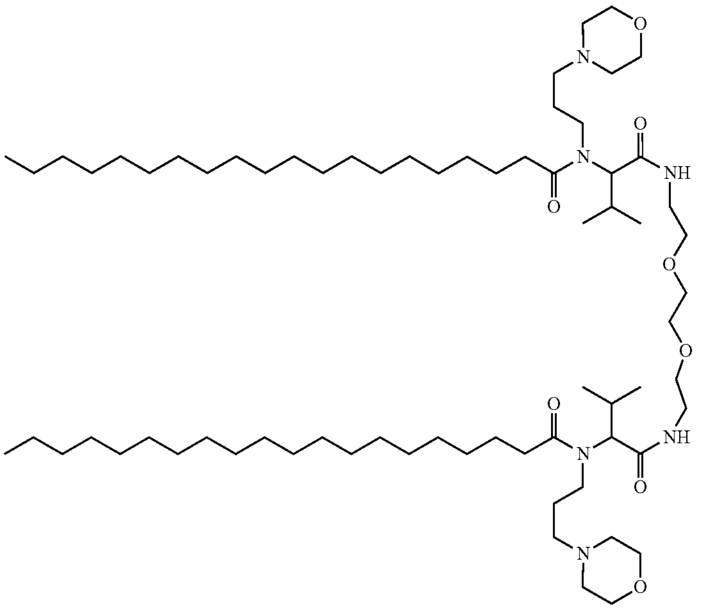

-continued
I2R5C18-1A1
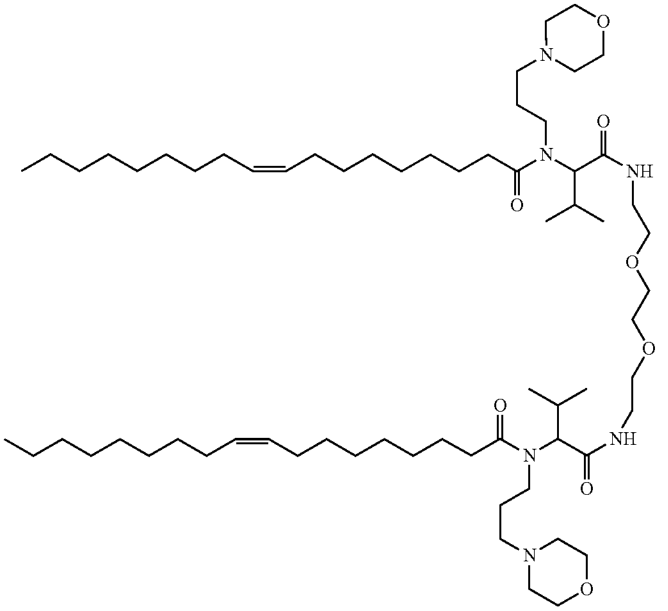
I2R5C18-2A1
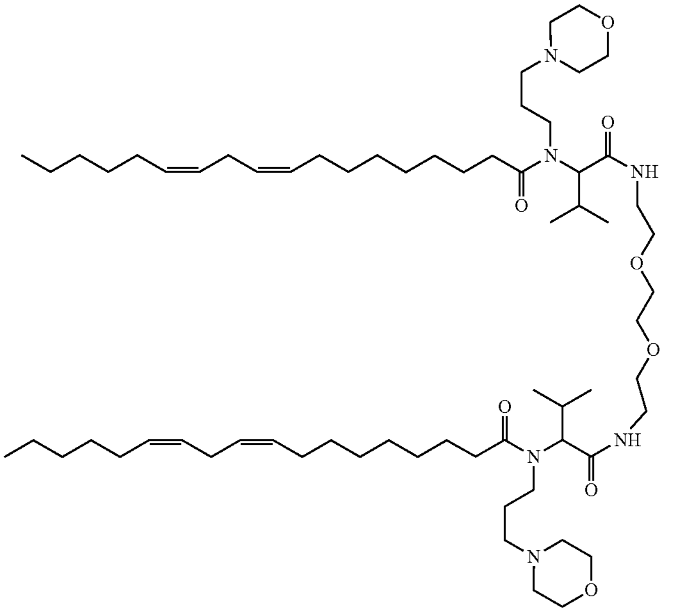

-continued
I2R11C12A1
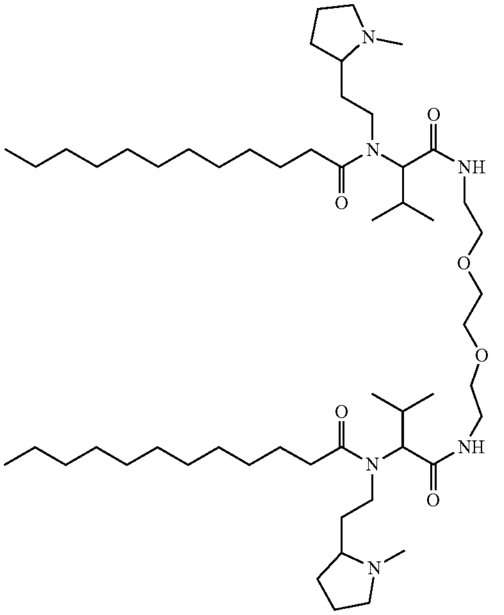
I2R11C14A1
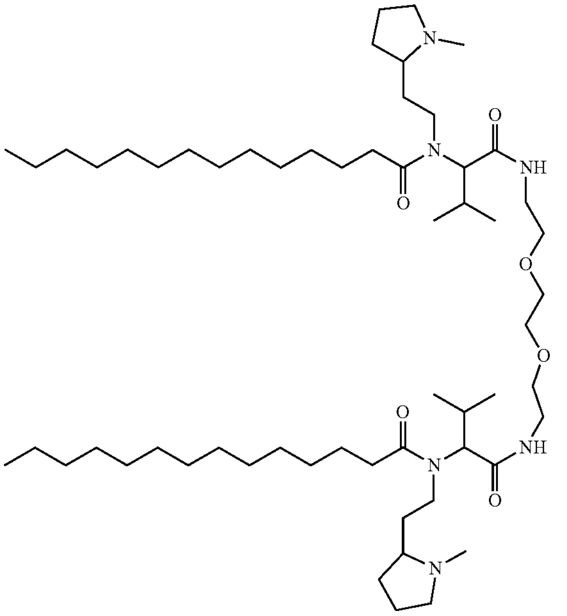

-continued
I2R11C16A1
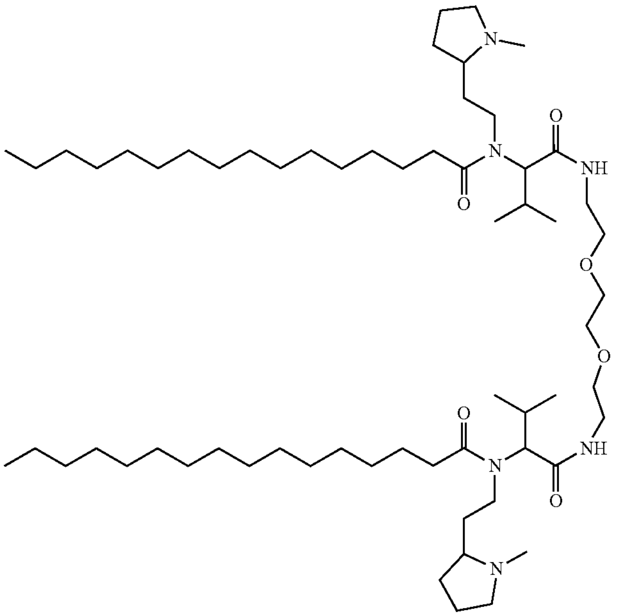
I2R11C18A1
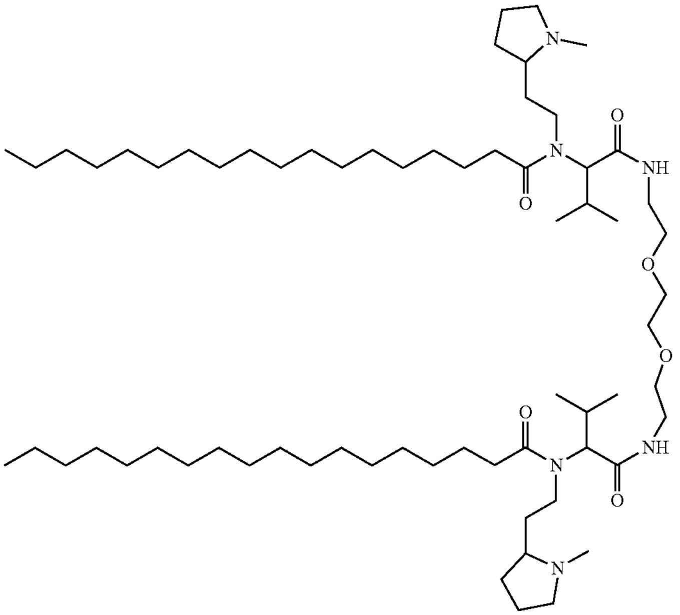

-continued
I2R11C20A1
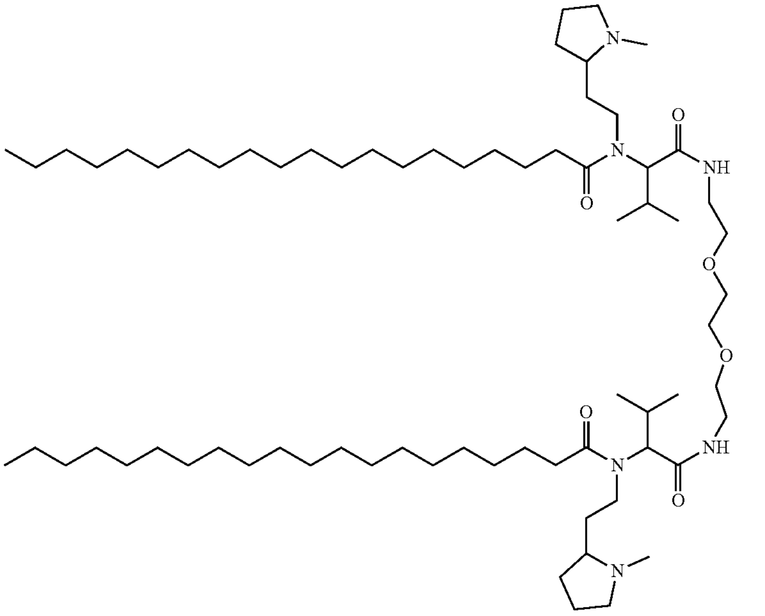
I2R11C18-1A1
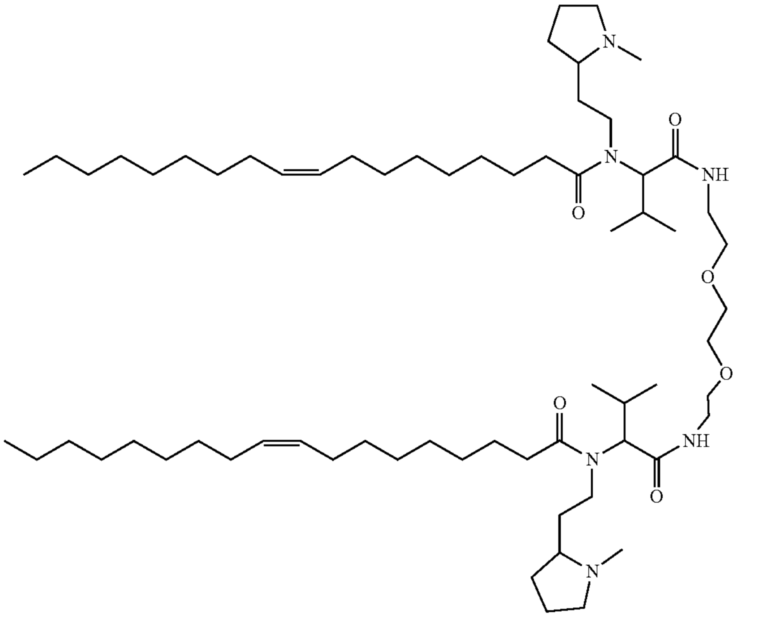

-continued
I2R11C18-2A1
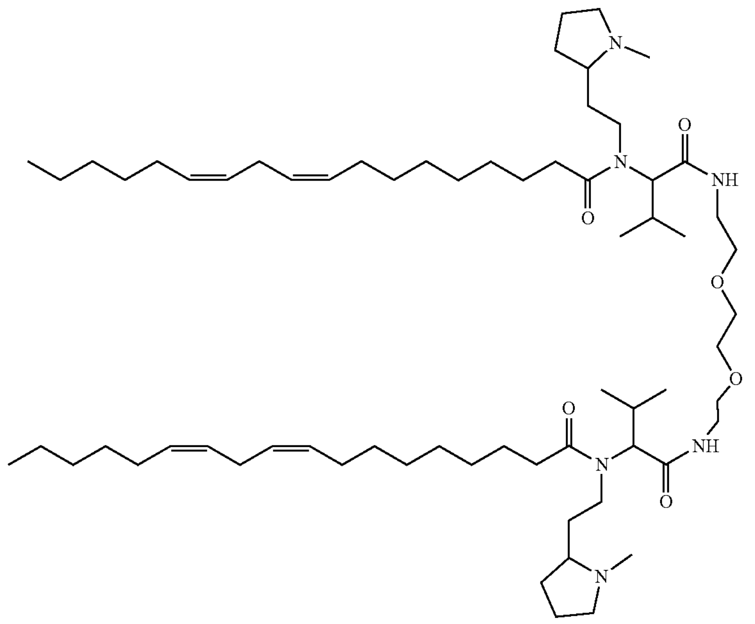
I2-1R2C18A1
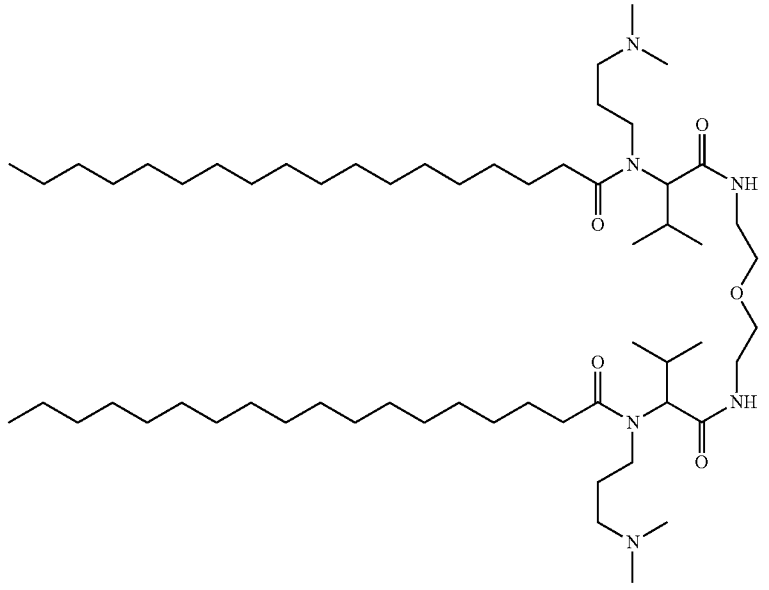

-continued

I2-3R2C18A1

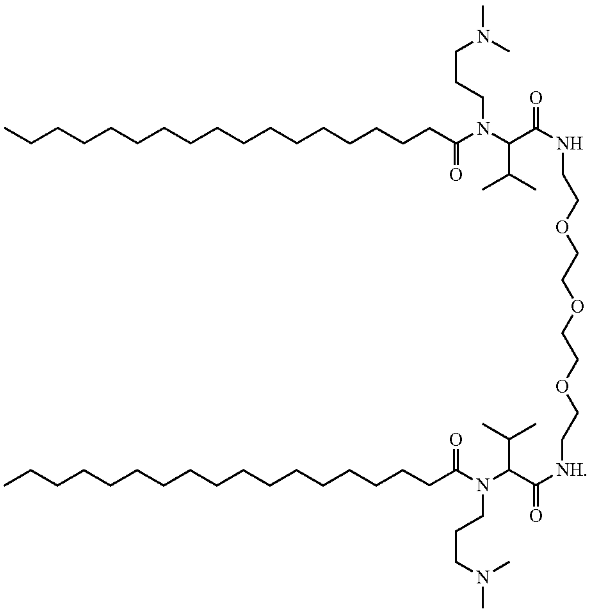

10. A preparation method of the ionizable cationic lipid analog material according to claim 1, comprising: adding an aldehyde compound and an amine compound to an organic solution; allowing to react for 10 min to 120 min before sequentially adding a carboxylic acid compound and an isocyanide compound; allowing to react at 4° C. to 60° C. for 6 h to 72 h; and separating and purifying a product by column chromatography after completion of reaction to obtain the ionizable cationic lipid analog material.

11. The preparation method of the ionizable cationic lipid analog material according to claim 10, wherein a molar ratio of the aldehyde compound, the amine compound, the carboxylic acid compound, and the isocyanide compound is (0.1-1):(0.1-1):(0.1-1):(0.1-1).

12. The preparation method of the ionizable cationic lipid analog material according to claim 11, wherein the molar ratio of the aldehyde compound, the amine compound, the carboxylic acid compound, and the isocyanide compound is 1:1:1:0.5.

13. The preparation method of the ionizable cationic lipid analog material according to claim 10, wherein the aldehyde compound is one selected from the group consisting of compounds A1 to A3:

A1

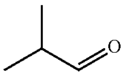

A2

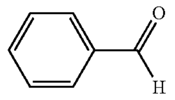

A3

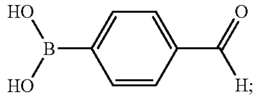

and the amine compound is one selected from the group consisting of compounds R1 to R11:

R1

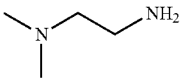

R2

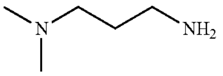

R3

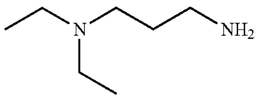

R4

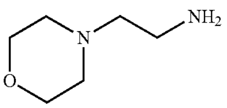

R5

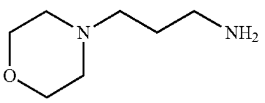

R6

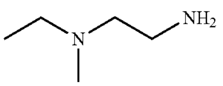

R7

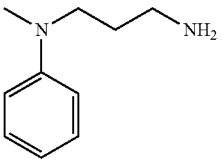

-continued

R8

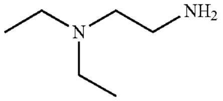

R9

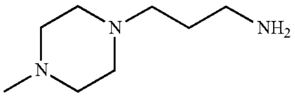

R10

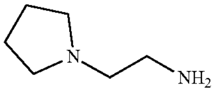

R11

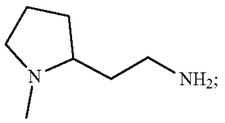

the carboxylic acid compound is one selected from the group consisting of compounds CHS, C18-1, C18-2, and C8 to C20:

C8

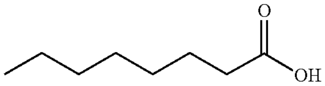

C9

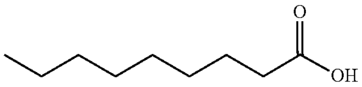

C10

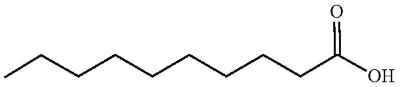

C11

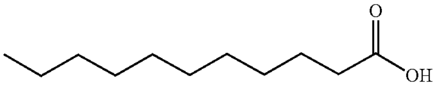

C12

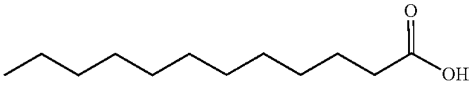

C13

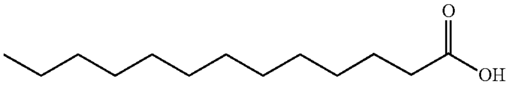

C14

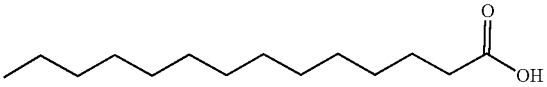

C15

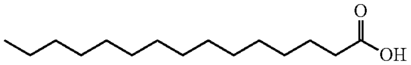

C16

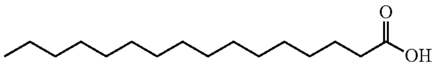

C17

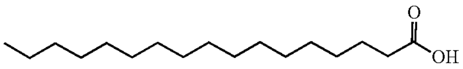

-continued

C18

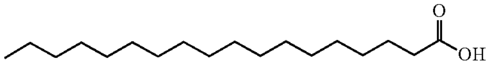

C19

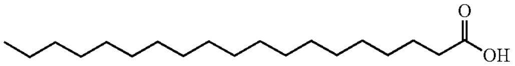

C20

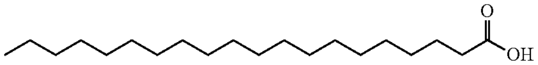

C18-1

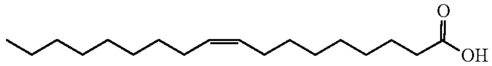

C18-2

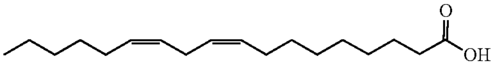

CHS

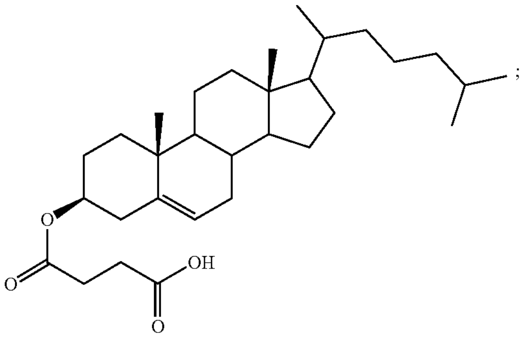

and the isocyanide compound is one selected from the group consisting of compounds I1, I2-1, I2, I2-3, and I3:

I1

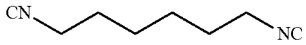

I2-1

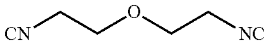

I2

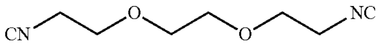

I2-3

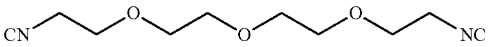

I3

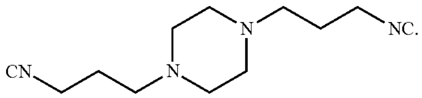

14. The preparation method of the ionizable cationic lipid analog material according to claim 13, wherein the aldehyde compound is compound A1.

15. A drug delivery system comprising a carrier and a drug wrapped around the carrier or loaded on the carrier, wherein the carrier is the ionizable cationic lipid analog material according to claim 1.

16. A preparation method of the ionizable cationic lipid analog material according to claim 2, comprising: adding an aldehyde compound and an amine compound to an organic solution; allowing to react for 10 min to 120 min before sequentially adding a carboxylic acid compound and an isocyanide compound; allowing to react at 4° C. to 60° C. for 6 h to 72 h; and separating and purifying a product by column chromatography after completion of reaction to obtain the ionizable cationic lipid analog material.

17. A preparation method of the ionizable cationic lipid analog material according to claim 3, comprising: adding an aldehyde compound and an amine compound to an organic solution; allowing to react for 10 min to 120 min before sequentially adding a carboxylic acid compound and an isocyanide compound; allowing to react at 4° C. to 60° C. for 6 h to 72 h; and separating and purifying a product by column chromatography after completion of reaction to obtain the ionizable cationic lipid analog material.

18. A preparation method of the ionizable cationic lipid analog material according to claim 4, comprising: adding an aldehyde compound and an amine compound to an organic solution; allowing to react for 10 min to 120 min before sequentially adding a carboxylic acid compound and an isocyanide compound; allowing to react at 4° C. to 60° C. for 6 h to 72 h; and separating and purifying a product by column chromatography after completion of reaction to obtain the ionizable cationic lipid analog material.

19. A preparation method of the ionizable cationic lipid analog material according to claim 5, comprising: adding an aldehyde compound and an amine compound to an organic solution; allowing to react for 10 min to 120 min before sequentially adding a carboxylic acid compound and an isocyanide compound; allowing to react at 4° C. to 60° C. for 6 h to 72 h; and separating and purifying a product by column chromatography after completion of reaction to obtain the ionizable cationic lipid analog material.

20. A preparation method of the ionizable cationic lipid analog material according to claim 6, comprising: adding an aldehyde compound and an amine compound to an organic solution; allowing to react for 10 min to 120 min before sequentially adding a carboxylic acid compound and an isocyanide compound; allowing to react at 4° C. to 60° C. for 6 h to 72 h; and separating and purifying a product by column chromatography after completion of reaction to obtain the ionizable cationic lipid analog material.

* * * * *